United States Patent [19]
Meyer et al.

[11] Patent Number: 5,891,882
[45] Date of Patent: Apr. 6, 1999

[54] BENZOPYRANOPYRROLE AND BENZOPYRANOPYRIDINE α-1 ADENERGIC COMPOUNDS

[75] Inventors: Michael D. Meyer, Lake Villa; Robert J. Altenbach, Chicago; Fatima Z. Basha, Lake Forest; William A. Carroll, Evanston; Irene Drizin, Wadsworth; James F. Kerwin, Jr., Grayslake; Michael D. Wendt, North Chicago, all of Ill.

[73] Assignee: Abbott Laboratories, Abbott Park, Ill.

[21] Appl. No.: 975,979

[22] Filed: Nov. 21, 1997

Related U.S. Application Data

[63] Continuation of Ser. No. 761,423, Dec. 6, 1996, abandoned.
[51] Int. Cl.$^6$ .................... A61K 31/505; C07D 239/00; C07D 471/00; C07D 487/00
[52] U.S. Cl. .................... 514/267; 544/250; 544/251
[58] Field of Search ................... 544/249, 250, 544/251; 546/89; 548/430; 514/267

[56] References Cited

U.S. PATENT DOCUMENTS

| | | | |
|---|---|---|---|
| 3,888,946 | 6/1975 | Pars et al. | 260/326.5 B |
| 4,117,140 | 9/1978 | Brown et al. | 424/267 |
| 4,385,056 | 5/1983 | Loozen | 424/248.55 |
| 5,387,591 | 2/1995 | Lavielle et al. | 514/307 |
| 5,597,823 | 1/1997 | Meyer et al. | 514/250 |

FOREIGN PATENT DOCUMENTS

| | | |
|---|---|---|
| 0095666 | 12/1983 | European Pat. Off. |
| 0556119 | 8/1993 | European Pat. Off. |

OTHER PUBLICATIONS

Pars, H. G., et al., "Drugs Derived from Cannabinoids. 1. Nitrogen Analogs, Benzopyranopyridines and Benzopyranopyrroles", *Journal of Medicinal Chemistry*, 19(4):445–453 (1976).

Caine, et al., "Adrenergic and Cholinergic Receptors in the Human Prostate, Prostatic Capsule and Bladder Neck", *British Journal of Urology*, 47:193–202 (1975.

Chapple, "Medical treatment for benigh prostatic hyperplasia", *BMJ*, 1198–1199 (1992).

Chapple, et al., "Characterisation of Human Prostatic Adrenoceptors using Pharmacology receptor Binding and Localisation", *British Journal of Urology*, 63:487–496 (1989).

Chapple, et al., "A Twelve–Week Placebo–Controlled Study of Prazosin in the Treatment of Prostatic Obstruction", *Urol Int*, 45(1):47–55 (1990).

Chow, et al,., "Multicentre Controlled Trail of Indoramin in the Symptomatic Relief of Benigh Prostatic Hypertrophy", *British Journal of Urology*, 65:36–38 (1990).

Gittes. et al., "Female Urethral Syndrome A Female Prostatitis?", *WJM*, 164(5):435–438 (1996).

Hoffman, et al., "Alpha Adrenergic Receptor Subtypes in Rabbit Uterus: Mediation of Myometrial Contraction and Regulation by Estrogens", *The Journal of Pharmacology and Experimental Therapeutics*, 219(2):290–295 (1981).

Janknegt, et al., "Efficacy and Safety of the Alpha–1 Blocker Doxazosin in the Treatment of Benigh Prostatic Hyperplasia", *Eur Urol*,24:319–326 (1993).

Lepor, "Alpha Blockade for the Treatment of Benigh Prostatic Hyperplasia", *Urologic Clinics of North America*, 22(2):375–386 (1995).

Miller, et al., "Uterine response to nerve stimulation; relation to hormonal status and catecholamines", *American Journal of Physiology*, 209:859–863 (1965).

Roberts, et al., Regulation of Myometrial Adrenoreceptors and Adrenergic Response by Sex Steroids:, *Molecular Pharmacology*, 20:52–58 (1981).

Rosier, et al., "Is Detrusor Instability in Elderly Males Related to the Grade of Obstruction?", *Neurourology and Urodynamics*, 14:625–633 (1995).

Thien, et al., "Urinary incontinence caused by prazosin", *British Medical Journal*, 622–623 (1978).

*Primary Examiner*—Richard L. Raymond
*Assistant Examiner*—Bruck Kifle
*Attorney, Agent, or Firm*—Michael J. Ward

[57] ABSTRACT

The present invention relates to a compound of the formula and the pharmaceutically acceptable salts thereof wherein W is a bicyclic heterocyclic ring system. The compounds are α-1 adrenergic antagonists and are useful in the treatment of BPH; also disclosed are α-1 antagonist compositions and a method for antagonizing α-1 adrenoreceptors and tr

33 Claims, No Drawings

BENZOPYRANOPYRROLE AND BENZOPYRANOPYRIDINE α-1 ADENERGIC COMPOUNDS

This application is a continuation of U.S. patent application Ser. No. 08/761,423, filed Dec. 6, 1996, which is abandoned.

TECHNICAL FIELD

The present invention relates to novel organic compounds and compositions which are alpha-1 (α-1) adrenoreceptor antagonists, processes for making such compounds, synthetic intermediates employed in these processes, and a method for inhibiting alpha-1 adrenoreceptors and treating benign prostatic hyperplasia (BPH), also called benign prostatic hypertrophy, or other urological diseases such as bladder outlet obstruction and neurogenic bladder, or gynecological syndromes such as dysmenorrhea, also called benign prostatic hypertrophy.

BACKGROUND OF THE INVENTION

Adrenergic neurons play a major role in the innervation of heart, blood vessel and smooth muscle tissue. Compounds capable of interacting with adrenoreceptor sites within adrenergic nerves can initiate a variety of physiological responses, including vasoconstriction, vasodilation, and increased or decreased heart rate (chronotropic), contractility (inotropic) and metabolic activity. In the past, various adrenergic compounds have been employed to affect these and other physiological responses. However, many adrenergic compounds do not possess significant selectivity to enable desirable interactions with adrenergic adrenoreceptor sites. That is, these adrenergic compounds do not demonstrate a high degree of specificity for differing adrenoreceptor types within adrenergic neurons in order to obtain a desired physiological response separate from other possible, and perhaps less desirable, responses of the system.

Benign prostatic hyperplasia (BPH) is a condition which develops in middle-aged and elderly males and refers to the benign overgrowth of the stromal and epithelial elements of the prostate associated with aging. Symptoms of BPH include increased frequency of urination, nocturia, a weak urine stream and hesitancy or delay in starting the urine flow. Chronic consequences of BPH can include hypertrophy of bladder smooth muscle, a decompensated bladder and an increased incidence of urinary tract infection.

Typically, BPH begins at an age in the mid-fifties and is the most common cause of urinary tract problems of men of this age. BPH is apparently rare in men prior to age 40, but at age 60, approximately 50% of men have histological evidence of BPH. The prevalence of BPH continues to increase with age until, at age 80, approximately 80% of men have pathological evidence of BPH.

Although prostatic hyperplasia is a common finding in older men, the presence of urinary symptoms is the essential feature that distinguishes simple anatomic enlargement of the prostate from prostatism, which is the clinical syndrome whereby the patient experiences significant obstruction of urinary flow. It is not uncommon in older men to have a palpably enlarged prostate without showing the symptoms of prostatism. From the patient's perspective, however, the incidence and progression of urinary symptoms are more important than the mere presence of an enlarged prostate.

The discovery in the 1970's (M. Caine, et al., *Brit. J. Urol.*, 47: 193–202 (1975)) of large numbers of alpha-adrenergic adrenoreceptors in the smooth muscle of the prostatic capsule and bladder neck led to the conclusion that there is both a static and a dynamic component to bladder outlet obstruction associated with BPH. The static component derives from the progressive hyperplasia of the prostate with aging, leading to urethral narrowing which causes symptoms of urinary obstruction. Superimposed on this essentially mechanical problem is the variable degree of smooth muscle contraction controlled by the sympatheic nervous system and which is affected by factors such as stress, cold and sympathomimetic drugs. It is this dynamic component which explains the often rapid fluctuations in symptoms observed in patients with prostatism.

The currently most effective treatment for BPH is the surgical procedure of transurethral resection of the prostate (TURP) Since it removes the obstructing tissue (C. Chapple, *Br. Med. Journal* 304: 1198–1199 (1992)) it is a treatment which is directed to the static and dynamic components of BPH. However, this surgical treatment is associated with rates of mortality (1%) and adverse event (incontinence 2–4%, infection 5–10%, and impotence 5–10%). A non-invasive alternative treatment would thus be highly desirable.

The incidental clinical observation that urinary incontinence developed in women during antihypertensive treatment with prazosin (T. Thien, K. P. Delacre, F. M. J. Debruyne, R. A. P. Koene, *Br. Med. Journal*, 622–623 (1978)) and the experimental work of Caine (op cit.) contributed to the recognition of the potential role of selective α-1 adrenoreceptor blockade in diseases of the lower urinary tract. Subsequent studies by several groups have documented the functional role of α-1 adrenoreceptors relative to α-2 adrenoreceptors in the stromal compartment of the prostate, thereby providing a putative molecular basis for the use of specific α-1 adrenoreceptor blockers in the non-surgical management of BPH (C. R. Chapple, M. L. Aubry, S. James, M. Greengrass, G. Burnstock, R. T. Turner-Warwick, *Br. J. Urol.* 63, 487–496 (1989)). Clinical efficacy of α-1 antagonists in BPH has been demonstrated with several non-selective α-1 blockers, including terazosin (Hytrin®), prazosin, and doxazosin. Treatment periods as short as two to four weeks with α-1 adrenoreceptor blockers have shown objective improvements in the mean and maximum urinary flow rates (14–96%) with subjective improvements in patients' symptom scores (R. A. Janknegt, C. R. Chapple, *Eur. Urol.* 24: 319–326 (1993)). Longer term studies with terazosin, indoramin, prazosin, and doxazosin have similarly demonstrated significant improvements in urinary flow rates and subjective symptom scores (R. A. Janknegt, op. cit., H. Lepor, G. Knapp-Maloney, *J. Urol.* 145: 263A (1991), W. Chow, D. Hahn, D. Sandhu, *Br. J. Urol.* 65: 36–38 (1990) and C. R. Chapple, T. J. Christmas, E. J. G. Milroy, *Urol. Int.* 45: 47–55 (1990)). However, these agents possess similar dose limiting side effects: hypotension, dizziness, and muscle fatigue.

In recent years, it has become clear that BPH and bladder outlet obstruction (BOO) are clinically differentiable, and that the severity of clinical BPH is related to many factors in addition to BOO (Lepor, H., *Alpha Blockade for the Treatment of Benign Prostatic Hyperplasia*, Urol. Clin. N. Amer., 22: 375–386, 1995.). For example, BOO may be related to other urological symptoms such as detrusor instability (Rosier, P. F. W. M., J. J. M. C. H. de la Rosette, H. Wijkstra, Ph. E. V. Van Kerrebroeck and F. M. J. Debruyne, *Is Detrusor Instability in Elderly Males Related to the Grade of Obstruction?*, Neurourol. Urodynam., 14: 625–633, 1995). In addition, the role of extraprostatic α-1 adrenoreceptors has been postulated as important in the etiology of lower urinary tract symptoms, such that antagonism of these receptors in spinal cord, ganglia, nerve terminals, bladder and bladder neck or the external urethral sphincter could be important in pharmacotherapy of urological conditions such as BOO and neurogenic bladder (Andersson, K.-E., *Prostatic and extraprostatic α-adrenoceptors-Contributions to the Lower Urinary Tract Symptoms in Benign Prostatic Hyperplasia,* Scand. J. Urol. and Nephrol., 30: 105–111, 1996). The recognition that women possess paraurethral glands which have anatomical, histological and biochemical similarities to the male prostate (Gittes, R. F. and R. M. Nakamura, *Female urethral syndrome: A female prostatitis?,* Western J. Medicine, 164: 435–438, 1996) suggests a potential role for α-1 adrenoreceptor antagonist pharmacotherapy for amelioration of some symptoms of female urethral syndromes. In addition, α-adrenoreceptors are functionally important to smooth muscle contraction in the uterus (Miller, M. D. and J. M. Marshall, *Uterine response to nerve stimulation: relation to hormonal status and catecholamines,* Am. J. Physiol., 209: 859–863, 1965) and the modulation of sympathetic responses to catecholamines is enhanced by elevations in the levels of estrogens (Miller and Marshall, *Uterine response to nerve stimulation: relation to hormonal status and catecholamines,* Am. J. Physiol., 209: 859–863, 1965). Consistent with this observation are data showing increasing levels of α-adrenoreceptor responses and receptor density following estrogen administration to animals (Hoffman, B. B., T. N. Lavin, R. J. Lefkowitz and R. R. Ruffolo, Jr., *Alpha adrenergic receptor subtypes in rabbit uterus: Mediation of myometrial contraction and regulation by estrogens,* J. Pharmacol. Exp. Ther., 219: 290–295, 1981, and Roberts, J. M., P. A. Insel and A. Goldfein, *Regulation of myometrial adrenoreceptors and adrenergic response by sex steroids,* Mol. Pharmacol., 20: 52–58, 1981). Thus hormonal regulation of α-1 adrenoreceptor sensitivity could play a role in enhanced uterine contractions in dysmenorrhea, a condition for which selective α-1 adrenoreceptor antagonists could have therapeutic potential.

There thus exists a need for a "uroselective" α-1 antagonist with reduced side effect liabilities.

SUMMARY OF THE INVENTION

In its principle embodiment, the present invention provides certain benzopyranopyrrole and benzopyranopyridine compounds of formula I:

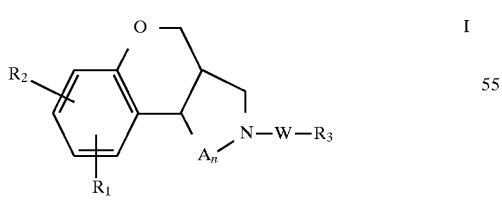

or a pharmaceutically acceptable salt thereof, wherein $R_1$ and $R_2$ are independently selected from the group consisting of hydrogen, alkyl, alkenyl, alkynyl, alkoxyalkyl, alkoxy, alkoxycarbonyl, hydroxy, hydroxyalkyl, carboxy, carboxyalkyl, halogen, nitro, amino, and aminoalkyl, A is methylene, n is 1 or 2, W is alkylene of from 2 to 10 carbon atoms, and $R_3$ is selected from the group consisting of,

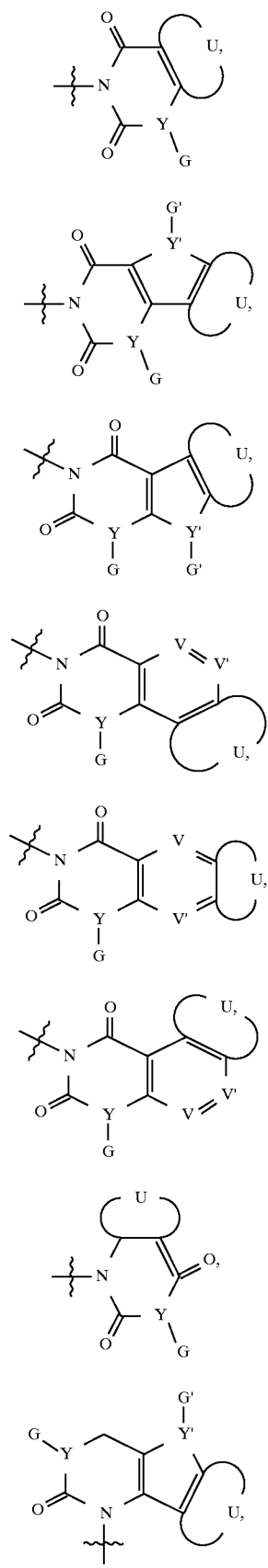

-continued

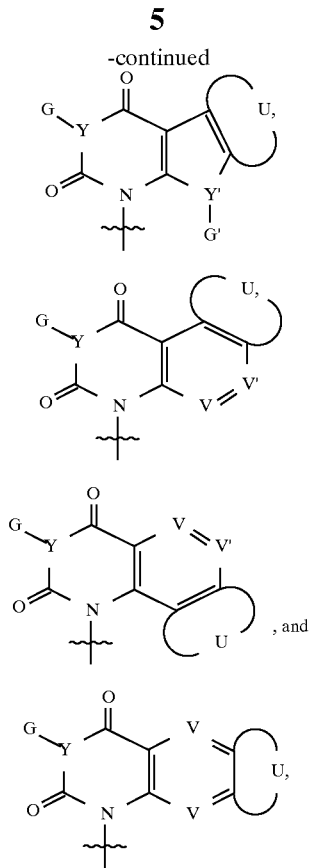

wherein G and G' are independently selected from the group consisting of hydrogen, alkyl, alkenyl, alkynyl, alkoxy, alkoxyalkyl, alkoxycarbonyl, hydroxy, hydroxyalkyl, carboxy, carboxyalkyl, halogen, alkylsulfonyl, and aminoalkyl, Y and Y' are independently selected from the group consisting of oxygen, nitrogen, and sulfur, with the proviso that when Y is oxygen or sulfur, G is absent and when Y' is oxygen or sulfur, G' is absent, V and V' are independently selected from the group of nitrogen and methine, and U is a ring that is fused to its adjacent ring and is selected from the group consisting of (a) an unsubstituted or substituted five member ring having five carbon atoms; (b) an unsubstituted or substituted five membered ring having four carbon atoms and one heteroatom selected from the group consisting of nitrogen, oxygen, and sulfur; (c) an unsubstituted or substituted five membered ring having three carbon atoms and two heteroatoms independently selected from the group consisting of nitrogen, oxygen, and sulfur; (d) a substituted or unsubstituted six membered ring having six carbon atoms; (e) a substituted or unsubstituted six membered ring having 5 carbon atoms and one heteroatom selected from the group consisting of nitrogen, oxygen, and sulfur; (f) a substituted or unsubstituted 6 membered ring having 4 carbon atoms and two heteroatom selected from the group consisting of nitrogen, oxygen, and sulfur; and (g) a substituted or unsubstituted 6 membered ring having three carbon atoms and three heteroatoms selected from the group consisting of nitrogen, oxygen, and sulfur. The five membered rings constituting U may contain 0, 1, or 2 double bonds. The six membered rings constituting U may contain 0, 1, 2, or 3 double bonds. The rings (a)–(g) of the group constituting U may be mono or di-substituted with substituents independently selected from the group consisting of alkyl, alkoxy, cyano, nitro, carboxy, alkoxycarbonyl of two to eight carbon atoms, halogen, cycloalkyl, aryl, and heterocyclic.

The present invention also relates to pharmaceutical compositions which comprise a therapeutically effective amount of a compound of formula I in combination with a pharmaceutically effective carrier.

The present invention also relates to a method of antagonizing alpha-1 adrenoreceptor binding in a host mammal, in particular humans, by administering a therapeutically effective amount of a composition comprising a compound of formula I. In particular, the present invention relates to a method of treating BPH in a mammal, in particular humans, by administering to a mammal an effective amount of a compound of formula I.

DETAILED DESCRIPTION OF THE INVENTION

In one embodiment, the present invention provides a compound of the formula I,

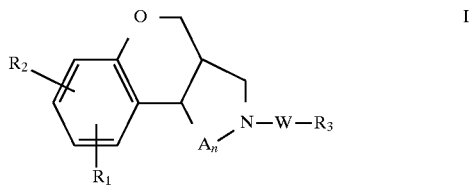

or a pharmaceutically acceptable salt thereof, wherein $R_1$ and $R_2$ are independently selected from the group consisting of hydrogen, alkyl, alkenyl, alkynyl, alkoxyalkyl, alkoxy, alkoxycarbonyl, hydroxy, hydroxyalkyl, carboxy, carboxyalkyl, halogen, nitro, amino, and aminoalkyl, A is methylene, n is 1 or 2, W is alkylene of from 2 to 10 carbon atoms, and $R_3$ is selected from the group consisting of,

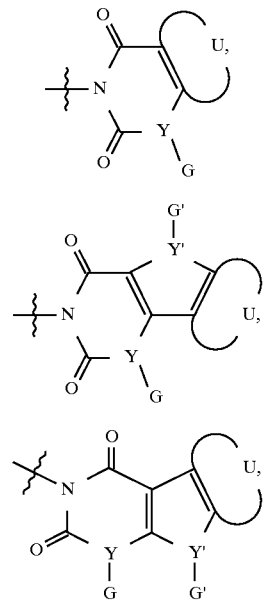

7
-continued

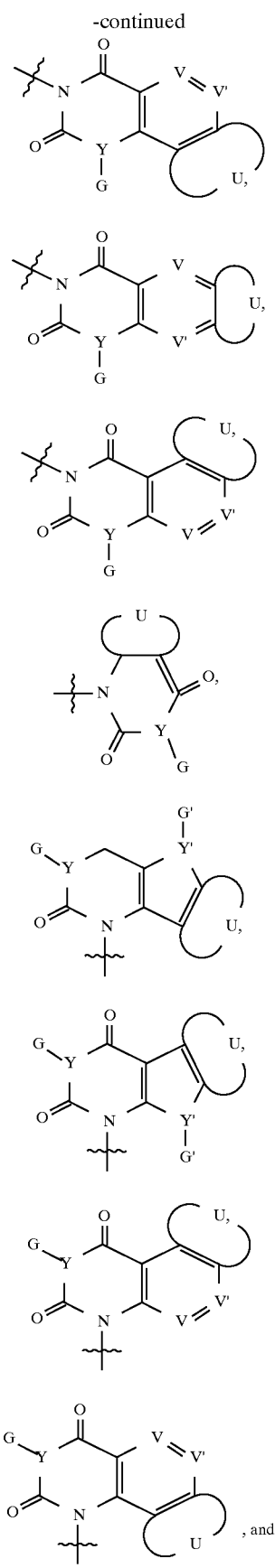

, and

8
-continued

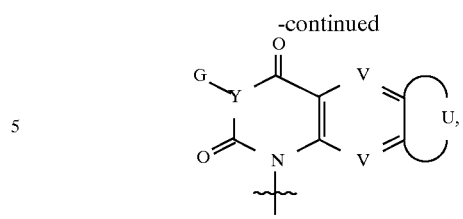

wherein G and G' are independently selected from the group consisting of hydrogen, alkyl, alkenyl, alkynyl, alkoxy, alkoxyalkyl, alkoxycarbonyl, hydroxy, hydroxyalkyl, carboxy, carboxyalkyl, halogen, alkylsulfonyl, and aminoalkyl, Y and Y' are independently selected from the group consisting of oxygen, nitrogen, and sulfur, with the proviso that when Y is oxygen or sulfur, G is absent and when Y' is oxygen or sulfur, G' is absent, V and V' are independently selected from the group of nitrogen and methine, and U is a ring that is fused to its adjacent ring and is selected from the group consisting of (a) an unsubstituted or substituted five member ring having five carbon atoms; (b) an unsubstituted or substituted five membered ring having four carbon atoms and one heteroatom selected from the group consisting of nitrogen, oxygen, and sulfur; (c) an unsubstituted or substituted five membered ring having three carbon atoms and two heteroatoms independently selected from the group consisting of nitrogen, oxygen, and sulfur; (d) a substituted or unsubstituted six membered ring having six carbon atoms; (e) a substituted or unsubstituted six membered ring having 5 carbon atoms and one heteroatom selected from the group consisting of nitrogen, oxygen, and sulfur; (f) a substituted or unsubstituted 6 membered ring having 4 carbon atoms and two heteroatom selected from the group consisting of nitrogen, oxygen, and sulfur; and (g) a substituted or unsubstituted 6 membered ring having three carbon atoms and three heteroatoms selected from the group consisting of nitrogen, oxygen, and sulfur. The five membered rings constituting U may contain 0,1, or 2 double bonds. The six membered rings constituting U may contain 0,1,2, or 3 double bonds. The rings (a)–(g) of the group constituting U may be mono or di-substituted with substituents indepedently selected from the group consisting of alkyl, alkoxy, cyano, nitro, carboxy, alkoxycarbonyl of two to eight carbon atoms, halogen, cycloalkyl, aryl, and heterocyclic.

In a preferred embodiment, the present invention provides a compound of formula II:

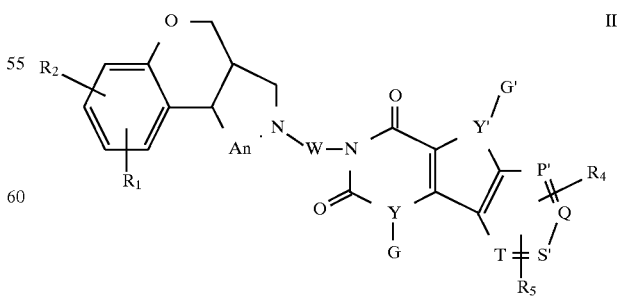

II wherein
R$_1$ and R$_2$ are independently selected from the group consisting of hydrogen, alkyl, alkenyl, alkynyl, alkoxyalkyl, alkoxy, alkoxycarbonyl, hydroxy, hydroxyalkyl, carboxy, carboxyalkyl, halogen, nitro, amino, and aminoalkyl, A is methylene, n is 1 or 2, W is alkylene of from 2 to 10 carbon atoms, G and G' are independently selected from the group consisting of hydrogen, alkyl, alkenyl, alkynyl, alkoxy, alkoxyalkyl, alkoxycarbonyl, hydroxy, hydroxyalkyl, carboxy, carboxyalkyl, halogen, alkylsulfonyl, and aminoalkyl, Y and Y' are independently selected from the group consisting of oxygen, nitrogen, and sulfur, with the proviso that when Y is oxygen or sulfur, G is absent and when Y' is oxygen or sulfur, G' is absent, P', Q, S', and T are independently selected from the group consisting of nitrogen and methine, with the proviso that no more than two of P', Q, S', and T can be nitrogen, and $R_4$ and $R_5$ are independently selected from hydrogen, alkyl, alkoxy, halogen, hydroxy, amino, cycloalkyl, aryl and heterocyclic.

In another preferred embodiment, the present invention provides a compound of the formula III:

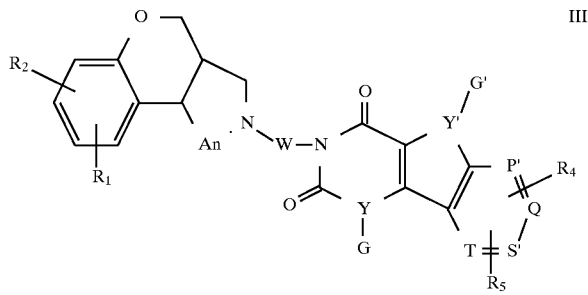

III wherein $R_1$ and $R_2$ are independently selected from the group consisting of hydrogen, alkyl, alkenyl, alkynyl, alkoxyalkyl, alkoxy, alkoxycarbonyl, hydroxy, hydroxyalkyl, carboxy, carboxyalkyl, halogen, nitro, amino, and aminoalkyl, A is methylene, n is 1 or 2, W is alkylene of from 2 to 10 carbon atoms, G and G' are independently selected from the group consisting hydrogen, alkyl, alkenyl, alkynyl, alkoxy, alkoxyalkyl, alkoxycarbonyl, hydroxy, hydroxyalkyl, carboxy, carboxyalkyl, halogen, alkylsulfonyl, and aminoalkyl, Y and Y' are independently selected from the group consisting of oxygen, nitrogen, and sulfur, with the proviso that when Y is oxygen or sulfur, G is absent and when Y' is oxygen or sulfur, G' is absent, P' and T are nitrogen, Q and S' are methine, and $R_4$ and $R_5$ are independently selected from hydrogen, alkyl, alkoxy, halogen, hydroxy, amino, cycloalkyl, aryl and heterocyclic.

In yet another preferred embodiment, the present invention provides compound of formula IV:

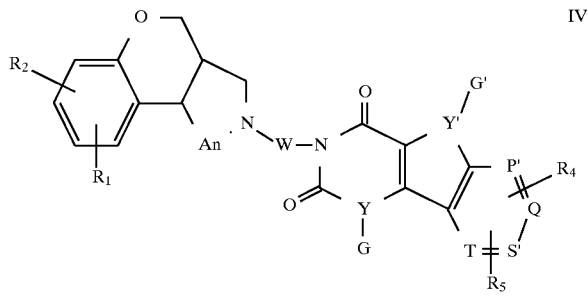

IV wherein $R_1$ and $R_2$ are independently selected from the group consisting of hydrogen, alkyl, alkenyl, alkynyl, alkoxyalkyl, alkoxy, alkoxycarbonyl, hydroxy, hydroxyalkyl, carboxy, carboxyalkyl, halogen, nitro, amino, and aminoalkyl, A is methylene, n is 1 or 2, W is alkylene of from 2 to 10 carbon atoms, G and G' are independently selected from the group consisting hydrogen, alkyl, alkenyl, alkynyl, alkoxy, alkoxyalkyl, alkoxycarbonyl, hydroxy, hydroxyalkyl, carboxy, carboxyalkyl, halogen, alkylsulfonyl, and aminoalkyl, Y and Y' are independently selected from the group consisting of oxygen, nitrogen, and sulfur, with the proviso that when Y is oxygen or sulfur, G is absent and when Y' is oxygen or sulfur, G' is absent, P' is nitrogen, Q, S', and T are methine, and $R_4$ and $R_5$ are independently selected from hydrogen, alkyl, halogen, hydroxy, amino, cycloalkyl, aryl and heterocyclic.

In yet another preferred embodiment, the present invention provides compound of formula V:

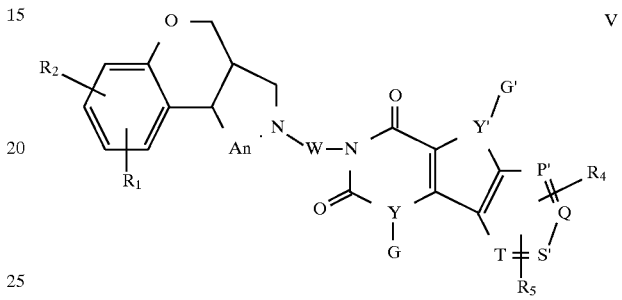

V wherein $R_1$ and $R_2$ are independently selected from the group consisting of hydrogen, alkyl, alkenyl, alkynyl, alkoxyalkyl, alkoxy, alkoxycarbonyl, hydroxy, hydroxyalkyl, carboxy, carboxyalkyl, halogen, nitro, amino, and aminoalkyl, A is methylene, n is 1 or 2, W is alkylene of from 2 to 10 carbon atoms, G and G' are independently selected from the group consisting hydrogen, alkyl, alkenyl, alkynyl, alkoxy, alkoxyalkyl, alkoxycarbonyl, hydroxy, hydroxyalkyl, carboxy, carboxyalkyl, halogen, alkylsulfonyl, and aminoalkyl, Y and Y' are independently selected from the group consisting of oxygen, nitrogen, and sulfur, with the proviso that when Y is oxygen or sulfur, G is absent and when Y' is oxygen or sulfur, G' is absent, Q is nitrogen, P', S', and T are methine, and $R_4$ and $R_5$ are independently selected from hydrogen, alkyl, alkoxy, halogen, hydroxy, amino, cycloalkyl, aryl and heterocyclic.

In yet another preferred embodiment, the present invention provides compound of formula VI:

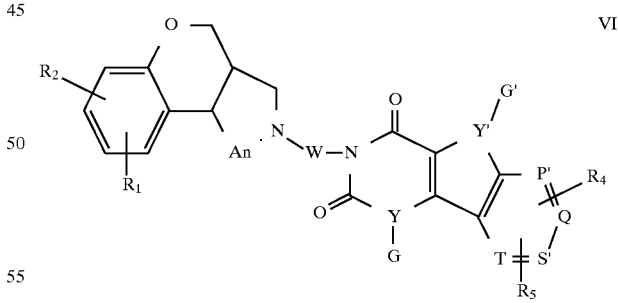

VI wherein $R_1$ and $R_2$ are independently selected from the group consisting of hydrogen, alkyl, alkenyl, alkynyl, alkoxyalkyl, alkoxy, alkoxycarbonyl, hydroxy, hydroxyalkyl, carboxy, carboxyalkyl, halogen, nitro, amino, and aminoalkyl, A is methylene, n is 1 or 2, W is alkylene of from 2 to 10 carbon atoms, G and G' are independently selected from the group consisting hydrogen, alkyl, alkenyl, alkynyl, alkoxy, alkoxyalkyl, alkoxycarbonyl, hydroxy, hydroxyalkyl, carboxy, carboxyalkyl, halogen, alkylsulfonyl, and aminoalkyl, Y and Y' are independently selected from the group consisting of oxygen, nitrogen, and sulfur, with the proviso that when Y is oxygen or sulfur, G is absent and when Y' is oxygen or sulfur, G' is absent, S' is nitrogen, P', Q, and T are methine, and R$_4$ and R$_5$ are independently selected from hydrogen, alkyl, alkoxy, halogen, hydroxy, amino, cycloalkyl, aryl and heterocyclic.

In yet another preferred embodiment, the present invention provides compound of formula VII:

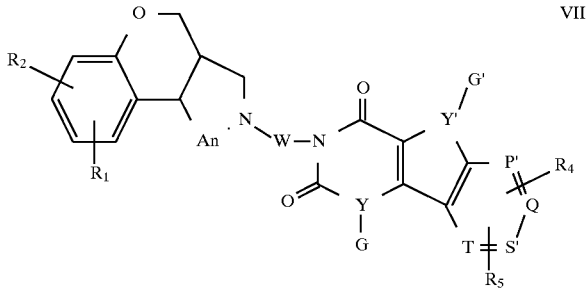

VII wherein R$_1$ and R$_2$ are independently selected from the group consisting of hydrogen, alkyl, alkenyl, alkynyl, alkoxyalkyl, alkoxy, alkoxycarbonyl, hydroxy, hydroxyalkyl, carboxy, carboxyalkyl, halogen, nitro, amino, and aminoalkyl, A is methylene, n is 1 or 2, W is alkylene of from 2 to 10 carbon atoms, G and G' are independently selected from the group consisting hydrogen, alkyl, alkenyl, alkynyl, alkoxy, alkoxyalkyl, alkoxycarbonyl, hydroxy, hydroxyalkyl, carboxy, carboxyalkyl, halogen, alkylsulfonyl, and aminoalkyl, Y and Y' are independently selected from the group consisting of oxygen, nitrogen, and sulfur, with the proviso that when Y is oxygen or sulfur, G is absent and when Y' is oxygen or sulfur, G' is absent, T is nitrogen, P', Q, and S' are methine, and R$_4$ and R$_5$ are independently selected from hydrogen, alkyl, alkoxy, halogen, hydroxy, amino, cycloalkyl, aryl and heterocyclic.

In yet another preferred embodiment, the present invention provides compound of formula VIII:

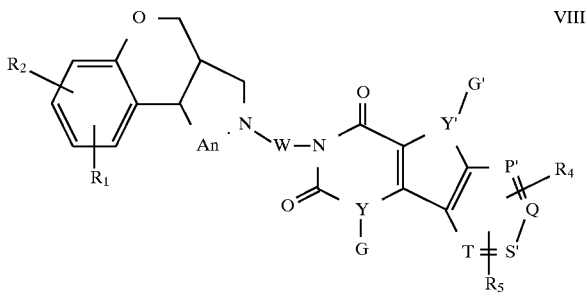

VIII wherein R$_1$ and R$_2$ are independently selected from the group consisting of hydrogen, alkyl, alkenyl, alkynyl, alkoxyalkyl, alkoxy, alkoxycarbonyl, hydroxy, hydroxyalkyl, carboxy, carboxyalkyl, halogen, nitro, amino, and aminoalkyl, A is methylene, n is 1 or 2, W is alkylene of from 2 to 10 carbon atoms, G and G' are independently selected from the group consisting hydrogen, alkyl, alkenyl, alkynyl, alkoxy, alkoxyalkyl, alkoxycarbonyl, hydroxy, hydroxyalkyl, carboxy, carboxyalkyl, halogen, alkylsulfonyl, and aminoalkyl, Y and Y' are independently selected from the group consisting of oxygen, nitrogen, and sulfur, with the proviso that when Y is oxygen or sulfur, G is absent and when Y' is oxygen or sulfur, G' is s absent, P', Q, S', and T are methine, and R$_4$ and R$_5$ are independently selected from hydrogen, alkyl, alkoxy, halogen, hydroxy, amino, cycloalkyl, aryl and heterocyclic.

In yet another preferred embodiment, the present invention provides compound of formula IX:

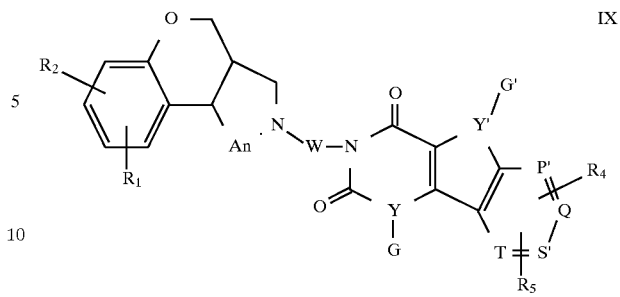

IX wherein R$_1$ and R$_2$ are independently selected from the group consisting of hydrogen, and alkoxy, A is methylene, n is 1, W is an alkylene of 2 to 10 carbon atoms, G is hydrogen, G' is absent, Y is nitrogen, Y' is sulfur, P', Q, S', are methine, T is nitrogen, and R$_4$ and R$_5$ are independently selected from hydrogen, alkyl, alkoxy, halogen, hydroxy, amino, cycloalkyl, aryl and heterocyclic.

In yet another preferred embodiment, the present invention provides compound of formula X:

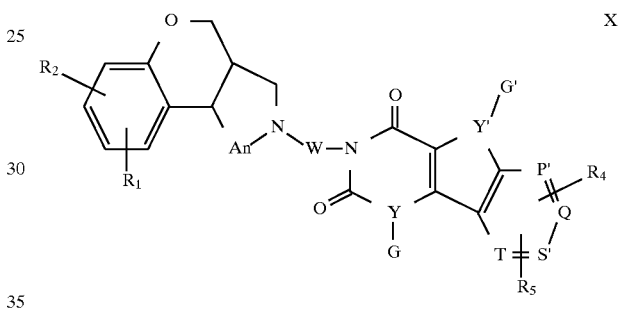

X wherein R$_1$ and R$_2$ are independently selected from the group consisting of hydrogen, and alkoxy, A is methylene, n is 2, W is an alkylene of 2 to 10 carbon atoms, G is hydrogen, G' is absent, Y is nitrogen, Y' is sulfur, P', Q, and S' are methine, T is nitrogen, and R$_4$ and R$_5$ are independently selected from hydrogen, alkyl, alkoxy, halogen, hydroxy, amino, cycloalkyl, aryl and heterocyclic.

In yet another preferred embodiment, the present invention provides compound of formula XI:

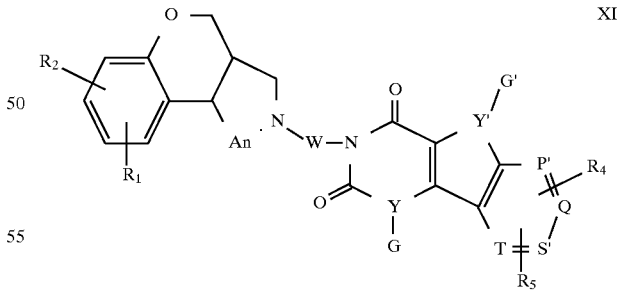

XI wherein R$_1$ and R$_2$ are independently selected from the group consisting of hydrogen, and alkoxy, A is methylene, n is 2, W is an alkylene of 2 to 10 carbon atoms, G is hydrogen, G' is absent, Y is nitrogen, Y' is sulfur, Q and S' are methine, P' and T are nitrogen, and R$_4$ and R$_5$ are independently selected from hydrogen, alkyl, alkoxy, halogen, hydroxy, amino, cycloalkyl, aryl and heterocyclic.

In yet another preferred embodiment, the present invention provides compound of formula XII:

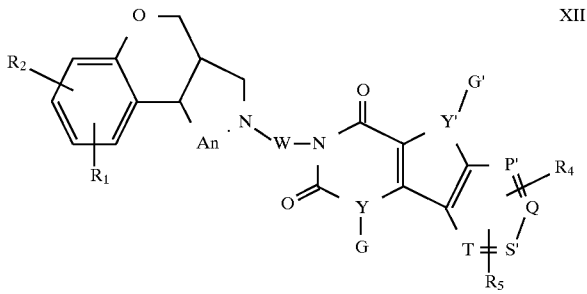

XII wherein $R_1$ and $R_2$ are independently selected from the group consisting of hydrogen, and alkoxy, A is methylene, n is 1, W is an alkylene of 2 to 10 carbon atoms, G is hydrogen, G' is absent, Y is nitrogen, Y' is sulfur, Q and S', are methine, P' and T are nitrogen, and $R_4$ and $R_5$ are independently selected from hydrogen, alkyl, alkoxy, halogen, hydroxy, amino, cycloalkyl, aryl and heterocyclic.

In yet another preferred embodiment, the present invention provides compound of formula XIII:

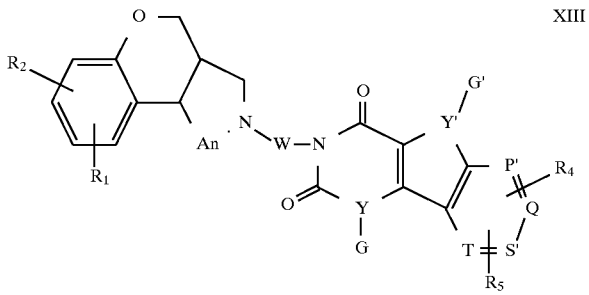

XIII wherein $R_1$ and $R_2$ are independently selected from the group consisting of hydrogen, and alkoxy, A is methylene, n is 1, W is an alkylene of 2 to 10 carbon atoms, G is hydrogen, G' is absent, Y is nitrogen, Y' is sulfur, Q, S', and T are methine, P' is nitrogen, and $R_4$ and $R_5$ are independently selected from hydrogen, alkyl, alkoxy, halogen, hydroxy, amino, cycloalkyl, aryl and heterocyclic.

In yet another preferred embodiment, the present invention provides compound of formula XIV:

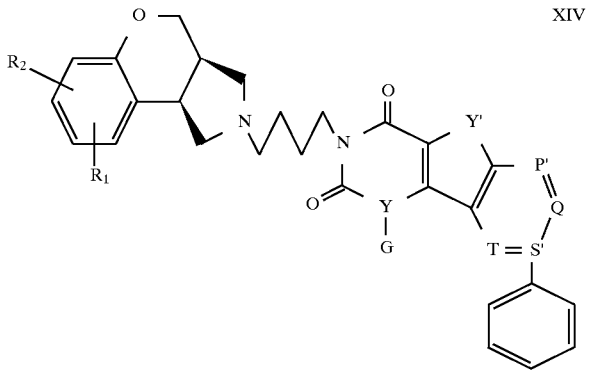

XIV wherein $R_1$ and $R_2$ are independently selected from the group consisting of hydrogen, and alkoxy, Y is nitrogen, G is hydrogen, Y' is sulphur, P' and T are nitrogen, and Q and S' are methine.

The present invention also relates to pharmaceutical compositions which comprise a therapeutically effective amount of a compound of formulae I–XIV in combination with a pharmaceutically acceptable carrier.

The invention further relates to a method of antagonizing α-1 adrenoreceptors in a host mammal, in particular humans, in need of such treatment by administering a therapeutically effective amount of a compound of formulae I–XIV.

The invention still further relates to a method of treating BPH in a host mammal, in particular humans, in need of such treatment by administering a therapeutically effective amount of a compound of formulae I–XIV.

The invention still further relates to a method of treating bladder outlet obstruction (BOO) in a host mammal, in particular humans, in need of such treatment by administering a therapeutically effective amount of a compound of formulae I–XIV.

The invention still further relates to a method of treating neurogenic bladder in a host mammal, in particular humans, in need of such treatment by administering a therapeutically effective amount of a compound of formulae I–XIV.

The invention still further relates to a method of treating uterine smooth muscle contraction in a female host mammal, in particular humans, in need of such treatment by administering a therapeutically effective amount of a compound of formulae I–XIV.

As used throughout this specification and the appended claims, the following terms have the following meanings:

The term "alkenyl" as used herein refers to a hydrocarbon containing at least one carbon-carbon double bond. Alkenyl groups include, for example, vinyl (ethenyl), allyl (propenyl), butenyl, 1-methyl-2-buten-1-yl and the like.

The terms "alkyl" or "loweralkyl" as used herein refer to straight or branched chain alkyl radicals containing from 1 to 6 carbon atoms including, but not limited to, methyl, ethyl, n-propyl, iso-propyl, n-butyl, iso-butyl, sec-butyl, t-butyl, n-pentyl, 1-methylbutyl, 2,2-dimethylbutyl, 2-methylpentyl, 2,2-dimethylpropyl, n-hexyl and the like.

The term "alkylamino" as used herein refers to $R_{10}NH$— wherein $R_{10}$ is an alkyl group, for example, ethylamino, butylamino, and the like.

The term "alkylene" denotes a divalent group derived from a straight or branched chain saturated hydrocarbon of from 2 to 10 carbon atoms by the removal of two hydrogen atoms, for example methylene, 1,2-ethylene, 1,1-ethylene, 1,3-propylene, 2,2-dimethylpropylene, and the like.

The term "alkoxy" as used herein refers to $R_{11}O$— wherein $R_{11}$ is an alkyl group, as defined above. Examples of alkoxy include, but are not limited to, methoxy, ethoxy, tert-butoxy, and the like.

The term "alkoxyalkyl" as used herein refers to an alkoxy group as previously defined appended to an alkyl radical as previously defined. Examples of alkoxyalkyl include, but are not limited to, methoxymethyl, methoxyethyl, isopropoxymethyl and the like.

The term "alkoxyalkoxy" refers to $R_{12}O$—$R_{13}O$— wherein $R_{12}$ is alkyl $R_{13}$ is alkylene. Examples of alkoxyalkoxy include methoxymethoxy, methoxyethoxy and the like.

The term "alkoxycarbonyl" as used herein refers to $R_{14}O$—C(O)— wherein $R_{14}$ is an alkyl group. Examples of alkoxycarbonyl include methoxycarbonyl, ethoxycarbonyl, isopropoxycarbonyl and the like.

The term "alkylsulfonyl" refers to $R_{15}S(O)_2$— wherein $R_{15}$ is an alkyl group.

The term "alkynyl" refers to a straight or branched chain hydrocarbon containing a carbon-carbon triple bond. Examples of alkynyl include —C≡C—, —C≡C—$CH_2$—, —C≡C—$CH(CH_3)$— and the like.

The term "amino" as used herein refers to —$NH_2$.

The term "aminoalkyl" as used herein refers to an alkyl radical to which is appended an amino group (—$NH_2$).

The term "aryl" as used herein refers to a mono- or bicyclic carbocyclic ring system having one or more aromatic rings including, but not limited to, phenyl, naphthyl, tetrahydronaphthyl, indanyl, indenyl and the like. Aryl groups can be unsubstituted or substituted with one, two or three substituents independently selected from loweralkyl, haloalkyl, alkoxy, thioalkoxy, amino, alkylamino, dialkylamino, hydroxy, halo, nitro, carboxy, alkoxycarbonyl and carboxamide.

The term "carboxamide" as used herein refers to —C(O)NH$_2$ wherein the carboxylic acid hydroxy moiety has been replaced by an amine.

The term "carboxyalkyl" as used herein refers to a carboxy group (—C(O)OH) appended to an alkyl radical as previously defined. Examples of carboxyalkyl include carboxymethyl, carboxyethyl and the like.

The term "dialkylamino" as used herein refers to $R_{16}R_{17}N$— wherein $R_{16}$ and $R_{17}$ are independently alkyl, for example diethylamino, methyl propylamino, and the like.

The term "carboxy" as used herein refers to a carboxylic acid radical, —C(O)OH.

The term "cycloalkyl" as used herein refers to an aliphatic ring system having 3 to 10 carbon atoms and 1 to 3 rings including, but not limited to, cyclopropyl, cyclopentyl, cyclohexyl, norbornyl, adamantyl, and the like. Cycloalkyl groups can be unsubstituted or substituted with one, two or three substituents independently selected from alkyl, haloalkyl, alkoxy, thioalkoxy, amino, alkylamino, dialkylamino, hydroxy, halo, mercapto, nitro, carboxaldehyde, carboxy, alkoxycarbonyl and carboxamide.

The term "halogen" or "halo" as used herein refers to I, Br, Cl, or F.

The term "haloalkyl" as used herein refers to a lower alkyl radical, as defined above, bearing at least one halogen substituent, for example, chloromethyl, fluoroethyl or trifluoromethyl and the like.

The terms "heterocyclic ring" or "heterocyclic" or "heterocycle" as used herein refers to any 3- or 4-membered ring containing a heteroatom selected from oxygen, nitrogen and sulfur; or a 5-, 6- or 7-membered ring containing one, two or three heteroatoms wherein the heteroatoms are independently selected from nitrogen, oxygen and sulfur. The 5-membered ring has from 0–2 double bonds and the 6- and 7-membered ring have from 0–3 double bonds. The nitrogen heteroatoms can be optionally quaternized. The term "heterocyclic" also includes bicyclic groups in which any of the above heterocyclic rings is fused to a benzene ring or a cyclohexane ring or another heterocyclic ring (for example, indolyl, quinolyl, isoquinolyl, tetrahydroquinolyl, benzofuryl or benzothienyl and the like). Heterocyclics include: azetidinyl, pyrrolyl, pyrrolinyl, pyrrolidinyl, pyrazolyl, pyrazolinyl, pyrazolidinyl, imidazolyl, imidazolinyl, imidazolidinyl, pyridyl, piperidinyl, homopiperidinyl, pyrazinyl, piperazinyl, pyrimidinyl, pyridazinyl, oxazolyl, oxazolidinyl, isoxazolyl, isoxazolidinyl, morpholinyl, thiazolyl, thiazolidinyl, isothiazolyl, isothiazolidinyl, indolyl, quinolinyl, isoquinolinyl, benzimidazolyl, benzothiazolyl, benzoxazolyl, furyl, thienyl and benzothienyl.

Heterocyclics can be unsubstituted or monosubstituted or disubstituted with substituents independently selected from hydroxy, halo, oxo (═O), alkylimino ($R_{18}N$═ wherein $R_{18}$ is a loweralkyl group), amino, alkylamino, dialkylamino, alkoxy, alkoxyalkoxy, haloalkyl, cycloalkyl, aryl, arylalkyl, —COOH, —SO$_3$H and loweralkyl. In addition, nitrogen containing heterocycles can be N-protected.

The term "(heterocyclic)alkyl" as used herein refers to a heterocyclic group as defined above appended to a loweralkyl radical as defined above.

The term "hydroxy" as used herein refers to —OH.

The term "hydroxyalkyl" as used herein refers to alkyl radical which is appended to an hydoxy group.

The term "methine" as used herein refers to —CH═.

The term "nitro" as used herein refers to —NO$_2$.

The term "thioalkoxy" as used herein refers to $R_{19}S$— wherein $R_{19}$ is alkyl. Examples of thioalkoxy include, but are not limited to, methylthio, ethylthio and the like.

By "pharmaceutically acceptable salt" is meant those salts which are, within the scope of sound medical judgement, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge, et al. describe pharmaceutically acceptable salts in detail in *J. Pharm. Sciences,* 66: 1–19 (1977), which is hereby incorporated by reference. The compounds of the present invention can be used in the form of salts derived from inorganic or organic acids. The salts can be prepared in situ during the final isolation and purification of the compounds of the invention, or separately by reacting the free base function with a suitable organic acid. These salts include, but are not limited to, the following: acetate, adipate, alginate, citrate, aspartate, benzoate, benzenesulfonate, bisulfate, butyrate, camphorate, camphorsulfonate, digluconate, cyclopentanepropionate, dodecylsulfate, ethanesulfonate, glucoheptanoate, glycerophosphate, hemisulfate, heptanoate, hexanoate, fumarate, hydrochloride, hydrobromide, hydroiodide, 2-hydroxy-ethanesulfonate, lactate, maleate, methanesulfonate, nicotinate, 2-naphthalenesulfonate, oxalate, pamoate, pectinate, persulfate, 3-phenylpropionate, picrate, pivalate, propionate, succinate, tartrate, thiocyanate, p-toluenesulfonate and undecanoate. Also, the basic nitrogen-containing groups can be quaternized with such agents as alkyl halides, such as methyl, ethyl, propyl, and butyl chloride, bromides, and iodides; dialkyl sulfates like dimethyl, diethyl, dibutyl, and diamyl sulfates, long chain halides such as decyl, lauryl, myristyl and stearyl chlorides, bromides and iodides, aralkyl halides like benzyl and phenethyl bromides, and others. Water or oil-soluble or dispersible products are thereby obtained.

Examples of acids which may be employed to form pharmaceutically acceptable acid addition salts include such inorganic acids as hydrochloric acid, sulphuric acid and phosphoric acid and such organic acids as oxalic acid, maleic acid, succinic acid and citric acid. Basic addition salts can be prepared in situ during the final isolation and purification of the compounds of formula (I), or separately by reacting the carboxylic acid function with a suitable base such as the hydroxide, carbonate or bicarbonate of a pharmaceutically acceptable metal cation or with ammonia, or an organic primary, secondary or tertiary amine. Pharmaceutically acceptable salts include, but are not limited to, cations based on the alkali and alkaline earth metals, such as sodium, lithium, potassium, calcium, magnesium, aluminum salts and the like, as well as nontoxic ammonium, quaternary ammonium, and amine cations, including, but not limited to ammonium, tetramethylammonium, tetraethylammonium, methylamine, dimethylamine, trimethylamine, triethylamine, ethylamine, and the like. Other representative organic amines useful for the formation of base addition salts include diethylamine, ethylenediamine, ethanolamine, diethanolamine, piperazine and the like.

Asymmetric centers may exist in the compounds of the present invention. The present invention comtemplates the various stereoisomers and mixtures thereof. Starting compounds of particular stereochemistry are either commercially available or are made by the methods detailed below and resolved by techniques well known in the art of organic chemistry.

Representative compounds falling within the scope of formula I include:

3-[4-((3aR,9bR)-cis-9-Methoxy-1,2,3,3a,4,9b-hexahydro-[1]-benzopyrano[3,4-c]pyrrol-2-yl)butyl]-pyrido[2',3':4,5]thieno[3,2-d]pyrimidine-2,4(1H,3H)-dione, 3-[4-((3aS,9bS)-cis-9-Methoxy-1,2,3,3a,4,9b-hexahydro-[1]-benzopyrano[3,4-c]pyrrol-2-yl)butyl]-pyrido[2',3':4,5]thieno[3,2-d]pyrimidine-2,4(1H,3H)-dione, 3-[4-((3aS,9bR)-trans-9-Methoxy-1,2,3,3a,4,9b-hexahydro-[1]-benzopyrano[3,4-c]pyrrol-2-yl)butyl]-pyrido[2',3':4,5]thieno[3,2-d]pyrimidine-2,4(1H,3H)-dione, 3-[4-((3aR,9bS)-trans-9-Methoxy-1,2,3,3a,4,9b-hexahydro-[1]-benzopyrano[3,4-c]pyrrol-2-yl)butyl]-pyrido[2',3':4,5]thieno[3,2-d]pyrimidine-2,4(1H,3H)-dione, 3-[4-((3aR,9bS)-trans-9-Methoxy-1,2,3,3a,4,9b-hexahydro-[1]-benzopyrano[3,4-c]pyrrol-2-yl)butyl]-6-chloro-pyrido[2',3':4,5]thieno[3,2-d]pyrimidine-2,4(1H,3H)-dione, 3-[4-((3aR,9bS)-trans-9-Methoxy-1,2,3,3a,4,9b-hexahydro-[1]-benzopyrano[3,4-c]pyrrol-2-yl)butyl]-8-chloro-pyrido[2',3':4,5]thieno[3,2-d]pyrimidine-2,4(1H,3H)-dione, 3-[4-((3aR,9bS)-trans-9-Methoxy-1,2,3,3a,4,9b-hexahydro-[1]-benzopyrano[3,4-c]pyrrol-2-yl)butyl]-8-methoxy-pyrido[2',3':4,5]thieno[3,2-d]pyrimidine-2,4(1H,3H)-dione, 3-[4-((3aR,9bS)-trans-9-Methoxy-1,2,3,3a,4,9b-hexahydro-[1]-benzopyrano[3,4-c]pyrrol-2-yl)butyl]-6-methoxy-pyrido[2',3':4,5]thieno[3,2-d]pyrimidine-2,4(1H,3H)-dione, 3-[4-(3aR,9bS)-trans-9-Methoxy-1,2,3,3a,4,9b-hexahydro-[1]-benzopyrano[3,4-c]pyrrol-2-yl)butyl]-8-phenyl-pyrazino[2',3':4,5]thieno[3,2-d]pyrimidine-2,4(1H,3H)-dione 3-[4-((3aR,9bS)-trans-9-Methoxy-1,2,3,3a,4,9b-hexahydro-[1]-benzopyrano[3,4-c]pyrrol-2-yl)butyl]-8-chloro-pyrazino[2',3':4,5]thieno[3,2-d]pyrimidine-2,4(1H,3H)-dione, 3-[4-((3aR,9bS)-trans-9-Methoxy-1,2,3,3a,4,9b-hexahydro-[1]-benzopyrano[3,4-c]pyrrol-2-yl)butyl]-1-(2-Methoxyethyl)-pyrazino[2',3':4,5]thieno[3,2-d]pyrimidine-2,4(1H,3H)-dione, 3-[4-((3aR,9bS)-trans-9-Methoxy-1,2,3,3a,4,9b-hexahydro-[1]-benzopyrano[3,4-c]pyrrol-2-yl)butyl]-pyrazino[2',3':4,5]thieno[3,2-d]pyrimidine-2,4(1H,3H)-dione, 3-[4-((3aS,9bR)-trans-9-Methoxy-1,2,3,3a,4,9b-hexahydro-[1]-benzopyrano[3,4-c]pyrrol-2-yl)butyl]-8-chloro-pyrazino[2',3':4,5]thieno[3,2-d]pyrimidine-2,4(1H,3H)-dione, 3-[4-((3aS,9bR)-trans-9-Methoxy-1,2,3,3a,4,9b-hexahydro-[1]-benzopyrano[3,4-c]pyrrol-2-yl)butyl]-pyrazino[2',3':4,5]thieno[3,2-d]pyrimidine-2,4(1H,3H)-dione, 3-[4-((3aR,9bR)-cis-9-Methoxy-1,2,3,3a,4,9b-hexahydro-[1]-benzopyrano[3,4-c]pyrrol-2-yl)butyl]-pyrazino[2',3':4,5]thieno[3,2-d]pyrimidine-2,4(1H,3H)-dione, 3-[4-((3aR,9bR)-cis-9-Methoxy-1,2,3,3a,4,9b-hexahydro-[1]-benzopyrano[3,4-c]pyrrol-2-yl)butyl]-8-chloro-pyrazino[2',3':4,5]thieno[3,2-d]pyrimidine-2,4(1H,3H)-dione, 3-[4-((3aS,9bR)-trans-9-Methoxy-1,2,3,3a,4,9b-hexahydro-[1]-benzopyrano[3,4-c]pyrrol-2-yl)butyl]-6-methoxy-pyrido[2',3':4,5]thieno[3,2-d]pyrimidine-2,4(1H,3H)-dione, 3-[4-((3aR,9bR)-cis-9-Methoxy-1,2,3,3a,4,9b-hexahydro-[1]-benzopyrano[3,4-c]pyrrol-2-yl)butyl]-6-methoxy-pyrido[2',3':4,5]thieno[3,2-d]pyrimidine-2,4(1H,3H)-dione, 3-[4-((3aS,9bR)-trans-9-Methoxy-1,2,3,3a,4,9b-hexahydro-[1]-benzopyrano[3,4-c]pyrrol-2-yl)butyl]-6-chloro-pyrido[2',3':4,5]thieno[3,2-d]pyrimidine-2,4(1H,3H)-dione, 3-[4-((3aR,9bR)-cis-9-Methoxy-1,2,3,3a,4,9b-hexahydro-[1]-benzopyrano[3,4-c]pyrrol-2-yl)butyl]-6-chloro-pyrido[2',3':4,5]thieno[3,2-d]pyrimidine-2,4(1H,3H)-dione, 3-[4-((3aS,9bR)-trans-9-Methoxy-1,2,3,3a,4,9b-hexahydro-[1]-benzopyrano[3,4-c]pyrrol-2-yl)butyl]-[1]benzthieno[3,2-d]pyrimidine-2,4(1H,3H)-dione, 3-[4-((3aR,9bR)-cis-9-Methoxy-1,2,3,3a,4,9b-hexahydro-[1]-benzopyrano[3,4-c]pyrrol-2-yl)butyl]-[1]benzthieno[3,2-d]pyrimidine-2,4(1H,3H)-dione, 3-[5-((3aS,9bR)-trans-9-Methoxy-1,2,3,3a,4,9b-hexahydro-[1]-benzopyrano[3,4-c]pyrrol-2-yl)pentyl]-[1]benzthieno[3,2-d]pyrimidine-2,4(1H,3H)-dione, 3-[5-((3aR,9bR)-cis-9-Methoxy-1,2,3,3a,4,9b-hexahydro-[1]-benzopyrano[3,4-c]pyrrol-2-yl)pentyl]-[1]benzthieno[3,2-d]pyrimidine-2,4(1H,3H)-dione, 3-[4-((3aS,9bR)-trans-9-Methoxy-1,2,3,3a,4,9b-hexahydro-[1]-benzopyrano[3,4-c]pyrrol-2-yl)butyl]-8-chloro-pyrido[2',3':4,5]thieno[3,2-d]pyrimidine-2,4(1H,3H)-dione, 3-[4-((3aS,9bR)-trans-9-Methoxy-1,2,3,3a,4,9b-hexahydro-[1]-benzopyrano[3,4-c]pyrrol-2-yl)butyl]-8-methoxy-pyrido[2',3':4,5]thieno[3,2-d]pyrimidine-2,4(1H,3H)-dione, 3-[4-((3aS,9bR)-trans-9-Methoxy-1,2,3,3a,4,9b-hexahydro-[1]-benzopyrano[3,4-c]pyrrol-2-yl)butyl]-7-methoxy-pyrido[2',3':4,5]thieno[3,2-d]pyrimidine-2,4(1H,3H)-dione, 3-[4-((3aR,9bR)-cis-9-Methoxy-1,2,3,3a,4,9b-hexahydro-[1]-benzopyrano[3,4-c]pyrrol-2-yl)butyl]-pyrido[3',4':4,5]thieno[3,2-d]pyrimidine-2,4(1H,3H)-dione, 3-[4-((3aR,9bR)-cis-9-Methoxy-1,2,3,3a,4,9b-hexahydro-[1]-benzopyrano[3,4-c]pyrrol-2-yl)butyl]-pyrido[4',3':4,5]thieno[3,2-d]pyrimidine-2,4(1H,3H)-dione, 3-[4-((3aR,9bR)-cis-9-Methoxy-1,2,3,3a,4,9b-hexahydro-[1]-benzopyrano[3,4-c]pyrrol-2-yl)butyl]-8-methoxy-pyrido[2',3':4,5]thieno[3,2-d]pyrimidine-2,4(1H,3H)-dione, 3-[4-((3aR,9bR)-cis-9-Methoxy-1,2,3,3a,4,9b-hexahydro-[1]-benzopyrano[3,4-c]pyrrol-2-yl)butyl]-8-methoxy-pyrazino[2',3':4,5]thieno[3,2-d]pyrimidine-2,4(1H,3H)-dione, 3-[4-((3aR,9bR)-cis-9-Methoxy-1,2,3,3a,4,9b-hexahydro-[1]-benzopyrano[3,4-c]pyrrol-2-yl)butyl]-7-chloro-pyrido[3',2':4,5]thieno[3,2-d]pyrimidine-2,4(1H,3H)-dione, 3-[4-((3aR,9bR)-cis-9-Methoxy-1,2,3,3a,4,9b-hexahydro-[1]-benzopyrano[3,4-c]pyrrol-2-yl)butyl]-7-methoxy-pyrido[3',2':4,5]thieno[3,2-d]pyrimidine-2,4(1H,3H)-dione, 3-[4-((3aR,9bR)-cis-9-Methoxy-1,2,3,3a,4,9b-hexahydro-[1]-benzopyrano[3,4-c]pyrrol-2-yl)butyl]-pyrido[3',2':4,5]thieno[3,2-d]pyrimidine-2,4(1H,3H)-dione, 3-[4-((3aR,9bR)-cis-9-Methoxy-1,2,3,3a,4,9b-hexahydro-[1]-benzopyrano[3,4-c]pyrrol-2-yl)butyl]-7-methyl-pyrido[3',2':4,5]thieno[3,2-d]pyrimidine-2,4(1H,3H)-dione, 3-[4-((3aR,9bR)-cis-9-Methoxy-1,2,3,3a,4,9b-hexahydro-[1]-benzopyrano[3,4-c]pyrrol-2-yl)butyl]-9- methoxy-pyrido[3',2':4,5]thieno[3,2-d]pyrimidine-2,4 (1H,3H)-dione,

3-[4-((3aR,9bR)-cis-9-Methoxy-1,2,3,3a,4,9b-hexahydro-[1]-benzopyrano[3,4-c]pyrrol-2-yl)butyl]-8-chloro-pyrido[2',3':4,5]thieno[3,2-d]pyrimidine-2,4(1H,3H)-dione, 3-[4-((3aR,9bR)-cis-9-Methoxy-1,2,3,3a,4,9b-hexahydro-[1]-benzopyrano[3,4-c]pyrrol-2-yl)butyl]-7-chloro-pyrido[2',3':4,5]thieno[3,2-d]pyrimidine-2,4(1H,3H)-dione, 3-[4-((3aR,9bR)-cis-9-Methoxy-1,2,3,3a,4,9b-hexahydro-[1]-benzopyrano[3,4-c]pyrrol-2-yl)butyl]-8-phenyl-pyrazino[2',3':4,5]thieno[3,2-d]pyrimidine-2,4(1H,3H)-dione, 3-[4-((3aR,9bR)-cis-9-Methoxy-1,2,3,3a,4,9b-hexahydro-[1]-benzopyrano[3,4-c]pyrrol-2-yl)butyl]-7-phenyl-pyrazino[2',3':4,5]thieno[3,2-d]pyrimidine-2,4(1H,3H)-dione, 3-[4-((3aS,9bR)-trans-9-Methoxy-1,2,3,3a,4,9b-hexahydro-[1]-benzopyrano[3,4-c]pyrrol-2-yl)butyl]-pyrido[3',4':4,5]thieno[3,2-d]pyrimidine-2,4(1H,3H)-dione, 3-[4-((3aS,9bR)-trans-9-Methoxy-1,2,3,3a,4,9b-hexahydro-[1]-benzopyrano[3,4-c]pyrrol-2-yl)butyl]-pyrido[4',3':4,5]thieno[3,2-d]pyrimidine-2,4(1H,3H)-dione, 3-[4-((3aS,9bR)-trans-9-Methoxy-1,2,3,3a,4,9b-hexahydro-[1]-benzopyrano[3,4-c]pyrrol-2-yl)butyl]-8-methoxy-pyrazino[2',3':4,5]thieno[3,2-d]pyrimidine-2,4(1H,3H)-dione, 3-[4-((3aS,9bR)-trans-9-Methoxy-1,2,3,3a,4,9b-hexahydro-[1]-benzopyrano[3,4-c]pyrrol-2-yl)butyl]-pyrido[3',2':4,5]thieno[3,2-d]pyrimidine-2,4(1H,3H)-dione, 3-[4-((3aS,9bR)-trans-9-Methoxy-1,2,3,3a,4,9b-hexahydro-[1]-benzopyrano[3,4-c]pyrrol-2-yl)butyl]-7-methyl-pyrido[3',2':4,5]thieno[3,2-d]pyrimidine-2,4(1H,3H)-dione, 3-[4-((3aS,9bR)-trans-9-Methoxy-1,2,3,3a,4,9b-hexahydro-[1]-benzopyrano[3,4-c]pyrrol-2-yl)butyl]-7-methoxy-pyrido[3',2':4,5]thieno[3,2-d]pyrimidine-2,4(1H,3H)-dione, 3-[4-((3aS,9bR)-trans-9-Methoxy-1,2,3,3a,4,9b-hexahydro-[1]-benzopyrano[3,4-c]pyrrol-2-yl)butyl]-7-chloro-pyrido[3',2':4,5]thieno[3,2-d]pyrimidine-2,4(1H,3H)-dione, 3-[4-((3aS,9bR)-trans-9-Methoxy-1,2,3,3a,4,9b-hexahydro-[1]-benzopyrano[3,4-c]pyrrol-2-yl)butyl]-9-methoxy-pyrido[3',4':4,5]thieno[3,2-d]pyrimidine-2,4(1H,3H)-dione, 3-[4-((3aR,9bR)-cis-9-Methoxy-1,2,3,3a,4,9b-hexahydro-[1]-benzopyrano[3,4-c]pyrrol-2-yl)butyl]-9-chloro-pyrido[3',4':4,5]thieno[3,2-d]pyrimidine-2,4(1H,3H)-dione, 3-[4-((3aS,9bR)-trans-9-Methoxy-1,2,3,3a,4,9b-hexahydro-[1]-benzopyrano[3,4-c]pyrrol-2-yl)butyl]-8-phenyl-pyrazino[2',3':4,5]thieno[3,2-d]pyrimidine-2,4(1H,3H)-dione, 3-[4-((3aS,9bR)-trans-9-Methoxy-1,2,3,3a,4,9b-hexahydro-[1]-benzopyrano[3,4-c]pyrrol-2-yl)butyl]-8-isopropoxy-pyrido[2',3':4,5]thieno[3,2-d]pyrimidine-2,4(1H,3H)-dione, 3-[4-((3aS,9bR)-trans-9-Methoxy-1,2,3,3a,4,9b-hexahydro-[1]-benzopyrano[3,4-c]pyrrol-2-yl)butyl]-8-phenyl-pyrido[2',3':4,5]thieno[3,2-d]pyrimidine-2,4(1H,3H)-dione, 3-[4-((3aR,9bR)-cis-9-Methoxy-1,2,3,3a,4,9b-hexahydro-[1]-benzopyrano[3,4-c]pyrrol-2-yl)butyl]-6-chloro-pyrido[4',3':4,5]thieno[3,2-d]pyrimidine-2,4(1H,3H)-dione, 3-[4-((3aS,9bR)-trans-9-Methoxy-1,2,3,3a,4,9b-hexahydro-[1]-benzopyrano[3,4-c]pyrrol-2-yl)butyl]-6-chloro-pyrido[4',3':4,5]thieno[3,2-d]pyrimidine-2,4(1H,3H)-dione, 3-[4-((3aS,9bR)-trans-9-Methoxy-1,2,3,3a,4,9b-hexahydro-[1]-benzopyrano[3,4-c]pyrrol-2-yl)butyl]-8-methoxy-pyrido[3',2':4,5]thieno[3,2-d]pyrimidine-2,4(1H,3H)-dione, 3-[4-((3aR,9bR)-cis-9-Methoxy-1,2,3,3a,4,9b-hexahydro-[1]-benzopyrano[3,4-c]pyrrol-2-yl)butyl]-8-(3-pyridyl)-pyrido[2',3':4,5]thieno[3,2-d]pyrimidine-2,4(1H,3H)-dione, 3-[4-((3aR,9bR)-cis-9-Methoxy-1,2,3,3a,4,9b-hexahydro-[1]-benzopyrano[3,4-c]pyrrol-2-yl)butyl]-8-(3-thienyl)-pyrazino[2',3':4,5]thieno[3,2-d]pyrimidine-2,4(1H,3H)-dione, 3-[4-((3aS,9bR)-trans-9-Methoxy-1,2,3,3a,4,9b-hexahydro-[1]-benzopyrano[3,4-c]pyrrol-2-yl)butyl]-8-(3-pyridyl)-pyrido[2',3':4,5]thieno[3,2-d]pyrimidine-2,4(1H,3H)-dione, 3-[4-((3aS,9bR)-trans-9-Methoxy-1,2,3,3a,4,9b-hexahydro-[1]-benzopyrano[3,4-c]pyrrol-2-yl)butyl]-8-(3-thienyl)-pyrazino[2',3':4,5]thieno[3,2-d]pyrimidine-2,4(1H,3H)-dione, 3-[4-((3aS,9bR)-trans-9-Methoxy-1,2,3,3a,4,9b-hexahydro-[1]-benzopyrano[3,4-c]pyrrol-2-yl)butyl]-8-(3-pyridyl)-pyrazino[2',3':4,5]thieno[3,2-d]pyrimidine-2,4(1H,3H)-dione, 3-[4-((3aR,9bR)-cis-9-Methoxy-1,2,3,3a,4,9b-hexahydro-[1]-benzopyrano[3,4-c]pyrrol-2-yl)butyl]-8-(3-pyridyl)-pyrazino[2',3':4,5]thieno[3,2-d]pyrimidine-2,4(1H,3H)-dione, 3-[4-((3aR,9bR)-cis-9-Methoxy-1,2,3,3a,4,9b-hexahydro-[1]-benzopyrano[3,4-c]pyrrol-2-yl)butyl]-8-(3-furyl)-pyrazino[2',3':4,5]thieno[3,2-d]pyrimidine-2,4(1H,3H)-dione, 3-[2-((±)-cis-7-Methoxy-1,2,3,3a,4,9b-hexahydro-[1]-benzopyrano[3,4-c]pyrrol-2-yl)ethyl]-[1]benzthieno[3,2-d]pyrimidine-2,4(1H,3H)-dione, 3-[3-((±)-cis-7-Methoxy-1,2,3,3a,4,9b-hexahydro-[1]-benzopyrano[3,4-c]pyrrol-2-yl)propyl]-[1]benzthieno[3,2-d]pyrimidine-2,4(1H,3H)-dione, 3-[2-((±)-cis-9-Methoxy-1,2,3,3a,4,9b-hexahydro-[1]-benzopyrano[3,4-c]pyrrol-2-yl)propyl]-[1]benzthieno[3,2-d]pyrimidine-2,4(1H,3H)-dione, 3-[3-((±)-cis-9-Methoxy-1,2,3,3a,4,9b-hexahydro-[1]-benzopyrano[3,4-c]pyrrol-2-yl)propyl]-[1]benzthieno[3,2-d]pyrimidine-2,4(1H,3H)-dione, 3-[2-((±)-cis-6-Methoxy-1,2,3,3a,4,9b-hexahydro-[1]-benzopyrano[3,4-c]pyrrol-2-yl)ethyl]-[1]benzthieno[3,2-d]pyrimidine-2,4(1H,3H)-dione, 3-[3-((±)-cis-6-Methoxy-1,2,3,3a,4,9b-hexahydro-[1]-benzopyrano[3,4-c]pyrrol-2-yl)propyl]-[1]benzthieno[3,2-d]pyrimidine-2,4(1H,3H)-dione, 3-[2-((±)-cis-1,2,3,3a,4,9b-hexahydro-[1]-benzopyrano[3,4-c]pyrrol-2-yl)ethyl]-[1]benzthieno[3,2-d]pyrimidine-2,4(1H,3H)-dione, 3-[4-((±)-cis-1,2,3,3a,4,9b-hexahydro-[1]-benzopyrano[3,4-c]pyrrol-2-yl)butyl]-pyrido[2',3':4,5]thieno[3,2-d]pyrimidine-2,4(1H,3H)-dione, 3-[4-((±)-trans-1,2,3,3a,4,9b-hexahydro-[1]-benzopyrano[3,4-c]pyrrol-2-yl)butyl]-pyrido[2',3':4,5]thieno[3,2-d]pyrimidine-2,4(1H,3H)-dione, 3-[4-((±)-trans-9-Methoxy-1,2,3,3a,4,9b-hexahydro-[1]-benzopyrano[3,4-c]pyrrol-2-yl)butyl]-pyrido[2',3':4,5]thieno[3,2-d]pyrimidine-2,4(1H,3H)-dione, 3-[4-((±)-cis-9-Methoxy-1,2,3,3a,4,9b-hexahydro-[1]-benzopyrano[3,4-c]pyrrol-2-yl)butyl]-pyrido[2',3':4,5]thieno[3,2-d]pyrimidine-2,4(1H,3H)-dione, 3-[4-((±)-trans-9-Methoxy-1,2,3,3a,4,9b-hexahydro-[1]-benzopyrano[3,4-c]pyrrol-2-yl)butyl]-pyrazino[2',3':4,5]thieno[3,2-d]pyrimidine-2,4(1H,3H)-dione, 3-[4-((±)-cis-8-Methoxy-1,2,3,3a,4,9b-hexahydro-[1]-benzopyrano[3,4-c]pyrrol-2-yl)butyl]-pyrido[3',2':4,5]thieno[3,2-d]pyrimidine-2,4(1H,3H)-dione, 3-[4-((±)-cis-8-Methoxy-1,2,3,3a,4,9b-hexahydro-[1]-benzopyrano[3,4-c]pyrrol-2-yl)butyl]-pyrazino[2',3':4,5]thieno[3,2-d]pyrimidine-2,4(1H,3H)-dione, 3-[3-((±)-cis-8-Methoxy-1,2,3,3a,4,9b-hexahydro-[1]-benzopyrano[3,4-c]pyrrol-2-yl)propyl]-pyrido[3',2':4,5]thieno[3,2-d]pyrimidine-2,4(1H,3H)-dione, 3-[2-((±)-cis-8-Methoxy-1,2,3,3a,4,9b-hexahydro-[1]-benzopyrano[3,4-c]pyrrol-2-yl)ethyl]-pyrido[3',2':4,5]thieno[3,2-d]pyrimidine-2,4(1H,3H)-dione, 3-[4-((±)-cis-9-Methoxy-1,2,3,3a,4,9b-hexahydro-[1]-benzopyrano[3,4-c]pyrrol-2yl)butyl]-6,7-dimethoxy-quinazoline-2,4(1H,3H)-dione, 3-[4-((±)-trans-1,2,3,3a,4,9b-hexahydro-[1]-benzopyrano[3,4c]pyrrol-2-yl)butyl]-6,7-dimethoxy-quinazoline-2,4(1H,3H)-dione, 3-[4-((±)-cis-1,2,3,3a,4,9b-hexahydro-[1]-benzopyrano[3,4-c]pyrrol-2-yl)butyl]-6,7-dimethoxy-quinazoline-2,4(1H,3H)-dione, 3-[4-((±)-trans-9-Methoxy-1,2,3,3a,4,9b-hexahydro-[1]-benzopyrano[3,4-c]pyrrol-2-yl)butyl]-6,7-dimethoxy-quinazoline-2,4(1H,3H)-dione, 3-[3-((±)-trans-10-Methoxy-1,3,4,4a,5,10b-hexahydro-2H-[1]-benzopyrano[3,4-c]pyrido-3-yl)propyl]-6,7-dimethoxy-quinazoline-2,4(1H,3H)-dione, 3-[3-((±)-trans-10-Methoxy-1,3,4,4a,5, 10b-hexahydro-2H-[1]-benzopyrano[3,4-c]pyrido-3-yl)propyl]-pyrido[3',2':4,5]thieno[3,2-d]pyrimidine-2,4(1H,3H)-dione, 3-[4-((±)-trans-10-Methoxy-1,3,4,4a,5,10b-hexahydro-2H-[1]-benzopyrano[3,4-c]pyrido-3-yl)butyl]-pyrido[3',2':4,5]thieno[3,2-d]pyrimidine-2,4(1H,3H)-dione, 3-[4-((±)-trans-10-Methoxy-1,3,4,4a,5,10b-hexahydro-2H-[1]-benzopyrano[3,4-c]pyrido-3-yl)butyl]-6,7-dimethoxy-quinazoline-2,4(1H,3H)-dione, 3-[4-((±)-trans-10-Methoxy-1,3,4,4a,5,10b-hexahydro-2H-[1]-benzopyrano[3,4-c]pyrido-3-yl)butyl]-[1]benzthieno[3,2-d]pyrimidine-2,4(1H,3H)-dione, 3-[4-((±)-trans-10-Methoxy-1,3,4,4a,5,10b-hexahydro-2H-[1]-benzopyrano[3,4-c]pyrido-3-yl)butyl]-pyrido[2',3':4,5]thieno[3,2-d]pyrimidine-2,4(1H,3H)-dione, 3-[3-((±)-trans-10-Methoxy-1,3,4,4a,5,10b-hexahydro-2H-[1]-benzopyrano[3,4-c]pyrido-3-yl)propyl]-[1]benzthieno[3,2-d]pyrimidine-2,4(1H,3H)-dione, 3-[2-((±)-trans-10-Methoxy-1,3,4,4a,5,10b-hexahydro-2H-[1]-benzopyrano[3,4-c]pyrido-3-yl)ethyl]-[1]benzthieno[3,2-d]pyrimidine-2,4(1H,3H)-dione, 3-[2-((±)-trans-10-Methoxy-1,3,4,4a,5,10b-hexahydro-2H-[1]-benzopyrano[3,4-c]pyrido-3-yl)ethyl]-6,7-dimethoxy-quinazoline-2,4(1H,3H)-dione, 3-[3-((4aS,10bR)-trans-10-Methoxy-1,3,4,4a,5,10b-hexahydro-2H-[1]-benzopyrano[3,4-c]pyrido-3-yl)propyl]-pyrido[2',3':4,5]thieno[3,2-d]pyrimidine-2,4(1H,3H)-dione, 3-[3-((4aR,10bS)-trans-10-Methoxy-1,3,4,4a,5,10b-hexahydro-2H-[1]-benzopyrano[3,4-c]pyrido-3-yl)propyl]-pyrido[2',3':4,5]thieno[3,2-d]pyrimidine-2,4(1H,3H)-dione, 3-[4-((4aR,10bS)-trans-10-Methoxy-1,3,4,4a,5,10b-hexahydro-2H-[1]-benzopyrano[3,4-c]pyrido-3-yl)butyl]-pyrido[2',3':4,5]thieno[3,2-d]pyrimidine-2,4(1H,3H)-dione, 3-[4-((4aS,10bR)-trans-10-Methoxy-1,3,4,4a,5,10b-hexahydro-2H-[1]-benzopyrano[3,4-c]pyrido-3-yl)butyl]-pyrido[2',3':4,5]thieno[3,2-d]pyrimidine-2,4(1H,3H)-dione, 3-[4-((4aR,10bS)-trans-10-Methoxy-1,3,4,4a,5,10b-hexahydro-2H-[1]-benzopyrano[3,4-c]pyrido-3-yl)butyl]-8-chloro-pyrazino[2',3':4,5]thieno[3,2-d]pyrimidine-2,4(1H,3H)-dione, 3-[4-((4aS,10bR)-trans-10-Methoxy-1,3,4,4a,5,10b-hexahydro-2H-[1]-benzopyrano[3,4c]pyrido-3-yl)butyl]-8-chloro-pyrazino[2',3':4,5]thieno[3,2-d]pyrimidine-2,4(1H,3H)-dione, 3-[4-((4aS,10bR)-trans-10-Methoxy-1,3,4,4a,5,10b-hexahydro-2H-[1]-benzopyrano[3,4-c]pyrido-3-yl)butyl]-8-methoxy-pyrido[2',3':4,5]thieno[3,2-d]pyrimidine-2,4(1H,3H)-dione, 3-[4-((4aS,10bR)-trans-10-Methoxy-1,3,4,4a,5,10b-hexahydro-2H-[1]-benzopyrano[3,4-c]pyrido-3-yl)butyl]-8-methoxy-pyrazino[2',3':4,5]thieno[3,2-d]pyrimidine-2,4(1H,3H)-dione, 3-[4-((4aS,10bR)-trans-10-Methoxy-1,3,4,4a,5,10b-hexahydro-2H-[1]-benzopyrano[3,4-c]pyrido-3-yl)butyl]-8-phenyl-pyrazino[2',3':4,5]thieno[3,2-d]pyrimidine-2,4(1H,3H)-dione, 3-[4-((4aS,10bR)-trans-10-Methoxy-1,3,4,4a,5,10b-hexahydro-2H-[1]-benzopyrano[3,4-c]pyrido-3-yl)butyl]-8-phenyl-pyrido[2',3':4,5]thieno[3,2-d]pyrimidine-2,4(1H,3H)-dione, 3-[4-((4aS,10bR)-trans-10-Methoxy-1,3,4,4a,5,10b-hexahydro-2H-[1]-benzopyrano[3,4-c]pyrido-3-yl)butyl]-7-chloro-pyrido[3',2':4,5]thieno[3,2-d]pyrimidine-2,4(1H,3H)-dione, 3-[4-((4aS,10bR)-trans-10-Methoxy-1,3,4,4a,5,10b-hexahydro-2H-[1]-benzopyrano[3,4-c]pyrido-3-yl)butyl]-7-methoxy-pyrido[3',2':4,5]thieno[3,2-d]pyrimidine-2,4(1H,3H)-dione, or a pharmaceutically acceptable salt thereof.

Preferred compounds falling within the scope of formula (I) include:

3-[4-((3aR,9bR)-cis-9-Methoxy-1,2,3,3a,4,9b-hexahydro-[1]-benzopyrano[3,4-c]pyrrol-2-yl)butyl]-pyrido[2',3':4,5]thieno[3,2-d]pyrimidine-2,4(1H,3H)-dione, 3-[4-((3aS,9bR)-trans-9-Methoxy-1,2,3,3a,4,9b-hexahydro-[1]-benzopyrano[3,4-c]pyrrol-2-yl)butyl]-pyrido[2',3':4,5]thieno[3,2-d]pyrimidine-2,4(1H,3H)-dione, 3-[4-((3aS,9bR)-trans-9-Methoxy-1,2,3,3a,4,9b-hexahydro-[1]-benzopyrano[3,4-c]pyrrol-2-yl)butyl]-8-chloro-pyrazino[2',3':4,5]thieno[3,2-d]pyrimidine-2,4(1H,3H)-dione, 3-[4-((3aR,9bR)-cis-9-Methoxy-1,2,3,3a,4,9b-hexahydro-[1]-benzopyrano[3,4-c]pyrrol-2-yl)butyl]-8-chloro-pyrazino[2',3':4,5]thieno[3,2-d]pyrimidine-2,4(1H,3H)-dione, 3-[4-((3aR,9bR)-cis-9-Methoxy-1,2,3,3a,4,9b-hexahydro-[1]-benzopyrano[3,4-c]pyrrol-2-yl)butyl]-8-methoxy-pyrido[2',3':4,5]thieno[3,2-d]pyrimidine-2,4(1H,3H)-dione, 3-[4-((3aR,9bR)-cis-9-Methoxy-1,2,3,3a,4,9b-hexahydro-[1]-benzopyrano[3,4-c]pyrrol-2-yl)butyl]-8-methoxy-pyrazino[2',3':4,5]thieno[3,2-d]pyrimidine-2,4(1H,3H)-dione, 3-[4-((3aR,9bR)-cis-9-Methoxy-1,2,3,3a,4,9b-hexahydro-[1]-benzopyrano[3,4-c]pyrrol-2-yl)butyl]-7-methoxy-pyrido[3',2':4,5]thieno[3,2-d]pyrimidine-2,4(1H,3H)-dione, 3-[4-((3aR,9bR)-cis-9-Methoxy-1,2,3,3a,4,9b-hexahydro-[1]-benzopyrano[3,4-c]pyrrol-2-yl)butyl]-7-chloro-pyrido[3',2':4,5]thieno[3,2-d]pyrimidine-2,4(1H,3H)-dione, 3-[4-((3aR,9bR)-cis-9-Methoxy-1,2,3,3a,4,9b-hexahydro-[1]-benzopyrano[3,4-c]pyrrol-2-yl)butyl]-8-chloro-pyrido[2',3':4,5]thieno[3,2-d]pyrimidine-2,4(1H,3H)-dione, 3-[4-((3aR,9bR)-cis-9-Methoxy-1,2,3,3a,4,9b-hexahydro-[1]-benzopyrano[3,4-c]pyrrol-2-yl)butyl]-8-phenyl-pyrazino[2',3':4,5]thieno[3,2-d]pyrimidine-2,4(1H,3H)-dione, 3-[4-((3aS,9bR)-trans-9-Methoxy-1,2,3,3a,4,9b-hexahydro-[1]-benzopyrano[3,4-c]pyrrol-2-yl)butyl]-8-methoxy-pyrazino[2',3':4,5]thieno[3,2-d]pyrimidine-2,4(1H,3H)-dione, 3-[4-((3aS,9bR)-trans-9-Methoxy-1,2,3,3a,4,9b-hexahydro-[1]-benzopyrano[3,4-c]pyrrol-2-yl)butyl]-7-methoxy-pyrido[3',2':4,5]thieno[3,2-d]pyrimidine-2,4(1H,3H)-dione, 3-[4-((3aS,9bR)-trans-9-Methoxy-1,2,3,3a,4,9b-hexahydro-[1]-benzopyrano[3,4-c]pyrrol-2-yl)butyl]-7-chloro-pyrido[3',2':4,5]thieno[3,2-d]pyrimidine-2,4(1H,3H)-dione, 3-[4-((3aS,9bR)-trans-9-Methoxy-1,2,3,3a,4,9b-hexahydro-[1]-benzopyrano[3,4-c]pyrrol-2-yl)butyl]-8-phenyl-pyrazino[2',3':4,5]thieno[3,2-d]pyrimidine-2,4(1H,3H)-dione, 3-[4-((3aS,9bR)-trans-9-Methoxy-1,2,3,3a,4,9b-hexahydro-[1]-benzopyrano[3,4-c]pyrrol-2-yl)butyl]-8-isopropoxy-pyrido[2',3':4,5]thieno[3,2-d]pyrimidine-2,4(1H,3H)-dione, 3-[4-((3aS,9bR)-trans-9-Methoxy-1,2,3,3a,4,9b-hexahydro-[1]-benzopyrano[3,4-c]pyrrol-2-yl)butyl]-8-phenyl-pyrido[2',3':4,5]thieno[3,2-d]pyrimidine-2,4(1H,3H)-dione, 3-[3-((4aS,10bR)-trans-10-Methoxy-1,3,4,4a,5,10b-hexahydro-2H-[1]-benzopyrano[3,4-c]pyrido-3-yl)propyl]-pyrido[2',3':4,5]thieno[3,2-d]pyrimidine-2,4(1H,3H)-dione, 3-[4-((4aS,10bR)-trans-10-Methoxy-1,3,4,4a,5,10b-hexahydro-2H-[1]-benzopyrano[3,4-c]pyrido-3-yl)butyl]-pyrido[2',3':4,5]thieno[3,2-d]pyrimidine-2,4(1H,3H)-dione, 3-[4-((4aS,10bR)-trans-10-Methoxy-1,3,4,4a,5,10b-hexahydro-2H-[1]-benzopyrano[3,4-c]pyrido-3-yl)butyl]-8-methoxy-pyrido[2',3':4,5]thieno[3,2-d]pyrimidine-2,4(1H,3H)-dione, 3-[4-((4aS,10bR)-trans-10-Methoxy-1,3,4,4a,5,10b-hexahydro-2H-[1]-benzopyrano[3,4-c]pyrido-3-yl)butyl]-8-methoxy-pyrazino[2',3':4,5]thieno[3,2-d]pyrimidine-2,4(1H,3H)-dione, 3-[4-((4aS,10bR)-trans-10-Methoxy-1,3,4,4a,5,10b-hexahydro-2H-[1]-benzopyrano[3,4-c]pyrido-3-yl)butyl]-8-phenyl-pyrazino[2',3':4,5]thieno[3,2-d]pyrimidine-2,4(1H,3H)-dione, 3-[4-((4aS,10bR)-trans-10-Methoxy-1,3,4,4a,5,10b-hexahydro-2H-[1]-benzopyrano[3,4-c]pyrido-3-yl)butyl]-8-phenyl-pyrido[2',3':4,5]thieno[3,2-d]pyrimidine-2,4(1H,3H)-dione, 3-[4-((3aR,9bR)-cis-9-Methoxy-1,2,3,3a,4,9b-hexahydro-[1]-benzopyrano[3,4-c]pyrrol-2-yl)butyl]-8-(3-thienyl)-pyrazino[2',3':4,5]thieno[3,2-d]pyrimidine-2,4(1H,3H)-dione, 3-[4-((3aR,9bR)-cis-9-Methoxy-1,2,3,3a,4,9b-hexahydro-[1]-benzopyrano[3,4-c]pyrrol-2-yl)butyl]-8-(3-pyridyl)-pyrido[2',3':4,5]thieno[3,2-d]pyrimidine-2,4(1H,3H)-dione, 3-[4-((3aR,9bR)-cis-9-Methoxy-1,2,3,3a,4,9b-hexahydro-[1]-benzopyrano[3,4-c]pyrrol-2-yl)butyl]-8-(3-pyridyl)-pyrazino[2',3':4,5]thieno[3,2-d]pyrimidine-2,4(1H,3H)-dione, 3-[4-((3aS,9bR)-trans-9-Methoxy-1,2,3,3a,4,9b-hexahydro-[1]-benzopyrano[3,4-c]pyrrol-2-yl)butyl1-8-(3-pyridyl)-pyrazino[2',3':4,5]thieno[3,2-d]pyrimidine-2,4(1H,3H)-dione, 3-[4-((3aR,9bR)-cis-9-Methoxy-1,2,3,3a,4,9b-hexahydro-[1]-benzopyrano[3,4-c]pyrrol-2-yl)butyl]-8-(3-furyl)-pyrazino[2',3':4,5]thieno[3,2-d]pyrimidine-2,4(1H,3H)-dione, and 3-[4-((3aS,9bR)-trans-9-Methoxy-1,2,3,3a,4,9b-hexahydro-[1]-benzopyrano[3,4-c]pyrrol-2-yl)butyl]-8-(3-thienyl)-pyrazino[2',3':4,5]thieno[3,2-d]pyrimidine-2,4(1H,3H)-dione, or a pharmaceutically acceptable salt thereof.

The following compounds may be prepared by the methods described in the synthetic Schemes and Examples contained herein:

3-[4-((3aR,9bR)-cis-9-Methoxy-1,2,3,3a,4,9b-hexahydro-[1]-benzopyrano[3,4-c]pyrrol-2-yl)butyl]-pyrido[2,3-g]quinazoline-2,4(1H,3H)-dione, 3-[4-((3aR,9bR)-cis-9-Methoxy-1,2,3,3a,4,9b-hexahydro-[1]-benzopyrano[3,4-c]pyrrol-2-yl)butyl]-pyrido[3,4-g]quinazoline-2,4(1H,3H)-dione, 3-[4-((3aR,9bR)-cis-9-Methoxy-1,2,3,3a,4,9b-hexahydro-[1]-benzopyrano[3,4-c]pyrrol-2-yl)butyl]-pyrido[4,3-g]quinazoline-2,4(1H,3H)-dione, 3-[4-((3aR,9bR)-cis-9-Methoxy-1,2,3,3a,4,9b-hexahydro-[1]-benzopyrano[3,4-c]pyrrol-2-yl)butyl]-pyrido[3,2-g]quinazoline-2,4(1H,3H)-dione, 3-[4-((3aR,9bR)-cis-9-Methoxy-1,2,3,3a,4,9b-hexahydro-[1]-benzopyrano[3,4-c]pyrrol-2-yl)butyl]-pyrido[2,3-f]quinazoline-2,4(1H,3H)-dione, 3-[4-((3aR,9bR)-cis-9-Methoxy-1,2,3,3a,4,9b-hexahydro-[1]-benzopyrano[3,4-c]pyrrol-2-yl)butyl]-pyrido[3,4-f]quinazoline-2,4(1H,3H)-dione, 3-[4-((3aR,9bR)-cis-9-Methoxy-1,2,3,3a,4,9b-hexahydro-[1]-benzopyrano[3,4-c]pyrrol-2-yl)butyl]-pyrido[3,2-a]quinazoline-2,4(1H,3H)-dione, 3-[4-((3aR,9bR)-cis-9-Methoxy-1,2,3,3a,4,9b-hexahydro-[1]-benzopyrano[3,4-c]pyrrol-2yl)butyl]-pyrido[4,3-f]quinazoline-2,4(1H,3H)-dione, 3-[4-((3aR,9bR)-cis-9-Methoxy-1,2,3,3a,4,9b-hexahydro-[1-benzopyrano[3,4-c]pyrrol-2-yl)butyl]-pyrido[2,3-h]quinazoline-2,4(1H,3H)-dione, 3-[4-((3aR,9bR)-cis-9-Methoxy-1,2,3,3a,4,9b-hexahydro-[1]-benzopyrano[3,4-c]pyrrol-2-yl)butyl]-pyrido[3,4-h]quinazoline-2,4(1H,3H)-dione, 3-[4-((3aR,9bR)-cis-9-Methoxy-1,2,3,3a,4,9b-hexahydro-[1]-benzopyrano[3,4-c]pyrrol-2-yl)butyl]-pyrido[3,2-h]quinazoline-2,4(1H,3H)-dione, 3-[4-((3aR,9bR)-cis-9-Methoxy-1,2,3,3a,4,9b-hexahydro-[1]-benzopyrano[3,4-c]pyrrol-2-yl)butyl]-pyrido[4,3-h]quinazoline-2,4(1H,3H)-dione, 3-[4-((3aR,9bR)-cis-9-Methoxy-1,2,3,3a,4,9b-hexahydro-[1]-benzopyrano[3,4-c]pyrrol-2-yl)butyl]-benz[g]quinazoline-2,4(1H,3H)-dione, 3-[4-((3aR,9bR)-cis-9-Methoxy-1,2,3,3a,4,9b-hexahydro-[1]-benzopyrano[3,4-c]pyrrol-2-yl)butyl]-benz[h]quinazoline-2,4(1H,3H)-dione, 3-[4-((3aR,9bR)-cis-9-Methoxy-1,2,3,3a,4,9b-hexahydro-[1]-benzopyrano[3,4-c]pyrrol-2-yl)butyl]-benz[f]quinazoline-2,4(1H,3H)-dione, 3-[4-((3aR,9bR)-cis-9-Methoxy-1,2,3,3a,4,9b-hexahydro-[1]-benzopyrano[3,4-c]pyrrol-2-yl)butyl]-pyrazino[2,3-f]quinazoline-2,4(1H,3H)-dione, 3-[4-((3aR,9bR)-cis-9-Methoxy-1,2,3,3a,4,9b-hexahydro-[1]-benzopyrano[3,4-c]pyrrol-2-yl)butyl]-pyrazino[2,3-g]quinazoline-2,4(1H,3H)-dione, 3-[4-((3aR,9bR)-cis-9-Methoxy-1,2,3,3a,4,9b-hexahydro-[1]-benzopyrano[3,4-c]pyrrol-2-yl)butyl]-pyrazino[2,3-h]quinazoline-2,4(1H,3H)-dione, 3-[4-((3aR,9bR)-cis-9-Methoxy-1,2,3,3a,4,9b-hexahydro-[1]-benzopyrano[3,4-c]pyrrol-2-yl)butyl]-pyridazino[3,4-f]quinazoline-2,4(1H,3H)-dione, 3-[4-((3aR,9bR)-cis-9-Methoxy-1,2,3,3a,4,9b-hexahydro-[1]-benzopyrano[3,4-c]pyrrol-2-yl)butyl]-pyridazino[4,3-f]quinazoline-2,4(1H,3H)-dione, 3-[4-((3aR,9bR)-cis-9-Methoxy-1,2,3,3a,4,9b-hexahydro-[1]-benzopyrano[3,4-c]pyrrol-2-yl)butyl]-pyridazino[4,5-f]quinazoline-2,4(1H,3H)-dione, 3-[4-((3aR,9bR)-cis-9-Methoxy-1,2,3,3a,4,9b-hexahydro-[1]-benzopyrano[3,4-c]pyrrol-2-yl)butyl]-pyridazino[3,4-g]quinazoline-2,4(1H,3H)-dione, 3-[4-((3aR,9bR)-cis-9-Methoxy-1,2,3,3a,4,9b-hexahydro-[1]-benzopyrano[3,4-c]pyrrol-2-yl)butyl]-pyridazino[4,3-g]quinazoline-2,4(1H,3H)-dione, 3-[4-((3aR,9bR)-cis-9-Methoxy-1,2,3,3a,4,9b-hexahydro-[1 1-benzopyrano[3,4-c]pyrrol-2-yl)butyl]-pyridazino[4,5-g]quinazoline-2,4(1H,3H)-dione, 3-[4-((3aR,9bR)-cis-9-Methoxy-1,2,3,3a,4,9b-hexahydro-[1]-benzopyrano[3,4-c]pyrrol-2-yl)butyl]-pyridazino[3,4-h]quinazoline-2,4(1H,3H)-dione, 3-[4-((3aR,9bR)-cis-9-Methoxy-1,2,3,3a,4,9b-hexahydro-[1]-benzopyrano[3,4-c]pyrrol-2-yl)butyl]-pyridazino[4,3-h]quinazoline-2,4(1H,3H)-dione, 3-[4-((3aR,9bR)-cis-9-Methoxy-1,2,3,3a,4,9b-hexahydro-[1]-benzopyrano[3,4-c]pyrrol-2-yl)butyl3-pyridazino[4,5-h]quinazoline-2,4(1H,3H)-dione, 3-[4-((3aR,9bR)-cis-9-Methoxy-1,2,3,3a,4,9b-hexahydro-[1]-benzopyrano[3,4-c]pyrrol-2-yl)butyl]-pyrimidino[4,5-f]quinazoline-2,4(1H,3H)-dione, 3-[4-((3aR,9bR)-cis-9-Methoxy-1,2,3,3a,4,9b-hexahydro-[1]-benzopyrano[3,4-c]pyrrol-2-yl)butyl]-pyrimidino[5,4-f]quinazoline-2,4(1H,3H)-dione, 3-[4-((3aR,9bR)-cis-9-Methoxy-1,2,3,3a,4,9b-hexahydro-[1]-benzopyrano[3,4-c]pyrrol-2-yl)butyl]-pyrimidino[4,5-g]quinazoline-2,4(1H,3H)-dione, 3-[4-((3aR,9bR)-cis-9-Methoxy-1,2,3,3a,4,9b-hexahydro-[1]-benzopyrano[3,4-c]pyrrol-2-yl)butyl]-pyrimidino[5,4-g]quinazoline-2,4(1H,3H)-dione, 3-[4-((3aR,9bR)-cis-9-Methoxy-1,2,3,3a,4,9b-hexahydro-[1]-benzopyrano[3,4-c]pyrrol-2-yl)butyl]-pyrimidino[4,5-h]quinazoline-2,4(1H,3H)-dione, 3-[4-((3aR,9bR)-cis-9-Methoxy-1,2,3,3a,4,9b-hexahydro-[1]-benzopyrano[3,4-c]pyrrol-2-yl)butyl]-pyrimidino[5,4-h]quinazoline-2,4(1H,3H)-dione, 3-[4-((3aS,9bR)-trans-9-Methoxy-1,2,3,3a,4,9b-hexahydro-[1]-benzopyrano[3,4-c]pyrrol-2-yl)butyl]-pyrido[2,3-g]quinazoline-2,4(1H,3H)-dione, 3-[4-((3aS,9bR)-trans-9-Methoxy-1,2,3,3a,4,9b-hexahydro-[1]-benzopyrano[3,4-c]pyrrol-2-yl)butyl]-pyrido[3,4-g]quinazoline-2,4(1H,3H)-dione, 3-[4-((3aS,9bR)-trans-9-Methoxy-1,2,3,3a,4,9b-hexahydro-[1]-benzopyrano[3,4-c]pyrrol-2-yl)butyl]-pyrido[4,3-g]quinazoline-2,4(1H,3H)-dione, 3-[4-((3aS,9bR)-trans-9-Methoxy-1,2,3,3a,4,9b-hexahydro-[1]-benzopyrano[3,4-c]pyrrol-2-yl)butyl]-pyrido[3,2-g]quinazoline-2,4(1H,3H)-dione, 3-[4-((3aS,9bR)-trans-9-Methoxy-1,2,3,3a,4,9b-hexahydro-[1]-benzopyrano[3,4-c]pyrrol-2-yl)butyl]-pyrido[2,3-f]quinazoline-2,4(1H,3H)-dione, 3-[4-((3aS,9bR)-trans-9-Methoxy-1,2,3,3a,4,9b-hexahydro-[1]-benzopyrano[3,4-c]pyrrol-2-yl)butyl]-pyrido[3,4-f]quinazoline-2,4(1H,3H)-dione, 3-[4-((3aS,9bR)-trans-9-Methoxy-1,2,3,3a,4,9b-hexahydro-[1]-benzopyrano[3,4-c]pyrrol-2-yl)butyl]-pyrido[3,2-f]quinazoline-2,4(1H,3H)-dione, 3-[4-((3aS,9bR)-trans-9-Methoxy-1,2,3,3a,4,9b-hexahydro-[1]-benzopyrano[3,4-c]pyrrol-2-yl)butyl]-pyrido[4,3-f]quinazoline-2,4(1H,3H)-dione, 3-[4-((3aS,9bR)-trans-9-Methoxy-1,2,3,3a,4,9b-hexahydro-[1]-benzopyrano[3,4-c]pyrrol-2-yl)butyl]-pyrido[2,3-h]quinazoline-2,4(1H,3H)-dione, 3-[4-((3aS,9bR)-trans-9-Methoxy-1,2,3,3a,4,9b-hexahydro-[1]-benzopyrano[3,4-c]pyrrol-2-yl)butyl]-pyrido[3,4-h]quinazoline-2,4(1H,3H)-dione, 3-[4-((3aS,9bR)-trans-9-Methoxy-1,2,3,3a,4,9b-hexahydro-[1]-benzopyrano[3,4-c]pyrrol-2-yl)butyl]-pyrido[3,2-h]quinazoline-2,4(1H,3H)-dione, 3-[4-((3aS,9bR)-trans-9-Methoxy-1,2,3,3a,4,9b-hexahydro-[1 -benzopyrano[3,4-c]pyrrol-2-yl)butyl]-pyrido[4,3-h]quinazoline-2,4(1H,3H)-dione, 3-[4-((3aS,9bR)-trans-9-Methoxy-1,2,3,3a,4,9b-hexahydro-[1]-benzopyrano[3,4-c]pyrrol-2-yl)butyl]-benz[g]quinazoline-2,4(1H,3H)-dione, 3-[4-((3aS,9bR)-trans-9-Methoxy-1,2,3,3a,4,9b-hexahydro-[1]-benzopyrano[3,4-c]pyrrol-2-yl)butyl]-benz[h]quinazoline-2,4(1H,3H)-dione, 3-[4-((3aS,9bR)-trans-9-Methoxy-1,2,3,3a,4,9b-hexahydro-[1]-benzopyrano[3,4-c]pyrrol-2-yl)butyl]-benz[f]quinazoline-2,4(1H,3H)-dione, 3-[4-((3aS,9bR)-trans-9-Methoxy-1,2,3,3a,4,9b-hexahydro-[1]-benzopyrano[3,4-c]pyrrol-2-yl)butyl]-pyrazino[2,3-f]quinazoline-2,4(1H,3H)-dione, 3-[4-((3aS,9bR)-trans-9-Methoxy-1,2,3,3a,4,9b-hexahydro-[1]-benzopyrano[3,4-c]pyrrol-2-yl)butyl]-pyrazino[2,3-g]quinazoline-2,4(1H,3H)-dione, 3-[4-((3aS,9bR)-trans-9-Methoxy-1,2,3,3a,4,9b-hexahydro-[1]-benzopyrano[3,4-c]pyrrol-2-yl)butyl]-pyrazino[2,3-h]quinazoline-2,4(1H,3H)-dione, 3-[4-((3aS,9bR)-trans-9-Methoxy-1,2,3,3a,4,9b-hexahydro-[1]-benzopyrano[3,4-c]pyrrol-2-yl)butyl]-pyridazino[3,4-f]quinazoline-2,4(1H,3H)-dione, 3-[4-((3aS,9bR)-trans-9-Methoxy-1,2,3,3a,4,9b-hexahydro-[1]-benzopyrano[3,4-c]pyrrol-2-yl)butyl]-pyridazino[4,3-f]quinazoline-2,4(1H,3H)-dione, 3-[4-((3aS,9bR)-trans-9-Methoxy-1,2,3,3a,4,9b-hexahydro-[1]-benzopyrano[3,4-c]pyrrol-2-yl)butyl]-pyridazino[4,5-f]quinazoline-2,4(1H,3H)-dione, 3-[4-((3aS,9bR)-trans-9-Methoxy-1,2,3,3a,4,9b-hexahydro-[1]-benzopyrano[3,4-c]pyrrol-2-yl)butyl]-pyridazino[3,4-g]quinazoline-2,4(1H,3H)-dione, 3-[4-((3aS,9bR)-trans-9-Methoxy-1,2,3,3a,4,9b-hexahydro-[1]-benzopyrano[3,4-c]pyrrol-2-yl)butyl]-pyridazino[4,3-g]quinazoline-2,4(1H,3H)-dione, 3-[4-((3aS,9bR)-trans-9-Methoxy-1,2,3,3a,4,9b-hexahydro-[1]-benzopyrano[3,4-c]pyrrol-2-yl)butyl]-pyridazino[4,5-g]quinazoline-2,4(1H,3H)-dione, 3-[4-((3aS,9bR)-trans-9-Methoxy-1,2,3,3a,4,9b-hexahydro-[1]-benzopyrano[3,4-c]pyrrol-2-yl)butyl]-pyridazino[3,4-h]quinazoline-2,4(1H,3H)-dione, 3-[4-((3aS,9bR)-trans-9-Methoxy-1,2,3,3a,4,9b-hexahydro-[1]-benzopyrano[3,4-c]pyrrol-2-yl)butyl]-pyridazino[4,3-h]quinazoline-2,4(1H,3H)-dione, 3-[4-((3aS,9bR)-trans-9-Methoxy-1,2,3,3a,4,9b-hexahydro-[1 1-benzopyrano[3,4-c]pyrrol-2-yl)butyl]-pyridazino[4,5-h]quinazoline-2,4(1H,3H)-dione, 3-[4-((3aS,9bR)-trans-9-Methoxy-1,2,3,3a,4,9b-hexahydro-[1]-benzopyrano[3,4-c]pyrrol-2-yl)butyl]-pyrimidino[4,5-f]quinazoline-2,4(1H,3H)-dione, 3-[4-((3aS,9bR)-trans-9-Methoxy-1,2,3,3a,4,9b-hexahydro-[1]-benzopyrano[3,4-c]pyrrol-2-yl)butyl]-pyrimidino[5,4-f]quinazoline-2,4(1H,3H)-dione, 3-[4-((3aS,9bR)-trans-9-Methoxy-1,2,3,3a,4,9b-hexahydro-[1]-benzopyrano[3,4-c]pyrrol-2-yl)butyl]-pyrimidino[4,5-g]quinazoline-2,4(1H,3H)-dione, 3-[4((3aS,9bR)-trans-9-Methoxy-1,2,3,3a,4,9b-hexahydro-[1]-benzopyrano[3,4-c]pyrrol-2-yl)butyl]-pyrimidino[5,4-g]quinazoline-2,4(1H,3H)-dione, 3-[4((3aS,9bR)-trans-9-Methoxy-1,2,3 ,3a,4,9b-hexahydro-[1]-benzopyrano[3,4-c]pyrrol-2-yl)butyl]-pyrimidino[4,5-h]quinazoline-2,4(1H,3H)-dione, and 3-[4((3aS,9bR)-trans-9-Methoxy-1,2,3,3a,4,9b-hexahydro-[1]-benzopyrano[3,4-c]pyrrol-2-yl)butyl]-pyrimidino[5,4-h]quinazoline-2,4(1H,3H)-dione, or a pharmaceutically acceptable salt thereof.

Representative compounds of the present invention were evaluated for their ability to displace prazosin from its adrenoreceptor.

In vitro Binding Assays

In the following, for purposes of discussing alpha-1 adrenoreceptor subtypes, the IUPHAR convention of using lower case letters to define molecular clones and upper case letters to indicate pharmacologically defined adrenoreceptors has been followed. Moreover, the newly recommended nomenclature for alpha-1 ($\alpha_{1a}$, $\alpha_{1b}$, $\alpha_{1d}$) has been used.

Representative compounds of the invention were evaluated for α-adrenoreceptor binding affinity in vitro using [$^3$H]-prazosin as the radioligand and three cloned α-1 adrenoreceptors expressed in LTK cells: α-1a (bovine), α-1b (hamster), and α-1d (rat). Additionally, binding affinity against the pharmacologically defined α-1A adrenoreceptor (rat submaxillary gland) was measured.

The cDNA clones encoding the α-1 adrenoreceptors (α-1a, α-1b, and α-1d) were obtained from TULCO (Triangle Universities Licensing Consortium, Research Triangle Park, N.C.) and inserted into the eukaryotic expression vector SnaB30. In this vector, expression of the adrenoreceptor gene is under the transcriptional control of an SV40 early promoter. Positive drug selection is provided by a neomycin-resistance gene. Mouse fibroblast cells (LTK) were transfected with the $\alpha_1$ expression plasmids and grown in Dulbecco's modified Eagle's medium (DMEM) containing 10% fetal calf serum and 30 μM G418. Stable G418-resistant parental lines were generated, with successful expression of adrenoreceptor protein monitored using radioligand binding techniques. Stable single cell clones derived from the parental lines were screened in adrenoreceptor binding assays to identify clones having high adrenoreceptor density. Roller bottle cultures of the cloned lines were used to provide cell membranes for subsequent adrenoreceptor binding characterization studies. A cell line containing the SnaB30 vector expressing the human erythropoietin gene served as a negative control.

For adrenoreceptor binding assays, large scale membrane preparations were utilized in which 6 million cells were seeded into small (450 cm$^2$) Corning tissue culture roller bottles. 200 mL of DMEM containing 10% fetal calf serum and 300 μM G418 were added to each roller bottle. A 95% air/5% CO$_2$ gas mixture (sterile) was injected into each roller bottle prior to sealing. The bottles were then incubated at 37° C. on a roller rack for 5 days. Cells were re-fed with fresh medium after 3 days in culture.

On the fifth day of culture, growth medium was removed from cells grown in roller bottles, and the cells were washed twice with PBS (Sigma, 120 mM NaCl, 2.7 mM KCl, 10 mM Na$_2$HPO$_4$—NaH$_2$PO$_4$, pH=7.4). Cells were detached from the roller bottles by incubating for 15 minutes at 37° C. in a Tris-EDTA solution (10 mM Tris, 100 mM NaCl, 1 mM EDTA, pH=7.4). The cell suspension from each roller bottle was decanted into tared centrifuge tubes and kept on ice. An aliquot of each cell suspension was generally taken for cell counting. Cells were centrifuged at 3000×G for 5 min at 2°–4° C., washed with PBS and recentrifuged. The supernatant was decanted and the pellet weighed to determine the wet weight of cells. Cells were washed a final time in 40 vol 5 mM Tris-HCl, 5 mM EDTA, pH=7.7, and centrifuged at 40,000×G for 10 minutes. Cells were homogenized in 10 mL of 50 mM Tris-HCl, 5 mM EDTA (pH=7.4) and diluted to 40 mL/tube. Homogenates were centrifuged at 40,000×G for 10 minutes. The supernatant was decanted and the pellets rehomogenized in 50 mM Tris-HCl (pH=7.4) and centrifuged as before. The supernatant was decanted and the homogenate resuspended in 6.25 volumes (per gram wet weight) of 50 mM Tris-HCl and aliquots of the pooled homogenates frozen in liquid N$_2$ and stored at −70° C. until the time of assay. Rat submaxillary glands were used for α-1A adrenoreceptors and were prepared essentially as described (Michel, A. D., Loury, D. N. and Whiting, R. L., *Brit. J. Pharmacol.* 98: 83–889 (1989)).

Receptor binding assays for α-1 adrenoreceptors were performed essentially as described by Greengrass and Bremner (*Eur. J. Pharmacol.* 55: 323–326 (1979)). Briefly, plastic Bioblocks® (DBM Scientific, Valencia, Calif.) were incubated at 25° C. for 50 minutes with 500 μL of membrane homogenate (diluted with an additional 96 volumes [for cloned adrenoreceptors, 12 volumes for submaxillary gland] in 50 mM Tris-HCl buffer (pH=7.7 at the time of assay), 450 μL of [$^3$H]prazosin (0.2 nM final concentration, 75–85 Ci/mmole, DuPont-NEN Corp., Boston, Mass.) and 50 μL of either water (for total binding) or 10 μM phentolamine (final concentration, for non-specific binding). Following equilibration, bound radioligand was separated from free on GF/B filters (presoaked in 0.5% polyethyleneimine) using either a Brandel or Packard cell harvester. Radioactivity was determined by standard liquid scintillation techniques. Data were analyzed as previously described (Hancock, A. A., Kyncl, J. J., Martin, Y. C. and DeBernardis, J. F., *J Receptor Res.* 8: 23–46 (1988)).

Canine prostate strips were used in vitro as previously described (Hieble, J. P., Boyce, Caine, M., *Fed Proc.,* 45: 2609–2614 (1986)), to determine antagonist potencies phenylephrine-induced contractions.

The results are shown in Table 1. The results show that the compounds of the invention bind to the α-1 adrenoreceptor and show varying degrees of specificity for the α-1a adrenoreceptor.

TABLE 1

In Vitro Data for Binding to α-1 Adrenoceptors

| | Radioligand Binding (Ki; nM) | | | |
|---|---|---|---|---|
| | 1A (Rat) | 1a (Bovine) | 1b (Hamster) | 1d (Rat) |
| 1 | 0.045 | 0.024 | 1.144 | 0.223 |
| 2 | 0.95 | 0.193 | 9.23 | 2.716 |
| 3 | 0.026 | 0.02 | 0.286 | 0.041 |
| 4 | 0.097 | 0.049 | 0.867 | 0.377 |
| 5 | 0.268 | 0.086 | 2.008 | 0.638 |
| 6 | 0.409 | 0.173 | 1.997 | 0.302 |
| 7 | 0.53 | 0.215 | 1.606 | 0.438 |
| 8 | 0.762 | 0.362 | 4.187 | 1.419 |
| 9 | 2.267 | 0.325 | 17.75 | 1.551 |
| 10 | 0.662 | 0.406 | 10.45 | 1.597 |
| 11 | 0.374 | 0.243 | 3.784 | 1.461 |
| 12 | 0.52 | 0.375 | 5.255 | 2.167 |
| 13 | 0.1 | 0.041 | 2.492 | 0.112 |
| 14 | 0.105 | 0.038 | 1.37 | 0.145 |
| 15 | 0.227 | 0.068 | 4.406 | 0.928 |
| 16 | 0.373 | 0.073 | 8.636 | 0.729 |
| 17 | 0.175 | 0.068 | 1.2475 | 0.19 |

TABLE 1-continued

In Vitro Data for Binding to α-1 Adrenoceptors

| | Radioligand Binding (Ki; nM) | | | |
|---|---|---|---|---|
| | 1A (Rat) | 1a (Bovine) | 1b (Hamster) | 1d (Rat) |
| 18 | 0.284 | 0.069 | 5.055 | 0.79 |
| 19 | 0.059 | 0.025 | 1.13 | 0.108 |
| 20 | 0.208 | 0.038 | 3.505 | 0.439 |
| 21 | 0.03 | 0.018 | 0.326 | 0.03 |
| 22 | 0.196 | 0.031 | 1.163 | 0.138 |
| 23 | 0.743 | 0.046 | 0.973 | 0.639 |
| 24 | 5.37 | 0.616 | 5.557 | 4.512 |
| 25 | 0.061 | 0.03 | 0.591 | 0.039 |
| 26 | 0.09 | 0.022 | 0.376 | 0.017 |
| 27 | 0.121 | 0.044 | 0.974 | 0.094 |
| 28 | 0.273 | 0.092 | 3.694 | 0.195 |
| 29 | 0.252 | 0.095 | 3.69 | 0.466 |
| 30 | 0.264 | 0.066 | 2.673 | 0.222 |
| 31 | 0.224 | 0.06 | 4.787 | 0.344 |
| 32 | 1.011 | 0.093 | 9.952 | 0.86 |
| 33 | 0.811 | 0.082 | 10.451 | 0.701 |
| 34 | 0.474 | 0.079 | 3.367 | 0.339 |
| 35 | 0.312 | 0.057 | 5.121 | 0.436 |
| 36 | 0.539 | 0.124 | 2.854 | 0.36 |
| 37 | 0.264 | 0.069 | 3.343 | 0.195 |
| 38 | 0.376 | 0.057 | 5.63 | 0.897 |
| 39 | 0.343 | 0.226 | 31.915 | 2.145 |
| 40 | 22.845 | 3.015 | 33.778 | 7.123 |
| 41 | 0.069 | 0.031 | 0.603 | 0.041 |
| 42 | 0.073 | 0.028 | 0.829 | 0.066 |
| 43 | 0.114 | 0.037 | 1.485 | 0.063 |
| 44 | 0.043 | 0.043 | 0.622 | 0.081 |
| 45 | 0.125 | 0.066 | 1.341 | 0.104 |
| 46 | 0.353 | 0.033 | 2.577 | 0.114 |
| 47 | 0.245 | 0.038 | 2.402 | 0.189 |
| 49 | 0.037 | 0.007 | 0.129 | 0.019 |
| 48 | 0.475 | 0.048 | 5.749 | 0.467 |
| 50 | 1.934 | 0.335 | 20.787 | 0.391 |
| 51 | 1.188 | 0.064 | 0.868 | 0.371 |
| 52 | 3.981 | 1.083 | 13.575 | 0.597 |
| 53 | 0.872 | 0.037 | 9.419 | 0.664 |
| 54 | 0.077 | 0.187 | 1.004 | 0.173 |
| 55 | 0.111 | 0.103 | 1.458 | 0.02 |
| 56 | 0.614 | 0.078 | 10.202 | 1.307 |
| 57 | 0.682 | 0.078 | 19.3 | 0.507 |
| 58 | 0.273 | 0.188 | 2.079 | 0.039 |
| 59 | 0.166 | 0.049 | 6.74 | 0.257 |
| 60 | 0.187 | 0.078 | 14.155 | 1.821 |
| 61 | 0.152 | 0.15 | 8.851 | 0.336 |
| 62 | 982.857 | 52.015 | 1147.067 | 411.328 |
| 63 | 51.225 | 11.213 | 92.216 | 70.056 |
| 64 | 4.198 | 1.633 | 9.298 | 10.356 |
| 65 | 15.023 | 1.821 | 20.715 | 25.011 |
| 66 | 214.086 | 24.756 | 532.739 | 87.712 |
| 67 | 115.856 | 77.208 | 247.773 | 64.982 |
| 68 | 40.585 | 7.82 | 23.6 | 42.499 |
| 69 | 0.665 | 0.344 | 4.347 | 1.63 |
| 70 | 0.17 | 0.082 | 0.724 | 0.482 |
| 71 | 0.065 | 0.068 | 0.634 | 0.169 |
| 72 | 0.107 | 0.133 | 3.543 | 0.804 |
| 73 | 0.087 | 0.038 | 1.312 | 0.187 |
| 74 | 3.286 | 1.532 | 14.325 | 2.939 |
| 75 | 5.727 | 1.893 | 52.108 | 18.34 |
| 76 | 11.652 | 6.213 | 78.559 | 12.922 |
| 77 | 99.715 | 26.984 | 10000 | 105.832 |
| 78 | 0.297 | 0.122 | 1.883 | 0.478 |
| 79 | 0.199 | 0.174 | 0.821 | 0.361 |
| 80 | 0.442 | 0.17 | 2.504 | 0.765 |
| 81 | 0.045 | 0.052 | 0.192 | 0.108 |
| 82 | 0.577 | 0.361 | 4.898 | 1.577 |
| 83 | 0.383 | 0.217 | 3.069 | 0.807 |
| 84 | 0.479 | 0.617 | 4.916 | 1.123 |
| 85 | 0.419 | 0.336 | 1.886 | 0.566 |
| 86 | 0.54 | 0.202 | 1.707 | 0.398 |
| 87 | 0.371 | 0.227 | 2.857 | 0.704 |
| 88 | 0.188 | 0.11 | 0.791 | 0.259 |
| 89 | 0.133 | 0.038 | 0.111 | 0.061 |
| 90 | 0.323 | 0.135 | 2.294 | 0.439 |
| 91 | 0.102 | 0.066 | 1.459 | 0.495 |
| 92 | 3.845 | 2.196 | 45.066 | 18.494 |
| 93 | 4.044 | 1.204 | 3.667 | 11.524 |
| 94 | 0.185 | 0.097 | 1.967 | 0.361 |
| 95 | 8.834 | 1.804 | 21.594 | 23.036 |
| 96 | 0.816 | 0.211 | 10.382 | 0.816 |
| 97 | 0.892 | 0.097 | 4.696 | 0.247 |
| 98 | 1.023 | 0.121 | 2.654 | 0.324 |
| 99 | 14.939 | 1.726 | 57.075 | 5.808 |
| 100 | 30.546 | 5.826 | 26.984 | 7.59 |
| 101 | 1.267 | 0.063 | 8.415 | 0.597 |
| 102 | 1.894 | 0.113 | 6.26 | 0.651 |
| 103 | 0.909 | 0.115 | 3.327 | 0.243 |
| Prazosin | 0.112 | 0.195 | 0.223 | 0.054 |
| Terazosin | 0.829 | 3.311 | 2.027 | 0.689 |
| Doxazosin | 0.423 | 0.912 | 0.793 | 0.231 |

Functional Antagonism at α-1 Adrenoceptors

Functional assays indicative of pharmacologically defined α-1 adrenoreceptors were used to further characterize compounds. Inhibition of phenylephrine (PE)-induced contraction of canine prostate smooth muscle can be correlated with α-1A adrenoreceptor activation. Inhibition of PE-induced contraction of rat spleen is representative of α-1B adrenoreceptor antagonism and inhibition of PE-induced contraction of rat vas deferens correlates with α-1A adrenoreceptor antagonism (R. P. Burt, C. R. Chapple and I. Marshall, *Br. J. Pharmacol.* 107: P324 (1992)). For each of these models, agonist dose response curves were repeated against increasing concentrations of test agent to derive a Schild plot [log $(EC_{50}-1)$ against log (molarity of test agent)] to determine the $pA_2$. Data for prazosin, terazosin and doxazosin actually demonstrate a more potent effect on spleen smooth muscle by approximately an order of magnitude.

Canine prostate strips were used in vitro as previously described (Hieble, J. P., Boyce, A. J. and Caine, M., *Fed. Proc.*, 45: 2609–2614 (1986)), to determine antagonist potencies against phenylephrine-induced contractions.

The results are shown in Tables 2. The results show that the compounds of the invention exhibit functional antagonism of α-1 adrenoreceptors.

TABLE 2

In Vitro Data for Functional Antagonism at α-1 Adrenoceptors

| | In Vitro Characterization (pA2) | | | |
|---|---|---|---|---|
| Ex. No | Rat Vas | Rat Spleen | Dog Prostate | Rat Aorta |
| 1 | | | 8.69 | |
| 2 | | | 7.95 | |
| 3 | | | 9.43 | |
| 13 | 9.8 | 8.39 | 9.91 | 10.39 |
| 17 | 9.95 | 7.96 | | 9.2 |
| 18 | 9.13 | 7.71 | | 9.34 |
| 25 | 9.92 | 8.7 | | 10.86 |
| 26 | 10.34 | 8.5 | 9.15 | 10.18 |
| 28 | 9.39 | 8.36 | | 9.71 |
| 29 | 9.36 | 7.91 | | 9.3 |
| 30 | 9.6 | 7.67 | | 9.33 |
| 31 | 9.64 | 7.85 | | 9.1 |
| 32 | 9.46 | 7.24 | | 9.31 |
| 33 | 9.02 | 7.83 | | 9.15 |

TABLE 2-continued

In Vitro Data for Functional Antagonism at α-1 Adrenoceptors

| Ex. No | In Vitro Characterization (pA2) | | | |
|---|---|---|---|---|
| | Rat Vas | Rat Spleen | Dog Prostate | Rat Aorta |
| 34 | 9.23 | 8.12 | | 9.19 |
| 35 | 8.9 | 7.96 | | 9.13 |
| 36 | 9.27 | 8.09 | | 9.43 |
| 37 | 9.69 | 8.03 | | 9.64 |
| 38 | 9.55 | 7.71 | | 8.94 |
| 39 | 9.79 | 6.83 | 8.52 | 7.89 |
| 40 | 8.52 | 6.12 | | 8.35 |
| 41 | 9.45 | 8.4 | | 10.77 |
| 42 | 9.59 | 8.56 | | 10.41 |
| 43 | | 7.66 | | |
| 44 | 9.96 | 8.35 | | 10.4 |
| 45 | 9.59 | 8.89 | | 9.68 |
| 46 | 9.79 | 8.12 | | 9.81 |
| 47 | 8.95 | 7.95 | | 9.69 |
| 49 | | 8.14 | | |
| 48 | | 7.4 | | |
| 50 | 10.35 | 6.5 | 8.45 | 9.41 |
| 51 | 9.2 | 7.47 | | 9.74 |
| 53 | 9.31 | 7.2 | | 8.97 |
| 54 | | 7.31 | | |
| 63 | | | 6.65 | |
| 64 | | | 6.92 | |
| 65 | | | 7.76 | |
| 66 | | | 7.48 | |
| 67 | | 6.83 | 7.33 | |
| 68 | | | 7.02 | |
| 69 | | | 6.91 | |
| 70 | 8.2 | 7.06 | | |
| 74 | 9.1 | 8.19 | | 9.03 |
| 81 | | 7.41 | | |
| 85 | | | 8.6 | |
| 87 | 8.67 | 7.14 | | |
| 88 | 8.74 | 7.14 | 8.09 | |
| 95 | | 7.72 | 8.58 | |
| 97 | 8.81 | 7.76 | 8.6 | |
| Prazosin | 8.78 | 10.02 | 8.46 | 9.35 |
| Terazosin | 8.04 | 8.60 | 7.44 | 8.65 |
| Doxazosin | 8.69 | 9.51 | 7.59 | 8.97 |

In Vivo Determination of Intraurethral Pressure (IUP) in Canines

The intraurethral pressure (IUP) model in aged canines is an accepted model of measuring the effect of prostate smooth muscle contraction on urethral tone. Canines also have an enclosed prostate covering the urethral shaft thus providing an anatomical correlate with humans.

Beagle dogs (Marshall Farms) greater that 2 years of age and weighing between 12 and 15 kg were pre-anesthetized with thiopental sodium 15 mg/kg i.v. (Pentothal™, Abbott) and then placed under general anesthesia (isoflurane). A 7F Swan-Ganz balloon catheter (Multiflex—list no. 41224-01, Abbott) was lubricated with a water soluble jelly, inserted into the urethral orifice and advanced approximately 40 cm in male dogs (considerably less in females) until the balloon tip was placed well inside the bladder. The balloon was then inflated with 1 mL of room air and the catheter slowly withdrawn just past the first resistance that is felt at the bladder neck. Preliminary experiments in which dogs were sacrificed after such placement confirmed that this technique results in consistent positioning of the balloon within the prostatic urethra in males or the corresponding location in females. The balloon port of the catheter was connected to a Gould Statham P23Dd pressure transducer interfaced to a computerized data acquisition system (Modular Instruments, Inc., Malvern, Pa.) for the measurement of intraurethral pressure (IUP).

Dogs were then treated with propranolol to block the β-adrenoreceptor agonist effects of test agonists. Dose-response curves of the intraurethral pressor effect of epinephrine (EPI) were obtained before and after each of up to 3 increasing doses of a test antagonist (i.v.). Fifteen minutes was allowed after each antagonist dose for equilibration before the next agonist dose-response was initiated. The increase in IUP caused by a given agonist dose was allowed to return to baseline before the next dose was given. The estimated antagonist dissociation constant (in vivo pseudo $pA_2$) was determined by Schild analysis (Brune, et al., Drug Development Research, 34:267–275 (1995).

The results are shown in Table 3. The results indicate that the compounds of the invention inhibit EPI induced increases in IUP.

TABLE 3

Inhibition of EPI Induced Increase in Canine IUP

| Ex. No. | In Vivo Characterization (pseudo pA2) IUP |
|---|---|
| 13 | 8.61 |
| 26 | 8.22 |
| 39 | 8.10 |
| 67 | 6.70 |
| Prazosin | 7.88 |
| Terazosin | 6.91 |
| Doxazosin | 6.90 |

Spontaneously Hypertensive Rat (SHR) Model

The SHR model historically has been used as a predictor for the hypotensive effects of α-1 adrenoreceptor antagonists. Male spontaneously hypertensive rats were anesthetized and the left femoral artery and vein catheterized for the measurement of mean arterial pressure (MAP) and drug administration respectively. The arterial catheter was connected to a Gould Statham p23ID transducer and the pressure waveform was recorded. MAP (mm Hg) and heart rate (HR, beats/min) were determined on-line using a BUXCO Cardiovascular Analyzer. After a 30 minute pre-dose control period, each rat was given one dose of a test antagonist i.v. and the MAP and HR were monitored for an additional 2.5 hours. The area under the hypotensive response curve up to 60 minutes post dosing ($T_{60}AUC$) was determined using a trapezoidal rule integration of the percent change from control arterial pressure dataset. The results are expressed as a $pED_{50}$ value, which is defined as the negative log of the dose that produced a hypotensive response of −1250, which constitutes 50% of the area under the curve between SHR and normotensive rats.

The results are shown in Table 4. The results show that the compounds of the invention are weakly hypotensive.

TABLE 4

Spontaneously Hypertensive Rat (SHR) Assay

| Ex. No. | In Vivo Characterization (pseudo pA2) SHR |
|---|---|
| 13 | 6.15 |
| 26 | 6.4 |
| 39 | 5.2 |
| 67 | 4 |
| 97 | 5.9 |
| Prazosin | 7.4 |
| Terazosin | 6.59 |
| Doxazosin | 6.74 |

Pharmaceutical Compositions

The present invention also provides pharmaceutical compositions which comprise compounds of the present invention formulated together with one or more non-toxic pharmaceutically acceptable carriers. The pharmaceutical compositions may be specially formulated for oral administration in solid or liquid form, for parenteral injection, or for rectal administration.

The pharmaceutical compositions of this invention can be administered to humans and other animals orally, rectally, parenterally, intracisternally, intraperitoneally, topically (as by powders, ointments, or drops), bucally, or as an oral or nasal spray. The term "parenteral" administration as used herein refers to modes of administration which include intravenous, intramuscular, intraperitoneal, intrasternal, subcutaneous and intraarticular injection and infusion.

Pharmaceutical compositions of this invention for parenteral injection comprise pharmaceutically acceptable sterile aqueous or nonaqueous solutions, dispersions, suspensions or emulsions as well as sterile powders for reconstitution into sterile injectable solutions or dispersions just prior to use. Examples of suitable aqueous and nonaqueous carriers, diluents, solvents or vehicles include water, ethanol, polyols (such as glycerol, propylene glycol, polyethylene glycol, and the like), and suitable mixtures thereof, vegetable oils (such as olive oil), and injectable organic esters such as ethyl oleate. Proper fluidity can be maintained, for example, by the use of coating materials such as lecithin, by the maintenance of the required particle size in the case of dispersions, and by the use of surfactants.

These compositions may also contain adjuvants such as preservative, wetting agents, emulsifying agents, and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents such as sugars, sodium chloride, and the like, Prolonged absorption of the injectable pharmaceutical form may be brought about by the inclusion of agents which delay absorption such as aluminum monostearate and gelatin.

In some cases, in order to prolong the effect of the drug, it is desirable to slow the absorption of the drug from subcutaneous or intramuscular injection. This may be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle.

Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include poly (orthoesters) and poly(anhydrides). Depot injectable formulations are also prepared by entrapping the drug in liposomes or microemulsions which are compatible with body tissues.

The injectable formulations can be sterilized, for example, by filtration through a bacterial-retaining filter, or by incorporating sterilizing agents in the form of sterile solid compositions which can be dissolved or dispersed in sterile water or other sterile injectable medium just prior to use.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like.

The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions which can be used include polymeric substances and waxes.

The active compounds can also be in micro-encapsulated form, if appropriate, with one or more of the above-mentioned excipients.

Liquid dosage forms for oral administration include pharmaceutically acceptable emulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethyl formamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, and perfuming agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar, and tragacanth, and mixtures thereof.

Compositions for rectal administration are preferably suppositories which can be prepared by mixing the compounds of this invention with suitable non-irritating excipients or carriers such as cocoa butter, polyethylene glycol or a suppository wax which are solid at room temperature but liquid at body temperature and therefore melt in the rectum and release the active compound.

Compounds of the present invention can also be administered in the form of liposomes. As is known in the art, liposomes are generally derived from phospholipids or other lipid substances. Liposomes are formed by mono- or multi-lamellar hydrated liquid crystals that are dispersed in an aqueous medium. Any non-toxic, physiologically acceptable and metabolizable lipid capable of forming liposomes can be used. The present compositions in liposome form can contain, in addition to a compound of the present invention, stabilizers, preservatives, excipients, and the like. The preferred lipids are the phospholipids and the phosphatidyl cholines (lecithins), both natural and synthetic.

Methods to form liposomes are known in the art. See, for example, Prescott, Ed., *Methods in Cell Biology*, Volume XIV, Academic Press, New York, N.Y. (1976), p. 33 et seq.

Dosage forms for topical administration of a compound of this invention include powders, sprays, ointments and inhalants. The active compound is mixed under sterile conditions with a pharmaceutically acceptable carrier and any needed preservatives, buffers, or propellants which may be required. Opthalmic formulations, eye ointments, powders and solutions are also contemplated as being within the scope of this invention.

Actual dosage levels of active ingredients in the pharmaceutical compositions of this invention may be varied so as to obtain an amount of the active compound(s) that is effective to achieve the desired therapeutic response for a particular patient, compositions, and mode of administration. The selected dosage level will depend upon the activity of the particular compound, the route of administration, the severity of the condition being treated, and the condition and prior medical history of the patient being treated. However, it is within the skill of the art to start doses of the compound at levels lower than required for to achieve the desired therapeutic effect and to gradually increase the dosage until the desired effect is achieved.

Generally dosage levels of about 0.01 to about 50, more preferably of about 0.05 to about 5 mg of active compound per kilogram of body weight per day are administered orally to a mammalian patient. If desired, the effective daily dose may be divided into multiple doses for purposes of administration, e.g. two to four separate doses per day.

Methods for preparing the compounds of the invention are shown in Schemes 1–6. In the following Schemes, $R_1$ and $R_2$ are independently selected from the group consisting of hydrogen, alkyl, alkenyl, alkynyl, alkoxyalkyl, alkoxy, alkoxycarbonyl, hydroxy, hydroxyalkyl, carboxy, carboxyalkyl, halogen, nitro, amino, and aminoalkyl. In the following schemes, n=1 or 2, and m=1–6, Y, G, U, and U' are as defined previously.

Scheme 1 illustrates the general procedure for the preparation of the compounds of this invention. The secondary amine 1 is elaborated to the compounds of this invention (7) by one of two general methods. Alkylation of 1 with a haloalkyl nitrile in the presence of a non-nucleophilic base, such as ethyldiisopropylamine, $K_2CO_3$, or the like to yield an intermediate nitrile (2) which is then reduced using $LiAlH_4$, $AlH_3$, $BH_3$, catalytic hydrogenation, or the like produces the intermediate aminoalkyl substituted analog 3. Treatment of this amine with a heterocyclic isocyanate of the general formula 5 yields an intermediate urea, which either spontaneously cyclizes to the pyrimidinedione product 7, or does so under base catalysis. Alternatively, when R is other than H, the carbamoyl chloride 6 replaces the isocyanate 5. Alternatively, the secondary amine 1 can be reacted with the haloalkyl heterocyclic urea of the general formula 4 in the presence of a non-nucleophilic base such as ethyldiisopropylamine, $K_2CO_3$, or the like to the yield the title compounds of the invention (7) directly.

The amine 1, where n=1, is prepared as outlined in Scheme 2 (for cis ring fusion) and Scheme 3 (for trans ring fusion). For the cis fused product, treatment of the appropriately substituted coumarin 8 with the azomethine ylide precursor N-trimethylsilylmethyl-N-methoxymethyl-benzylamine 9 produces the cyclized product 10 selectively as the cis isomer. Reduction of the lactone with $LiAiH_4$, $BH_3$, $AlH_3$ or the like yield the alcohol 11. Activation of the primary alcohol as a chloride 12, bromide, mesylate, or the like, followed by treatment with a base, such as KOtBu, NaOMe, NaOH, $K_2CO_3$, or the like results in cyclization to the cis fused benzopyranopyrrole nucleus 13. Removal of the benzyl group from the amine, most conveniently achieved by catalytic hydrogenation, yields the cis fused secondary amine 14.

For the trans fused product, treatment of the appropriately substituted trans cinnamate (Scheme 3) with the azomethine ylide precursor N-trimethylsilylmethyl-N-methoxymethyl-benzylamine 9 produces the cyclized product 16 selectively as the trans isomer. Reduction of the ester with $LiAlH_4$, $BH_3$, $AlH_3$ or the like, followed by hydrolysis of the phenol protecting group, yields the alcohol 17. Activation of the primary alcohol as a chloride 18, bromide, mesylate, or the like, followed by treatment with a base, such as KOtBu, NaOMe, NaOH, $K_2CO_3$, or the like results in cyclization to the trans fused benzopyranopyrrole nucleus 19. Removal of the benzyl group from the amine, most conveniently achieved by catalytic hydrogenation, yields the trans fused secondary amine 20.

In a preferred embodiment of this invention, substitution of the azomethine ylide precursor 21, derived from (R)-α-methylbenzyl amine, for 9, derived from benzyl amine, allows for synthesis of the preferred (3aR, 9bR) amine 22 from 5-methoxycoumarin (Scheme 4), and the preferred (3aS,9bR) amine 23 from the ethyl 2-methoxy-6-methoxymethyl-trans-cinnamate (Scheme 5).

In another preferred embodiment of this invention, a precursor of a compound of formula 1 wherein n=2, (4aR, 10bS)-trans-10-Methoxy-1,3,4,4a,5,10b-hexahydro-2H-[1]-benzopyrano[3,4-c]pyridine (28) is prepared as show in Scheme 6. The imide 24 is prepared from ethyl 2-methoxy-6-methoxymethyl cinnamate and ethyl N-benzylamidomalonate according to the method of Faruk and Martin, U.S. Pat. No. 4,902,801. Reduction with $LiAlH_4$, $AlH_3$, $BH_3$, or the like, followed by conversion of the primary alcohol to a suitable leaving group, such as chloro, bromo, mesylate, or the like; hydrolysis of the protected phenol, and intramolecular cyclization, followed by debenzylation yields the racemic trans-10-Methoxy-1,3,4,4a,5,10b-hexahydro-2H-[1]-benzopyrano[3,4-c]pyridine 25. Reaction of the secondary amine with a chiral chloroformate, such as menthyl chloroformate, yields a mixture of diastereomeric carbamates, which can then be separated chromatographically. Removal of the carbamate group by treatment with n-BuLi then yields the enantiomerically resolved secondary amine 28.

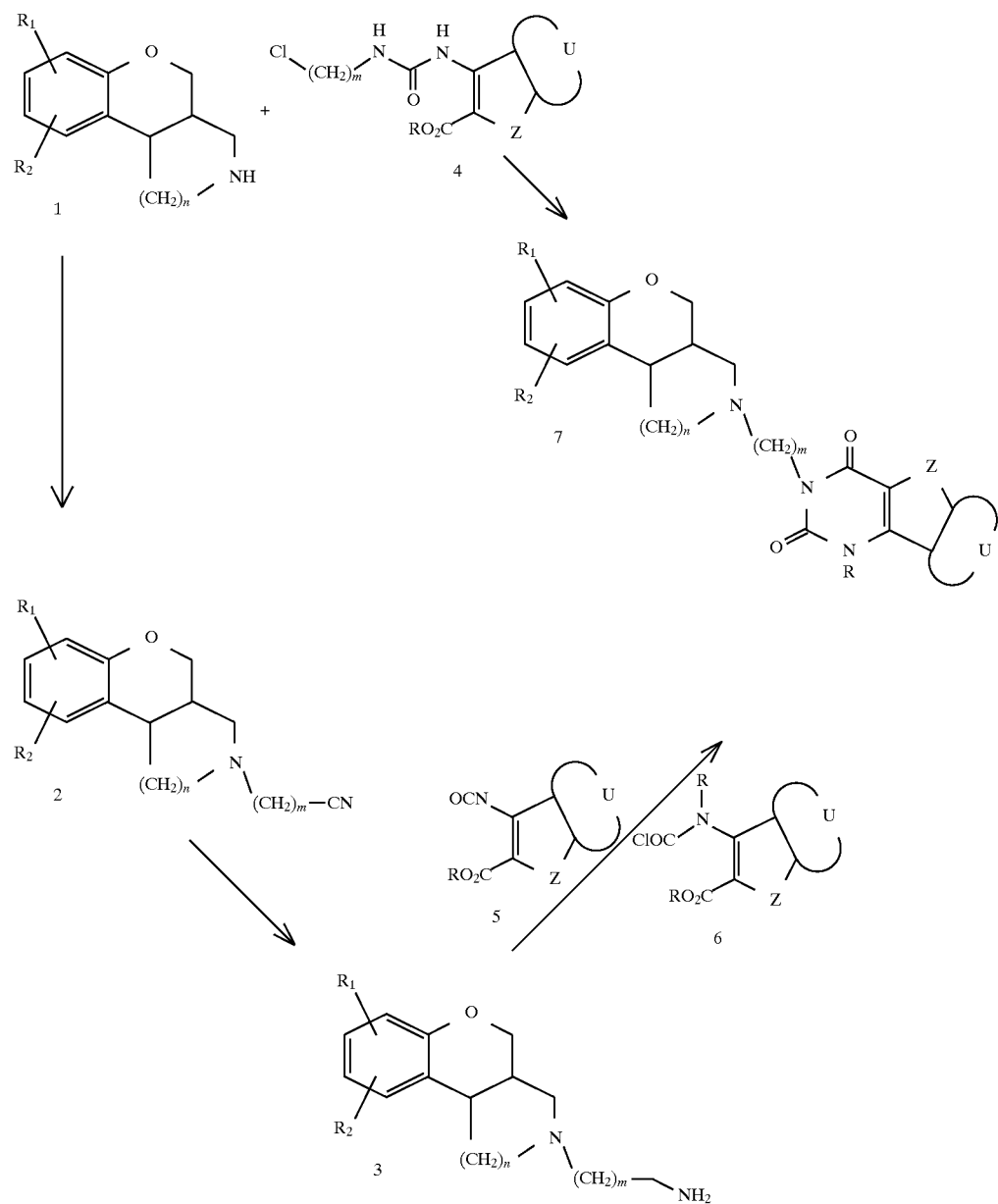
Scheme 1
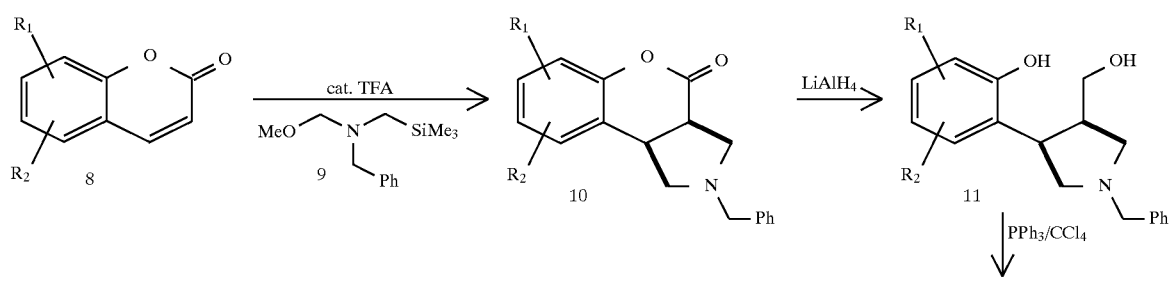
Scheme 2

-continued
Scheme 2
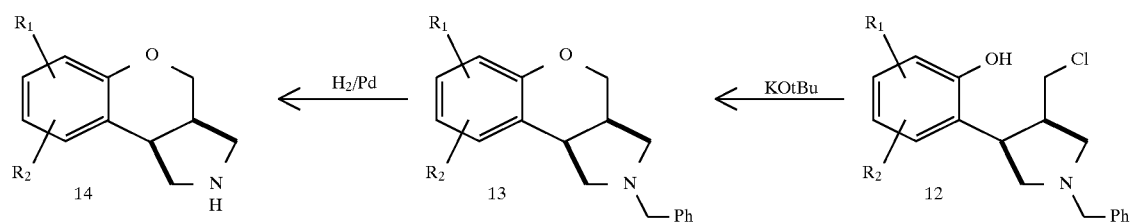
Scheme 3
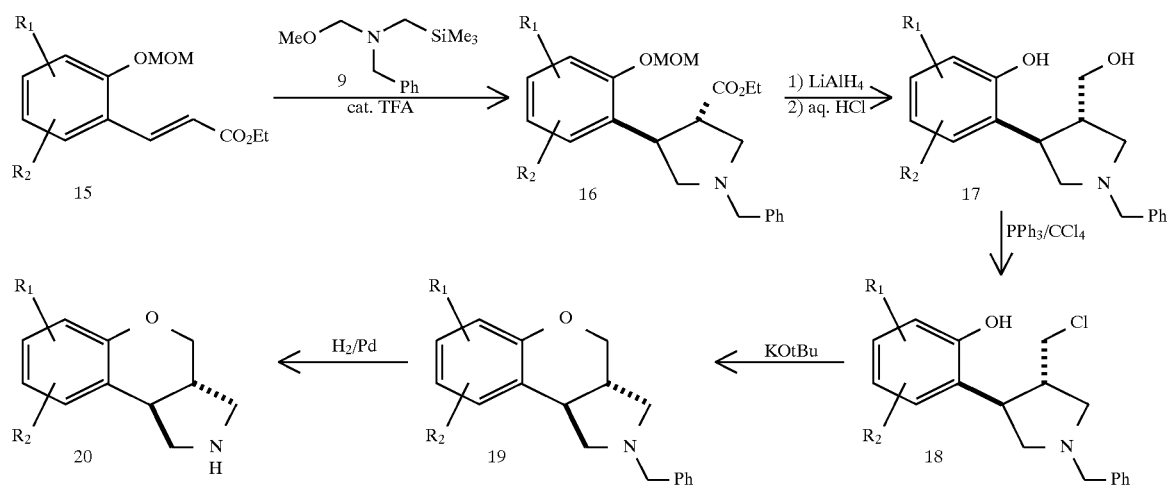
Scheme 4
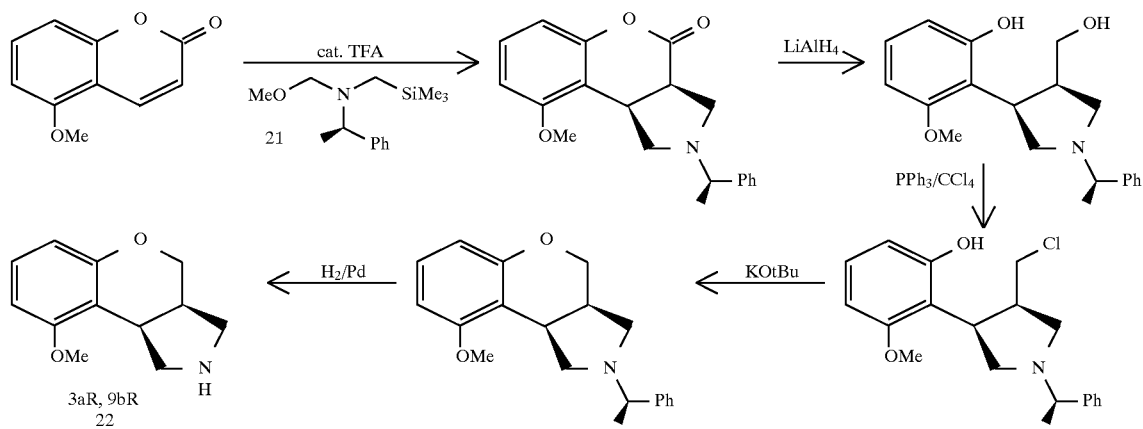

Scheme 5

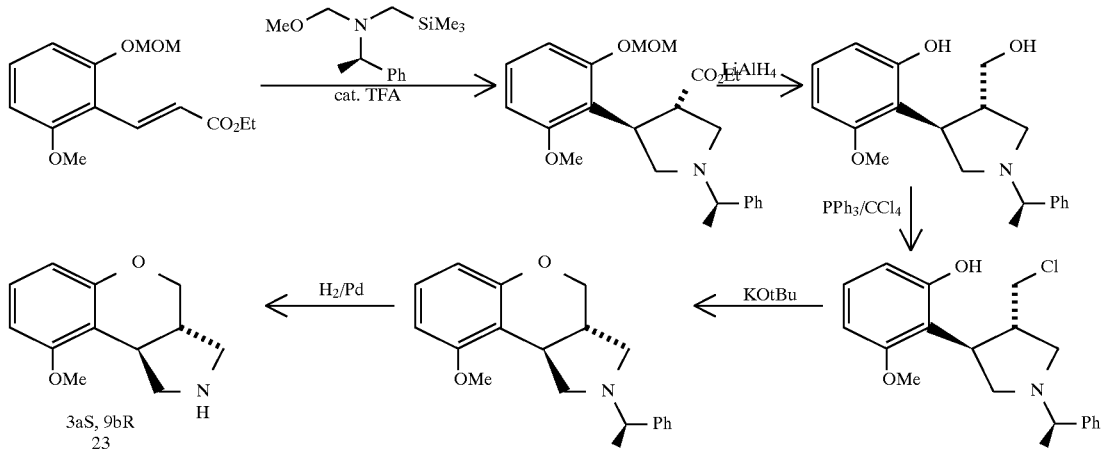

Scheme 6

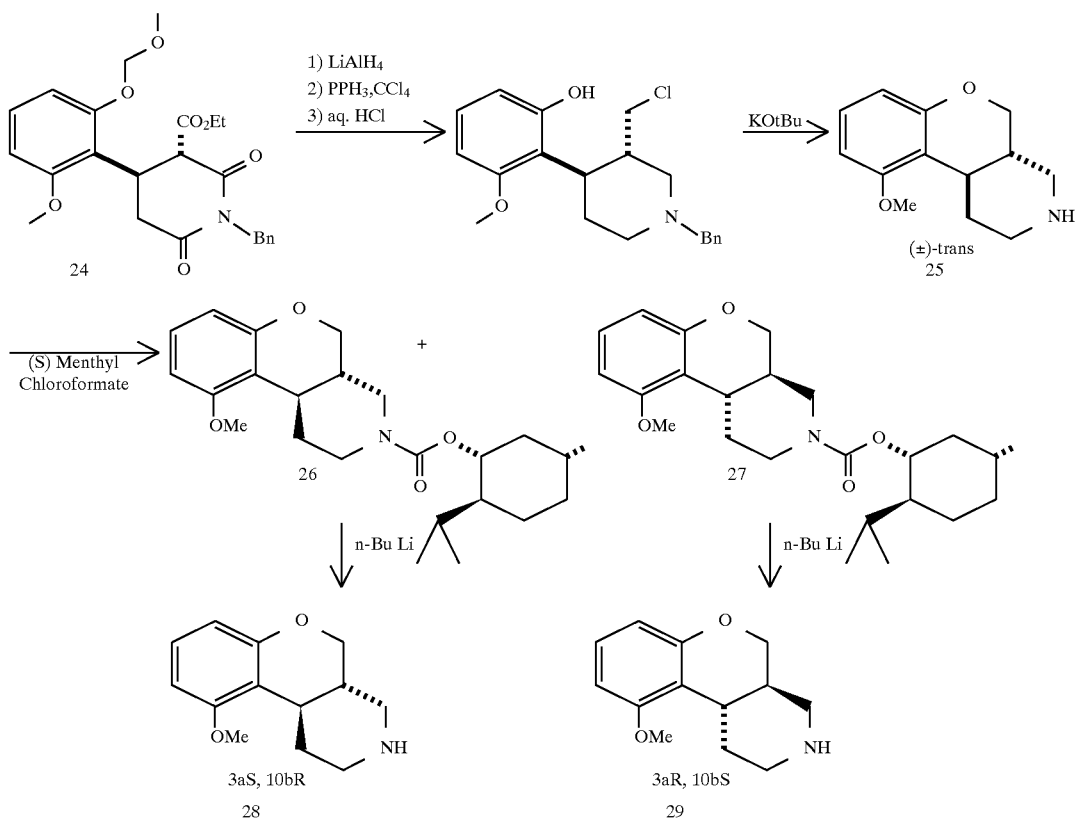

The forgoing may be better understood by reference to the following examples which are provided for illustration and not intended to limit the scope of the inventive concept.

The following abbreviations are used: $K_2CO_3$ for potassium carbonate, $LiAlH_4$ for lithium aluminum hydride, $AlH_3$ for aluminum hydrate, $BH_3$ for borane, $BH_3.DMS$ for borane dimethylsulfide complex, DMF for dimethylformamide, DMSO for dimethylsulfoxide, $Et_3N$ for triethylamine, $Et_2O$ for diethyl ether, EtOAc for ethyl acetate, EtOH for ethanol, KOtBu for potassium tert-butoxide, LDA for lithium diisopropylamide, MeOH for methanol, NaOMe for sodium methoxide, NaOH for sodium hydroxide, HCl for hydrochloric acid, $H_2$/Pd for hydrogen and a palladium catalyst, iPrOH for isopropyl alcohol and THF for tetrahydrofuran, cat. TFA for catalytic trifluoroacetic acid, $PPh_3/CCl_4$ for triphenyl phosphine/carbon tetrachloride, and n-BuLi for n-butyllithium.

EXAMPLE 1

3-[4-((3aR,9bR)-cis-9-Methoxy-1,2,3,3a,4,9b-hexahydro-[1]-benzopyrano[3,4-c]pyrrol-2-yl)butyl]-pyrido[2',3':4,5]thieno[3,2-d]pyrimidine-2,4(1H,3H)-dione hydrochloride

EXAMPLE 1A (3aR,9bR)-cis-9-Methoxy-2-(R)-α-methylbenzyl-1,2,3,3a,4,9b-hexahydro-[1]-benzopyrano[3,4-c]pyrrol-4-one 5-Methoxycoumarin (22.3 g, 126 mmol) and trifluoroacetic acid (0.97 mL, 12.6 mmol) were combined in $CH_2Cl_2$ (200 mL) and cooled to 0° C. To the stirred solution was added N-methoxymethyl-N-trimethylsilylmethyl-(R)-α-methylbenzylamine (63.4 g, 252 mmol) over 30 min. The reaction was stirred an additional 30 min at 0° C., and then 1 hr at 25° C. The reaction mixture was washed with 5% $NaHCO_3$, the organic layer was dried and evaporated. The resulting oil was suspended in diethyl ether, and after 2 hr, the title compound was collected by filtration, (15.4 g, 38%). $^1H$ NMR (300 MHz, $CDCl_3$) δ 1.36 (d, 3H), 2.41 (dd, 1H), 3.04 (d, 1H), 3.05–3.15 (m, 2H), 3.23 (m, 1H), 3.32 (1, 1H), 3.75 (m, 1H), 3.79 (s, 3H), 6.61 (d, 1H), 6.67 (d, 1H), 7.18 (t, 1H), 7.20–7.35 (m, 5H).

EXAMPLE 1B (3aR,9bR)-cis-9-Methoxy-2-(R)-α-methylbenzyl-1,2,3,3a,4,9b-hexahydro-[1]-benzopyrano[3,4-c]pyrrole The resulting product from Example 1A (15.3 g, 47 mmol) in THF (200 mL) was added to a suspension of $LiAlH_4$ (3.6 g, 94 mol) in THF (200 mL) over 15 min. After 2 hr at 25° C., the reaction was quenched (Fieser workup), and the intermediate alcohol isolated by evaporation of solvent. The alcohol (15.2 g, 46 mmol) was combined with triphenylphosphine (24.3 g, 93 mmol) in a 4:1 mixture of acetonitrile and $CCl_4$, and the resulting solution was heated to reflux for 1 hr. The solvent was evaporated and the resulting product was isolated as a mixture of the title compound and an intermediate chlorophenol. The mixture was treated with 1M potassium t-butoxide (12 mmol) in THF (50 mL). Solvent was evaporated and the product was partitioned between dil aq. NaOH and ethyl actetate. The organic phase was dried and evaporated to yield, after chromatographic purification, 11.9 g (84%) of the title compound: $^1H$ NMR (300 MHz, $CDCl_3$) δ 1.36 (d, 3H), 2.23–2.31 (m, 2H), 2.59 (m, 1H), 3.04 (dd, 1H), 3.20 (q, 1H), 3.23 (q, 1H), 3.38 (q, 1H), 3.77 (s, 3H), 3.81 (q, 1H), 4.01 (q, 1H), 6.41 (d, 1H), 6.52 (d, 1H), 7.04 (t, 1H), 7.20–7.35 (m, 5H).

EXAMPLE 1C (3aR,9bR)-cis-9-Methoxy-1,2,3,3a,4,9b-hexahydro-[1]-benzopyrano[3,4-c]pyrrole The product from Example 1B (7.7 g, 24.9 mmol) was dissolved in methanol (300 mL) and palladium hydroxide on charcoal (1.5 g) was added. The reaction was stirred rapidly under one atomsphere of $H_2$ for 18 hr. The reaction was filtered and evaporated to yield the title compound (4.6 g, 90%): $^1H$ NMR (300 MHz, $CDCl_3$) δ 2.55 (m, 1H), 2.67 (dd, 1H), 2.80 (dd, 1H), 3.21 (q, 1H), 3.32 (dd, 1H), 3.62 (dd, 1H), 3.70 (m, 1H), 3.81 (s, 3H), 4.10 (dd, 1H), 6.46 (d, 1H), 6.55 (d, 1H), 7.17 (t, 1H); $[\alpha]_D$ –95.7° (MeOH).

EXAMPLE 1D (3aR,9bR)-cis-2-(3-cyanopropyl)-9-Methoxy-1,2,3,3a,4,9b-hexahydro-[1]-benzopyrano[3,4-c]pyrrole The product from Example 1C (7.0 g, 34 mmol) was combined with 4-bromobutyronitrile (5.6 g, 37.5 mmol) and ethyldiisopropylamine (8.9 mL, 51 mmol) in acetonitrile (50 mL), and the reaction was stirred at 80° C. for 4 hr. The reaction was quenched in 5% aq. $NaHCO_3$ and extracted with $CH_2Cl_2$. The organic extracts were washed with brine, dried and evaporated. The resulting product was purified by column chromatography to yield the title compound (7.5 g, 81%): $^1H$ NMR (300 MHz, $CDCl_3$) δ 1.82 (m, 2H), 2.30 (m, 2H), 2.43 (t, 2H), 2.45–2.65 (m, 3H), 3.04 (dd, 1H), 3.23–3.42 (m, 2H), 3.79 (dd, 1H), 3.82 (s, 3H), 4.06 (dd, 1H), 6.46 (d, 1H), 6.54 (d, 1H), 7.07 (t, 1H).

EXAMPLE 1E (3aR,9bR)-cis-2-(4-aminobutyl)-9-Methoxy-1,2,3,3a,4,9b-hexahydro-[1]-benzopyrano[3,4-c]pyrrole $LiAlH_4$ (7.8 g, 207 mmol) was suspended in THF (200 mL) and cooled to 0° C. To the suspension was added $AlCl_3$ (9.2 g, 69 mmol) in small portions over 15 min. The product from Example 1D (7.5 g, 27.5 mmol) in THF (50 mL) was then added over 15 min, and the reaction was allowed to warm to 25° C. and stir for 1.5 hr. The reaction was quenched by the addition of 10.5 mL $H_2O$, 10.5 mL 15% aq. KOH, and 42 mL $H_2O$. The reaction was filtered though celite, and the solvent evaporated to yield the title compound (6.6 g, 87%): $^1H$ NMR (300 MHz, $CDCl_3$) δ 1.65–1.80 (m, 4H), 2.19 (m, 1H), 2.25 (dd, 1H), 2.42 (m, 1H), 2.52 (t, 2H), 3.14 (dd, 1H), 3.18–3.30 (m, 2H), 3.79 (dd, 1H), 3.80 (s, 3H), 4.04 (dd, 1H), 6.46 (d, 1H), 6.54 (d, 1H), 7.07 (t, 1H).

EXAMPLE 1F

3-[4-((3aR,9bR)-cis-9-Methoxy-1,2,3,3a,4,9b-hexahydro-[1]-benzopyrano[3,4-c]pyrrol-2-yl)butyl]-pyrido[2',3':4,5]thieno[3,2-d]pyrimidine-2,4(1H,3H)-dione hydrochloride Methyl 3-amino-thieno[3,2-b]pyridine-2-carboxylate, prepared by the procedure described in *J. Heterocyclic Chem.*, 24: 85 (1987), (0.624 g, 3.00 mmol) and triethylamine (0.84 mL, 6.0 mmol) were dissolved in THF (20 mL), and to the solution was added 1.7 mL of a 1.93M solution of phosgene in toluene (3.3 mmol). After 2 h, the product from Example 1E (0.78 g, 2.8 mmol) was added. After 4 h, the reaction was quenched in aq. 5% $NaHCO_3$, and extracted with $CH_2Cl_2$. The organic extracts were dried, and evaporated. The resulting urea was dissolved in toluene (100 mL) and heated to reflux for 18 h. The cooled reaction mixture was filtered, and the resulting free base of the title compound was treated with anhydrous HCl in ethanol. Addition of diethyl ether resulted in crystallization of the title compound (0.76 g, 57%): m.p. 241–243° (dec); $^1H$ NMR (300 MHz, $CDCl_3$ (free base)) δ 1.56–1.99 (m, 2H), 1.71–1.83 (m, 2H), 2.26 (t, J=9 Hz, 1H), 2.34 (dd, J=6, 10 Hz, 1H), 2.50–2.70 (m, 3H), 3.26 (dd, J=7, 10 Hz, 1H), 3.43 (q, J=8 Hz, 1H), 3.63 (t, J=8 Hz, 1H), 3.79 (s, 3H), 3.76–3.86 (m, 1H), 4.01 (dd, J=4, 11 Hz, 1H), 4.11 (t, J=7 Hz, 1H), 6.43 (d, J=8 Hz, 1H), 6.49 (d, J=8 Hz, 1H), 7.04 (t, J=8 Hz, 1H), 7.49 (dd, J=4, 8 Hz, 1H), 8.23 (dd, J=1, 8 Hz, 1H), 8.78 (dd, J=1, 4 Hz, 1H); MS (DCI($NH_3$)) m/e 479 (M+H)$^+$; Analysis calc'd for $C_{25}H_{26}N_4O_4S \cdot HCl \cdot (H_2O)_{0.25}$: C, 57.80; H, 5.34; N, 10.78; found: C, 57.72; H, 5.46; N, 10.58.

EXAMPLE 2

3-[4-((3aS,9bS)-cis-9-Methoxy-1,2,3,3a,4,9b-hexahydro-[1]-benzopyrano[3,4-c]pyrrol-2-yl)butyl]-pyrido[2',3':4,5]thieno[3,2-d]pyrimidine-2,4(1H,3H)-dione hydrochloride

EXAMPLE 2A (3aS,9bS)-cis-9-Methoxy-2-(S)-α-methylbenzyl-1,2,3,3a,4,9b-hexahydro-[1]-benzopyrano[3,4-c]pyrrol-4-one 5-Methoxycoumarin and N-methoxymethyl-N-trimethylsilylmethyl-(S)-α-methylbenzylamine were treated in an analogous manner as described in Example 1A. $^1$H NMR (300 MHz, CDCl$_3$) δ 1.36 (d, 3H), 2.41 (dd, 1H), 3.04 (d, 1H), 3.05–3.15 (m, 2H), 3.23 (m, 1H), 3.32 (1, 1H), 3.75 (m, 1H), 3.79 (s, 3H), 6.61 (d, 1H), 6.67 (d, 1H), 7.18 (t, 1H), 7.20–7.35 (m, 5H).

EXAMPLE 2B (3aS,9bS)-cis-9-Methoxy-2-(S)-α-methylbenzyl-1,2,3,3a,4,9b-hexahydro-[1]-benzopyrano[3,4-c]pyrrole The resulting product from Example 2A was treated in an analogous manner as described in Example 1B. $^1$H NMR (300 MHz, CDCl$_3$) δ 1.36 (d, 3H), 2.23–2.31 (m, 2H), 2.59 (m, 1H), 3.04 (dd, 1H), 3.20 (q, 1H), 3.23 (q, 1H), 3.38 (q, 1H), 3.77 (s, 3H), 3.81 (q, 1H), 4.01 (q, 1H), 6.41 (d, 1H), 6.52 (d, 1H), 7.04 (t, 1H), 7.20–7.35 (m, 5H).

EXAMPLE 2C (3aS,9bS)-cis-9-Methoxy-1,2,3,3a,4,9b-hexahydro-[1]-benzopyrano[3,4-c]pyrrole The product from Example 2B was treated in an analogous manner as described in Example 1C. $^1$H NMR (300 MHz, CDCl$_3$) δ 2.55 (m, 1H), 2.67 (dd, 1H), 2.80 (dd, 1H), 3.21 (q, 1H), 3.32 (dd, 1H), 3.62 (dd, 1H), 3.70 (m, 1H), 3.81 (s, 3H), 4.10 (dd, 1H), 6.46 (d, 1H), 6.55 (d, 1H), 7.17 (t, 1H); [α]$_D$ MeOH+95.2°.

EXAMPLE 2D (3aS,9bS)-cis-2-(3-cyanopropyl)-9-Methoxy-1,2,3,3a,4,9b-hexahydro-[1]-benzopyrano[3,4-c]pyrrole The product from Example 2C was treated in an analogous manner as described in Example 1D. $^1$H NMR (300 MHz, CDCl$_3$) δ 1.82 (m, 2H), 2.30 (m, 2H), 2.43 (t, 2H), 2.45–2.65 (m, 3H), 3.04 (dd, 1H), 3.23–3.42 (m, 2H), 3.79 (dd, 1H), 3.82 (s, 3H), 4.06 (dd, 1H), 6.46 (d, 1H), 6.54 (d, 1H), 7.07 (t, 1H).

EXAMPLE 2E (3aS,9bS)-cis-2-(4-aminobutyl)-9-Methoxy-1,2,3,3a,4,9b-hexahydro-[1]-benzopyrano[3,4-c]pyrrole The product from Example 2D was treated in an analogous manner as described in Example 1E. $^1$H NMR (300 MHz, CDCl$_3$) δ 1.65–1.80 (m, 4H), 2.19 (m, 1H), 2.25 (dd, 1H), 2.42 (m, 1H), 2.52 (t, 2H), 3.14 (dd, 1H), 3.18–3.30 (m, 2H), 3.79 (dd, 1H), 3.80 (s, 3H), 4.04 (dd, 1H), 6.46 (d, 1H), 6.54 (d, 1H), 7.07 (t, 1H).

EXAMPLE 2F

3-[4-((3aS,9b S)-cis-9-Methoxy-1,2,3,3a,4,9b-hexahydro-[1]-benzopyrano[3,4-c]pyrrol-2-yl)butyl]-pyrido[2',3':4,5]thieno[3,2-d]pyrimidine-2,4(1H,3H)-dione hydrochloride The product from Example 2E (0.800 g, 2.9 mmol) and methyl 3-amino-thieno[3,2-b]pyridine-2carboxylate (0.624 g, 3.00 mmol) were treated as described in Example 1F to yield 1.1 g (79%) of the title compound: m.p. 241–243° (dec); $^1$H NMR (300 MHz, CDCl$_3$ (free base)) δ 1.56–1.99 (m, 2H), 1.71–1.83 (m, 2H), 2.26 (t, J=9 Hz, 1H), 2.34 (dd, J=6, 10 Hz, 1H), 2.50–2.70 (m, 3H), 3.26 (dd, J=7, 10 Hz, 1H), 3.43 (q, J=8 Hz, 1H), 3.63 (t, J=8 Hz, 1H), 3.79 (s, 3H), 3.76–3.86 (m, 1H), 4.01 (dd, J=4, 11 Hz, 1H), 4.11 (t, J=7 Hz, 1H), 6.43 (d, J=8 Hz, 1H), 6.49 (d, J=8 Hz, 1H), 7.04 (t, J=8 Hz, 1H), 7.49 (dd, J=4, 8 Hz, 1H), 8.23 (dd, J=1, 8 Hz, 1H), 8.78 (dd, J=1, 4 Hz, 1H); MS (DCI(NH$_3$)) m/e 479 (M+H)$^+$; Analysis calc'd for C$_{25}$H$_{26}$N$_4$O$_4$S.HCl.(H$_2$O)$_{0.25}$: C, 57.80; H, 5.34; N, 10.78; found: C, 57.85; H, 5.46; N, 10.65.

EXAMPLE 3

3-[4-((3aS,9bR)-trans-9-Methoxy-1,2,3,3a,4,9b-hexahydro-[1]-benzopyrano[3,4-c]pyrrol-2-yl)butyl]-pyrido]2',3':4,5]thieno[3,2-d]pyrimidine-2.4(1H,3H)-dione hydrochloride

EXAMPLE 3A 3-(R)-(2-Hydroxy-6-methoxy)phenyl-4-(S)-hydroxymethyl-N-(R)-α-methylbenzyl-pyrrolidine Ethyl 2-methoxy-6-methoxymethyl-cinnamate (36 g, 160 mmol) and trifluoroacetic acid (1.23 mL, 16 mmol) were combined in CH$_2$Cl$_2$ (800 mL) and cooled to 0° C. To the stirred solution was added N-methoxymethyl-N-trimethylsilylmethyl-(R)-α-methylbenzylamine (80 g, 320 mmol) in 200 mL CH$_2$Cl$_2$ over 30 min. The reaction was stirred an additional 2.5 hr at 0° C. The reaction mixture was washed with 5% NaHCO$_3$, the organic layer was dried and evaporated. The crude product was dissolved in THF (150 mL) and added to a stirred suspension of LiAlH$_4$ (12.1 g, 320 mmol). The reaction was quenched, (Fieser workup), filtered through celite, and evaporated. The product was dissolved in methanol (850 mL) and 4N HCl (120 mL) was added. After heating at reflux for 2 h, the solvent was evaporated, and the residue was partitioned between sat. NaHCO$_3$ solution and ethyl acetate. The organic extracts were dried and evaporated. The crude product was purified by chromatography, eluting 2:1 diethyl ether:hexane to yield 22.1 g (42%) of the title compound as the faster moving diastereomer: $^1$H NMR (300 MHz, CDCl$_3$) δ 1.48 (d, 3H), 1,81 (t, 1H), 2.16 (m, 1H), 2.36 (m, 1H), 2.58 (t, 1H), 3.05 (t, 1H), 3.40 (m, 2H), 3.53 (m, 2H), 3.80 (dd, 1H), 3.83 (s,3H), 6.38 (d, 1H), 6.60 (d, 1H), 7.05 (t, 1H), 7.22–7.40 (m, 5H), 12.62 (br s, 1H).

EXAMPLE 3B (3aS,9bR)-trans-9-Methoxy-2-(R)-α-methylbenzyl-1,2,3,3a,4,9b-hexahydro-[1]-benzopyrano[3,4-c] pyrrole The product from Example 3A (22.1 g, 67.0 mmol) was dissolved in 290 mL of a 4:1 mixture of acetonitrile and CCl$_4$. To the solution was added triphenylphosphine (35.4 g, 135 mmol) and the reaction was heated to 80° C. for 20 min. The reaction was concentrated, and passed through a silica gel column, eluting with 1:1 hexane:diethyl ether. The product, which contained a mixture of the title compound and the chloro intermediate, was dissolved in THF (300 mL) and 41 mL of 1.0M potassium t-butoxide in THF was added. After 18 hr, the THF was evaporated and the resulting product partitioned between 1N NaOH and diethyl ether. The organic extracts were dried and evaporated, and the resulting product was chromatographed over silica gel, eluting 1:1 hexane:diethyl ether to yield 13.2 g (63%) of the title compound: $^1$H NMR (300 MHz, CDCl$_3$) δ 1.45 (d, 3H), 2.28 (m, 1H), 2.44 (dd, 1H), 2.70–2.90 (m, 2H), 3.54 (m, 1H), 3.69 (s, 3H), 3.70 (q, 1H), 3.99 (dd, 1H), 4.38 (dd, 1H), 6.37 (d, 1H), 6.47 (d, 1H), 7.04 (t, 1H), 7.20–7.40 (m, 5H).

EXAMPLE 3C (3aS,9bR)-trans-9-Methoxy-1,2,3,3a,4,9b-hexahydro-[1]-benzopyrano[3,4-c]pyrrole The product from Example 3B (13.0 g, 42 mmol) was treated as described in Example 1C to yield 8.08 g (94%) of the title compound: $^1$H NMR (300 MHz, CDCl$_3$) δ 2.07 (br s, 1H), 2.24 (m, 1H), 2.70 (m, 2H), 2.84 (t, 1H), 3.21 (dd, 1H), 3.77 (s, 3H), 3.83 (dd, 1H), 4.07 (dd, 1H), 4.53 (dd, 1H), 6.40 (d, 1H), 6.51 (d, 1H), 7.06 (t, 1H); [α]$_D$ MeOH −94.8°.

EXAMPLE 3D (3aS,9bR)-trans-2-(3-cyanopropyl)-9-Methoxy-1,2,3,3a,4,9b-hexahydro-[1]-benzopyrano[3,4-c]pyrrole The product from Example 3C (8.0 g, 39 mmol), 4-bromobutyronitrile (6.3 g, 43 mmol), and diisopropylethylamine (7.6 g, 58 mmol) were treated as described in Example 1D to yield 7.1 g (67%) of the title compound: $^1$H NMR (300 MHz, CDCl$_3$) δ 1.84 (m, 2H), 2.30 (m, 1H), 2.46 (t, 2H), 2.55 (dd, 1H), 2.70–2.85 (m, 4H), 2.91 (dd, 1H), 3.52 (m, 1H), 3.78 (s, 3H), 4.06 (dd, 1H), 4.45 (dd, 1H), 6.39 (d, 1H), 6.49 (d, 1H), 7.05 (t, 1H).

EXAMPLE 3E (3aS,9bR)-trans-2-(4-aminobutyl)-9-Methoxy-1,2,3,3a,4,9b-hexahydro-[1]-benzopyrano[3,4-c]pyrrole The product from Example 3D (7.1 g, 26 mmol) was treated as described in Example 1E to yield 6.29 g (87%) of the title compound: $^1$H NMR (300 MHz, CDCl$_3$) δ 1.40–1.80 (m, 4H), 2.32 (m, 1H), 2.57 (t, 1H), 2.62–2.90 (m, 4H), 2.95 (t, 1H), 3.60 (m, 1H), 3.78 (s, 3H), 4.06 (dd, 1H), 4.45 (dd, 1H), 6.40 (d, 1H), 6.49 (d, 1H), 7.04 (t, 1H).

EXAMPLE 3F

3-[4-((3aS,9bR)-trans-9-Methoxy-1,2,3,3a,4,9b-hexahydro-[1]-benzopyrano[3,4-c]pyrrol-2-yl)butyl]-pyrido[2',3':4,5]thieno[3,2-d]pyrimidine-2,4(1H,3H)-dione hydrochloride The product from Example 3E (0.800 g, 2.9 mmol) and methyl 3-amino-thieno[3,2-b]pyridine-2-carboxylate (0.624 g, 3.00 mmol) were treated as described in Example 1F to yield 0.70 g (50%) of the title compound: m.p. >255°; $^1$H NMR (300 MHz, DMSO-d$_6$ (free base)) δ 1.42–1.54 (m, 2H), 1.60–1.72 (m, 2H), 2.04–2.18 (m, 1H), 2.25–2.89 (m, 4H), 3.10–3.48 (m, 3H), 3.68 (s, 3H), 3.95 (t, J=7 Hz, 2H), 4.02 (dd, J=10, 12 Hz, 1H), 4.39 (dd, J=4, 10 Hz, 1H), 6.39 (dd, J=1, 8 Hz, 1H), 6.44 (dd, J=1, 8 Hz, 1H), 7.01 (t, J=8 Hz, 1H), 7.64 (dd, J=5, 8 Hz, 1H), 8.63 (dd, J=1, 8 Hz, 1H), 8.83 (dd, J=1, 5 Hz, 1, 5 Hz, 1H); MS (DCI(NH$_3$)) m/e 479 (M+H)$^+$; Analysis calc'd for C$_{25}$H$_{26}$N$_4$O$_4$S.HCl.(H$_2$O)$_{0.5}$: C, 57.30; H, 5.39; N, 10.69; found: C, 57.08; H, 5.43; N, 10.80.

EXAMPLE 4

3-[4-((3aR,9bS)-trans-9-Methoxy-1,2,3,3a,4,9b-hexahydro-[1]-benzopyrano[3,4-c]pyrrol-2-yl)butyl]-pyrido[2',3':4,5]thieno[3,2-d]pyrimidine-2,4(1H,3H)-dione hydrochloride

EXAMPLE 4A (3aR,9bS)-trans-2-(4-aminobutyl)-9-Methoxy-1,2,3,3a,4,9b-hexahydro-[1]-benzopyrano[3,4-c]pyrrole Ethyl 2-methoxy-6-methoxymethyl-cinnamate and N-methoxymethyl-N-trimethylsilylmethyl-(S)-α-methylbenzylamine were treated, in an analogous manner as described in Examples 3A–E: $^1$H NMR (300 MHz, CDCl$_3$) δ 1.40–1.80 (m, 4H), 2.32 (m, 1H), 2.57 (t, 1H), 2.62–2.90 (m, 4H), 2.95 (t, 1H), 3.60 (m, 1H), 3.78 (s, 3H), 4.06 (dd, 1H), 4.45 (dd, 1H), 6.40 (d, 1H), 6.49 (d, 1H), 7.04 (t, 1H).

EXAMPLE 4B

3-[4-((3aR,9bS)-trans-9-Methoxy-1,2,3,3a,4,9b-hexahydro-[1]-benzopyrano[3,4-c]pyrrol-2-yl)butyl]-pyrido[2',3':4,5]thieno[3,2-d]pyrimidine-2,4(1H,3H)-dione hydrochloride The product from Example 4A (680 mg, 2.5 mmol) and methyl 3-amino-thieno[3,2-b]pyridine-2-carboxylate (520 mg, 2.5 mmol) were treated as described in Example 1F to yield 0.75 g (63%).: m.p. >255°; $^1$H NMR (300 MHz, DMSO-d$_6$ (free base)) δ 1.42–1.54 (m, 2H), 1.60–1.72 (m, 2H), 2.04–2.18 (m, 1H), 2.25–2.89 (m, 4H), 3.10–3.48 (m, 3H), 3.68 (s, 3H), 3.95 (t, J=7 Hz, 2H), 4.02 (dd, J=10, 12 Hz, 1H), 4.39 (dd, J=4, 10 Hz, 1H), 6.39 (dd, J=1, 8 Hz, 1H), 6.44 (dd, J=1, 8 Hz, 1H), 7.01 (t, J=8 Hz, 1H), 7.64 (dd, J=5, 8 Hz, 1H), 8.63 (dd, J=1, 8 Hz, 1H), 8.83 (dd, J=1, 5 Hz, 1H); MS (DCI(NH$_3$)) m/e 479 (M+H)$^+$; Analysis calc'd for C$_{25}$H$_{26}$N$_4$O$_4$S.HCl.(H$_2$O)$_{0.25}$: C, 57.80; H, 5.34; N, 10.78; found: found: C, 57.45; H, 5.35; N, 10.80.

EXAMPLE 5

3-[4-((3aR,9bS)-trans-9-Methoxy-1,2,3,3a,4,9b-hexahydro-[1]-benzopyrano[3,4-c]pyrrol-2-yl)butyl]-6-chloro-pyrido[2',3':4,5]thieno[3,2-d]pyrimidine-2,4(1H,3H)-dione dihydrochloride

EXAMPLE 5A

Methyl 3-amino-5-chlorothieno[3,2-b]pyridine-2-carboxylate and Methyl 3-amino-7-chlorothieno[3,2-b]pyridine-2-carboxylate To a solution of 3-chloro-2-cyanopyridine (40 g, 0.29 mol) in 500 mL acetic acid was added hydrogen peroxide (30%, 52 g, 0.45 mol) dropwise. After stirring at 90° C. for 18 h, the reaction is cooled to 25° C. and a solution of sodium sulfite (57 g, 0.45 mol) in H$_2$O was added dropwise. The reaction was concentrated to remove the bulk of the acetic acid and the residue is partitioned between 1M NaOH and CH$_2$Cl$_2$. The CH$_2$Cl$_2$ layer was dried (MgSO4), filtered, concentrated, and recrystallized from EtOAc to provide 23 g (51%) of 3-chloro-2-cyanopyridine-N-oxide. The resulting N-oxide (12.2 g, 79 mmol) was dissolved in DMF (160 mL) at 0° C. Methyl thioglycolate (7.1 mL, 79 mmol) was added followed by sodium methoxide (8.5 g, 160 mmol) in portions. The reaction was stirred for 1 h. The reaction was poured onto ice and the resulting solid was collected by filtration, washed with water, dissolved in CH$_2$Cl$_2$, dried (MgSO4), filtered, concentrated, and recrystallized from EtOAc. 10.6 g (60%) of methyl 3-amino-thieno[3,2-b]pyridine-4-oxide carboxylate was obtained. The pyridine-N-oxide (10.6 g, 47 mmol) was mixed with phosphorous oxychloride (100 mL). The reaction was heated to 80° C. for 30 min. The reaction was concentrated and partitioned between CH$_2$Cl$_2$ and 5% aq.NaHCO$_3$ solution. The CH$_2$Cl$_2$ layer was dried (MgSO4), filtered, concentrated, and chromatographed (5:1 hex:EtOAc) to yield methyl 3-amino-5-chloro-thieno[3,2-b]pyridine-2-carboxylate (8.3 g, 73%): $^1$H NMR (300 MHz, CDCl$_3$) d 3.92 (s, 3H), 6.15 (bs, 2H), 7.37 (d, 1H), 7.99 (d, 1H); MS (DCI/NH3) m/e 243 (M+H)$^+$; followed by methyl 3-amino-7-chloro-thieno[3,2-b]

pyridine-2-carboxylate (2.0 g, 18%): $^1$H NMR (300 MHz, CDCl3) δ 3.93 (s, 3H), 6.20 (bs, 2H), 7.41 (d, 1H), 8.54 (db, 1H); MS (DCI/NH3) m/e 243 (M+H)$^+$.

EXAMPLE 5B

3-[4-((3aR,9bS)-trans-9-Methoxy-1,2,3,3a,4,9b-hexahydro-[1]-benzopyrano[3,4-yl)butyl]-6-chloro-pyrido[2',3':4,5]thieno[3,2-d]pyrimidine-2,4(1H,3H)-dione dihydrochloride The product from Example 4A (0.27 g, 1.0 mmol) and methyl 3-amino-7-chloro-thieno[3,2-b]pyridine-2-carboxylate were treated as described in Example 1F to yield 0.12 g (24%) of the title compound: m.p. 265–267°; $^1$H NMR (300 MHz, CDCl$_3$(free base)) δ 8.63 (d, 1H), 7.51 (d, 1H), 7.08 (t, 1H), 6.48 (d, 1H), 6.38 (d, 1H), 4.93 (dd, 1H), 4.02–4.18 (m, 3H), 3.99 (m, 1H), 3.38 (t, 1H), 2.88–3.12 (m, 5H), 2.45 (m, 1H), 1.8 (m, 4H); MS (DCI/NH$_3$) m/e 513 (M+H)$^+$; Analysis calc'd for C$_{25}$H$_{25}$N$_4$O$_4$SCl.2HCl: C, 51.25; H, 4.64; N, 9.56; found: C, 51.28; H, 4.96; N, 9.45.

EXAMPLE 6

3-[4-((3aR,9bS)-trans-9-Methoxy-1,2,3,3a,4,9b-hexahydro-[1]-benzopyrano[3,4-c]pyrrol-2-yl)butyl]-8-chloro-pyrido[2',3':4,5]thieno[3,2-d]pyrimidine-2,4(1H,3H)-dione hydrochloride The product from Example 4A (0.27 g, 1.0 mmol) and methyl 3-amino-5-chloro-thieno[3,2-b]pyridine-2-carboxylate were treated as described in Example 1F to yield 0.10 g (19%) of the title compound: m.p. >250°; $^1$H NMR (300 MHz, CDCl$_3$(free base)) δ 8.1 (d, 1H), 7.41 (d, 1H), 7.05 (t, 1H), 6.48 (d, 1H), 6.35 (d, 1H), 4.57 (dd, 1H), 4.11 (m, 3H), 3.95 (m, 1H), 3.73 (s, 3H), 3.37 (m, 2H), 2.9–3.1 (m, 4H), 2.48 (m, 1H), 1.18 (m, 4H); MS (DCI/NH$_3$) m/e 513(M+H)$^+$; Analysis calc'd for C$_{25}$H$_{25}$ClN$_4$O$_4$S.2HCl: C, 51.25; H, 4.64; N, 9.56; found: C, 51.22; H, 4.77; N, 9.32.

EXAMPLE 7

3-[4-((3aR,9bS)-trans-9-Methoxy-1,2,3,3a,4,9b-hexahydro-[1]-benzopyrano[3,4-c]pyrrol-2-yl)butyl]-8-methoxy-pyrido[2',3':4,5]thieno[3,2-d]pyrimidine-2,4(1H,3H)-dione hydrochloride

EXAMPLE 7A

3-Amino-5-methoxy-thieno[3,2-b]pyridine-2-carboxylate

A solution of 3-amino-5-chloro-thieno[3,2-b]pyridine-2-carboxylate, (5 g, 21 mmol) and sodium methoxide (4.5 g, 82 mmol) in MeOH (150 mL) were refluxed for 18 h. The reaction was concentrated and partitioned between EtOAc and NaHCO$_3$ solution. The EtOAc layer was dried (MgSO$_4$), filtered, concentrated, and chromatographed (5:1 hex: EtOAc) to yield 2.5 g (51%) of the title compound: $^1$H NMR (300 MHz, CDCl$_3$) δ 3.80 (s, 3H), 4.02 (s, 3H), 6.05 (bs, 2H), 6.89 (d, 1H), 7.88 (d, 1H); MS (DCI/NH3) m/e 239 (M+H)$^+$.

EXAMPLE 7B

3-[4-((3aR,9bS)-trans-9-Methoxy-1,2,3,3a,4,9b-hexahydro-[1]-benzopyrano[3,4-c]pyrrol-2-yl) butyl]-8-methoxy-pyrido[2',3':4,5]thieno[3,2-d] pyrimidine-2,4(1H,3H)-dione hydrochloride To 0.10 g (0.42 mmol) of the product from Example 7A, dissolved in 10 mL of dry THF and cooled to 0° C. was add 2.2 equiv. of triethylamine (0.142 ml), followed by 0.23 ml of 1.93M solution of phosgene in toluene. The reaction was stirred for 3 hr and then 0.10 g (0.36 mmol) of the product from Example 4A was added. The reaction was stirred at room temperature overnight, and then partitioned between aq. NaHCO$_3$ and CH$_2$Cl$_2$. The organic phase was dried, concentrated, and dissolved in THF. Potassium t-butoxide (0.8 mmol in THF) was added. The reaction was stirred at room temperature for 2 hours, and then partitioned between aq. NaHCO$_3$ and CH$_2$Cl$_2$. After chromatographic purification and conversion to the hydrochloride salt, 0.09 g (48%) of the title compound was isolated:. m.p. 238–240°; $^1$H NMR (300 MHz, CDCl$_3$(free base)) δ 8.06 (d, 1H), 7.05 (t, 1H), 6.9 (d, 1H), 6.48 (d, 1H), 6.39 (d, 1H), 4.45 (dd, 1H), 4.12 (t, 1H), 4.03 (s, 3H), 4.02 (m, 1H), 3.76 (s, 3H), 3.59 (q, 1H), 2.96 (q, 1H), 2.78 (m, 4H), 2.56 (m, 1H), 2.31 (m, 1H), 1.79 (m, 2H), 1.63 (m, 2H); MS (DCI/NH$_3$) m/e 509(M+H)$^+$; Analysis calc'd for C$_{26}$H$_{28}$N$_4$O$_5$S.HCl.0.5H$_2$O: C, 56.36; H, 5.46; N, 10.11; found: C, 56.56; H, 5.41; N, 9.97.

EXAMPLE 8

3-[4-((3aR,9bS)-trans-9-Methoxy-1,2,3,3a,4,9b-hexahydro-[1]-benzopyrano[3,4-c]pyrrol-2-yl) butyl]-6-methoxy-pyrido[2',3':4,5]thieno[3,2-d] pyrimidine-2,4(1H,3H)-dione dihydrochloride

EXAMPLE 8A

3-Amino-7-methoxy-thieno[3,2-b]pyridine-2-carboxylate

Following the procedure described in Example 7A, 3-amino-7-chloro-thieno[3,2-b]pyridine-2-carboxylate (2.0 g, 8.2 mmol) provided 1.1 g (56%) of the title compound after chromatography with 1:1 hex:EtOAc.: $^1$H NMR (300 MHz, CDCl$_3$) δ 3.92 (s, 3H), 4.05 (s, 3H), 6.18 (bs, 2H), 6.81 (d, 2H), 8.52 (d, 2H); MS (DCI/NH3) m/e 239 (M+H)$^+$.

EXAMPLE 8B

3-[4-((3aR,9bS)-trans-9-Methoxy-1,2,3,3a,4,9b-hexahydro-[1]-benzopyrano[3,4-c]pyrrol-2-yl) butyl]-6-methoxy-pyrido[2',3':4,5]thieno[3,2-d] pyrimidine-2,4(1H,3H)-dione hydrochloride To 0.24 g (1 mmol) of the product from Example 8A, dissolved in 10ml of dry THF and cooled to 0° C. was added 2.2 equiv. of triethylamine (0.37 ml), followed by 0.6 ml of 1.93M solution of phosgene in toluene. The reaction was stirred for 3 hr and then 0.276 g (1.00 mmol) of the product from Example 4A was added. The reaction was stirred at room temperature overnight, and then partitioned between aq. NaHCO$_3$ and CH$_2$Cl$_2$. The organic phase was dried, concentrated, and dissolved in THF. Potassium t-butoxide (1 mmol in THF) was added. The reaction was stirred at room temperature for 2 hours, and then partitioned between aq. NaHCO$_3$ and CH$_2$Cl$_2$. After chromatographic purification and conversion to the dihydrochloride salt, 0.26 g (49%) of the title compound was isolated: m.p. 191–193°; $^1$H NMR (300 MHz, CDCl$_3$(free base)) δ 8.63 (d, 1H), 7.1 (t, 1H), 6.92 (d, 1H), 6.5 (d, 1H), 6.4 (d, 1H), 4.51 (dd, 1H), 4.15 (m, 6H), 3.78 (s, 3H), 3.6 (m, 1H), 3.0–3.3 (m, 6H), 2.52 (m, 1H), 1.85 (m, 4H); MS (DCI/NH$_3$) m/e 509(M+H)$^+$; Analysis calc'd for C$_{26}$H$_{28}$N$_4$O$_5$S.2HCl.H$_2$O: C, 52.09; H, 5.38; N, 9.34; found: C, 51.85; H, 5.47; N, 9.00.

EXAMPLE 9

3-[4-((3aR,9bS)-trans-9-Methoxy-1,2,3,3a,4,9b-hexahydro-[1]-benzopyrano[3,4-c]pyrrol-2-yl)butyl]-8-phenyl-pyrazino[2',3':4,5]thieno[3,2-d]pyrimidine-2,4(1H,3H)-dione hydrochloride

EXAMPLE 9A

2-Chloro-3-cyano-5-phenylpyrazine and 2-chloro-3-cyano-6-phenylpyrazine

A mixture of 5- and 6- phenyl regioisomers of 2-hydroxy-3-carboxamidopyrazines (7.2 g, 33.5 mmol) prepared by the method of R. G. Jones, *J. Am. Chem. Soc.* 71:78 (1949) was combined with phosphorous oxychloride (56 ml, 586 mmol) and triethylamine (9.3 mL, 67 mmol) and heated to reflux for 2 h. The mixture was evaporated to give a black oil which was extracted with ether (3×100 ml); the combined extracts were washed with 300 ml of 10% $Na_2CO_3$, after which the aqueous layer was back-extracted with ether. The combined organic layers were decolorized with activated carbon and filtered through Celite, then evaporated to give a white solid as a 60:40 mixture of the 5 and 6-phenyl isomers; mp: (mixture) 121–125° C. $^1$H NMR (300 MHz $CDCl_3$) δ 7.52 (m, 5H major and minor), 8.02 (d, 2H (major), 8.11 (d, 2H (minor)), 9.0 (s, 1H (major)), 9.05 (s, 1H (minor)). MS (DCI/$NH_3$) m/e 215 (M)+.

EXAMPLE 9B

Methyl 7-amino-3-phenylthieno[2,3-b]pyrazine-6-carboxylate

The product from Example 9A (1.20 g, 5.58 mmol) was treated sequentially with methyl thioglycolate (0.65 g, 6.14 mmol), and sodium methoxide (0.60 g, 11.2 mmol) in anhydrous DMF (5 ml) and the reaction was stirred at 25° for 1 h. The reaction mixture was diluted with water, the product collected by filtration and purified by column chromatography on silica gel eluting with $CH_2Cl_2$ to yield 0.80 g (first eluting isomer) (47%) of the title compound as a yellow solid: $^1$H NMR (300 MHz, $CDCl_3$) δ 3.75 (s, 3H), 6.25 (br s, 2H), 7.53 (m, 3H), 8.09 (d, 2H), 9.09 (s, 1H). MS (DCI/$NH_3$) m/e 286 (M+H)$^+$.

EXAMPLE 9C

3-[4-((3aR,9bS)-trans-9-Methoxy-1,2,3,3a,4,9b-hexahydro-[1]-benzopyrano[3,4-c]pyrrol-2-yl)butyl]-8-phenyl-pyrazino[2',3':4,5]thieno[3,2-d]pyrimidine-2,4(1H,3H)-dione hydrochloride The product from Example 4A (0.10 g, 0.42 mmol) and the product from Example 9B (0.14 g, 0.43 mmol) were treated as described in Example 1F to yield 0.03 g (13%) of the title compound: m.p. >250°; $^1$H NMR (300 MHz, $CDCl_3$(free base)) δ 9.18 (s, 1H), 8.11 (m, 2H), 7.6 (m, 3H), 7.1 (t, 1H), 6.5 (d, 1H), 6.38 (d, 1H), 4.5 (dd, 1H), 4.18 (m, 3H), 4.1 (m, 1H), 3.8 (s, 3H), 3.18 (m, 6H), 2.5 (m, 1H), 1.7–1.9 (m, 4H); MS (DCI/$NH_3$) m/e 556(M+H)$^+$; Analysis calc'd for $C_{30}H_{29}N_5O_4S·HCl·2H_2O$: C, 57.36; H, 5.46; N, 11.15; found: C, 57.40; H, 5.27; N, 10.79.

EXAMPLE 10

3-[4-((3aR,9bS)-trans-9-Methoxy-1,2,3,3a,4,9b-hexahydro-[1]-benzopyrano[3,4-c]pyrrol-2-yl)butyl]-8-chloro-pyrazino[2',3':4,5]thieno[3,2-d]pyrimidine-2,4(1H,3H)-dione hydrochloride

EXAMPLE 10A

2-Chloro-3-cyano-pyrazine-4-oxide

2-Chloro-3-cyanopyrazine (5.00 g, 35.94 mmol) was dissolved in 35 ml concentrated $H_2SO_4$ under nitrogen and cooled to 0° C. To this was added 11.65 g (43.95 mmol) $K_2S_2O_8$ portionwise. The flask was fitted with a $CaCl_2$ drying tube, the reaction mixture allowed to warm to rt and stir for 24 h. After partitioning between $CHCl_3$ and ice water, the separated aqueous phase was extracted with $CHCl_3$. The combined organics were washed with water, saturated $NaHCO_3$, brine and dried over $MgSO_4$. Concentration gave 2.01 g (36%) of the title compound as an off-white solid. $^1$H NMR (300 MHz, $CDCl_3$) δ 8.12 (d, 1H), 8.38 (d, 1H). MS (DCI/$NH_3$) m/e 173 (M+$NH_4$)+.

EXAMPLE 10B

Ethyl-7-aminothieno[2,3-b]pyrazine-6-carboxylate-1-oxide

The compound resulting from Example 10A (2.90 g, 18.64 mmol) was dissolved in 100 ml DMF under nitrogen and treated with ethyl thioglycolate (2.24 g, 18.64 mmol). After cooling the solution to 0° C., it was treated with solid NaOEt (2.54 g, 37.29 mmol) allowed to warm to rt and then stirred for 13 h. The reaction mixture was partitioned between ethyl acetate and brine and the layers separated. After extracting the aqueous phase with ethyl acetate, the combined organics were washed with water, brine and dried over $MgSO_4$. Concentration gave a yellow solid that was purified by column chromatography on silica gel eluting with 2:1 then 1:1 hexanes:ethyl acetate to yield 3.50 g (78%) of the title compound as a yellow solid: mp: 126–127° C.; $^1$H NMR (300 MHz, $CDCl_3$) δ 1.40 (t, 3H), 4.38 (q, 2H), 7.25 (br s, 2H), 8.02 (d, 1H), 8.41 (d, 1H); MS (DCI/$NH_3$) m/e 240 (M+H)$^+$, 257 (M+$NH_4$)$^+$; Analysis calc'd. for $C_9H_9N_3O_3S$: C, 45.18; H, 3.79; N, 17.56; Found: C, 44.94; H, 3.77; N, 17.47.

EXAMPLE 10C

Ethyl-7-amino-2-chloro-thieno[2,3-b]pyrazine-6-carboxylate

The compound resulting from Example 88B (0.88 g, 3.68 mmol) was dissolved in 50 ml $POCl_3$ under nitrogen and heated to 95° C. for 3 h. The reaction mixture was concentrated and partitioned between ethyl acetate and water. After extracting the aqueous phase with ethyl acetate, the combined organics were washed with water, saturated $NaHCO_3$, brine and dried over $Na_2SO_4$. Concentration gave a two component mixture that was separated by column chromatography on silica gel using a gradient elution from 10:1 to 1:1 hexanes:ethyl acetate to give 0.56 g (59%) of the title compound: $^1$H NMR (300 MHz, $CDCl_3$) δ 1.41 (t, 3H), 4.40 (q, 2H), 6.11 (br s, 2H), 8.60 (s, 1H); MS (DCI/$NH_3$) m/e 258 (M+H)$^+$, 275 (M+$NH_4$)$^+$.

EXAMPLE 10D

3-[4-((3aR,9bS)-trans-9-Methoxy-1,2,3,3a,4,9b-hexahydro-[1]-benzopyrano[3,4-c]pyrrol-2-yl)butyl]-8-chloro-pyrazino[2',3':4,5]thieno[3,2-d]pyrimidine-2,4(1H,3H)-dione hydrochloride The product resulting from Example 4A (0.25 g, 0.95 mmol) and the product from Example 10C (0.25 g, 1.1 mmol) were treated as described in Example 1F to yield 0.15 g (29%) of the title compound: m.p. 266–267°; $^1$H NMR (300 MHz, $CDCl_3$ (free base)) δ 8.7 (d, 1H), 7.53 (d, 1H), 7.1 (t, 1H), 6.5 (d, 1H), 6.4 (d, 1H), 4.51 (dd, 1H), 4.14 (t, 2H), 3.78 (s, 3H), 3.68 (m, 1H), 3.55 (m, 1H), 3.02–3.32 (m, 5H), 2.58 (m, 2H), 1.85 (m, 4H), MS (DCI/$NH_3$) m/e 514(M+H)+; Analysis calc'd for C25H25ClN4O4S.HCl.1.5H2O: C, 52.09; H, 5.07; N, 9.72; found: C, 52.21; H, 4.87; N, 9.60.

EXAMPLE 11

3-[4-((3aR,9bS)-trans-9-Methoxy-1,2,3,3a,4,9b-hexahydro-[1]-benzopyrano[3,4-c]pyrrol-2-yl)butyl]-1-(2-Methoxyethyl)-pyrazino[2',3':4,5]thieno[3,2-d]pyrimidine-2,4(1H,3H)-dione hydrochloride

EXAMPLE 11A

Ethyl 7-(N-(2-methoxyethyl)amino)thieno[2,3-b]pyrazine-6-carboxylate

Ethyl 7-amino-thieno[2,3-b]pyrazine-6-carboxylate (1.0 g g, 4.48 mmol) prepared by the method of Schneller and Clough, J. Het. Chem., 12: 513 (1975), was treated with potassium bis(trimethylsilyl)amide (0.5M in toluene, 8.96 ml) in 15 ml THF at −70° C., and allowed to warm to room temperature. 2-Bromoethyl methyl ether (0.454 ml, 4.70 mmol) was added, and the reaction was stirred under $N_2$ at 60° C. overnight. The mixture was cooled and evaporated, then purified by column chromatography on silica gel eluting with 1:9 ethyl acetate:hexanes to yield 0.640 g (51%) of the title compound as a yellow solid: $^1$H NMR (300 MHz, DMSO-d6) d 1.32 (t, 3H), 3.3 (s, 3H), 3.56 (t, 2H), 4.25 (q, 2H), 4.32 (t, 2H), 7.70 (br t, 1H), 8.76 (s, 1H), 8.77 (s, 1H); MS (DCI/NH3) m/e 282 (M+H)+.

EXAMPLE 11B

Ethyl 7-(N-(2-methoxyethyl)-N-chlorocarbamoylamino)thieno[2,3-b]pyrazine-6-carboxylate The product from Example 11A (0.620 g, 2.20 mmol) was reacted with phosgene (1.93M in toluene, 3.41 ml, 6.6 mmol) and triethylamine (0.767 ml, 5.5 mmol) to yield the title compound (0.582 g, 81%) as a yellow oil: $^1$H NMR (300 MHz DMSO-d6) d 1.31 (t, 3H), 3.3 (s, 3H), 3.56 (t, 2H), 4.23 (q, 2H), 4.3 (q, 2H), 8.78 (2 singlets, 2H); MS (DCI/NH3) 344 (M+H)+.

EXAMPLE 11C

3-[4-((3aR,9bS)-trans-9-Methoxy-1,2,3,3a,4,9b-hexahydro-[1]-benzopyrano[3,4-c]pyrrol-2-yl)butyl]-1-(2-Methoxyethyl)-pyrazino[2',3':4,5]thieno[3,2-d]pyrimidine-2,4(1H,3H)-dione hydrochloride The product from Example 4A (0.25 g, 0.95 mmol) was refluxed overnight with 0.1 ml of triethylamine and 0.27 g (0.82 mmol) of the product from Example 11B. After workup and chromatography, 0.3 g (68%) of the title compound was isolated as its free base. The product was converted to its HCl-salt and recrystalized from ethanol/ether to yield the title compound: m.p. 200–202°; $^1$H NMR (300 MHz, CDCl3(free base)) δ 8.78 (d, 1H), 8.7 (d, 1H), 7.1 (t, 1H), 6.5 (d, 1H), 6.4 (d, 1H), 5.12 (t, 2H,), 4.5 (dd, 1H), 4.05–4.2 (m, 4H), 3.8 (m, 5H), 3.5 (m, 1H), 3.12 (m, 5H), 2.5 (m, 1H), 1.85 (m, 4H); MS (DCI/NH3) m/e 538(M+H)+; Analysis calc'd for C27H31N5O5S.HCl.0.75H2O: C, 55.19; H, 5.75; N, 11.92; found 55.19; H, 5.49; N, 11.88.

EXAMPLE 12

3-[4-((3aR,9bS)-trans-9-Methoxy-1,2,3,3a,4,9b-hexahydro-[1]-benzopyrano[3,4-c]pyrrol-2-yl)butyl]-pyrazino[2',3':4,5thieno[3,2-d]pyrimidine-2,4(1H,3H)-dione dihydrochloride Ethyl 7-amino-thieno[2,3-b]pyrazine-6-carboxylate (0.32 g, 1.35 mmol) prepared by the method of Schneller and Clough, J. Het. Chem., 12: 513 (1975) and the product from Example 4A (0.31 g, 1.13 mmol) were treated as described in Example 1F to yield 0.28 g of the title compound as its free base. The product was converted to its HCl salt and recrystallized from ethanol/ether to yield the title compound: m.p. >250°; $^1$H NMR (300 MHz, DMSO-d6(free base)) δ 8.98 (d, 1H), 8.89 (d, 1H), 7.11 (t, 1H), 6.52 (d, 1H), 6.45 (d, 1H), 4.5 (dd, 1H), 4.2 (m, 1H), 4.1 (m, 1H), 3.92 (m, 2H), 3.73 (s, 3H), 3.0 (m, 1H), 2.6 (m, 5H), 2.3 (m, 1H), 1.8 (m, 4H); MS (DCI/NH3) m/e 480(M+H)+; Analysis calc'd for C24H25N5O4S.2HCl.0.5H2O: C, 51.34; H, 5.03; N, 12.47; found: C, 51.34; H, 4.95; N, 12.32.

EXAMPLE 13

3-[4((3aS,9bR)-trans-9-Methoxy-1,2,3,3a,4,9b-hexahydro-[1]-benzopyrano[3,4-c]pyrrol-2-yl)butyl]-8-chloro-pyrazino[2',3':4,5]thieno[3,2-d]pyrimidine-2,4(1H,3H)-dione hydrochloride The product from Example 10C (0.27 g, 1.0 mmol) and the product from Example 3E (0.22 g, 0.8 mmol) were treated as described in Example 1F to yield 0.22 g (66%) of the title compound: m.p. >270°; $^1$H NMR (300 MHz, CDCl3(free base)) δ 8.61 (s, 1H), 7.05 (t, 1H), 6.48 (d, 1H), 6.45 (d, 1H), 4.6 (m, 1H), 4.45 (dd, 1H), 4.18 (m, 3H), 3.71 (s, 3H), 3.52 (m, 1H), 3.3 (m, 1H), 3.1 (m, 2H), 2.9 (m, 2H), 2.5 (m, 1H), 1.8 (m, 4H); MS (DCI/NH3) m/e 514(M+H)+; Analysis calc'd for C24H24ClN5O4S.HCl.0.5H2O: C, 51.52; H, 4.68; N, 12.52; found: C, 51.89; H, 4.38; N, 12.17.

EXAMPLE 14

3-[4((3aS,9bR)-trans-9-Methoxy-1,2,3,3a,4,9b-hexahydro-[1]-benzopyrano[3,4-c]pyrrol-2-yl)butyl]-pyrazino[2',3':4,5]thieno[3,2-d]pyrimidine-2,4(1H,3H)-dione dihydrochloride Ethyl 7-amino-thieno[2,3-b]pyrazine-6-carboxylate (0.24 g, 1.0 mmol) prepared by the method of Schneller and Clough, J. Het. Chem., 12: 513 (1975) and the product from Example 3E (0.22 g, 0.8 mmol) were treated as described in Example 1F to yield 0.16 g (43%) of the title compound: m.p. 219–222°; $^1$H NMR (300 MHz, CDCl3 (free base)) δ 8.62 (s, 1H), 8.45 (s, 1H), 7.05 (t, 1H), 6.48 (d, 1H), 6.4 (d, 1H), 4.5 (dd, 1H), 4.2 (m, 1H), 4.1 (m, 3H), 3.72 (s, 1H), 7.7 (m, 1H), 3.3 (m, 2H), 3.2 (m, 1H), 3.05 (m, 2H), 2.52 (m, 1H), 1.8 (m, 4H); MS (DCI/NH3) m/e 480(M+H)+; Analysis calc'd for C24H25N5O4S.2HCl.0.5H2O: C, 51.34; H, 4,96; N, 12.25; found: C, 51.45; H, 4,96; N, 12.25.

EXAMPLE 15

3-[4((3aR,9bR)-trans-9-Methoxy-1,2,3,3a,4,9b-hexahydro-[1]-benzopyrano[3,4-c]pyrrol-2-yl)butyl]-pyrazino[2',3':4,5]thieno[3,2-d]pyrimidine-2,4(1H,3H)-dione dihydrochloride Ethyl 7-amino-thieno[2,3-b]pyrazine-6-carboxylate (0.24 g, 1.0 mmol) prepared by the method of Schneller and Clough, J. Het. Chem., 12: 513 (1975) and the product from Example 1E (0.2 g, 0.75 mmol) were treated as described in Example 1F to yield 0.11 g (32%) of the title compound: m.p. 220–222°; $^1$H NMR (300 MHz, CDCl3(free base)) δ 8.7 (d, 1H), 8.6 (d, 1H), 7.02 (t, 1H), 6.4 (t, 2H), 4.1 (m, 2H), 3.7–4.0 (m, 4H), 3.7 (s, 3H), 3.52 (m, 2H), 2.6–2.9 (m, 4H), 1.6–1.82 (m, 4H); MS (DCI/NH3) m/e 480(M+H)+; Analysis calc'd for C24H25N5O4S.2HCl: C, 52.18; H, 4.93; N, 12.68; found: C, 52.56; H, 4.99; N, 12.64.

EXAMPLE 16

3-[4-((3aR,9bR)-cis-9-Methoxy-1,2,3,3a,4,9b-hexahydro-[1]-benzopyrano[3,4-c]pyrrol-2-yl)butyl]-8-chloro-pyrazino[2',3':4,5]thieno[3,2-d]pyrimidine-2,4(1H,3H)-dione hydrochloride

The product from Example 10C (0.27 g, 1.0 mmol) and the product from Example 1E (0.20 g, 0.73 mmol) were treated as described in Example 1F to yield 0.29 g (77%) of the title compound: m.p. 220–222°; $^1$H NMR (300 MHz, CDCl$_3$(free base)) δ 8.68 (s, 1H), 7.0 (t, 1H), 6.48 (d, 1H), 6.45 (d, 1H), 4.28 (m, 1H), 4.12 (m, 3H), 4.0 (m, 2H), 3.75 (s, 3H), 3.6 (m, 1H), 3.08 (m, 3H), 2.9 (m, 2H), 1.75 (m, 4H); MS (DCI/NH$_3$) m/e 514(M+H)$^+$; Analysis calc'd for C$_{24}$H$_{24}$ClN$_5$O$_4$S.HCl.0.75H$_2$O: C, 51.11; H, 4.74; N, 12.42; found: C, 51.09; H, 4.75; N, 12.43.

EXAMPLE 17

3-[4-((3aS,9bR)-trans-9-Methoxy-1,2,3,3a,4,9b-hexahydro-[1]-benzopyrano[3,4-c]pyrrol-2-yl)butyl]-6-methoxy-pyrido[2',3':4,5]thieno[3,2-d]pyrimidine-2,4(1H,3H)-dione dihydrochloride

The product from Example 8A (0.24 g, 1.0 mmol) and the product from Example 3E (0.276 g, 1.0 mmol) were treated as described in Example 1F to yield 0.26 g (51%) of the title compound: m.p. 173–174°; $^1$H NMR (300 MHz, CDCl$_3$(free base)) δ 8.64 (d, 1H), 7.08 (t, 1H), 6.92 (d, 1H), 6.5 (d, 1H), 6.4 (d, 1H), 6.5 (dd, 1H), 4.5 (dd, 1H), 4.12 (m, 8H), 3.76 (s, 3H), 3.02 (m, 4H), 2.45 (m, 2H), 1.82 (m, 4H); MS (DCI/NH$_3$) m/e 509(M+H)$^+$; Analysis calc'd for C$_{26}$H$_{28}$N$_4$O$_5$S.2HCl.0.25H$_2$O: C, 60.86; H, 5.60; N, 10.92; found: C, 60.84; H, 5.41; N, 10.62.

EXAMPLE 18

3-[4-((3aR,9bR)-cis-9-Methoxy-1,2,3,3a,4,9b-hexahydro-[1]-benzopyrano[3.4-c]pyrrol-2-yl)butyl]-6-methoxy-pyrido[2',3':4,5]thieno[3,2-d]pyrimidine-2,4(1H,3H)-dione dihydrochloride

The product from Example 8A (0.30 g, 1.26 mmol) and the product from Example 1E (0.345 g, 1.25 mmol) were treated as described in Example 1F to yield 0.37 g (58%) of the title compound: m.p. 204–206°; $^1$H NMR (300 MHz, CDCl$_3$(free base)) δ 8.64 (d, 1H), 7.05 (t, 1H), 6.92 (d, 1H), 6.51 (d, 1H), 6.44 (d, 1H), 4.0–4.18 ( m, 6H), 3.8 (s, 4H), 3.6 (m, 1H), 3.44 (m, 1H), 3.24 (m, 1H), 2.6 (m, 3H), 2.3 (m, 2H), 1.78 (m, 2H), 1.64 (m, 2H); MS (DCI/NH$_3$) m/e 509(M+H)$^+$; Analysis calc'd for C$_{26}$H$_{28}$N$_4$O$_5$S.2HCl.2H$_2$O: C, 50.57; H, 5.55; N, 9.07; found: C, 50.59; H, 5.74; N, 9.05.

EXAMPLE 19

3-[4-((3aS,9bR)-trans-9-Methoxy-1,2,3,3a,4,9b-hexahydro-[1]-benzopyrano[3,4-c]pyrrol-2-yl)butyl]-6-chloro-pyrido[2',3':4,51thieno[3,2-d]pyrimidine-2,4(1H,3H)-dione hydrochloride

The product from Example 5A (0.24 g, 1.0 mmol) and the product from Example 3E (0.27 g, 1.0 mmol) were treated as described in Example 1F to yield 0.08 g (15%) of the title compound: m.p. 266–267°; $^1$H NMR (300 MHz, CDCl$_3$(free base)) δ 8.7 (d, 1H), 7.53 (d, 1H), 7.1 (t, 1H), 6.5 (d, 1H), 6.4 (d, 1H), 4.51 (dd, 1H), 4.14 (t, 2H), 3.78 (s, 3H), 3.68 (m, 1H), 3.55 (m, 1H), 3.02–3.32 (m, 5H), 2.58 (m, 2H), 1.85 (m, 4H); MS (DCI/NH$_3$) m/e 514(M+H)$^+$; Analysis calc'd for C$_{25}$H$_{25}$ClN$_4$O$_4$S.HCl·1.5H$_2$O: C, 52.09; H, 5.07; N, 9.72; found: C, 52.21; H, 4.87; N, 9.60.

EXAMPLE 20

3-[4-((3aR,9bR)-cis-9-Methoxy-1,2,3,3a,4,9b-hexahydro-[1]-benzopyrano[3,4-c]pyrrol-2-yl)butyl]-6-chloro-pyrido[2',3':4,51thieno[3,2-d]pyrimidine-2,4(1H,3H)-dione hydrochloride

The product from Example 5A (0.24 g, 1.0 mmol) and the product from Example 1E (0.27 g, 1.0 mmol) were treated as described in Example 1F to yield 0.125 g (25%) of the title compound: m.p. 180–182°; $^1$H NMR (300 MHz, CDCl$_3$ (free base)) δ 8.63 (d, 1H), 7.51 (d, 1H), 7.05 (t, 1H), 6.48 (d, 1H), 6.42 (d, 1H), 4.1 (t, 2H), 4.0 (dd, 1H) 3.73 (m, 1H), 3.7 (s, 3H), 3.48 (q, 2H), 3.38 (m, 1H), 3.25 (m, 1H), 2.7 (m, 3H), 2.5 (m, 1H), 2.4 (m, 1H), 1.78 (m, 1H), 1.65 (m, 1H); MS (DCI/NH$_3$) m/e 513(M+H)$^+$; Analysis calc'd for C$_{25}$H$_{25}$ClN$_4$O$_4$S.HCl.0.75H$_2$O: C, 53.34; H, 4,92; N, 9.95; found: C, 53.42; H, 4.65; N, 9.55.

EXAMPLE 21

3-[4((3aS,9bR)-trans-9-Methoxy-1,2,3,3a,4,9b-hexahydro-[1]-benzopyrano[3,4-c]pyrrol-2-yl)butyl]-[1]benzthieno[3,2-d]pyrimidine-2,4)(1H,3H)-dione hydrochloride

Methyl-3-amino-benzo[b]thiophene-2-carboxylate (0.24 g, 0.97 mmol) and the product from Example 3E (0.18 g, 0.6 mmol) were treated as described in Example 1F to yield 0.22 g (77%) of the title compound: m.p. >250°; $^1$H NMR (300 MHz, CDCl$_3$(free base)) δ 8.28 (d, 1H), 7.39 (d, 1H), 7.56 (m, 2H), 7.04 (t, 1H), 6.46 (d, 1H), 6.38 (d, 1H), 4.4 (dd, 1H), 4.24 (t, 2H), 4.0 (t, 1H), 3.71 (s, 3H), 3.65 (m, 1H), 3.0 (t, 1H), 2.81 (m, 4H), 2.58 (t, 1H), 2.3 (m, 1H), 1.88 (m, 2H); MS (DCI/NH$_3$) m/e 478(M+H)$^+$; Analysis calc'd for C$_{26}$H$_{27}$N$_3$O$_4$S.HCl: C, 60.75; H, 5.49; N, 8.17; found: C, 60.65; H, 5.31; N, 8.03.

EXAMPLE 22

3-[4((3aR,9bR)-trans-9-Methoxy-1,2,3,3a,4,9b-hexahydro-[1]-benzopyrano[3,4-c]pyrrol-2-yl)butyl]-[1]benzthieno[3,2-d]pyrimidine-2,4)(1H,3H)-dione hydrochloride

Methyl-3-amino-benzo[b]thiophene-2-carboxylate (0.13 g, 0.52 mmol) and the product from Example 1E (0.10 g, 0.36 mmol) were treated as described in Example 1F to yield 0.11 g (64%) of the title compound: m.p. 198–199°; $^1$H NMR (300 MHz, CDCl$_3$) δ 8.22 (d, 1H), 8.4 (d, 1H), 7.55 (m, 2H), 7.04 (t, 1H), 6.5 (d, 1H), 6.43 (d, 1H), 4.22 (t, 2H), 4.0 (dd, 1H), 3.78 (s, 3H), 3.72 (m, 1H), 3.48 (m, 1H), 3.39 (m, 1H), 3.11 (m, 1H), 2.55 (m, 3H), 2.2 (m, 2H), 1.86 (m, 2H), 1.69 (m, 2H); MS (DCI/NH$_3$) m/e 478(M+H)$^+$; Analysis calc'd for C$_{26}$H$_{27}$N$_3$O$_4$S.HCl: C, 60.75; H, 5.49; N, 8.17; found: C, 60.62; H, 5.27; N, 8.03

EXAMPLE 23

3-[5-((3aS,9bR)-trans-9-Methoxy-1,2,3,3a,4,9b-hexahydro-[1]-benzopyrano[3,4-yl)pentyl]-1]benzthieno[3,2-d]pyrimidine-2,4(1H,3H)-dione hydrochloride

EXAMPLE 23A

(3aS,9bR)-trans-2-(4-cyanobutyl)-9-Methoxy-1,2,3,3a,4,9b-hexahydro-[1]-benzopyrano[3,4-c]pyrrole

The product from Example 3C (0.12 g, 0.6 mmol), 5-chlorovaleronitrile (0.08 g, 0.69 mmol) and 1.0 mL ethyldiisopropylamine were heated to reflux in 5 mL acetonitrile for 6 h. Solvent was evaporated, and the product partitioned between ethyl acetate and water. The organic layer was dried, evaporated, and purified by silica gel column chromatography to yield 0.11 g(64%) of the title compound: $^1$H NMR (300 MHz, CDCl$_3$) δ 7.05 (t, 1H), 6.49(d,1H), 6.39(d,1H),4.46(dd,1H), 3.77(s,3H), 3.56(q, 1H), 2.92(q,1H), 2.68–2.88(m, 4H), 2.57(q,1H), 2.42(t,2H), 2.32(m,1H), 1.71(m,4H); MS (DCI/NH$_3$) m/e 287(M+H)$^+$

EXAMPLE 23B (3aS,9bR)-trans-2-(5-aminopentyl)-9-Methoxy-1,2, 3,3a,4,9b-hexahydro-[1]-benzopyrano[3,4-c]pyrrole Lithium aluminum hydride (0.11 g, 2.88 mmol) was suspended in ether, and a solution of 0.13 g (0.96 mmol) of aluminum chloride in ether was added. To the reaction was then added a solution of the product from Example 23A (0.11 g, 0.38 mmol). The reaction was stirred at 25° for 3 h, and then isolated (Fieser workup) to yield 0.10 g (90%) of the title compound: $^1$H NMR (300 MHz, CDCl$_3$) δ 7.05 (t,1H), 6.49 (d,1H), 6.39 (d1H), 4.45 (dd, 1H), 4.05 (q,1H), 3.77 (s,3H), 3.58 (q,1H), 2.93 (q,1H), 2.61–2.88 (m,6H), 2.56 (m,1H), 2.3 (m,1H), 1.5 (m,2H), 1.48 (m,2H); MS (DCI/NH$_3$) m/e 291(M+H)$^+$:

EXAMPLE 23C

3-[5-((3aS,9bR)-trans-9-Methoxy-1,2,3,3a,4,9b-hexahydro-[1]-benzopyrano[3,4-c]pyrrol-2-yl) pentyl]-[1]benzthieno[3,2-d]pyrimidine-2,4(1H,3H)-dione hydrochloride Methyl-3-amino-benzo[b]thiophene-2-carboxylate (0.10 g, 0.40 mmol) and the product from Example 23B (0.11 g, 0.38 mmol) were treated as described in Example 1F to yield 0.11 g (60%) of the title compound: m.p. 196–198°; $^1$H NMR (300 MHz, CDCl$_3$(free base)) δ 8.22 (d, 1H), 7.89 (d, 1H), 7.53 (m, 2H), 7.03 (t, 1H), 6.48 (d, 1H), 6.38 (d, 1H), 4.41 (dd, 1H), 4.21 (t, 2H), 4.02 (dd, 1H), 3.71 (s, 3H), 3.56 (m, 1H), 2.92 (m, 1H), 2.63–2.86 (m, 3H), 2.52 (m, 1H), 2.3 (m, 1H), 1.87 (m, 2H), 1.62 (m, 2H), 1.55 (m, 2H), 1.4 (m, 1H); MS (DCI/NH$_3$) m/e 492(M+H)$^+$; Analysis calc'd for C$_{27}$H$_{29}$N$_3$O$_4$S.HCl.H$_2$O: C, 59.39; H, 5.91; N, 7.69; found: C, 59.83; H, 5.71; N, 7.48.

EXAMPLE 24

3-[5-((3aR,9bR)-trans-9-Methoxy-1,2,3,3a,4,9b-hexahydro-[1]-benzopyrano[3,4-c]pyrrol-2-yl) pentyl]-[1]benzthieno[3,2-d]pyrimidine-2,4(1H,3H)-dione hydrochloride

EXAMPLE 24A (3aR,9bR)-cis-2-(4-cyanobutyl)-9-Methoxy-1,2,3,3a, 4,9b-hexahydro-[1]-benzopyrano[3,4-c]pyrrole The product from Example 1C (0.10 g, 0.5 mmol), 5-chlorovaleronitrile (0.067 g, 0.57 mmol) and 1.0 mL ethyldiisopropylamine were heated to reflux in 5 mL acetonitrile for 6 h. Solvent was evaporated, and the product partitioned between ethyl acetate and water. The organic layer was dried, evaporated, and purified by silica gel column chromatography to yield 0.08 g(58%) of the title compound: $^1$H NMR (300 MHz, CDCl$_3$) δ 7.08 (t, 1H), 6.51 (d,1H), 6.45 (d,1H), 4.04 (dd,1H), 3.82 (s,3H), 3.78 (m,1H), 3.4 (m,2H), 3.06 (q,1H), 2.6 (m,1H), 2.48 (q,2H), 2.39 (t,2H), 2.25 (m,2H), 1.71 (m,4H); MS (DCI/NH$_3$) m/e 287(M+H)$^+$

EXAMPLE 24B (3aR,9bR)-cis-2-(5-aminopentyl)-9-Methoxy-1,2,3, 3a,4,9b-hexahydro-[1]-benzopyrano[3,4c]pyrrole Lithium aluminum hydride (0.10 g, 2.63 mmol) was suspended in ether, and a solution of 0.11 g (0.82 mmol) of aluminum chloride in ether was added. To the reaction was then added a solution of the product from Example 24A (0.08 g, 0.28 mmol). The reaction was stirred at 25° for 3 h, and then isolated (Fieser workup) to yield 0.07 g (86%) of the title compound: $^1$H NMR (300 MHz, CDCl$_3$) δ 7.08 (t,1H), 6.51 (d,1H), 6.45 (d1H), 4.03 (dd,1H), 3.8 (s,3H), 3.78 (m,1H), 3.45 (m,2H), 3.12 (q,1H), 2.68 (t,2H), 2.6 (m,1H), 2.43 (m,2H), 2.18 (m,2H), 1.5 (m2H), 1.38 (m,2H); MS (DCI/NH$_3$) m/e 291(M+H)$^+$.

EXAMPLE 24C

3-[5-((3aR,9bR)-cis-9-Methoxy-1,2,3,3a,4,9b-hexahydro-[1]-benzopyrano[3,4-c]pyrrol-2-yl) pentyl]-[1]benzthieno[3,2-d]pyrimidine-2,4(1H,3H)-dione hydrochloride Methyl 3-amino-benzo[b]thiophene-2-carboxylate (0.10 g, 0.40 mmol) and the product from Example 24B (0.07 g, 0.24 mmol) were treated as described in Example 1F to yield 0.08 g (69%) of the title compound: m.p. 128–130°; $^1$H NMR (300 MHz, CDCl$_3$(free base)) δ 8.12 (d, 1H), 7.72 (d, 1H), 7.4 (m, 2H), 7.08 (t, 1H), 6.52 (d, 1H), 6.47 (d, 1H), 4.4 (m, 2H), 4.3 (m, 1H), 4.04 (dd, 1H), 3.7 (s, 3H), 3.5 (m, 1H), 3.32 (m, 2H), 3.2 (m, 1H), 2.7 (m, 1H), 2.52 (m, 2H), 2.35 (m, 2H), 1.88 (m, 1H), 1.62 (m, 4H); MS (DCI/NH$_3$) m/e 492(M+H)$^+$; Analysis calc'd for C$_{27}$H$_{29}$N$_3$O$_4$S.HCl.H$_2$O: C, 59.39; H, 5.91; N, 7.69; found: C, 59.47; H, 5.94; N, 7.52.

EXAMPLE 25

3-[4-((3aS,9bR)-trans-9-Methoxy-1,2,3,3a,4,9b-hexahydro-[1]-benzopyrano[3,4-c]pyrrol-2-yl) butyl]-8-chloro-pyrido[2',3':4,5]thieno[3,2-d] pyrimidine-2,4(1H,3H)-dione dihydrochloride Methyl 3-amino-5-chloro-thieno[3,2-b]pyridine-2-carboxylate, prepared as described in Example 6A (0.24 g, 1.0 mmol) and the product from Example 3E (0.20 g, 0.7 mmol) were treated as described in Example 1F to yield 0.18 g (50%) of the title compound: m.p. >250°; $^1$H NMR (300 MHz, CDCl$_3$(free base)) δ 8.1 (d, 1H), 7.21 (d, 1H), 7.02 (t, 1H), 6.48 (d, 1H), 6.38 (d, 1H), 4.56 (dd, 1H), 4.1 (m, 2H), 3.88 (m, 1H), 3.73 (s, 3H), 3.3 (m, 2H), 2.85–3.12 (m, 4H), 2.44 (m, 2H), 1.8 (m, 4H); MS (DCI/NH$_3$) m/e 513(M+H)$^+$; Analysis calc'd for C$_{25}$H$_{25}$ClN$_4$O$_4$S.2HCl: C, 51.25; H, 4.64; N, 9.56; found: C, 51.04; H, 4.58; N, 9.27.

EXAMPLE 26

3-[4-((3aS,9bR)-trans-9-Methoxy-1,2,3,3a,4,9b-hexahydro-[1]-benzopyrano[3,4-c]pyrrol-2-yl) butyl]-8-methoxy-pyrido[2',3':4,5]thieno[3,2-d] pyrimidine-2,4(1H,3H)-dione dihydrochloride Methyl 3-amino-5-methoxy-thieno[3,2-b]pyridine-2-carboxylate, prepared as described in Example 7A (0.20 g, 0.84 mmol) and the product from Example 3E (0.23 g, 0.84 mmol) were treated as described in Example 1F to yield 0.30 g (70%) of the title compound: m.p. >250°; $^1$H NMR (300 MHz, CDCl$_3$(free base)) δ 8.06 (d, 1H), 7.05 (t, 1H), 6.9 (d, 1H), 6.48 (d, 1H), 6.39 (d, 1H), 4.45 (dd, 1H), 4.12 (t, 1H), 4.03 (s, 3H), 4.02 (m, 1H), 3.76 (s, 3H), 3.59 (q, 1H), 2.96

(q, 1H), 2.78 (m, 4H); MS (DCI/NH$_3$) m/e 509(M+H)$^+$; Analysis calc'd for C$_{26}$H$_{28}$N$_4$O$_5$S.HCl.0.25H$_2$O: C, 56.82; H, 5.41; N, 10.19; found: C, 56.68; H, 5.19; N, 10.09.

EXAMPLE 27

3-[4-((3aS,9bR)-trans-9-Methoxy-1,2,3,3a,4,9b-hexahydro-[1]-benzopyrano[3,4-c]pyrrol-2-yl)butyl]-7-methoxy-pyrido[2',3':4,5]thieno[3,2-d]pyrimidine-2,4(1H,3H)-dione dihydrochloride

EXAMPLE 27A

2-Cyano-3,5-dichloropyridine 3,5-Dichloropyridine-N-oxide (10.0 g, 61 mmol), trimethysilylcyanide (25 mL, 183 mmol) and triethylamine (17 mL, 122 mmol) combined in acetonitrile (60 mL) and heated to reflux for 6 hr. The solvent was evaporated and the residue was partitioned between diethyl ether and 5% aq. NaHCO$_3$. The organic phase was dried (MgSO$_4$), evaporated, and the product purified by chromatography over silica gel to yield 10.0 g (97%) of the title compound: $^1$H NMR (300 MHz, CDCl$_3$) δ 7.92 (d, 1H), 8.58 (d, 1H).

EXAMPLE 27B

3-Chloro-2-cyano-5-methoxypyridine

The product from Example 27A (0.865 g, 5.0 mmol) was dissolved in THF (10 mL) and 0.27 g NaOMe was added. After 3 h and 25° C., the reaction was quenched in 5% aq. NaHCO$_3$ solution and extracted with diethyl ether. The organic phase was dried, evaporated, and the residue purified by column chromatography, eluting with 70:30 hexanes:ethyl acetate to yield 0.27 g (32%, second eluting component) of the title compound: $^1$H NMR (300 MHz, CDCl$_3$) δ 3.95 (s, 3H), 7.29 (d, 1H), 8.28 (d, 1H).

EXAMPLE 27C

Methyl 3-amino-6-methoxy-thieno[3,2-b]pyridine-2-carboxylate

The product from Example 27B (0.168 g, 1.0 mmol) and methyl thioglycolate (0.09 mL, 1.0 mmol) were combined in DMF (2 mL). To the solution was added 0.054 g NaOMe. After 1 hr, and additional 0.07 g NaOMe was added. After an additional 1 hr, the reaction was quenched in sat aq. NH$_4$Cl and extracted with ethyl acetate. The organic phase was dried (MgSO$_4$), and evaporated to yield 0.17 g of the title compound: $^1$H NMR (300 MHz, CDCl$_3$) δ 3.90 (s, 3H), 3.93 (s, 3H), 6.15 (br s, 2H), 7.44 (d, 1H), 8.36 (d, 1H).

EXAMPLE 27D

3-[4-((3aS,9bR)-trans-9-Methoxy-1,2,3,3a,4,9b-hexahydro-[1]-benzopyrano[3,4-c]pyrrol-2-yl)butyl]-7-methoxy-pyrido[2',3':4,5]thieno[3,2-d]pyrimidine-2,4(1H,3H)-dione hydrochloride The product from Example 27C (0.12 g, 0.50 mmol) and the product from Example 3E (0.15 g, 0.47 mmol) were treated as described in Example 1F to yield 0.12 g (47%) of the title compound: m.p. 235–237°; $^1$H NMR (300 MHz, CDCl$_3$((free base)) δ 8.45 (d, 1H), 7.6 (d, 1H), 7.05 (t, 1H), 6.48 (d, 1H), 6.38 (d, 1H), 4.45 (dd, 1H), 4.1 (t, 2H), 4.05 (m, 1H), 3.98 (s, 3H), 3.78 (s, 3H), 3.72 (m, 1H), 3.05 (m, 1H), 2.85 (m, 4H), 2.65 (m, 1H), 2.38 (m, 1H), 1.8 (m, 2H), 1.7 (m, 2H); MS (DCI/NH$_3$) m/e 509(M+H)$^+$; Analysis calc'd for C$_{26}$H$_{28}$N$_4$O$_5$S.HCl.H$_2$O: C, 55.46; H, 5.55; N, 9.95; found: C, 55.22; H, 5.30; N, 9.75.

EXAMPLE 28

3-[4-((3aR,9bR)-cis-9-Methoxy-1,2,3,3a,4,9b-hexahydro-[1]-benzopyrano[3,4-c]pyrrol-2-yl)butyl]-pyrido[3',3':4,5]thieno[3,2-d]pyrimidine-2,4(1H,3H)-dione hydrochloride The product from Example 1E (400 mg, 1.5 mmol), 3-amino-2-carbomethoxythieno[3,2-c]pyridine (0.33 g, 1.6 mmol) (*J. Heterocyclic Chem,* 24, 85 (1987)), Et$_3$N (0.50 mL, 3.6 mmol), and phosgene (0.82 mL 1.93M solution in toluene, 1.6 mmol) were treated as described in Example 1F to yield 0.38 g (55%) of the title compound: m.p. 207–210°; $^1$H NMR (300 MHz, CDCl$_3$ (free base)) δ 1.62–1.75 (m, 2H), 1.80–1.92 (m, 2H), 2.20–2.33 (m, 2H), 2.49–2.65 (m, 3H), 3.15 (bt, J=8 Hz, 1H), 3.39 (q, J=8 Hz, 1H), 3.50 (t, J=8 Hz, 1H), 3.70–3.79 (m, 1H), 3.75 (s, 3H), 3.98 (dd, J=4, 9 Hz, 1H), 4.22 (t, J=7 Hz, 2H), 6.41 (dd, J=1, 8 Hz, 1H), 6.47 (dd, J=1, 8 Hz, 1H), 7.03 (t, J=8 Hz, 1H), 7.82 (dd, J=1, 5 Hz, 1H), 8.65 (d, J=5 Hz, 1H), 9.55 (s, 1H); MS (DCI/NH$_3$)) m/e 479 (M+H)$^+$; Analysis calc'd for C$_{25}$H$_{26}$N$_4$O$_4$S.(HCl)$_2$.(H$_2$O)$_{0.75}$: C, 53.15; H, 5.26; N, 9.22; found: C, 53.37; H, 5.11; N, 9.74.

EXAMPLE 29

3-[4-((3aR,9bR)-cis-9-Methoxy-1,2,3,3a,4,9b-hexahydro-[1]-benzopyrano[3,4-c]pyrrol-2-yl)butyl]-pyrido[4',3':4,5]thieno[3,2-d]pyrimidine-2,4(1H,3H)-dione hydrochloride The product from Example 1E (400 mg, 1.5 mmol), 3-amino-2-carbomethoxythieno[2,3-c]pyridine (0.33 g, 1.6 mmol) (*J. Heterocyclic Chem,* 24, 85 (1987)), Et$_3$N (0.50 mL, 3.6 mmol), and phosgene (0.82 mL 1.93M solution in toluene, 1.6 mmol) were treated as described in Example 1F to yield 0.50 g (72%) of the title compound: m.p. 212–214°; $^1$H NMR (300 MHz, CDCl$_3$ (free base)) δ 1.61–1.76 (m, 2H), 1.81–1.93 (m, 2H), 2.21–2.31 (m, 2H), 2.50–2.67 (m, 3H), 3.15 (dd, J=7, 9 Hz, 1H), 3.36–3.55 (m, 2H), 3.73–3.82 (m, 1H), 3.78 (s, 3H), 4.00 (dd, J=5, 11 Hz, 1H), 4.23 (t, J=7 Hz, 2H), 6.42 (d, J=8 Hz, 1H), 6.48 (d, J=8 Hz, 1H), 7.04 (t, J=8 Hz, 1H), 8.12 (d, J=6 Hz, 1H), 8.71 (d, J=6 Hz, 1H), 9.24 (s, 1H); MS (DCI/NH$_3$)) m/e 479 (M+H)$^+$; Analysis calc'd for C$_{25}$H$_{26}$N$_4$O$_4$S.(HCl)$_2$: C, 54.45; H, 5.12; N, 10.16; found: C, 54.05; H, 5.24; N, 10.05

EXAMPLE 30

3-[4-((3aR,9bR)-cis-9-Methoxy-1,2,3,3a,4,9b-hexahydro-[1]-benzopyrano[3,4-c]pyrrol-2-yl)butyl]-8-methoxy-pyrido[2',3':4,5]thieno[3,2-d]pyrimidine-2,4(1H,3H)-dione hydrochloride The product from Example 7A (0.30 g, 1.26 mmol) and the product from Example 1E (0.35 g, 1.26 mmol) were treated as described in Example 1F to yield 0.37 g (58%) of the title compound: m.p. 195–197°; $^1$H NMR (300 MHz, CDCl$_3$(free base)) δ 8.3 (d, 1H), 7.07 (t, 1H), 6.98 (d, 1H), 6.52 (d, 1H), 6.46 (d, 1H), 4.05 (t, 2H), 4.03 (m, 1H), 4.02 (s, 3H), 3.83 (m, 1H), 3.81 (s, 3H), 3.5 (m, 2H), 3.25 (m, 1H), 2.65 (m, 3H), 2.3 (m, 2H), 1.78 (m, 2H), 1.58 (m, 2H); MS (DCI/NH$_3$) m/e 509(M+H)$^+$; Analysis calc'd for C$_{26}$H$_{28}$N$_4$O$_5$S.HCl.H$_2$O: C, 55.46; H, 5.55; N, 9.95; found: C, 55.40; H, 5.62; N, 9.58.

EXAMPLE 31

3-[4-((3aR,9bR)-cis-9-Methoxy-1,2,3,3a,4,9b-hexahydro-[1]-benzopyrano[3,4-c]pyrrol-2-yl)butyl]-8-methoxy-pyrido[2',3':4,5]thieno[3,2-d]pyrimidine-2,4(1H,3H)-dione hydrochloride

EXAMPLE 31A

Ethyl 7-amino-2-methoxy-thieno[2,3-b]pyrazine-6-carboxylate

The compound from Example 10C (0.700 g, 2.72 mmol) was dissolved in 75 ml MeOH, treated with solid NaOMe (1.47 g, 27.2 mmol) and the resulting solution refluxed for 12 h. The reaction mixture was partitioned between saturated $NH_4Cl$ and $CHCl_3$. After extracting the aqueous phase with $CHCl_3$, the combined organics were washed with water then brine and dried over $Na_2SO_4$. Concentration gave 0.500 g (77%) pure title compound as a yellow solid: mp: 181°–182° C.; $^1H$ NMR (300 MHz, $CDCl_3$) δ 3.92 (s, 3H), 4.05 (s, 3H), 6.02 (br s, 2H), 8.30 (s, 1H); MS ($DCI/NH_3$) m/e 240 $(M+H)^+$, 257 $(M+NH4)^+$. Analysis calc'd. for $C_9H_9N_3O_3S$: C, 45.18; H, 3.79; N, 17.56; Found: C, 45.25; H, 3.48; N, 17.41.

EXAMPLE 31B

3-[4-((3aR,9bR)-cis-9-Methoxy-1,2,3,3a,4,9b-hexahydro-[1]-benzopyrano[3,4-c]pyrrol-2-yl)butyl]-8-methoxy-pyrido[2',3':4,5]thieno[3,2-d]pyrimidine-2,4(1H,3H)-dione hydrochloride The product from Example 31A (0.30 g, 1.26 mmol) and the product from Example 1E (0.35 g, 1.26 mmol) were treated as described in Example 1F to yield 0.33 g (52%) of the title compound: m.p. 182–184°; $^1H$ NMR (300 MHz, DMSO-$d_6$(free base)) δ 8.58 (s, 1H), 7.13 (t, 1H), 6.61 (d, 1H), 6.52 (d, 1H), 4.1 (m, 1H), 4.08 (s, 3H), 3.96 (t, 2H), 3.85 (m, 1H), 3.8 (s, 3H), 3.42 (m, 2H), 3.1 (m, 1H), 2.85 (m, 3H), 2.75 (m, 2H), 1.68 (m, 4H); MS ($DCI/NH_3$) m/e 510$(M+H)^+$; Analysis calc'd for $C_{25}H_{27}N_5O_5S \cdot HCl \cdot 2H_2O$: C, 51.59; H, 5.54; N, 12.03; found: C, 51.67; H, 5.43; N, 11.84.

EXAMPLE 32

3-[4-((3aR,9bR)-cis-9-Methoxy-1,2,3,3a,4,9b-hexahydro-[1]-benzopyrano[3,4-c]pyrrol-2-yl)butyl]-7-chloro-pyrido[2',3':4,5]thieno[3,2-d]pyrimidine-2,4(1H,3H)-dione hydrochloride

EXAMPLE 32A

Methyl 3-amino-5-chloro-thieno[2,3-b]pyridine-2-carboxylate

3-Cyano-2,6-dichloropyridine (5.19 g, 30 mmol) and 2.7 mL (30 mmol) methyl thioglycolate were combined in DMF (25 mL) and the solution was cooled to 0° C. To the reaction was added KOH (3.0 g, 54 mmol) in 12 mL $H_2O$. After 1.5 h at 0° C. the reaction was diluted with $H_2O$ (50 mL) and the precipitate collected. The product was recrystallized from ethyl acetate/hexane to yield 1.49 g (20%) of the title compound: $^1H$ NMR (300 MHz, $CDCl_3$) δ 3.92 (s, 3H), 5.90 (br s, 2H), 7.33 (d, 1H), 7.87 (d, 1H).

EXAMPLE 32B

3-[4-((3aR,9bR)-cis-9-Methoxy-1,2,3,3a,4,9b-hexahydro-[1]-benzopyrano[3,4-c]pyrrol-2-yl)butyl]-7-chloro-pyrido[2',3':4,5]thieno[3,2-d]pyrimidine-2,4(1H,3H)-dione hydrochloride The product from Example 1E (0.414 g, 1.5 mmol) and the product from Example 32A (0.382 g, 1.57 mmol) were treated as described in Example 1F to yield 0.30 g (25%) of the title compound.: m.p. 201–205°; $^1H$ NMR (300 MHz, $CDCl_3$) δ 1.6–1.9 (m, 4H), 2.2–2.44 (m, 2H), 2.5–5.8 (m, 4H), 3.1–3.9 (m, 4H), 3.78 (s, 3H), 4.02 (dd, 1H), 4.18 (t, 2H), 6.42 (d, 1H), 6.49 (d, 1H), 7.05 (t, 1H), 7.49 (d, 1H), 8.49 (d, 1H); MS (DC/NH3) m/e 513 (515 $(M+H)^+$); Analysis calc'd for $C_{25}H_{26}Cl_2N_4O_4S \cdot H_2O$: C, 52.91; H, 4,97; N, 9.87; Cl, 12.49; found: C, 53.17; H, 4.87; N, 9.52; Cl, 12.43.

EXAMPLE 33

3-[4-((3aR,9bR)-cis-9-Methoxy-1,2,3,3a,4,9b-hexahydro-[1]-benzopyrano[3,4-c]pyrrol-2-yl)butyl]-7-methoxy-pyrido[2',3':4,5]thieno[3,2-d]pyrimidine-2,4(1H,3H)-dione hydrochloride

EXAMPLE 33A

Methyl 3-amino-5-methoxy-thieno[2,3-b]pyridine-2-carboxylate

Sodium metal (0.46 g, 20 mmol) was added to methanol (20 mL) and allowed to react until metallic sodium was consumed. To the solution was added the product from Example 32A (0.485 g, 2.0 mmol) and the reaction was heated to reflux for 2 h. The reaction was quenched in sat. aq. $NH_4Cl$ and extracted with ethyl acetate. The organic phase was dried ($MgSO_4$) and evaporated to yield 0.410 g (86%) of the title compound: $^1H$ NMR (300 MHz, $CDCl_3$) δ 3.88 (s, 3H), 4.02 (s, 3H), 6.74 (d, 1H), 7.77 (d, 1H).

EXAMPLE 33B

3-[4-((3aR,9bR)-cis-9-Methoxy-1,2,3,3a,4,9b-hexahydro-[1]-benzopyrano[3,4-c]pyrrol-2-yl)butyl]-7-methoxy-pyrido[2',3':4,5]thieno[3,2-d]pyrimidine-2,4(1H,3H)-dione hydrochloride The product from Example 1E (0.414 g, 1.5 mmol) and the product from Example 33A (0.375 g, 1.57 mmol) were treated as described in Example 1F to yield 0.480 g (51%) of the title compound.: m.p. 210–14°; $^1H$ NMR (300 MHz, $CDCl_3$) δ 1.64–1.88 (m, 4H), 2.2–2.4 (m, 2H), 2.5–2.8 (m, 4H), 3.1–3.9 (m, 4H), 3.78 (s, 3H), 4.02 (dd, 1H), 4.07 (s, 3H), 4.15 (t, 2H), 6.44 (d, 1H), 6.53 (d, 1H), 6.88 (d, 1H), 7.07 (t, 1H), 8.54 (d, 1H); MS (DCI/NH3) m/e 509 $(M+H)^+$; Analysis calc'd for $C_{25}H_{29}ClN_4O_5S \cdot H_2O$: C, 55.46; H, 5.55; N, 9.95; Cl, 6.30; found: C, 55.64; H, 5.35; N, 9.91; Cl, 6.24.

EXAMPLE 34

3-[4-((3aR,9bR)-cis-9-Methoxy-1,2,3,3a,4,9b-hexahydro-[1]-benzopyrano[3,4-c]pyrrol-2-yl)butyl]-pyrido[2',3':4,5]thieno[3,2-d]pyrimidine-2,4(1H,3H)-dione hydrochloride The product from Example 1E (0.414 g, 1.5 mmol) and methyl 3-amino-thieno[2,3-b]pyridine-2-carboxylate (0.328 g, 1.57 mmol) were treated as described in Example 1F to yield 0.26 g (34%) of the title compound.: m.p. 195–200°; $^1H$ NMR (300 MHz, $CDCl_3$) δ 1.68–1.9 (m, 4H), 2.3–2.5 (m, 2H), 2.5–2.85 (m, 4H), 3,2–3.9 (m, 4H), 3.79 (s, 3H), 4.01 (dd, 1H), 4.19 (t, 2H), 6.42 (d, 1H), 6.52 (d, 1H), 7.07 (t, 1H), 7.48 (dd, 1H), 8.57 (m, 1H), 8.77 (dd, 1H); MS (DC/NH3) m/e 497 $(M+H)^+$; Analysis calc'd for $C_{25}H_{27}ClN_4O_4S \cdot H_2O$: C, 56.33; H, 5.48; N, 10.51; Cl, 6.65; found: C, 56.32; H, 5.36; N, 10.42; Cl, 6.54.

EXAMPLE 35

3-[4-((3aR,9bR)-cis-9-Methoxy-1,2,3,3a,4,9b-hexahydro-[1]-benzopyrano[3,4-c]pyrrol-2-yl)butyl]-pyrido[2',3':4,5]thieno[3,2-d]pyrimidine-2,4(1H,3H)-dione hydrochloride

EXAMPLE 35A

Methyl 3-amino-5-methyl-thieno[2,3-b]pyridine-2-carboxylate

2-Chloro-3-cyano-6-methyl pyridine (1.5 g, 9.8 mmol) and methyl thioglycolate (0.88 mL, 9.8 mmol) were dissolved in DMF (7 mL). To the solution was added 1.0 g KOH in 5 mL H$_2$O over 30 min. The reaction was then quenched by the addition of ice water, and the product collected by filtration to yield 1.72 g (79%) of the title compound: $^1$H NMR (300 MHz, CDCl$_3$) δ 2.88 (s, 3H), 3.91 (s, 3H), 5.90 (br s, 2H), 7.17 (d, 1H), 7.82 (d, 1H),

EXAMPLE 35B

3-[4-((3aR,9bR)-cis-9-Methoxy-1,2,3,3a,4,9b-hexahydro-[1]-benzopyrano[3,4-c]pyrrol-2-yl)butyl]-pyrido[2',3':4,5]thieno[3,2-d]pyrimidine-2,4(1H,3H)-dione hydrochloride The product from Example 1E (0.414 g, 1.5 mmol) and the product from Example 35A (0.350 g, 1.57 mmol) were treated as described in Example 1F to yield 0.27 g (34%) of the title compound.: m.p. 215–20°; $^1$H NMR (300 MHz, CDCl$_3$) δ 1.68–1.9 (m, 4H), 2.3–2.5 (m, 2H), 2.5–2.8 (m, 4H), 2.71 (s, 3H), 3.2–3.9 (m, 4H), 3.77 (s, 3H), 4.02 (dd, 1H), 4.17 (t, 2H), 6.44 (d, 1H), 6.53 (d, 1H), 7.07 (t, 1H), 7.34 (d, 1H), 8.41 (d, 1H); MS (DCI/NH3) m/e 493 (M+H)$^+$; Analysis calc'd for C$_{26}$H$_{29}$ClN$_4$O$_4$S.1.5H$_2$O: C, 56.16; H, 5.80; N, 10.08; Cl, 6.38; found: C, 56.00; H, 5.37; N, 10.01; Cl, 5.99.

EXAMPLE 36

3-[4-((3aR,9bR)-cis-9-Methoxy-1,2,3,3a,4,9b-hexahydro-[1]-benzopyrano[3,4-c]pyrrol-2-yl)butyl]-9-methoxy-pyrido[2',3':4,5]thieno[3,2-d]pyrimidine-2,4(1H,3H)-dione hydrochloride

EXAMPLE 36A

Methyl 3-amino-4-methoxy-thieno[2,3-b]pyridine-2-carboxylate

To 2-chloro-3-cyano-4-methoxypyridine (2.02 g) and methyl thioglycolate (1.1 mL) in DMF (24 mL) at 5° C. was added a 1.0M solution of KOtBu/THF (14.6 mL). The reaction was stirred 20 min at 5°, then 1 h at RT, quenched in saturated NH$_4$Cl, the solid collected, washed with water and sucked dry. This was recrystallized from EtOAc to give 0.89 g of the title compound.

EXAMPLE 36B

3-[4-((3aR,9bR)-cis-9-Methoxy-1,2,3,3a,4,9b-hexahydro-[1]-benzopyrano[3,4-c]pyrrol-2-yl)butyl]-9-methoxy-pyrido[2',3':4,5]thieno[3,2-d]pyrimidine-2,4(1H,3H)-dione hydrochloride The product from Example 1E (0.414 g, 1.5 mmol) and the product from Example 36A (0.350 g, 1.57 mmol) were treated as described in Example 1F to yield 0.40 g (44%) of the title compound: m.p. 180–200°; $^1$H NMR (300 MHz, CDCl$_3$) δ 1.61 (2H, br), 1.78 (2H, m), 2.23 (2H, br), 2.60 (3H, br), 3.20 (1H, br), 3.45 (2H, br), 3.75 (1H, m), 3.81 (3H, s), 4.03 (1H, dd), 4.10 (1H, t), 4.14 (3H, s), 6.44 (1H, d), 6.51 (1H, d), 6.82 (1H, d), 7.04 (1H, t), 8.60 (1H, d), 8.90 (1H, br s); MS (DCI/(NH$_3$) m/e 509; Analysis calc'd for C$_{26}$H$_{29}$ClN$_4$O$_5$S.HCl. (H$_2$O)$_2$.(C$_4$H$_8$O$_2$)$_{0.5}$: C, 53.80; H, 5.97; N, 8.96; Cl, 5.67; found: C, 53.54; H, 5.68; N, 8.92; Cl, 5.73.

EXAMPLE 37

3-[4((3aR,9bR)-cis-9-Methoxy-1,2,3,3a,4,9b-hexahydro-[1]-benzopyrano[3,4-c]pyrrol-2-yl)butyl]-8-chloro-pyrido[2',3':4,5]thieno[3,2-d]pyrimidine-2,4(1H,3H)-dione hydrochloride The product from Example 1E (0.357 g, 1.25 mmol) and the product from Example 6A (0.30 g, 1.24 mmol) were treated as described in Example 1F to yield 0.30 g (47%) of the title compound: m.p. 196–198°; $^1$H NMR (300 MHz, CDCl$_3$(free base)) δ 8.15 (d, 1H), 7.47 (d, 1H), 7.05 (t, 1H), 6.48 (d, 1H), 6.42 (d, 1H), 4.08 (t, 2H), 4.02 (dd, 1H), 3.85 (m, 1H), 3.78 (s, 3H), 3.5 (m, 2H), 2.78 (m, 4H), 2.5 (m, 2H), 1.76 (m, 4H); MS (DCI/NH$_3$) m/e 513(M+H)$^+$; Analysis calc'd for C$_{25}$H$_{25}$ClN$_4$O$_4$S.HCl.2H$_2$O: C, 51.09; H, 5.28; N, 9.25; found: C, 51.20; H, 5.33; N, 9.55.

EXAMPLE 38

3-[4((3aR,9bR)-cis-9-Methoxy-1,2,3,3a,4,9b-hexahydro-[1]-benzopyrano[3,4-c]pyrrol-2-yl)butyl]-7-chloro-pyrido[2',3':4,5]thieno[3,2-d]pyrimidine-2,4(1H,3H)-dione hydrochloride

EXAMPLE 38A

Methyl 3-amino-6-chloro-thieno[3,2-b]pyridine-2-carboxylate

The product from Example 27A (3.46 g, 20 mmol) and methyl thioglycolate (1.8 mL, 20 mmol) were combined in 40 mL THF. To the solution was added 1.08 g NaOMe (20 mmol) After 1.5 h, and additional 1.08 g NaOMe was added, and then after an additional 2 h, the reaction was quenched in 5% aq. NaHCO$_3$ and extracted with diethyl ether. The organic extracts were dried (MgSO$_4$), evaporated, and the product was purified by silica gel column chromatography to yield 1.23 g (25%) of the title compound: $^1$H NMR (300 MHz, CDCl$_3$) δ 3.92 (s, 3H), 6.20 (br s, 2H), 8.04 (d, 1H), 8.54 (d, 1H).

EXAMPLE 38B

3-[4((3aR,9bR)-cis-9-Methoxy-1,2,3,3a,4,9b-hexahydro-[1]-benzopyrano[3,4-c]pyrrol-2-yl)butyl]-7-chloro-pyrido[2',3':4,5]thieno[3,2-d]pyrimidine-2,4(1H,3H)-dione hydrochloride The product from Example 1E (0.357 g, 1.25 mmol) and the product from Example 38A (0.30 g, 1.24 mmol) were treated as described in Example 1F to yield 0.29 g (46%) of the title compound: m.p. 224–226°; $^1$H NMR (300 MHz, DMSO-d$_6$) δ 8.88 (m, 2H), 7.13 (t, 1H), 6.62 (d, 1H), 6.5 (d, 1H), 4.05 (dd, 1H), 3.96 (t, 2H), 3.82 (m, 1H), 3.8 (s, 3H), 3.2 (m, 2H), 2.95 (m, 1H), 2.85 (m, 3H), 2.3 (m, 2H), 1.7 (m, 4H); Analysis calc'd for C$_{25}$H$_{25}$ClN$_4$O$_4$S.HCl.0.75H$_2$O: C, 53.22; H, 5.16; N, 9.39; found: C, 53.24; H, 5.04; N, 9.93.

EXAMPLE 39

3-[4-((3aR,9bR)-cis-9-Methoxy-1,2,33a,4,9b-hexahydro-[1]-benzopyrano[3,4-c]pyrrol-2-yl)butyl]-8-phenyl-pyrazino[2',3':4,5]thieno[3,2-d]pyrimidine-2,4(1H,3H)-dione hydrochloride The product from Example 1E (0.357 g, 1.25 mmol) and the product from Example 9B (0.356 g, 1.25 mmol) were treated as described in Example 1F to yield, after recrystallization from methanol, 0.35 g (63%) of the title compound: m.p. 291°; $^1$H NMR (300 MHz, CDCl$_3$(free base)) δ 9.08 (s, 1H), 8.07 (dd, 2H), 7.58 (m, 3H), 6.88 (t, 1H), 6.30 (d, 1H), 6.20 (d, 1H), 4.18 (m, 2H), 3.88 (dd, 1H), 3.72 (s, 3H), 3.63 (m, 2H), 3.38 (m, 2H), 2.72 (m, 3H), 2.6 (m, 1H), 2.5 (m, 1H), 1.8 (m, 4H); MS (DCI/NH$_3$) m/e 556(M+H$^+$); Analysis calc'd for C$_{30}$H$_{29}$N$_5$SO$_4$.HCl: C, 60.85; H, 5.10; N, 11.82; Cl, 5.98. Found C, 60.50; H, 5.20; N, 11.69; Cl, 6.07.

EXAMPLE 40

3-[4-((3aR,9bR)-cis-9-Methoxy-1,2,33a,4,9b-hexahydro-[1]-benzopyrano[3,4-c]pyrrol-2-yl)butyl]-7-phenyl-pyrazino[2',3':4,5]thieno[3,2-d]pyrimidine-2,4(1H,3H)-dione hydrochloride

EXAMPLE 40A

3-Cyano-2-chloro-6-phenylpyrazine

3-Carboxamido-2-hydroxy-6-phenylpyrazine (7.56 g, 35.13 mmol), prepared by the method of Dick and Wood, *J.*

*Chem. Soc.*, 1379 (1955), was suspended in triethylamine (7.11 g, 70.26 mmol), cooled to 0° C. and dissolved in 50 ml $POCl_3$. The mixture was refluxed for 3 h before concentrating in vacuo. The resulting black oil was extracted 5×100 ml $Et_2O$ and the combined extracts treated with 250 ml cold 10% $Na_2CO_3$. The layers were separated and the organic phase washed with water, brine and dried over $Na_2SO_4$. Concentration gave the title compound (3.20 g, 42%) as a tan solid. mp: 143–145° C.; $^1H$ NMR (300 MHz, $CDCl_3$) δ 7.57 (m, 3H), 8.10 (m, 2H), 9.05 (s, 1H); MS ($DCI/NH_3$) m/e 233 $(M+NH_4)^+$.

EXAMPLE 40B

Ethyl-7-amino-3-phenyl-thieno[2,3-b]pyrazine-6-carboxylate

The compound resulting from Example 40A (1.00 g, 4.65 mmol) was treated with ethyl thioglycolate (0.56 g, 4.65 mmol) and $Na_2CO_3$ (0.49 g, 4.65 mmol) in 20 ml EtOH. Recrystallization of the crude product from $EtOH/H_2O$ gave the title compound (1.19 g, 86%) as a yellow-green solid. mp: 173–175° C. $^1H$ NMR (300 MHz, $CDCl_3$) δ 1.42 (t, 3H), 4.41 (q, 2H), 6.18 (br s, 2H), 7.55 (m, 3H), 8.12 (m, 2H), 9.03 (s, 1H). MS ($DCI/NH_3$) m/e 300 $(M+H)^+$.

EXAMPLE 40C

3-[4-((3aR,9bR)-cis-9-Methoxy-1,2,3,3a,4,9b-hexahydro-[1]-benzopyrano[3,4-c]pyrrol-2-yl)butyl]-7-phenyl-pyrazino[2',3':4,5]thieno[3,2-d]pyrimidine-2,4(1H,3H)-dione hydrochloride The product from Example 1E (0.357 g, 1.25 mmol) and the product from Example 40B (0.356 g, 1.25 mmol) were treated as described in Example 1F to yield 0.30 g (59%) of the title compound: $^1H$ NMR (300 MHz, $CDCl_3$(free base)) δ 9.13 (s, 1H), 8.18 (dd, 2H), 7.79 (m, 3H), 7.04 (t, 1H), 6.45 (t, 2H), 4.12 (t, 2H), 4.01 (dd, 1H), 3.88 (m, 1H), 3.81 (s, 3H), 3.55 (m, 2H), 3.45 (m, 1H), 2.78 (m, 3H), 2.62 (m, 2H), 1.78 (m, 4H); MS ($DCI/NH_3$) m/e 556$(M+H)^+$; Analysis calc'd for $C_{30}H_{29}N_5SO_4.HCl.1.5H_2O$: C, 58.20; H, 5.37; N, 11.31; found: C, 58.51; H, 5.31; N, 11.33.

EXAMPLE 41

3-[4-((3aR,9bR)-trans-9-Methoxy-1,2,3,3a,4,9b-hexahydro-[1]-benzopyrano[3,4-c]pyrrol-2-yl)butyl]-pyrido[3',4':4,5]thieno[3,2-d]pyrimidine-2,4(1H,3H)-dione hydrochloride The product from Example 3E (210 mg, 0.75 mmol), 3-amino-2-carbomethoxythieno[3,2-c]pyridine (0.17 g, 0.83 mmol) (*J. Heterocyclic Chem.*, 24, 85 (1987)), $Et_3N$ (.40 mL, 2.9 mmol), and phosgene (0.43 mL 1.93M solution in toluene, 0.83 mmol) were treated as described in Example 1F to yield 0.20 g (56%) of the title compound: m.p. >250°; $^1H$ NMR (300 MHz, $CDCl_3$ (free base)) δ 1.72–1.93 (m, 4H), 2.29–2.43 (m, 1H), 2.74 (t, J=10 Hz, 1H), 2.83–2.98 (m, 4H), 3.16 (dd, J=8, 10 Hz, 1H), 3.73 (s, 3H), 3.75–3.83 (m, 1H), 4.03 (dd, J=1, 10 Hz, 1H), 4.21 (t, J=7 Hz, 2H), 4.43 (dd, J=4, 10 Hz, 1H), 6.36 (dd, J=1, 8 Hz, 1H), 6.46 (dd, J=1, 8 Hz, 1H), 7.05 (t, J=8 Hz, 1H), 7.80 (dd, J=1, 6 Hz, 1H), 8.61 (d, J=6 Hz, 1H), 9.54 (d, J=1 Hz, 1H); MS ($DCI/NH_3$)) m/e 479 $(M+H)^+$; Analysis calc'd for $C_{25}H_{26}N_4O_4S.(HCl)_2.H_2O.(CH_3OH)_{0.5}$: C, 52.31; H, 5.51; N, 9.57; found: C, 51.95; H, 5.22; N, 9.27.

EXAMPLE 42

3-[4-((3aR,9bR)-trans-9-Methoxy-1,2,3,3a,4,9b-hexahydro-[1]-benzopyrano[3,4-c]pyrrol-2-yl)butyl]-pyrido[3',4':4,5]thieno[3,2-d]pyrimidine-2,4(1H,3H)-dione hydrochloride The product from Example 3E (200 mg, 0.72 mmol), 3-amino-2-carbomethoxythieno[2,3-c]pyridine (0.16 g, 0.79 mmol) (*J. Heterocyclic Chem*, 24, 85 (1987)), $Et_3N$ (0.40 mL, 2.9 mmol), and phosgene (0.41 mL 1.93M solution in toluene, 0.79 mmol) were treated as described in Example 1F to yield 0.20 g (58%) of the title compound: m.p. 221–223°; $^1H$ NMR (300 MHz, $CDCl_3$ (free base)) δ 1.76–1.96 (m, 4H), 2.37–2.50 (m, 1H), 2.72–2.82 (m, 1H), 2.89–3.11 (m, 4H), 3.18–3.28 (m, 1H), 3.73 (s, 3H), 3.80–3.89 (m, 1H), 4.04 (dd, J=1, 9 Hz, 1H), 4.22 (t, J=7 Hz, 2H), 4.45 (dd, J=4, 10 Hz, 1H), 6.38 (d, J=8 Hz, 1H), 6.54 (d, J=8 Hz, 1H), 7.08 (t, J=8 Hz, 1H), 8.10 (d, J=6 Hz, 1H), 8.64 (d, J=6 Hz, 1H), 9.19 (s, 1H); MS ($DCI/NH_3$)) m/e 479 $(M+H)^+$; Analysis calc'd for $C_{25}H_{26}N_4O_4S.(HCl)_2.(H_2O)_{0.75}$: C, 53.15; H, 5.26; N, 9.92; found: C, 53.18; H, 5.18; N, 9.70.

EXAMPLE 43

3-[4-((3aR,9bR)-trans-9-Methoxy-1,2,3,3a,4,9b-hexahydro-[1]-benzopyrano[3,4-c]pyrrol-2-yl)butyl]-8-methoxy-pyrazino[2',3':4,5]thieno[3,2-d]pyrimidine-2,4(1H,3H)-dione hydrochloride The product from Example 3E (0.276 g, 1.00 mmol) and the product from Example 31A (0.25 g, 1.05 mmol) were treated as described in Example 1F to yield 0.10 g (50%) of the title compound: $^1H$ NMR (300 MHz, $CDCl_3$(free base)) δ 8.02 (d, 1H), 7.04 (t, 1H), 6.92 (d, 1H), 6.48 (d, 1H), 6.39 (d, 1H), 5.39 (m, 1H), 4.45 (dd, 1H), 4.11 (t, 2H), 4.04 (m, 1H), 3.76 (s, 3H), 3.59 (q, 1H), 2.96 (q, 1H), 2.76 (m, 4H), 2.58 (m, 1H), 2.3 (m, 1H), 1.77 (m, 4H), 1.42 (d, 6H); MS ($DCI/NH_3$) m/e 537$(M+H)^+$; Analysis calc'd for $C_{28}H_{32}N_4O_5S.HCl.1.5H_2O$: C, 56.04; H, 6.05; N, 9.34; found: C, 56.04; H, 5.70; N, 9.14.

EXAMPLE 44

3-[4-((3aS,9bR)-trans-9-Methoxy-1,2,3,3a,4,9b-hexahydro-[1]-benzopyrano[3,4-c]pyrrol-2-yl)butyl]-pyrido[3',2':4,5]thieno[3,2-d]pyrimidine-2,4(1H,3H)-dione hydrochloride The product from Example 3E (0.276 g, 1.0 mmol) and methyl 3-amino-thieno[2,3-b]pyridine-2-carboxylate (0.229 g, 1.1 mmol), as described in Example 35A, were treated as described in Example 1F to yield 0.185 g (36%) of the title compound: m.p. 217–8°; $^1H$ NMR (300 MHz, DMSO-$d_6$) δ 1.6–1.8 (m, 4H), 2.1–2.7 (m, 2H), 2.8–3.5 (m, 5H), 3.78 (s, 3H), 3.97 (m, 2H), 4.10 (q, 1H), 4.47 (m, 1H), 6.46 (d, 1H), 4.56 (d, 1H), 7.13 (t, 1H), 7.65 (dd, 1H), 8.75 (dt, 1H), 8.84 (dd, 1H), 10.55 (br s, 1H), 12.74 (d, 1H); MS (DCI/NH3)m/e 479$(M+H)^+$; Analysis calc'd for $C_{25}H_{27}ClN_4O_4S.1.5H_2O$: C, 55.39; H, 5.57; N, 10.33; found: C, 55.43; H, 5.17; N, 10.32.

EXAMPLE 45

3-[4-((3aS,9bR)-trans-9-Methoxy-1,2,3,3a,4,9b-hexahydro-[1]-benzopyrano[3,4-c]pyrrol-2-yl)butyl]-7-methyl-pyrido[3',2':4,5]thieno[3,2-d]pyrimidine-2,4(1H,3H)-dione hydrochloride The product from Example 3E (0.276 g, 1.0 mmol) and the product from Example 35A (0.244 g, 1.1 mmol) were treated as described in Example 1F to yield 0.090 g (17%) of the title compound: m.p. 243–5°; $^1H$ NMR (300 MHz, DMSO-$d_6$) δ 1.6–1.8 (m, 4H), 2.1–2.7 (m, 3H), 2.66 (s, 3H), 2.8–3.8 (m, 6H), 3.77 (s, 3H), 3.96 (m, 2H), 4.12 (m, 1H), 4.45 (m, 1H), 6.46 (d, 1H), 6.56 (d, 1H), 7.12 (t, 1H), 7.51 (d, 1H), 8.60 (d, 1H); MS (DCI/NH3) m/e 493 $(M+H)^+$;

EXAMPLE 46

3-[4-((3aS,9bR)-trans-9-Methoxy-1,2,3,3a,4,9b-hexahydro-[1]-benzopyrano[3,4-c]pyrrol-2-yl)butyl]-7-methoxy-pyrido[3',2':4,5]thieno[3,2-d]pyrimidine-2,4(1H,3H)-dione hydrochloride The product from Example 3E (0.248 g, 0.90 mmol) and the product from Example 33A (0.238 g, 1.0 mmol) were treated as described in Example 1F to yield 0.301 g (61%) of the title compound: m.p. 260–3°; $^1$H NMR (300 MHz, DMSO-d$_6$) δ 1.6–1.8 (m, 4H), 2.1–2.7 (m, 3H), 2.8–3.6 (m, 6H), 3.74 (s, 3H), 3.95 (m, 2H), 3.97 (s, 3H), 4.07 (t, 1H), 4.28 (m, 1H), 6.46 (d, 1H), 6.55 (d, 1H), 7.07 (d, 1H), 7.11 (t, 1H), 8.59 (d, 1H); MS (DCI/NH3) m/e 509 (M+H)$^+$; Analysis calc'd for $C_{26}H_{29}ClN_4O_5S\cdot\frac{3}{4}H_2O$: C, 55.91; H, 5.50; N, 10.03; Cl, 6.35; found: C, 55.75; H, 5.32; N, 10.00; Cl, 6.44.

EXAMPLE 47

3-[4-((3aS,9bR)-trans-9-Methoxy-1,2,3,3a,4,9b-hexahydro-[1]-benzopyrano[3,4-c]pyrrol-2-yl)butyl]-7-chloro-pyrido[3',2':4,5]thieno[3,2-d]pyrimidine-2,4(1H,3H)-dione hydrochloride The product from Example 3E (0.248 g, 0.90 mmol) and the product from Example 32A (0.242 g, 1.0 mmol) were treated as described in Example 1F to yield 0.285 g (58%) of the title compound: m.p. 245–50°; $^1$H NMR (300 MHz, DMSO-d$_6$) δ 1.6–1.8 (m, 4H), 2.1–2.7 (m, 2H), 2.8–3.6 (m, 5H), 3.77 (s, 3H), 3.8–4.2 (m, 2H), 3.95 (m, 2H), 4.10 (t, 1H), 4.47 (m, 1H), 6.46 (d, 1H), 6.54 (d, 1H), 7.11 (t, 1H), 7.78 (d, 1H), 8.75 ( d, 1H);MS (DCI/NH3) m/e 513 (515 (M+H)+); Analysis calc'd for $C_{25}H_{26}Cl_2N_4O_4S\cdot0.5H2O\cdot0.1HCl$: C, 53.42; H, 4.86; N, 9.97; Cl, 13.24; found: C, 53.25; H, 7.73; N, 9.68; Cl, 13.31.

EXAMPLE 48

3-[4-((3aR,9bR)-cis-9-Methoxy-1,2,3,3a,4,9b-hexahydro-[1]-benzopyrano[3,4-c]pyrrol-2-yl)butyl]-9-chloro-pyrido[3',3':4,5]thieno[3,2-d]pyrimidine-2,4(1H,3H)-dione hydrochloride

EXAMPLE 48A

Methyl 3-amino-4-chloro-thieno[3,2-c]pyridine-2-carboxylate

To 3-cyano-2,4dichloropyridine (653 mg) and methyl thioglycolate (340 μL) in DMF (12 mL) at 5° C. was added a solution of 1.0M KOtBu/THF (4.5 mL). The reaction was stirred 20 min at 5° then 1 h at RT, then quenched in sat'd NH$_4$Cl, the solid precipitate collected, washed with water and sucked dry to give 800 mg (88%) of the title compound.

EXAMPLE 48B

3-[4-((3aR,9bR)-cis-9-Methoxy-1,2,3,3a,4,9b-hexahydro-[1]-benzopyrano[3,4-c]pyrrol-2-yl)butyl]-9-chloro-pyrido[3',4':4,5]thieno[3,2-d]pyrimidine-2,4(1H,3H)-dione hydrochloride The product from Example 1E (0.276 g, 1.0 mmol) and the product from Example 48A (0.242 g, 1.0 mmol) were treated as described in Example 1F to yield 0.280 g (55%) of the title compound: $^1$H NMR (300 MHz, CDCl$_3$) δ 1.75 (4H, br m), 2.40 (2H, br), 2.65 (3H, br), 3.30 (1H, br), 3.50 (2H, br), 3.80 (3H, s), 3.86 (1H, br), 4.02 (1H, dd), 4.10 (1H, t), 6.45 (1H, d), 6.52 (1H, d), 7.08 (1H, t), 7.79 (1H, d), 8.40 (1H, d); MS (CI(NH3)) m/e 513 (M+H)$^+$; Analysis calc'd for $C_{25}H_{25}ClN_4O_4S\cdot HCl$: C, 52.49; H, 4.89; N, 9.79; found: C, 52.28; H, 4.55; N, 9.44.

EXAMPLE 49

3-[4-((3aS,9bR)-trans-9-Methoxy-1,2,3,3a,4,9b-hexahydro-[1]-benzopyrano[3,4-c]pyrrol-2-yl)butyl]-9-methoxy-pyrido[3',4':4,5]thieno[3,2-d]pyrimidine-2,4(1H,3H)-dione fumarate

EXAMPLE 49A

Methyl 3-amino-4-methoxy-thieno[3,2-c]pyridine-2-carboxylate

The product from Example 48A (1.2 g, 4.9 mmol) and sodium methoxide (1.0 g, 19 mmol) were refluxed in 30 mL MeOH for 6 h. The reaction was partitioned between water and CH$_2$Cl$_2$. The layers were separated and the aqueous layer was extracted with CH$_2$Cl$_2$. The combined organic layers were dried (MgSO$_4$), filtered, and concentrated. Silica gel chromatography (CH$_2$Cl$_2$) yielded 1.1 g (78%) of the title compound: $^1$H NMR (300 MHz, DMSO-d$_6$) δ 3.79 (s, 3H), 4.05 (s, 3H), 6.96 (bs, 2H), 7.47 (d, J=6 Hz, 1H), 8.07 (d, J=6 Hz, 1H); MS (DCI(NH$_3$)) m/e 239 (M+H)$^+$.

EXAMPLE 49B

3-[4-((3aS,9bR)-trans-9-Methoxy-1,2,3,3a,4,9b-hexahydro-[1]-benzopyrano[3,4-c]pyrrol-2-yl)butyl]-9-methoxy-pyrido[3',4':4,5]thieno[3,2-d]pyrimidine-2,4(1H,3H)-dione fumarate The product from Example 1E (0.140 g, 0.50 mmol), the product from Example 49A (0.145 g, 0.61 mmol), Et$_3$N (0.18 mL, 1.3 mmol), and phosgene (1.1 mL 1.93M solution in toluene, 2.1 mmol) were treated as described in Example 1F substituting fumaric acid for the salt forming step to yield 0.22 g (87%) of the title compound: m.p. 232–233°; $^1$H NMR (300 MHz, CDCl$_3$ (free base)) δ 1.60–1.84 (m, 4H), 2.24–2.40 (m, 1H), 2.55–2.65 (m, 1H), 2.72–2.90 (m, 4H), 2.95–3.03 (m, 1H), 3.60–3.69 (m, 1H), 3.76 (s, 3H), 4.05 (J=10, 11 Hz, 1H), 4.11 (t, J=7 Hz, 2H), 4.20 (s, 3H), 4.46 (dd, J=4, 9 Hz, 1H), 6.39 (d, J=8 Hz, 1H), 6.48 (d, J=8 Hz, 1H), 7.05 (t, J=8 Hz, 1H), 7.39 (d, J=6 Hz, 1H), 8.16 (d, J=6 Hz, 1H); MS (DCI(NH$_3$)) m/e 509 (M+H)$^+$; Analysis calc'd for $C_{26}H_{28}N_4O_5S\cdot C_4H_4O_4\cdot(H_2O)_{0.25}$: C, 57.27; H, 5.21; N, 8.90; found: C, 56.96; H, 4.95; N. 8.83.

EXAMPLE 50

3-[4-((3aS,9bR)-trans-9-Methoxy-1,2,3,3a,4,9b-hexahydro-[1]-benzopyrano[3,4-c]pyrrol-2-yl)butyl]-8-phenyl-pyrazino[2',3':4,5]thieno[3,2-d]pyrimidine-2,4(1H,3H)-dione hydrochloride The product from Example 3E (0.276 g, 1.0 mmol) and the product from Example 9B (0.308 g, 1.08 mmol) were treated as described in Example 1F to yield 0.41 g (73%) of the title compound: m.p. >250°; $^1$H NMR (300 MHz, CDCl$_3$(free base)) δ 9.03 (s, 1H), 8.02 (m, 2H), 7.58 (m, 3H), 7.0 (t, 1H), 6.31 (d, 1H), 3.98 (m, 2H), 4.05 (dd, 1H), 3.85 (t, 2H), 3.62 (m, 1H), 3.06 (m, 3H), 2.85 (m, 2H), 2.22 (m, 1H), 1.82 (m, 4H); MS (DCI/NH$_3$) m/e 556(M+H)$^+$;

Analysis calc'd for $C_{30}H_{29}N_5O_4S\cdot HCl\cdot 2H_2O$: C, 57.36; H, 5.46; N, 11.15; found: C, 57.31; H, 5.23; N, 10.99.

EXAMPLE 51

3-[4-((3aS,9bR)-trans-9-Methoxy-1,2,3,3a,4,9b-hexahydro-[1]-benzopyrano[3,4-c]pyrrol-2-yl)butyl]-8-isopropoxy-pyrido[2',3':4,5]thieno[3,2-d]pyrimidine-2,4(1H,3H)-dione hydrochloride

EXAMPLE 51A

Isopropyl 3-amino-5-isopropoxy-thieno[3,2-b]pyridine-2-carboxylate

Na metal (0.47 g, 20 mmol) was added to 2-propanol (150 mL) and the reaction was heated to reflux until all the sodium was consumed. To the resulting solution was added methyl 3-Amino-7-chloro-thieno[3,2-b]pyridine-2-carboxylate (prepared as described in Example 5A), (0.50 g, 2.06 mmol) and the solution was heated to reflux for 48 h. Solvent was evaporated and the product was partitioned between aq. $NH_4Cl$ and $CH_2Cl_2$. The organic phase was dried, concentrated, and the product purified by silica gel chromatography to yield 0.11 g (19%) of the title compound: $^1$H NMR (300 MHz, $CDCl_3$) 7.85 (d,1H), 6.91 (d, 1H), 5.98 (bs,1H), 5.42 (m, 1H), 5.25 (m, 1H), 1.42 (d, 6H), 1.38 (d,6H); MS ($DCI/NH_3$) m/e 295(M+H)$^+$:

EXAMPLE 51B

3-[4-((3aS,9bR)-trans-9-Methoxy-1,2,3,3a,4,9b-hexahydro-[1]-benzopyrano[3,4-c]pyrrol-2-yl)butyl]-8-isopropoxy-pyrido[2',3':4,5]thieno[3,2-d]pyrimidine-2,4(1H,3H)-dione hydrochloride The product from Example 3E (0.102 g, 0.37 mmol) and the product from Example 51A (0.11 g, 0.37 mmol) were treated as described in Example 1F to yield 0.10 g (50%) of the title compound: $^1$H NMR (300 MHz, $CDCl_3$(free base)) δ 8.02 (d, 1H), 7.04 (t, 1H), 6.92 (d, 1H), 6.48 (d, 1H), 6.39 (d, 1H), 5.39 (m, 1H), 4.45 (dd, 1H), 4.11 (t, 2H), 4.04 (m, 1H), 3.76 (s, 3H), 3.59 (q, 1H), 2.96 (q, 1H), 2.76 (m, 4H), 2.58 (m, 1H), 2.3 (m, 1H), 1.77 (m, 4H), 1.42 (d, 6H); MS ($DCI/NH_3$) m/e 537(M+H)$^+$; Analysis calc'd for $C_{28}H_{32}N_4O_5S\cdot HCl\cdot 1.5H_2O$: C, 56.04; H, 6.05; N, 9.34; found: C, 56.04; H, 5.70; N, 9.14.

EXAMPLE 52

3-[4-((3aS,9bR)-trans-9-Methoxy-1,2,3,3a,4,9b-hexahydro-[1]-benzopyrano[3,4-c]pyrrol-2-yl)butyl]-8-phenyl-pyrido[2',3':4,5]thieno[3,2-d]pyrimidine-2,4(1H,3H)-dione hydrochloride

EXAMPLE 52A

Methyl 3-amino-5-phenyl-thieno[3,2-b]pyridine-2-carboxylate

Methyl 3-amino-5-chloro-thieno[3,2-b]pyridine-2-carboxylate, prepared as described in Example 6A (0.243 g, 1.0 mmol), phenylboronic acid (0.134 g, 1.1 mmol) and triethylamine (0.20 mL) were added to 3 mL of DMF containing [1,1'-bis(diphenylphosphino)ferrocene]palladium(II) chloride (1:1 complex with $CH_2Cl_2$) under $N_2$. The mixture was stirred at 90° C. for 4 h. The reaction was then cooled and diluted with $Et_2O$. The organic layer was washed with $H_2O$, brine, dried ($MgSO_4$), concentrated and chromatographed (2:1 $CH_2Cl_2$:hexane) to yield the title compound (140 mg, 50%): $^1$H NMR (300 MHz, $CDCl_3$) δ 3.93 (s, 3H), 6.30 (bs, 2H), 7.41–7.55 (m, 3H), 7.84 (d, J=8 Hz, 1H), 8.07–8.13 (m, 3H); MS ($DCI(NH_3)$) m/e 285 (M+H)$^+$.

EXAMPLE 52B

3-[4-((3aS,9bR)-trans-9-Methoxy-1,2,3,3a,4,9b-hexahydro-[1]-benzopyrano[3,4-c]pyrrol-2-yl)butyl]-8-phenyl-pyrido[2',3':4,5]thieno[3,2-d]pyrimidine-2,4(1H,3H)-dione hydrochloride The product from Example 3E (0.21 g, 0.75 mmol), the product from Example 52A (235 mg, 0.83 mmol), $Et_3N$ (0.26 mL, 1.9 mmol), and phosgene (0.5 mL 1.93M solution in toluene, 0.95 mmol) were treated as described in Example 1F to yield 0.300 g (72%) of the title compound: m.p. >250°; $^1$H NMR (300 MHz, $CDCl_3$ (free base)) δ 1.59–1.71 (m, 2H), 1.74–1.87 (m, 2H), 2.19–2.34 (m, 1H), 2.59 (dd, J=9, 11 Hz, 1H), 2.72–2.84 (m, 4H), 3.00 (dd, J=7, 9 Hz, 1H), 3.55–3.67 (m, 1H), 3.73 (s, 3H), 4.00 (dd, J=10, 12 Hz, 1H), 4.18 (t, J=7 Hz, 2H), 4.38 (dd, J=4, 10 Hz, 1H), 6.38 (dd, J=1, 8 Hz, 1H), 6.46 (dd, J=1, 8 Hz, 1H), 7.08 (t, J=8 Hz, 1H), 7.44–7.56 (m, 3H), 7.92 (d, J=8 Hz, 1H), 8.04–8.11 (m, 2H), 8.26 (d, J=8 Hz, 1H); MS ($DCI(NH_3)$) m/e 555 (M+H)$^+$; Analysis calc'd for $C_{31}H_{30}N_4O_4S\cdot(HCl)_2\cdot(H_2O)_{0.5}$: C, 58.49; H, 5.23; N, 8.80; found: C, 58.18; H, 5.23; N, 8.47.

EXAMPLE 53

3-[4-((3aR,9bR)-cis-9-Methoxy-1,2,3,3a,4,9b-hexahydro-[1]-benzopyrano[3,4-c]pyrrol-2-yl)butyl]-6-chloro-pyrido[4',3':4,5]thieno[3,2-d]pyrimidine-2,4(1H,3H)-dione

EXAMPLE 53A

Methyl-3-amino-7-chloro-thieno[2,3-c]pyridine-2-carboxylate

3-Chloro-4-cyanopyridine, prepared as described in *J. Heterocyclic Chem.*, 15, 683 (1978), (2.9 g, 21 mmol) was dissolved in acetic acid (15 mL) and 30% $H_2O_2$ (15 mL) was added over 5 min. The reaction was stirred at 80° for 18 h. After cooling to room temp., the white solid product (2.5 g) was collected by filtration and dried. The N-oxide was then dissolved in DMF (50 mL) and methyl thioglycolate (1.45 mL, 16 mmol) was added. Sodium methoxide (0.86 g, 16 mmol) was then added. The reaction was stirred for 1 h, poured into ice/water, and the product collected by filtration, and dried. The resulting solid was suspended in $POCl_3$ (40 mL) and heated at reflux for 1 h. The reaction was quenched on ice, extracted with ether, and the organic extracts washed several times with aq. 5% $NaHCO_3$. Silica gel column chromatography (85:15 hexane:ethyl acetate) yielded 0.42 g of the minor isomer (methyl-3-amino-5-chloro-thieno[2,3-c]pyridine-2-carboxylate) and 1.05 g of the title compound.

EXAMPLE 53B

3-[4-((3aR,9bR)-cis-9-Methoxy-1,2,3,3a,4,9b-hexahydro-[1]-benzopyrano[3,4-yl)butyl]-6-chloro-pyrido[4',3':4.5]thieno[3,2-d]pyrimidine-2,4(1H,3H)-dione The product from Example 1E (0.42 g, 1.5 mmol), the product from Example 53A (0.364 g, 1.5 mmol), $Et_3N$ (0.5 mL, 3.0 mmol), and phosgene (1.6 mL 1.93M solution in toluene, 3.0 mmol) were treated as described in Example 1F to yield 0.26 g (33%) of the title compound: m.p. 191°; $^1$H NMR (300 MHz, CDCl$_3$) δ 1.7–1.8 (m, 2H), 1.8–1.9 (m, 2H), 2.32–2.55 (m, 2H), 2.60–2.80 (m, 3H), 3.27 (m, 1H), 3.40–3.90 (m, 4H), 3.78 (s, 3H), 4.01 (dd, 1H), 4.19 (t, 2H), 6.43 (d, 1H), 6.48 (d, 1H), 7.06 (t, 1H), 8.04 (d, 1H), 8.46 (d, 1H); MS (DCI/NH3) m/e 513, 515 (M+H)+; Analysis calc'd for C$_{25}$H$_{25}$ClN$_4$O$_4$S.H$_2$O: C, 56.55; H, 5.12; N, 10.55; found: C, 56.32; H, 5.03; N, 10.44.

EXAMPLE 54

3-[4-((3aS,9bR)-trans-9-Methoxy-1,2,3,3a,4,9b-hexahydro-[1]-benzopyrano[3,4-c]pyrrol-2-yl)butyl]-6-chloro-pyrido[4',3':4,5]thieno[3,2-d]pyrimidine-2,4(1H,3H)-dione The product from Example 3E (0.42 g, 1.5 mmol), the product from Example 53A (0.364 g, 1.5 mmol), Et$_3$N (0.5 mL, 3.0 mmol), and phosgene (1.6 mL 1.93M solution in toluene, 3.0 mmol) were treated as described in Example 1F to yield 0.31 g (40%) of the title compound: m.p. 230°; $^1$H NMR (300 MHz, CDCl$_3$) δ 1.50–1.75 (m, 4H), 2.18 (m, 1H), 2.66 (t, 1H), 2.82 (m, 4H), 3.07 (t, 1H), 3.1–3.9 (m, 5H), 3.71 (s, 3H), compound: m.p. 230°; $^1$H NMR (300 MHz, CDCl$_3$) δ 1.50–1.75 (m, 4H), 2.18 (m, 1H), (dd, 1H), 4.42 (dd, 1H), 6.40 (d, 1H), 6.47 (d, 1H), 7.04 (t, 1H), 8.21 (d, 1H), 8.50 (d, 1H); MS (DCI/NH3) m/e 513, 515 (M+H)+; Analysis calc'd for C$_{25}$H$_{25}$ClN$_4$O$_4$S.0.5H$_2$O: C, 1H); MS (DCI/NH3) m/e 513, 515 (M+H)+; Analysis calc'd for C$_{25}$H$_{25}$ClN$_4$O$_4$S.0.5H$_2$O: C; 57.52; H, 5.02; N, 10.73; found: C, 57.33; H, 4.72; N, 10.73.

EXAMPLE 55

3-[4-((3aS,9bR)-trans-9-Methoxy-1,2,3,3a,4,9b-hexahydro-[1]-benzopyrano[3,4-c]pyrrol-2-yl)butyl]-8-methoxy-pyrido[3',2':4,5]thieno[3,2-d]pyrimidine-2,4(1H,3H)-dione hydrochloride

EXAMPLE 55A

Methyl 2-amino-5-methoxy-thieno[2,3-b]pyridine-2-carboxylate

To 2-chloro-3-cyano-5-methoxypyridine (0.53 g) and methyl thioglycolate (280 μL) in DMF (10 mL) at 5° C. was added a 1.0M solution of KOtBu/THF (3.8 mL). The reaction was stirred 20 min at 5°, then 2 h at RT, quenched in sat'd NH$_4$Cl, the solid precipitate was collected, washed with water and dried to give 0.53 g (71%) of the title compound.

EXAMPLE 55B

3-[4-((3aS,9bR)-trans-9-Methoxy-1,2,3,3a,4,9b-hexahydro-[1]-benzopyrano[3,4-c]pyrrol-2-yl)butyl]-8-methoxy-pyrido[3',2':4,5]thieno[3,2-d]pyrimidine-2,4(1H,3H)-dione hydrochloride The product from Example 3E (0.223 g, 0.80 mmol) and the product from Example 55A (0.192 g, 0.80 mmol) were treated as described in Example 1F to yield 0.315 g (77%) of the title compound: m.p. 207–213°: $^1$H NMR (300 MHz, DMSO-d$_6$) δ 1.5 (2H, m), 1.65 (2H, m), 2.12 (1H, m), 2.57 (1H), 2.7 (4H, m), 2.9 (1H, t), 3.48 (1H, m), 3.7 (3H, s), 3.92 (3H, s), 3.94 (2H), 4.02 (1H, dd), 4.4 (1H, dd), 6.4 (1H, d), 6.45 (1H, d), 7.02 (1H), t), 8.32 (1H, d), 8.56 (1H, d); MS (CI(NH$_3$)) m/e 509; Analysis calc'd for C$_{26}$H$_{29}$ClN$_4$O$_5$: C, 54.59; H, 5.64; N, 9.79; found: C, 54.61; H, 5.60; N, 9.72.

EXAMPLE 56

3-[4-((3aR,9bR)-cis-9-Methoxy-1,2,3,3a,4,9b-hexahydro-[1]-benzopyrano[3,4-c]pyrrol-2-yl)butyl]-8-(3-pyridyl)-pyrido[2',3':4,5]thieno[3,2-d]pyrimidine-2,4(1H,3H)-dione dihydrochloride

EXAMPLE 56A

Methyl 3-amino-5-(3-pyridyl)thieno[3,2-b]pyridine-2-carboxylate

A solution of the methyl 3-amino-5-chloro-thieno[3,2-b]pyridine-2-carboxylate prepared as described in Example 5A (0.252 g), diethyl 3-pyridyl-borane (0.155 g), Pd(dppf)Cl$_2$ (0.082 g) and K$_2$CO$_3$ (420 mg) in degassed DMF (5 mL) was heated to 95° C. for 1.5 h, cooled, quenched in sat'd NH$_4$Cl, the solid precipitate collected and chromatographed 9:1 hexane/EtOAc to give 0.24 g (81%) of the title compound: $^1$H NMR (300MHz, CDCl$_3$) δ 3.95 (3H, s), 6.30 (2H, br s), 7.45 (1H, dd), 7.86 (1H, d), 8.19 (1H, d), 9:1 hexane/EtOAc to give 0.24 g (81%) of the title compound: $^1$H NMR (300MHz, CDCl$_3$) δ 3.95 (1H, dd), 9.32 (1H, br d).

EXAMPLE 56B

3-[4-((3aR,9bR)-cis-9-Methoxy-1,2,3,3a,4,9b-hexahydro-[1]-benzopyrano[3,4-c]pyrrol-2-yl)butyl]-8-(3-pyridyl)-pyrido[2',3':4,5]thieno[3,2-d]pyrimidine-2,4(1H,3H)-dione dihydrochloride The product from Example 1E (0.127 g, 0.46 mmol) and the product from Example 56A (0.14 g, 0.49 mmol) were treated as described in Example 1F to yield 0.09 g (33%) of the title compound: m.p. 210–211°; $^1$H NMR (300 MHz, CDCl$_3$) δ 9.3 (d, 1H), 8.73 (dd, 1H), 8.41 (dt, 1H), 8.37 (d, 1H), 7.99 (d, 1H), 7.48 (dd, 1H), 7.12 (t, 1H), 6.53 (d, 1H), 6.48 (d, 1H), 4.12 (t, 2H), 4.0 (dd, 1H), 3.81 (s, 3H), 3.78 (m, 1H), 3.42 (m, 2H), 3.1 (m, 1H), 2.6 (m, 3H), 2.2 (m, 2H), 1.85 (m, 2H), 1.68 (m, 2H); MS (DC/NH3) m/e 556(M+H)+; Analysis calc'd for C$_{30}$H$_{29}$N$_5$SO$_4$.2HCl: C, 57.33; H, 4,97; N, 11.14; found: C, 57.04; H, 5.09; N, 10.89.

EXAMPLE 57

3-[4-((3aR,9bR)-cis-9-Methoxy-1,2,3,3a,4,9b-hexahydro-[1]-benzopyrano[3,4-yl)butyl]-8-(3-thienyl)-pyrazino[2',3':4,5]thieno[3,2-d]pyrimidine-2,4(1H,3H)-dione dihydrochloride

EXAMPLE 57A

Methyl 7-amino-2-(3-thienyl)thieno[2,3-b]pyrazine-6-carboxylate

A solution of the methyl 7-amino-2-chloro-thieno[2,3-b]pyrazine-6-carboxylate prepared as described in Example 10C (0.190 g), thiophene-3-boronic acid (0.100 g), Pd(dppf)C12 (0.032 g) and triethylamine (0.22 mL) in degassed DMF was heated to 95° C. for 4 h, cooled, quenched in water and extracted with 1:1 Et$_2$O/EtOAc (3×). The organics were washed 3× with water, brine, dried (Na$_2$SO$_4$), filtered and solvent evaporated to give 0.200 g (88%) of the title compound: $^1$H NMR (300 MHz, CDCl$_3$) δ 3.95 (3H, s), 6.23 (2H, br s), 7.50 (1H, dd), 7.79 (1H, dd), 8.05 (1H, dd), 9.00 (1H, s).

EXAMPLE 57B

3-[4-((3aR,9bR)-cis-9-Methoxy-1,2,3,3a,4,9b-hexahydro-[1]-benzopyrano[3,4-c]pyrrol-2-yl)butyl]-8-(3-thienyl1-pyrazino[2',3':4,5]thieno[3,2-d]pyrimidine-2,4(1H,3H)-dione dihydrochloride The product from Example 1E (0.127 g, 0.46 mmol) and the product from Example 57A (0.13 g, 0.45 mmol) were treated as described in Example 1F to yield 0.09 g (36%) of the title compound: $^1$H NMR (300 MHz, CDCl$_3$(free base)) δ 9.06 (s, 1H), 8.1 (dd, 1H), 7.78 (dd, 1H), 7.53 (dd, 1H), 7.05 (t, 1H), 6.45 (dd, 2H), 4.13 (t, 2H), 4.01 (dd, 1H), 3.83 (m, 1H), 3.8 (s, 3H), 3.52 (m, 2H), 3.3 (m, 1H), 2.72 (m, 3H), 2.45 (m, 2H), 1.85 (m, 2H), 1.68 (m, 2H); MS (DCI/NH$_3$) m/e 562(M+H)+; Analysis calc'd for C$_{28}$H$_{27}$N$_5$O$_4$S$_2$.HCl.2H$_2$O: C, 53.00; H, 5.09; N, 11.04; found: C, 52.78; H, 4.84; N, 10.72.

EXAMPLE 58

3-[4-((3aS,9bR)-trans-9-Methoxy-1,2,3,3a,4,9b-hexahydro-[1]-benzopyrano[3,4-c]pyrrol-2-yl) butyl]-8-(3-pyridyl)-pyrido[2',3':4,5]thieno [3,2-d]primidine-2,4(1H,3H)-dione trihydrochloride The product from Example 3E (0.127 g, 0.46 mmol) and the product from Example 56A (0.14 g, 0.49 mmol) were treated as described in Example 1F to yield 0.095 g (35%) of the title compound: m.p. 238–241°; $^1$H NMR (300 MHz, CDCl$_3$(free base)) δ 9.34 (d, 1H), 8.76 (d, 1H), 8.47 (d, 1H), 8.38 (d, 1H), 7.99 (d, 1H), 7.52 (dd, 1H), 7.11 (t, 1H), 6.5 (d, 1H), 6.41 (d, 1H), 4.66 (dd, 1H), 4.51 (m, 2H), 4.2 (m, 1H), 3.85 (m, 1H), 3.78 (s, 3H), 2.83 (m, 1H), 2.64 (m, 4H), 2.52 (m, 1H), 2.3 (m, 1H), 1.78 (m, 2H), 1.72 (m, 2H); MS (DCI/NH3) m/e 456(M+H)+; Analysis calc'd for C$_{30}$H$_{29}$N$_5$SO$_4$.3HCl.2H$_2$O: C, 51.40; H, 5.18; N, 9.99; found: C, 51.24; H, 5.23; N, 9.82.

EXAMPLE 59

3-[4-((3aS,9bR)-trans-9-Methoxy-1,2,3,3a,4,9b-hexahydro-[1]-benzopyrano[3,4-c]pyrrol-2-yl) butyl]-8-(3-thienyl)-pyrazino[2',3':4,5]thieno [3,2-d]pyrimidine-2,4(1H,3H)-dione dihydrochloride The product from Example 3E (0.13 g, 0.44 mmol) and the product from Example 57A (0.13 g, 0.45 mmol) were treated as described in Example 1F to yield 0.045 g (17%) of the title compound: $^1$H NMR (300 MHz, CDCl$_3$(free base)) δ 9.09 (s, 1H), 8.12 (d, 1H), 7 (81, J=d Hz, 1H), 7.52 (dd, 1H), 7.11 (t, 1H), 6.51 (d, 1H), 6.42 (d, 1H), 4.52 (dd, 1H), 4.17 (m, 2H), 4.08 (m, 1H), 3.85 (m, 1H), 3.8 (s, 3H), 3.2 (m, 4H), 3.1 (m, 1H), 2.8 (m, 1H), 2.62 (m, 1H), 2.05 (m, 2H), 1.95 (m, 2H); MS (DCI/NH3) m/e 562(M+H)$^+$.

EXAMPLE 60

3-[4-((3aS,9bR)-trans-9-Methoxy-1,2,3,3a,4,9b-hexahydro-[1]-benzopyrano[3,4-c]pyrrol-2-yl) butyl]-8-(3-pyridyl)-pyrazino[2',3':4,5]thieno [3,2-d]pyrimidine-2,4(1H,3H)-dione dihydrochloride

EXAMPLE 60A

Methyl 7-amino-2-(3-pyridyl)thieno[2,3-b]pyrazine-6-carboxylate

EXAMPLE 60A

A solution of the methyl 7-amino-2-chloro-thieno[2,3-b] pyrazine-6-carboxylate prepared as described in Example 10C (0.468 g), diethyl(3-pyridyl)borane (0.293 g), Pd(dppf)Cl$_2$ (0.157 g), and K$_2$CO$_3$ (0.800 g) in degassed DMF (10 mL) was heated to 95° C. for 1.5 h, cooled, quenched in sat'd NH$_4$Cl, the solid precipitate collected, washed with water and dried. Purification by silica gel column chromatographed provided 0.44 g (80%) of the title compound. $^1$H NMR (DMSO-d6) δ 3.87 (3H, s), 7.25 (2H, br s), 7.6 (1H, dd), 8.75 (2H, m), 9.49 (1H, s), 9.58 (1H, m).

EXAMPLE 60B

3-[4-((3aS,9bR)-trans-9-Methoxy-1,2,3,3a,4,9b-hexahydro-[1]-benzopyrano[3,4-c]pyrrol-2-yl) butyl]-8-(3-pyridyl)-pyrazino[2',3':4,5]thieno [3,2-d]pyrimidine-2,4(1H,3H)-dione dihydrochloride The product from Example 3E (0.24 g, 0.87 mmol) and the product from Example 60A (0.25 g, 0.87 mmol) were treated as described in Example 1F to yield 0.14 g (29%) of the title compound: m.p. 235–240°; $^1$H NMR (300 MHz, CDCl$_3$) δ 1.9 (4H, br m), 2.4 (4H, br m), 3.05 (1H, br m), 3.10 (3H, br m), 3.65 (1H, m), 3.74 (3H, s), 4.03 (1H, t), 4.19 (2H, t), 4.40 (1H, dd), 6.38 (1H, d), 6.46 (1H, d), 7.07 (1H, t), 7.45 (1H, dd), 8.40 (1H, dt), 8.80 (1H, dd), 9.05 (1H, s), 9.36 (1H, d); MS (CI(NH3)) m/e 557; Analysis calc'd for C$_{29}$H$_{28}$N$_6$O$_6$S.1.75 HCl.2.75H$_2$O: C, 51.99; H, 5.30; N, 12.54; Cl, 9.26; found: C, 51.78; H, 5.12; N, 12.20; Cl, 9.14.

EXAMPLE 61

3-[4-((3aR,9bR)-cis-9-Methoxy-1,2,3,3a,4,9b-hexahydro-[1]-benzopyrano[3,4-c]pyrrol-2-yl) butyl]-8-(3-pyridyl)-pyrazino[2',3':4,5]thieno[3,2-d] pyrimidine-2,4(1H,3H)-dione dihydrochloride The product from Example 1E (0.18 g, 0.65 mmol) and the product from Example 60A (0.165 g, 0.58 mmol) were treated as described in Example 1F to yield 0.18 g (56%) of the title compound: m.p. 190–205°; $^1$H NMR (300 MHz, CDCl3) δ 1.84 (4H, br m), 2.7–3.05 (6H, br m), 3.5 (4H, br m), 3.72 (3H, s), 3.87 (1H, br d), 4.10 (2H, br m), 4.22 (1H, br m), 6.20 (1H, br s), 6.34 (1H, br d), 6.93 (1H, br t), 7.55 (1H, dd), 8.41 (1H, dt), 8.80 (1H, dd), 9.12 (1H, s), 9.34 (1H, d); MS (CI(NH3)) m/e 557; Analysis calc'd for C$_{29}$H$_{28}$N$_6$O$_4$S.1.7HCl.2.5H$_2$O: C, 52.48; H, 5.27; N, 12.66; Cl, 9.08; found: C, 52.21; H, 5.11; N, 12.42; Cl, 8.80.

EXAMPLE 62

3-[4-((3aR,9bR)-cis-9-Methoxy-1,2,3,3a,4,9b-hexahydro-[1]-benzopyrano[3,4-c]pyrrol-2-yl) butyl]-8-(3-furyl)-pyrazino[2',3':4,5]thieno [3,2-d]pyrimidine-2,4(1H,3H)-dione dihydrochloride

EXAMPLE 62A

Methyl 7-amino-2-(3-furyl)thieno[2,3-b]pyrazine-6-carboxylate

A solution of the methyl 7-amino-2-chloro-thieno[2,3-b] pyrazine-6-carboxylate prepared as described in Example 10C (0.300 g, 1.23 mmol), β-furanboronic acid (0.207 g, 1.85 mmol) were dissolved in 12 mL of anhydrous DMF. To this solution was added triethylamine (0.26 mL, 1.85 mMol, 1.5 equiv.), DPPP (153 mg, 0.37 mmol, 0.3 equiv.) and Pd(OAc)2 (83 mg, 0.37 mMol, 0.3 equiv.), followed by heating to 90° C. for 2 h. The solvent was evaporated and the resulting residue was chromatograghed (SiO2, 3:1 Hexanes/Ethyl Acetate) yielding the product as a light yellow solid (93 mg): $^1$H NMR (300 MHz, CDCl$_3$) δ 7.02 (m, 1H), 7.57 (t, J=3.0 Hz, 1H), 8.15 (m, 1H), 8.83 (s, 1H).

EXAMPLE 62B

3-[4-((3aR,9bR)-cis-9-Methoxy-1,2,3,3a,4,9b-hexahydro-[1]-benzopyrano[3,4-c]pyrrol-2-yl) butyl]-8-(3-furyl)-pyrazino[2',3':4,5]thieno [3,2-d]pyrimidine-2,4(1H,3H)-dione dihydrochloride The product from Example 1E (0.097 g, 0.35 mmol), the product from Example 62A (0.073 g, 0.27 mmol), Et$_3$N (0.1 mL, 0.68 mmol), and phosgene (0.7 mL 1.93M solution in toluene, 1.4 mmol) were treated as described in Example 1F to yield 0.040 g (26%) of the title compound: m.p. 183–186°; $^1$H NMR (300 MHz, DMSO-d6) δ 1.61–1.80 (m, 5H), 2.70–2.81 (m, 1H), 1.81–2.96 (m, 2H), 3.12–3.33 (m, 2H), 3.37–3.53 (m, 1H), 3.77–3.93 (m, 1H), 3.80 (s, 3H), 3.93–4.02 (m, 2H), 4.02–4.15 (m, 2H), 6.51 (d, J=8 Hz, 1H), 6.61 (d, J=8 Hz, 1H), 7.14 (t, J=8 Hz, 1H), 7.29 (d, J=2 Hz, 1H), 7.92 (d, J=2 Hz, 1H), 8.66 (s, 1H), 9.28 (s, 1H), 10.35 and 10.55 (bs and bs, 1H), 12.75 (bs, 1H); MS (CI(NH3)) m/e (M+H)+ at 546; Analysis calc'd for $C_{28}H_{27}N_5O_5S$.(HCl)$_2$: C, 54.37: H, 4.73; N, 11.32; found: C, 54.48; H, 5.03; N, 11.13.

EXAMPLE 63

3-[2-((±)-cis-7-Methoxy-1,2,3,3a,4,9b-hexahydro-[1]-benzopyrano[3,4-c]pyrrol-2-yl)ethyl]-[1]benzthieno[3,2-d]pyrimidine-2,4(1H,3H)-dione hydrochloride

EXAMPLE 63A

(±)-cis-7-Methoxy-1,2,3,3a,4,9b-hexahydro-[1]-benzopyrano[3,4-c]pyrrole

From 7-methoxy-coumarin and N-methoxymethyl-N-trimethylsilylmethyl-benzylamine in an analogous manner as described in Examples 1A–C: $^1$H NMR (300 MHz, CDCl$_3$) δ 1.92 (br s, 1H), 2.60 (m, 1H), 2.81 (m, 2H), 3.17 (q, 1H), 3.29 (dd, 1H), 3.40 (dd, 1H), (s, 3H), 3.78 (t, 1H), 4.10 (dd, 1H), 6.43 (d, 1H), 6.52 (dd, 1H), 7.03 (d, 1H).

EXAMPLE 63B

3-[2-((±)-cis-7-Methoxy-1,2,3,3a,4,9b-hexahydro-[1]-benzopyrano[3,4-c]pyrrol-2-yl)ethyl]-[1]benzthieno[3,2-d]pyrimidine-2,4(1H,3H)-dione hydrochloride The product from Example 63A (0.41 g, 2.00 mmol), N-(2-Chloroethyl)-N'-[3-[(2-methoxycarbonyl)benzothienyl]]-urea (0.654 g, 2.00 mmol), prepared by the procedure described in *Eur. J. Med. Chem.*, 28: 499–504 (1993), and ethyldiisopropylamine (0.44 mL, 2.5 mmol) were dissolved in DMSO (3 mL) and the reaction was heated to 100° C. for 3 h. The reaction was cooled to room temperature and 10 mL water added. The product was collected by filtration, recrystallized from 50% aqueous DMF, and the resulting product treated with excess anhydrous HCl in ethanol. After addition of anhydrous ether, the title compound was collected to yield 0.337 g: m.p. 204–7°; $^1$H NMR (300 MHz, DMSO-d$_6$) δ 2.75–2.9 (m, 1H), 2.9–3.2 (m, 2H), 3.4–3.7 (m, 3H), 3.71 (s, 3H), 3.85–4.4 (m, 6H), 6.44 (dd, J=1, 6.57, m Hz, 1H), 7.10 (d, 1H), 7.56 (m, 1H), 7.64 (m, 1H), 8.12 (b, 1H), 8.41 (d, 1H), 12.68 (br s, 1H); MS (DCI/NH3) m/e 450 (M+H)+; Analysis calc'd for $C_{24}H_{24}ClN_3O_4S$: C, 59.32; H, 4,98; N, 8.65; found: C, 59.06; H, 5.06; N, 8.45.

EXAMPLE 64

3-[3-((±)-cis-7-Methoxy-1,2,3,3a,4,9b-hexahydro-[1]-benzopyrano[3,4-c]pyrrol-2-yl)ethyl]-[1]benzthieno[3,2-d]pyrimidine-2,4(1H,3H)-dione hydrochloride The product from Example 63A (0.41 g, 2.00 mmol), N-(3-Chloropropyl)-N'-[3-[(2-methoxycarbonyl)benzothienyl]]-urea (0.750 g, 2.20 mmol), prepared by the procedure described in *Eur. J. Med. Chem.*, 28: 499–504 (1993), were treated as described in Example 63 to yield 0.296 g of the title compound: m.p. 220–2°; $^1$H NMR (300 MHz, DMSO-d$_6$) δ 1.95–2.15 (m, 2H), 2.7–3.0 (m, 3H), 3.1–3.7 (m, 4H), 3.70 (s, 3H), 3.86 (m, 1H), 3.91–4.17 (m, 4H), 6.42 (d, 1H), 6.55 (dd, J=1, 7.56, t Hz, 1H), 7.64 (t, 1H), 8.11 (d, 1H), 8.41 (d, 1H), 12.59 (br s, 1H); MS (DCI/NH3) m/e 464 (M+H)+; Analysis calc'd for $C_{24}H_{26}ClN_3O_4S$.½H$_2$O: C, 58.99; H, 5.34; N, 8.25; found: C, 59.10; H, 5.25; N, 8.09;

EXAMPLE 65

3-[2-((±)-cis-9-Methoxy-1,2,3,3a,4,9b-hexahydro-[1]-benzopyrano[3,4-c]pyrrol-2-yl)ethyl]-[1]-benzthieno[3,2-d]pyrimidine-2,4(1H, 3H)-dione hydrochloride

EXAMPLE 65A

3-[2-(±)-cis-9-Methoxy-1,2,3,3a,4,9b-hexahydro-[1]-benzopyrano[3,4-c]pyrrole From 5-methoxy-coumarin and N-methoxymethyl-N-trimethylsilylmethyl-benzylamine in an analogous manner as described in Examples 1A–C. $^1$H NMR (300 MHz, CDCl$_3$) δ 2.55 (m, 1H), 2.67 (dd, 1H), 2.80 (dd, 1H), 3.21 (q, 1H), 3.32 (dd, 1H), 3.62 (dd, 1H), 3.70 (m, 1H), 3.81 (s, 3H), 4.10 (dd, 1H), 6.46 (d, 1H), 6.55 (d, 1H), 7.17 (t, 1H).

EXAMPLE 65B

3-[2-((±)-cis-9-Methoxy-1,2,3,3a,4,9b-hexahydro-[1]-benzopyrano[3,4-c]pyrrol-2-yl)ethyl]-[1]-benzthieno[3,2-d]pyrimidine-2,4(1H,3H)-dione hydrochloride The product from Example 65A (515 mg, 2.5 mmol), N-(2-Chloroethyl)-N'-[3-[(2-methoxycarbonyl)benzothienyl]]-urea (915 mg, 2.8 mmol), prepared by the procedure described in *Eur. J. Med. Chem.*, 28: 499–504 (1993), and ethyldiisopropylamine (1.0 mL) were treated as described in Example 63B to yield 0.200 g (18%) of the title compound, m.p.: 224–228°; $^1$H NMR (300 MHz, CDCl$_3$ (free base)) δ 2.40–2.53 (m, 2H), 2.56–2.68 (m, 1H), 2.81–3.01 (m, 2H), 3.30 (dd, J=7, 9 Hz, 1H), 3.43 (q, J=8 Hz, 1H), 3.58 (t, J=9 Hz, 1H), 3.72 (s, 3H), 3.77 (dd, J=9, 11 Hz, 1H), 4.02 (dd, J=5, 11 Hz, 1H), 4.35 (t, J=7 Hz, 2H), 6.39 (d, J=8 Hz, 1H), 6.49 (d, J=8 Hz, 1H), 7.04 (t, J=8 Hz, 1H), 7.40 (t, J=8 Hz, 1H), 7.54 (t, J=8 Hz, 1H), 7.88 (d, J=8 Hz, 1H), 8.24 (d, J=8 Hz, 1H); MS (CI(NH$_3$)) m/e (M+H)$^+$ at 450; Analysis calc'd for $C_{24}H_{23}N_3O_4S.HCl.(H_2O)_{0.5}$: C, 58.24; H, 5.09; N, 8.49; found: C, 57.90; H, 4.76; N, 8.24.

EXAMPLE 66

3-[3-((±)-cis-9-Methoxy-1,2,3,3a,4,9b-hexahydro-[1]-benzopyrano[3,4-c]pyrrol-2-yl)propyl]-[1]-benzthieno[3,2-d]pyrimidine-2,4(1H,3H)-dione hydrochloride The product from Example 65A (500 mg, 2.4 mmol), N-(3-Chloropropyl)-N'-[3-[(2-methoxycarbonyl)benzothienyl]]-urea (1.7 g, 5.0 mmol), prepared by the procedure described in *Eur. J. Med. Chem.*, 28: 499–504 (1993), and ethyldiisopropylamine (1.0 mL) were treated as described in Example 63B to yield 300 mg (27%) of the title compound, m.p.: 197–199°; $^1$H NMR (300 MHz, CD$_3$OD)

δ 2.08–2.20 (m, 2H), 2.87–3.01 (m, 1H), 3.14–3.45 (m, 3H), 3.69 (q, J=8 Hz, 1H), 3.77–3.87 (m, 1H), 3.85 (s, 3H), 3.92 (dd, J=7, 12 Hz, 1H), 4.02–4.20 (m, 5H), 6.51 (dd, J=1, 8 Hz, 1H), 6.58 (dd, J=1, 8 Hz, 1H), 7.11 (t, J=8 Hz, 1H), 7.54 (t, J=8 Hz, 1H), 7.60–7.67 (m, 1H), 7.99 (d, J=8 Hz, 1H), 8.18 (d, J=8 Hz, 1H); MS (CI(NH$_3$)) m/e (M+H)$^+$ at 464; Analysis calc'd for C$_{25}$H$_{25}$N$_3$O$_4$S.HCl.CH$_3$OH: C, 58.69; H, 5.68; N, 7.90; found: C, 58.43; H, 5.23; N, 7.93.

EXAMPLE 67

3-[2-((±)-cis-6-Methoxy-1,2,3,3a,4,9b-hexahydro-[1]-benzopyrano[3,4-c]pyrrol-2-yl)ethyl]-[1]-benzthieno[3,2-d]pyrimidine-2,4(1H,3H)-dione hydrochloride

EXAMPLE 67A (±)-cis-6-Methoxy-1,2,3,3a,4,9b-hexahydro-[1]-benzopyrano[3,4-c]pyrrole From 8-methoxy-coumarin and N-methoxymethyl-N-trimethylsilylmethyl-benzylamine in an analogous manner as described in Examples 1A–C.

EXAMPLE 67B

3-[2-((±)-cis-6-Methoxy-1,2,3,3a,4,9b-hexahydro-[1]-benzopyrano[3,4-c]pyrrol-2-yl)ethyl]-[1]-benzthieno[3,2-d]pyrimidine-2,4(1H,3H)-dione hydrochloride The product from Example 67A (600 mg, 2.9 mmol), N-(2-Chloroethyl)-N'-[3-[(2-methoxycarbonyl)benzothienyl]]-urea (1.2 g, 3.7 mmol), prepared by the procedure described in Eur. J. Med. Chem., 28: 499–504 (1993), and ethyldiisopropylamine (1.5 mL) were treated as described in Example 63B to yield 320 mg (24%) of the title compound, m.p.: 251–254°; $^1$H NMR (300 MHz, CDCl$_3$ (free base)) δ 2.43–2.52 (m, 2H), 2.67–2.79 (m, 1H), 2.90 (t, J=7 Hz, 2H), 3.32–3.45 (m, 2H), 3.51 (t, J=8 Hz, 1H), 3.82 (dd, J=8, 11 Hz, 1H), 3.85 (s, 3H), 4.13 (dd, J=5, 9 Hz, 1H), 4.34 (t, J=7 Hz, 2H), 6.65–6.72 (m, 2H), 6.81 (t, J=8 Hz, 1H), 7.39 (t, J=8 Hz, 1H), 7.55 (t, J=8 Hz, 1H), 7.88 (d, J=8 Hz, 1H), 8.24 (d, J=8 Hz, 1H); MS (CI(NH$_3$)) m/e (M+H)$^+$ at 450; Analysis calc'd for C$_{24}$H$_{23}$N$_3$O$_4$S.HCl: C, 59.32; H, 4.98; N, 8.65; found: C, 59.18; H, 5.06; N, 8.54.

EXAMPLE 68

3-[3-((±)-cis-6-Methoxy-1,2,3,3a,4,9b-hexahydro-[1]-benzopyrano[3,4-c]pyrrol-2-yl)propyl]-[1]-benzthieno[3,2-d]pyrimidine-2,4(1H,3H)-dione hydrochloride The product from Example 67A (500 mg, 2.4 mmol), N-(3-Chloropropyl)-N'-[3-[(2-methoxycarbonyl)benzothienyl]]-urea (1.7 g, 5.0 mmol), prepared by the procedure described in Eur. J. Med. Chem., 28: 499–504 (1993), and ethyldiisopropylamine (1.5 mL) were treated as described in Example 63B to yield 610 mg (54%) of the title compound, m.p.: 191–195°; $^1$H NMR (300 MHz, CDCl$_3$ (free base)) δ 1.95–2.07 (m, 2H), 2.20–2.34 (m, 2H), 2.57–2.74 (m, 3H), 3.21 (dd, J=8, 9 Hz, 1H), 3.28–3.40 (m, 2H), 3.76 (dd, J=8, 11 Hz, 1H), 3.83 (s, 3H), 4.10 (dd, J=5, 11 Hz, 1H), 4.27 (t, J=7 Hz, 2H), 6.61–6.70 (m, 2H), 6.80 (t, J=8 Hz, 1H), 7.47 (dd, J=1, 8 Hz, 1H), 7.56 (dd, J=1, 8 Hz, 1H), 7.88 (d, J=8 Hz, 1H), 8.26 (d, J=8 Hz, 1H); MS (CI(NH$_3$)) m/e (M+H)$^+$ at 464; Analysis calc'd for C$_{24}$H$_{25}$N$_3$O$_4$S.HCl.(H$_2$O)$_{0.25}$: C, 59.52; H, 5.29; N, 8.33; found: C, 59.17; H, 5.22; N, 8.24.

EXAMPLE 69

3-[2-((±)-cis-1,2,3,3a,4,9b-hexahydro-[1]-benzopyrano[3,4-c]pyrrol-2-yl)ethyl]-[1]-benzthieno[3,2-d]pyrimidine-2,4(1H,3H)-dione hydrochloride

EXAMPLE 69A (±)-cis-1,2,3,3a,4,9b-hexahydro-[1]-benzopyrano[3,4-c]pyrrole

From coumarin and N-methoxymethyl-N-trimethylsilylmethyl-benzylamine in an analogous manner as described in Examples 1A–C.

EXAMPLE 69B

3-[2-((±)-cis-1,2,3,3a,4,9b-hexahydro-[1]-benzopyrano[3,4-c]pyrrol-2-yl)ethyl]-[1]-benzthieno[3,2-d]pyrimidine-2,4(1H,3H)-dione hydrochloride The product from Example 69A (540 mg, 2.8 mmol), N-(2-Chloroethyl)-N'-[3-[(2-methoxycarbonyl)benzothienyl]]-urea (0.89 g, 3.6 mmol), prepared by the procedure described in Eur. J. Med. Chem., 28: 499–504 (1993) and ethyldiisopropylamine (1.5 mL) were treated as described in Example 63B to yield 410 mg (35%) of the title compound, m.p.: 256–257°; $^1$H NMR (300 MHz, CD$_3$OD) δ 3.00–3.13 (m, 1H), 3.23–3.70 (m, 3H), 3.58 (t, J=6 Hz, 1H), 3.72–3.80 (m, 1H), 3.87–4.20 (m, 2H), 4.03 (dd, J=6, 12 Hz, 1H), 4.15 (dd, J=4, 12 Hz, 1H), 4.41 (t, J=6 Hz, 2H), 6.89 (dd, J=1, 8 Hz, 1H), 6.96–7.02 (m, 1H), 7.18 (dt, J=2, 8 Hz, 1H), 7.25 (dd, J=1, 8 Hz, 1H), 7.51–7.58 (m, 1H), 7.60–7.67 (m, 1H), 7.99 (d, J=8 Hz, 1H), 8.18 (d, J=8 Hz, 1H); MS (CI(NH$_3$)) m/e (M+H)$^+$ at 420; Analysis calc'd for C$_{23}$H$_{21}$N$_3$O$_3$S.HCl: C, 60.59; H, 4.86; N, 9.22; found: C, 60.38; H, 4.83; N, 9.14.

EXAMPLE 70

3-[4-((±)-cis-1,2,3,3a,4,9b-hexahydro-[1]-benzopyrano[3,4-c]pyrrol-2-yl)butyl]-pyrido[2',3':4,5]thieno[3,2-d]pyrimidine-2,4(1H,3H)-dione dihydrochloride

EXAMPLE 70A (±)-cis-2-(4-aminobutyl)-1,2,3,3a,4,9b-hexahydro-[1]-benzopyrano[3,4-c]pyrrole The product from Example 69A (1.0 g, 5.71 mmol) was treated as described in Examples 1D and 1E to yield 1.1 g (98%) of the title compound: $^1$H NMR (300 MHz, CDCl$_3$) δ 1.4–1.8 (m, 6H), 2.20 (dd, 1H), 2.27 (t, 1H), 2.45 (m, 2H), 2.68–2.80 (m, 3H), 3.19 (dd, 1H), 3.37 (m, 2H), 3.75 (dd, 1H), 4.07 (dd, 1H), 6.9 (m, 2H), 7.12 (m, 1H).

EXAMPLE 70B

3-[4-((±)-cis-1,2,3,3a,4,9b-hexahydro-[1]-benzopyrano[3,4-c]pyrrol-2-yl)butyl]-pyrido[2',3':4,5]thieno[3,2-d]pyrimidine-2,4(1H,3H)-dione hydrochloride The product from Example 70A (0.24 g, 1 mmol) and methyl 3-amino-thieno[3,2-b]pyridine-2-carboxylate (0.30 g, 1.2 mmol) were treated as described in Example 1F to yield 0.20 g (44%) of the title compound: m.p. 203–205°; $^1$H NMR (300 MHz, CDCl$_3$(free base)) δ 8.78 (d, 1H), 8.28 (d, 1H), 8.48 (bs, 1H), 7.52 (dd, 1H), 7.13 (m, 2H), 6.92 (m, 2H), 4.08 (m, 4H), 3.92 (m, 1H), 3.82 (m, 1H), 3.68 (q, 1H), 2.98 (m, 3H), 2.73 (m, 2H), 1.78 (m, 4H); MS (DCI/NH$_3$) m/e 449 (M+H)$^+$; Analysis calc'd for C$_{24}$H$_{24}$N$_4$O$_3$S.2HCl.H$_2$O: C, 53.43; H, 5.23; N, 10.39; found: C, 53.24; H, 4.83; N, 10.25.

EXAMPLE 71

3-[4-((±)-trans-1,2,3,3a,4,9b-hexahydro-[1]-benzopyrano[3,4-c]pyrrol-2-yl)butyl]-pyrido[2',3':4,5]thieno[3,2-d]pyrimidine-2,4(1H,3H)-dione hydrochloride

EXAMPLE 71A (±)-trans-1,2,3,3a,4,9b-hexahydro-[1]-benzopyrano[3,4-c]pyrrole

Ethyl 2-methoxymethyl-cinnamate and N-methoxymethyl-N-trimethylsilylmethyl-benzylamine were treated, in an analogous manner as described in Examples 3A–C.

EXAMPLE 71B (±)-trans-2-(4-aminobutyl)-1,2,3,3a,4,9b-hexahydro-[1]-benzopyrano[3,4-c]pyrrole The product from Example 71A (1.22 g, 6.97 mmol) was treated as described in Examples 1D and 1E to yield 0.58 g (34%) of the title compound: $^1$H NMR (300 MHz, CDCl$_3$) δ 1.45–1.8 (m, 6H), 2.29 (m, 1H), 2.60–2.83 (m, 6H), 2.95 (m, 2H), 3.39 (dd, 1H), 4.12 (dd, 1H), 4.50 (dd, 1H), 6.83 (m, 2H), 6.91 (m, 1H), 7.13 (m, 1H).

EXAMPLE 71C

3-[4-((±)-trans-1,2,3,3a,4,9b-hexahydro-[1]-benzopyrano[3,4-c]pyrrol-2-yl)butyl]-pyrido[2',3':4,5]thieno[3,2-d]pyrimidine-2,4(1H,3H)-dione hydrochloride The product from Example 71B (0.24 g, 1.0 mmol) and methyl 3-amino-thieno[3,2-b]pyridine-2-carboxylate (0.35 g, 1.35 mmol) were treated as described in Example 1F to yield 0.18 g (38%) of the title compound: m.p. >250°; $^1$H NMR (300 MHz, CDCl$_3$ (free base)) δ 8.78 (d, 1H), 8.3 (bs, 1H), 8.29 (d, 1H), 7.53 (dd, 1H), 7.18 (t, 1H), 6.88 (m, 3H), 4.45 (dd, 1H), 4.12 (m, 3H), 4.05 (m, 1H), 3.51 (m, 1H), 3.23 (m, 4H), 3.08 (m, 1H), 2.48 (m, 1H), 1.85 (m, 4H); MS (DCI/NH$_3$) m/e 452(M+H)$^+$; Analysis calc'd for C$_{24}$H$_{24}$N$_4$O$_3$S.HCl.0.5H$_2$O: C, 58.35; H, 5.30; N, 11.34; found: C, 58.43; N, 11.34.

EXAMPLE 72

3-[4-(±)-trans-9-Methoxy-1,2,3,3a,4,9b-hexahydro-[1]-benzopyrano[3,4-c]pyrrol-2-yl)butyl]-pyrido[2',3':4,5]thieno[3,2-d]pyrimidine-2,4(1H,3H)-dione dihydrochloride

EXAMPLE 72A (±)-trans-2-9-Methoxy-1,2,3,3a,4,9b-hexahydro-[1]-benzopyrano[3,4-c]pyrrole From ethyl 2-methoxy-6-methoxymethyl-cinnamate and N-methoxymethyl-N-trimethylsilylmethyl-benzylamine, in an analogous manner as described in Examples 3A–C: $^1$H NMR (300 MHz, CDCl$_3$) δ 2.07 (br s, 1H), 2.24 (m, 1H), 2.70 (m, 2H), 2.84 (t, 1H), 3.21 (dd, 1H), 3.77 (s, 3H), 3.83 (dd, 1H), 4.07 (dd, 1H), 4.53 (dd, 1H), 6.40 (d, 1H), 6.51 (d, 1H), 7.06 (t, 1H).

EXAMPLE 72B (±)-trans-2-(4-aminobutyl)-9-Methoxy-1,2,3,3a,4,9b-hexahydro-[1]-benzopyrano[3,4-c]pyrrole The product from Example 72A (1.2, 4.75 mmol) was treated as described in Examples 3D–E to yield 1.0 g (64%) of the title compound: $^1$H NMR (300 MHz, CDCl$_3$) δ 1.40–1.80 (m, 4H), 2.32 (m, 1H), 2.57 (t, 1H), 2.62–2.90 (m, 4H), 2.95 (t, 1H), 3.60 (m, 1H), 3.78 (s, 3H), 4.06 (dd, 1H), 4.45 (dd, 1H), 6.40 (d, 1H), 6.49 (d, 1H), 7.04 (t, 1H).

EXAMPLE 72C

3-[4-((±)-trans-9-Methoxy-1,2,3,3a,4,9b-hexahydro-[1]-benzopyrano[3,4-c]pyrrol-2-yl)butyl]-pyrido[2',3':4,5]thieno[3,2-d]pyrimidine-2,4(1H,3H)-dione dihydrochloride The product from Example 72B (0.28 g, 1.0 mmol) and methyl 3-amino-thieno[3,2-b]pyridine-2-carboxylate (0.27 g, 1.15 mmol) were treated as described in Example 1F to yield 0.22 g (46%) of the title compound: m.p. >250°; $^1$H NMR (300 MHz, DMSO-d$_6$(free base)) δ 1.42–1.54 (m, 2H), 1.60–1.72 (m, 2H), 2.04–2.18 (m, 1H), 2.25–2.89 (m, 4H), 3.10–3.48 (m, 3H), 3.68 (s, 3H), 3.95 (t, J=7 Hz, 2H), 4.02 (dd, J=10, 12 Hz, 1H), 4.39 (dd, J=4, 10 Hz, 1H), 6.39 (dd, J=1, 8 Hz, 1H), 6.44 (dd, J=1, 8 Hz, 1H), 7.01 (t, J=8 Hz, 1H), 7.64 (dd, J=5, 8 Hz, 1H), 8.63 (dd, J=1, 8 Hz, 1H), 8.83 (dd, J=1, 5 Hz, 1H); MS (DCI(NH$_3$)) m/e 479(M+H)$^+$; Analysis calc'd for C$_{25}$H$_{26}$N$_4$O$_4$S.2HCl.0.5H$_2$O: C, 53.57; H, 5.21; N, 10.00; found: C, 53.49; H, 5.35; N, 9.88.

EXAMPLE 73

3-[4-((±)-cis-9-Methoxy-1,2,3,3a,4,9b-hexahydro-[1]-benzopyrano[3,4-c]pyrrol-2-yl)butyl]-pyrido[2',3':4,5]thieno[3,2-d]pyrimidine-2,4(1H,3H)-dione dihydrochloride

EXAMPLE 73A (±)-cis-2-(4-aminobutyl)-9-Methoxy-1,2,3,3a,4,9b-hexahydro-[1]-benzopyrano[3,4-c]pyrrole From 5-methoxycoumarin and N-methoxymethyl-N-trimethylsilylmethyl-benzylamine, in an analogous manner as described in Examples 1A–C: $^1$H NMR (300 MHz, CDCl$_3$) δ 2.55 (m, 1H), 2.67 (dd, 1H), 2.80 (dd, 1H), 3.21 (q, 1H), 3.32 (dd, 1H), 3.62 (dd, 1H), 3.70 (m, 1H), 3.81 (s, 3H), 4.10 (dd, 1H), 6.46 (d, 1H), 6.55 (d, 1H), 7.17 (t, 1H).

EXAMPLE 73B (±)-cis-2-(4-aminobutyl)-9-Methoxy-1,2,3,3a,4,9b-hexahydro-[1]-benzopyrano[3,4-c]pyrrole The product from Example 73A (0.2, 1.0 mmol) was treated as described in Examples 1D–E to yield 0.08 g (29%) of the title compound: $^1$H NMR (300 MHz, CDCl$_3$) δ 1.65–1.80 (m, 4H), 2.19 (m, 1H), 2.25 (dd, 1H), 2.42 (m, 1H), 2.52 (t, 2H), 3.14 (dd, 1H), 3.18–3.30 (m, 2H), 3.79 (dd, 1H), 3.80 (s, 3H), 4.04 (dd, 1H), 6.46 (d, 1H), 6.54 (d, 1H), 7.07 (t, 1H).

EXAMPLE 73C

3-[4-((±)-cis-9-Methoxy-1,2,3,3a,4,9b-hexahydro-[1]-benzopyrano[3,4-c]pyrrol-2-yl)butyl]-pyrido[2',3':4,5]thieno[3,2-d]pyrimidine-2,4(1H,3H)-dione dihydrochloride The product from Example 73B (0.28 g, 1.0 mmol) and methyl 3-amino-thieno[3,2-b]pyridine-2-carboxylate (0.27 g, 1.15 mmol) were treated as described in Example 1F to yield 0.20 g (42%) of the title compound: m.p. 198–200°; $^1$H NMR (300 MHz, CDCl$_3$ (free base)) δ 1.56–1.99 (m, 2H), 1.71–1.83 (m, 2H), 2.26 (t, J=9 Hz, 1H), 2.34 (dd, J=6, 10 Hz, 1H), 2.50–2.70 (m, 3H), 3.26 (dd, J=7, 10 Hz, 1H), 3.43 (q, J=8 Hz, 1H), 3.63 (t, J=8 Hz, 1H), 3.79 (s, 3H), 3.76–3.86 (m, 1H), 4.01 (dd, J=4, 11 Hz, 1H), 4.11 (t, J=7 Hz, 1H), 6.43 (d, J=8 Hz, 1H), 6.49 (d, J=8 Hz, 1H), 7.04 (t, J=8 Hz, 1H), 7.49 (dd, J=4, 8 Hz, 1H), 8.23 (dd, J=1, 8 Hz, 1H), 8.78 (dd, J=1, 4 Hz, 1H); MS (DCI/NH$_3$) m/e 479(M+H)$^+$; Analysis calc'd for C$_{25}$H$_{26}$N$_4$O$_4$S.2HCl.0.5H$_2$O: C, 53.57; H, 5.21; N, 10.00; found: C, 53.41; H, 5.24; N, 9.88.

EXAMPLE 74

3-[4-((±)-trans-9-Methoxy-1,2,3,3a,4,9b-hexahydro-[1]-benzopyrano[3,4-c]pyrrol-2-yl)butyl]-pyrazino[2',3':4,5]thieno[3,2-d]pyrimidine-2,4(1H,3H)-dione dihydrochloride Ethyl 7-amino-thieno[2,3-b]pyrazine-6-carboxylate (0.25 g, 1.0 mmol) prepared by the method of Schneller and Clough, *J. Het. Chem.*, 12: 513 (1975) and the product from Example 72B (0.28 g, 1.0 mmol) were treated as described in Example 1F to yield 0.18 g (38%) of the title compound: m.p. 193–195°; $^1$H NMR (300 MHz, DMSO-d$_6$(free base)) δ 8.98 (d, 1H), 8.89 (d, 1H), 7.11 (t, 1H), 6.52 (d, 1H), 6.45 (d, 1H), 4.5 (dd, 1H), 4.2 (m, 1H), 4.1 (m, 1H), 3.92 (m, 2H), 3.73 (s, 3H), 3.0 (m, 1H), 2.6 (m, 5H), 2.3 (m, 1H), 1.8 (m, 4H); MS (DCI/NH$_3$) m/e 4809(M+H)$^+$; Analysis calc'd for C$_{24}$H$_{25}$N$_5$SO$_{4.2}$HCl.2H$_2$O: C, 48.98; H, 5.31; N, 11.90; found: C, C48.48; H, 5.80; N, 11.94.

EXAMPLE 75

3-[4-((±)-cis-8-Methoxy-1,2,3,3a,4,9b-hexahydro-[1]-benzopyrano[3,4-c]pyrrol-2-yl)butyl]-pyrido[3',2':4,5]thieno[3,2-d]pyrimidine-2,4(1H,3H)-dione dihydrochloride

EXAMPLE 75A (±)-cis-2-8-Methoxy-1,2,3,3a,4,9b-hexahydro-1]-benzopyrano[3,4-c]pyrrole From 6-methoxycoumarin and N-methoxymethyl-N-trimethylsilylmethyl-benzylamine, in an analogous manner as described in Examples 1A–C.

EXAMPLE 75B (±)-cis-2-(4-aminobutyl)-8-Methoxy-1,2,3,3a,4,9b-hexahydro-[1]-benzopyrano[3,4-c]pyrrole The product from Example 75A (1.0 g, 4.9 mmol) was treated as described in Examples 1D–E to yield 0.72 g (54%) of the title compound.

EXAMPLE 75C

3-[4-((±)-cis-8-Methoxy-1,2,3,3a,4,9b-hexahydro-[1]-benzopyrano[3,4-c]pyrrol-2-yl)butyl]-pyrido[3',2':4,5]thieno[3,2-d]pyrimidine-2,4(1H,3H)-dione dihydrochloride Methyl 3-amino-thieno[2,3-b]pyridine-2-carboxylate (0.25 g, 1.07 mmol) and the product from Example 75B (0.26 g, 1.0 mmol) were treated as described in Example 1F to yield 0.20 g (46%) of the title compound: m.p. 203–204°; $^1$H NMR (300 MHz, CDCl$_3$(free base)) δ 8.72 (dd, 1H), 8.6 (d, 1H), 8.38 (bs, 1H), 7.41 (dd, 1H), 6.82 (d, 1H), 6.71 (dd, 1H), 6.6 (d, 1H), 4.12 (m, 4H), 3.98 (m, 2H), 3.78 (m, 1H), 3.73 (s, 3H), 3.12 (m, 2H), 3.05 (m, 1H), 2.92 (m, 1H), 2.85 (m, 1H), 1.82 (m, 4H); MS (DCI/NH$_3$) m/e 479(M+H)$^+$; Analysis calc'd for C$_{25}$H$_{26}$N$_4$O$_4$S.2HCl.0.5H$_2$O: C, 53.57; H, 5.22; N, 10.00; found: C, 53.81; H, 5.06; N, 9.91.

EXAMPLE 76

3-[4-((±)-cis-8-Methoxy-1,2,3,3a,4,9b-hexahydro-[1]-benzopyrano[3,4-c]pyrrol-2-yl)butyl]-pyrazino[2',3':4,5]thieno[3,2-d]pyrimidine-2,4(1H,3H)-dione hydrochloride Ethyl 7-amino-thieno[2,3-b]pyrazine-6-carboxylate (0.25 g, 1.05 mmol) prepared by the method of Schneller and Clough, *J. Het. Chem.*, 12: 513 (1975) and the product from Example 75B (0.28 g, 1.0 mmol) were treated as described in Example 1F to yield 0.30 g (62%) of the title compound: m.p. 218–220°; $^1$H NMR (300 MHz, CDCl$_3$(free base)) δ 8.72 (m, 2H), 6.8 (d, 1H), 6.68 (dd, 1H), 6.61 (d, 1H), 4.12 (t, 2H), 4.0 (dd, 1H), 3.82 (m, 1H), 3.75 (s, 3H), 3.58 (m, 3H), 2.89 (m, 1H), 2.79 (m, 2H), 2.52 (m, 2H), 1.75 (m, 4H); MS (DCI/NH$_3$) m/e 480(M+H)$^+$; Analysis calc'd for C$_{24}$H$_{25}$N$_5$O$_4$S.HCl.2H$_2$O: C, 52.22; H, 5.48; N, 12.69; found: C, 52.68; H, 5.22; N, 12.63.

EXAMPLE 77

3-[3-(±)-cis-8-Methoxy-1,2,3,3a,4,9b-hexahydro-[1]-benzopyrano[3,4-c]pyrrol-2-yl)propyl]-pyrido[3',2':4,5]thieno[3,2-d]pyrimidine-2,4(1H,3H)-dione hydrochloride

EXAMPLE 77A (±)-cis-2-(3-aminopropyl)-8-Methoxy-1,2,3,3a,4,9b-hexahydro-[1]-benzopyrano[3,4-c]pyrrole The product from Example 75A (1.26 g, 6.14 mmol) was treated with 0.61 mL (7.36 mmol) 3-bromopropionitrile, followed by LiAlH$_4$ and AlCl$_3$ in an analagous manner as described in Examples 1D–E to yield 0.85 g (52%) of title compound.

EXAMPLE 77B

3-[3-(±)-cis-8-Methoxy-1,2,3,3a,4,9b-hexahydro-[1]-benzopyrano[3,4-c]pyrrol-2-yl)propyl]-pyrido[3',2':4,5]thieno[3,2-d]pyrimidine-2,4(1H,3H)-dione hydrochloride Methyl 3-amino-thieno[2,3-b]pyridine-2-carboxylate (0.25 g, 1.07 mmol) and the product from Example 78A (0.26 g, 1.0 mmol) were treated as described in Example 1F to yield 0.23 g (50%) of the title compound: $^1$H NMR (300 MHz, CDCl$_3$(free base)) δ 8.64 (dd, 1H), 8.43 (dd, 1H), 8.45 (s, 1H), 7.32 (dd, 1H), 6.82 (d, 1H), 6.7 (dd, 1H), 6.61 (d, 1H), 4.2 (m, 1H), 4.13 (t, 2H), 3.98 (m, 3H), 3.73 (m, 1H), 3.72 (s, 3H), 3.22 (m, 2H), 3.0 (m, 1H), 2.95 (d, 1H), 2.85 (m, 1H), 2.48 (m, 2H); MS (DCI/NH$_3$) m/e 465(M+H)$^+$; Analysis calc'd for C$_{24}$H$_{24}$N$_4$O$_4$S.HCl.H$_2$O: C, 55.54; H, 5.24; N, 10.79; found: C, 55.18; H, 4.98; N, 10.63.

EXAMPLE 78

3-[2-((±)-cis-8-Methoxy-1,2,3,3a,4,9b-hexahydro-[1]-benzopyrano[3,4-c]pyrrol-2-yl)ethyl]-pyrido[2',3':4,5]thieno[3,2-d]pyrimidine-2,4(1H,3H)-dione hydrochloride

EXAMPLE 78A (±)-cis-2-(2-aminoethyl)-8-Methoxy-1,2,3,3a,4,9b-hexahydro-[1]-benzopyrano[3,4-c]pyrrole The product from Example 75A (1.0 g, 4.88 mmol) was treated with 0.34 mL (5.36 mmol) 2-chloroacetonitrile,

EXAMPLE 78B

3-[2-((±)-cis-8-Methoxy-1,2,3,3a,4,9b-hexahydro-[1]-benzopyrano[3,4-c]pyrrol-2-yl)ethyl]-pyrido[3',2':4,5]thieno[3,2-d]pyrimidine-2,4(1H,3H)-dione hydrochloride followed by LiAlH$_4$ and AlCl$_3$ in an analagous manner as described in Examples 1D–E to yield 0.72 g (59%) of title compound: $^1$H NMR (300 MHz, CDCl$_3$) δ 2.1 (br s, 2H), 2.25–2.45 (m, 2H), 2.52–2.65 (m, 2H), 2.72 (m, 1H), 2.83 (t, 2H), 3.17 (dd, 1H), 3.28–3.45 (m, 2H), 3.75 (dd, 1H), 3.77 (s, 3H), 4.01 (dd, 1H), 6.63 (d, 1H), 6.68 (dd, 1H), 6.81 (d, 1H).

Methyl 3-amino-thieno[2,3-b]pyridine-2-carboxylate (0.25 g, 1.07 mmol) and the product from Example 78A (0.25 g, 1.0 mmol) were treated as described in Example 1F to yield 0.20 g (44%) of the title compound: $^1$H NMR (300 MHz, CDCl$_3$(free base)) δ 8.7 (dd, 1H), 8.48 (dd, 1H), 8.3 (bs, 1H), 7.32 (dd, 1H), 6.81 (d, 1H), 6.7 (dd, 1H), 6.65 (d, 1H), 4.5–4.7 (m, 3H), 4.0 (m, 3H), 3.76 (s, 3H), 3.4 (m, 2H), 3.1 (m, 2H), 2.9 (m, 2H); MS (DCI/NH$_3$) m/e 451(M+H)$^+$; Analysis calc'd for C$_{23}$H$_{22}$N$_4$O$_4$S.HCl.0.5H$_2$O: C, 55.70; H, 4.88; N, 11.30; found: C, 55.61; H, 4.66; N, 11.19.

EXAMPLE 79

3-[4-((±)-cis-9-Methoxy-1,2,3,3a,4,9b-hexahydro-[1]-benzopyrano[3,4-c]pyrrol-2-yl)butyl]-6,7-dimethoxy-quinazoline-2,4(1H,3H)-dione hydrochloride Methyl 2-amino-4,5-dimethoxybenzoate (0.28 g, 1.18 mmol) and the product from Example 73A (0.28 g, 1.0 mmol) were treated as described in Example 1F to yield the intermediate urea, which was treated with 1.5 mL of 1.0M KOtBu in 20 mL THF to yield the title compound (0.19 g, 40%): m.p. 178–180° (dec.); $^1$H NMR (300 MHz, CDCl$_3$ (free base)) δ 7.44 (s, 1H), 7.06 (t, 1H), 6.48 (m, 2H), 6.42 (s, 1H), 4.06 (m, 3H), 4.0 (m, 1H), 3.95 (s, 3H), 3.92 (s, 3H), 3.83 (m, 1H), 3.8 (s, 3H), 3.48 (m, 1H), 3.2 (m, 1H), 2.58 (m, 3H), 2.3 (m, 2H), 1.75 (m, 2H), 1.65 (m, 2H); MS (DCI/NH$_3$) m/e 482(M+H)$^+$; Analysis calc'd for C$_{26}$H$_{31}$N$_3$O$_6$.HCl.2H$_2$O: C, 56.37; H, 6.55; N, 7.58; found: C, 56.61; H, 6.30; N, 7.47.

EXAMPLE 80

3-[4-((±)-trans-1,2,3,3a,4,9b-hexahydro-[1]-benzopyrano[3,4-c]pyrrol-2-yl)butyl]-6,7-dimethoxy-quinazoline-2,4(1H,3H)-dione hydrochloride Methyl 2-amino-4,5-dimethoxybenzoate (0.27 g, 1.15 mmol) and the product from Example 71B (0.25 g, 1.0 mmol) were treated as described in Example 1F to yield the intermediate urea, which was treated with 1.5 mL of 1.0M KOtBu in 20 mL THF to yield the title compound (0.12 g, 26%): m.p. 182–184°; $^1$H NMR (300 MHz, CDCl$_3$(free base)) δ 7.41 (s, 1H), 7.18 (m, 1H), 6.88 (s, 1H), 6.86 (m, 2H), 6.71 (s, 1H), 4.55 (dd, 1H), 4.18 (t, 1H), 4.08 (t, 2H), 3.95 (s, 3H), 3.91 (s, 3H), 3.9 (m, 1H), 3.48 (m, 1H), 3.22 (m, 4H), 3.08 (m, 1H), 2.5 (m, 1H), 1.82 (m, 4H); MS (DCI/NH$_3$) m/e 452(M+H)$^+$; Analysis calc'd for C$_{25}$H$_{29}$N$_3$O$_5$.HCl.H$_2$O: C, 59.34; H, 6.37; N, 8.32; found: C, 59.12; H, 6.21; N, 7.82.

EXAMPLE 81

3-[4-((±)-cis-1,2,3,3a,4,9b-hexahydro-[1]-benzopyrano[3,4-c]pyrrol-2-yl)butyl]-6,7-dimethoxy-quinazoline-2,4(1H,3H)-dione hydrochloride Methyl 2-amino-4,5-dimethoxybenzoate (0.27 g, 1.15 mmol) and the product from Example 70A (0.25 g, 1.0 mmol) were treated as described in Example 1F to yield the intermediate urea, which was treated with 1.5 mL of 1.0M KOtBu in 20 mL THF to yield the title compound (0.18 g, 39%): $^1$H NMR (300 MHz, CDCl$_3$(free base)) δ 8.3 (b s, 1H), 7.46 (s, 1H), 7.08 (m, 2H), 6.88 (m, 2H), 6.39 (s, 1H), 4.08 (m, 3H), 3.96 (s, 3H), 3.94 (s, 3H), 3.72 (m, 1H), 3.38 (m, 2H), 3.21 (m, 1H), 2.72 (m, 1H), 2.52 (m, 2H), 2.28 (m, 2H), 1.75 (m, 2H), 1.62 (m, 2H); MS (DCI/NH$_3$) m/e 452(M+H)$^+$; Analysis calc'd for C$_{25}$H$_{29}$N$_3$O$_5$.HCl.2H$_2$O: C, 57.19; H, 6.1; N, 8.00; found: C, 56.63; H, 6.08; N, 7.51.

EXAMPLE 82

3-[4-((±)-trans-9-Methoxy-1,2,3,3a,4,9b-hexahydro-[1]-benzopyrano[3,4-c]pyrrol-2-yl)butyl]-6,7-dimethoxy-quinazoline-2,4(1H,3H)-dione dihydrochloride Methyl 2-amino-4,5-dimethoxybenzoate (0.28 g, 1.18 mmol) and the product from Example 72A (0.28 g, 1.0 mmol) were treated as described in Example 1F to yield the intermediate urea, which was treated with 1.5 mL of 1.0M KOtBu in 20 mL THF to yield the title compound (0.38 g, 79%): m.p. 189–191°; $^1$H NMR (300 MHz, CDCl$_3$(free base)) δ 7.44 (s, 1H), 7.05 (t, 1H), 6.49 (d, 1H), 6.41 (s, 1H), 6.39 (d, 1H), 4.44 (dd, 1H), 4.1 (m, 3H), 3.96 (s, 3H), 3.93 (s, 3H), 3.76 (s, 3H), 3.6 (m, 1H), 2.99 (t, 1H), 2.78 (m, 4H), 2.58 (t, 1H), 2.3 (m, 1H), 1.75 (m, 2H), 1.65 (m, 2H); MS (DCI/NH$_3$) m/e 482(M+H)$^+$; Analysis calc'd for C$_{26}$H$_{31}$N$_3$O$_6$.2HCl.2H$_2$O: C, 52.89; H, 6.32; N, 7.12; found: C, 52.89; H, 5.99; N, 7.02.

EXAMPLE 83

3-[3-((±)-trans-10-Methoxy-1,3,4,4a,5,10b-hexahydro-2H-[1]-benzopyrano[3,4-c]pyrido-3-yl)propyl]-6,7-dimethoxy-quinazoline-2,4(1H,3H)-dione hydrochloride

EXAMPLE 83A (±)-trans-N-benzyl-3-carboethoxy-4-(2-methoxy-6-methoxymethyl)phenyl-piperidine-2,5-dione Ethyl 2-methoxy-6-methoxymethyl-cinnamate (13.2 g, 59.7 mmol) was treated with ethyl N-benzylamidomalonate according to the method of Faruk and Martin, U.S. Pat. No. 4,902,801, to yield the title compound (8.34 g, 38%). $^1$H NMR (300 MHz, DMSO) δ 7.47–7.24 (m, 5H), 7.19 (dd, 1H), 6.71 (d, 1H), 6.68 (d, 1H), 5.19 (dd, 2H), 4.88 (s, 2H), 4.70 (d, 2H), 4.25 (dt, 1H), 3.90 (dq, 2H), 3.78 (s, 3H), 3.41 (dd, 1H), 3.40 (s, 3H), 2.63 (dd, 1H), 0.87 (t, 3H). MS (DCI/NH$_3$) m/e 442(M+H)$^+$.

EXAMPLE 83B (±)-trans-N-benzyl-3-chloromethyl-4-(2-hydroxy-6-methoxy)phenyl-piperidine To a solution of LiAlH$_4$ (2.45 g, 64.6 mmol) in THF (250 mL) was added dropwise at 0° C. a solution of the product from Example 83A (9.50 g, 21.5 mmol) in THF (50 mL). The reaction was warmed to room temperature, and then refluxed for 3 hours. The reaction was cooled to 0° C. and quenched by the consecutive addition of water (4 mL), 1M NaOH (4 mL), and water (10 mL), and stirred for 1 hour. The mixture was filtered through a pad of Celite and rinsed with EtOAc (500 mL). The organic layer was dried over MgSO$_4$, and condensed in vacuo to yield 8.0 g of a clear oil.

The oil was taken up in methanol (250 mL) and concentrated HCl (15 mL) and stirred at reflux for 6 hours. The mixture was cooled, condensed in vacuo, and the residue was partitioned between EtOAc and a saturated solution of NaHCO$_3$. The layers were separated and the aqueous layer extracted with 2× EtOAc. The combined organic layers were dried over MgSO$_4$, and condensed in vacuo to yield 7.0 g of a clear oil. To a solution of this oil in CCl$_4$ (75 mL) and CH$_3$CN (75 mL) was added triphenylphosphine (11.3 g, 43.1 mmol), and the solution was refluxed for 1 hour. The mixture was cooled and condensed in vacuo, and the residue was chromatographed on SiO$_2$ using NH$_3$-saturated 35% EtOAc/hexanes to yield the title compound (5.30 g, 71%). $^1$H NMR (300 MHz, DMSO) δ 9.32 (br s, 1H), 7.35–7.22 (m, 5H), 6.96 (dd, 1H), 6.44 (br d, 2H), 3.72 (s, 3H), 3.5 (dd, 2H), 3.26 (m, 1H), 3.16 (m, 2H), 2.98 (dt, 1H), 2.85 (m, 2H), 2.24 (m, 1H), 1.93 (m, 1H), 1.78 (m, 1H), 1.39 (m, 1H). MS (DCI/NH$_3$) m/e 346(M+H)$^+$.

EXAMPLE 83C (±)-trans-10-Methoxy-1,3,4a,5,10b-hexahydro-2H-[1]-benzopyrano[3,4-c]pyridine To a solution of the product from Example 83B (5.30 g, 15.3 mmol) in THF (125 mL) was added a 1.0M solution of potassium t-butoxide (16 mL), and the reaction was refluxed for 2 hours. The reaction was cooled, poured into water, and extracted with 3× EtOAc. The extracts were dried over MgSO$_4$, and condensed in vacuo to yield 4.7 g of a clear oil. To a solution of the oil and 10% Pd on carbon (2 g) in MeOH (125 mL) was added ammonium formate (4.7 g, 75 mmol), and the reaction was refluxed for 2 h. The reaction mixture was cooled, filtered through a small pad of Celite, and rinsed with EtOAc (200 mL). The filtrate was dried over Na$_2$SO$_4$, and condensed in vacuo to yield the title compound (3.01 g, 90%). $^1$H NMR (300 MHz, DMSO) δ 7.02 (dd, 1H), 6.48 (d, 1H), 6.36 (d, 1H), 4.03 (dd, 1H), 3.72 (s, 3H), 3.55 (dd, 1H), 3.01 (m, 1H), 2.94 (dd, 1H), 2.83 (ddd, 1H), 2.62 (dt, 1H), 2.51 (dt, 1H), 2.29 (t, 1H), 1.64 (ddt, 1H), 1.05 (ddd, 1H). MS (DCI/NH$_3$) m/e 220(M+H)$^+$.

EXAMPLE 83D (±)-trans-3-(2-cyanoethyl)-10-Methoxy-1,3,4,4a,5,10b-hexahydro-2H-[1]-benzopyrano[3,4-c]pyridine A mixture of the product from Example 83C (340 mg, 1.55 mmol), 3-bromopropionitrile (193 μL, 2.33 mmol), and ethyldiisopropylamine (675 μL, 3.88 mmol) in acetonitrile (4 mL) was refluxed for 18 hours. The reaction was cooled, and partitioned between EtOAc and 1M NaOH. The organic layer was dried over MgSO$_4$, the solvent was condensed in vacuo, and the crude product was chromatographed on SiO$_2$ using EtOAc to yield the title compound (0.335 g, 79%). $^1$H NMR (300 MHz, DMSO) δ 7.03 (dd, 1H), 6.49 (d, 1H), 6.38 (d, 1H), 4.08 (dd, 1H), 3.73 (s, 3H), 3.62 (t, 1H), 3.04–2.86 (m, 3H), 2.65 (m, 4H), 2.41 (m, 1H), 2.16 (m, 1H), 1.81 (m, 2H), 1.18 (m, 1H). MS (DCI/NH$_3$) m/e 273(M+H)$^+$.

EXAMPLE 83E (±)-trans-3-(3-Aminopropyl)-10-Methoxy-1,3,4,4a,5,10b-hexahydro-2H-[1]-benzopyrano[3,4-c]pyridine The product from Example 83D (355 mg, 1.30 mmol) was treated with 7.5 equivalents of LiAlH$_4$ and 2.5 equivalents of AlCl$_3$ by the procedure described in Example 1E to yield the title compound (0.347 g, 96%). $^1$H NMR (300 MHz, DMSO) δ 7.02 (dd, 1H), 6.48 (d, 1H), 6.37 (d, 1H), 4.08 (dd, 1H), 3.73 (s, 3H), 3.62 (t, 1H), 2.96 (m, 2H), 2.89 (m, 1H), 2.57 (m, 2H), 2.39 (m, 1H), 2.33 (m, 2H), 2.01 (dt, 1H), 1.77 (m, 1H), 1.66 (t, 1H), 1.51 (m, 2H), 1.17 (m, 1H). MS (DCI/NH$_3$) m/e 277(M+H)$^+$.

EXAMPLE 83F

3-[3-((±)-trans-10-Methoxy-1,3,4,4a,5,10b-hexahydro-2H-[1]-benzopyrano[3,4-c]pyrido-3-yl) propyl]-6,7-dimethoxy-quinazoline-2,4(1H,3H)-dione hydrochloride Methyl 2-amino-4,5-dimethoxybenzoate (258 mg, 1.09 mmol) and the product from Example 83E (250 mg, 0.905 mmol) were treated as described in Example 1F to yield the title compound (347 mg, 71%): m.p. 230° C. $^1$H NMR (300 MHz, DMSO) δ 11.35 (s, 1H), 10.61 (br s, 1H), 7.31 (s, 1H), 7.08 (t, 1H), 6.74 (s, 1H), 6.54 (d, 1H), 6.42 (d, 1H), 4.13 (dd, 1H), 3.98 (m, 2H), 3.84 (s, 3H), 3.81 (s, 3H), 3.75 (s, 3H), 3.63 (m, 1H), 3.58 (m, 2H), 3.10 (m, 4H), 2.84 (m, 1H), 2.76 (m, 1H), 2.24 (m, 1H), 2.19 (m, 2H), 1.57 (m, 1H). MS (DCI/NH$_3$) m/e 482 (M+H)$^+$. Anal calcd for C$_{26}$H$_{31}$N$_3$O$_6$·1.6HCl: C, 57.85; H, 6.09; N, 7.78. Found: C, 57.73; H, 5.99; N, 7.57.

EXAMPLE 84

3-[3-(±)-trans-10-Methoxy-1,3,3,4a,5,10b-hexahydro-2H-[1]-benzopyrano[3,4-c]pyrido-3-yl) propyl]-pyrido[3',2':4,5]thieno[3,2-d]pyrimidine-2,4 (1H,3H)-dione hydrochloride Methyl 3-amino-thieno[2,3-b]pyridine-2-carboxylate (254 mg, 1.09 mmol) and the product from Example 83E (250 mg, 0.904 mmol) were treated as described in Example 1F to yield the title compound (281 mg, 59%). m.p. >300° C. $^1$H NMR (300 MHz, DMSO) δ 12.80 (s, 1H), 10.44 (br s, 1H), 8.83 (d, 1H), 8.78 (d, 1H), 7.67 (dd, 1H), 7.09 (t, 1H), 6.53 (d, 1H), 6.42 (d, 1H), 4.14 (dd, 1H), 4.03 (m, 2H), 3.76 (s, 3H), 3.64 (m, 1H), 3.59 (m, 2H), 3.24–3.02 (m, 4H), 2.85 (m, 1H), 2.76 (m, 1H), 2.22 (m, 1H), 2.13 (m, 2H), 1.53 (m, 1H). MS (DCI/NH$_3$) m/e 479 (M+H)$^+$. Anal calcd for C$_{25}$H$_{26}$N$_4$O$_4$S·1.35HCl: C, 56.89; H, 5.22; N, 10.62. Found: C, 57.03; H, 5.06; N, 10.45.

EXAMPLE 85

3-[4-((±)-trans-10-Methoxy-1,3,4,4a,5,10b-hexahydro-2H-[1]-benzopyrano[3,4-c]pyrido-3-yl) butyl]-pyrido[3',2':4,5]thieno[3,2-d]pyrimidine-2,4 (1H,3H)-dione dihydrochloride

EXAMPLE 85A (±)-trans-3-(3-Cyanopropyl)-10-Methoxy-1,3,4,4a,5, 10b-hexahydro-2H-[1]-benzopyrano[3,4-c]pyridine The product from Example 83C (380 mg, 1.73 mmol) was treated with 1.5 equivalents of 4-bromobutyronitrile and 2.5 equivalents of ethyldiisopropylamine by the procedure described in Example 83D to yield the title compound (0.38 g, 71%). $^1$H NMR (300 MHz, DMSO) δ 7.03 (dd, 1H), 6.49 (d, 1H), 6.38 (d, 1H), 4.09 (dd, 1H), 3.73 (s, 3H), 3.62 (t, 1H), 2.93 (m, 3H), 2.39 (m, 2H), 2.08 (m, 1H), 1.74 (m, 3H), 1.30 (m, 1H). MS (DCI/NH$_3$) m/e 287 (M+H)$^{30}$.

EXAMPLE 85B (±)-trans-3-(4-Aminobutyl)-10-Methoxy-1,3,4,4a,5, 10b-hexahydro-2H-[1]-benzopyrano[3,4-c]pyridine The product from Example 85A (380 mg, 1.33 mmol) was treated with 7.5 equivalents of LiAlH$_4$ and 2.5 equivalents of AlCl₃ by the procedure described in Example 83E to yield the title compound (0.358 g, 93%). ¹H NMR (300 MHz, DMSO) δ 7.02 (dd, 1H), 6.48 (d, 1H), 6.37 (d, 1H), 4.08 (dd, 1H), 3.73 (s, 3H), 3.62 (t, 1H), 2.97 (m, 2H), 2.89 (m, 1H), 2.53 (m, 2H), 2.38 (m, 1H), 2.29 (m, 2H), 2.01 (dt, 1H), 1.78 (m, 1H), 1.67 (t, 1H), 1.46 (m, 2H), 1.34 (m, 2H), 1.18 (m, 1H). MS (DCI/NH₃) m/e 291 (M+H)⁺.

EXAMPLE 85C

3-[4-((±)-trans-10-Methoxy-1,3,4,4a,5,10b-hexahydro-2H-[1]-benzopyrano[3,4-c]pyrido-3-yl) butyl]-pyrido[3',2':4,5]thieno[3,2-d]pyrimidine-2,4 (1H,3H)-dione hydrochloride Methyl 3-amino-thieno[2,3-b]pyridine-2-carboxylate (0.194 g, 1.09 mmol) and the product from Example 85B (0.200 g, 0.69 mmol) were treated as described in Example 1F to yield the title compound (0.245 g, 59%): m.p. 251–4° C; ¹H NMR (300 MHz, DMSO) δ 12.72 (s, 1H), 10.76 (br s, 1H), 8.77 (d, 1H), 8.74 (d, 1H), 7.61 (dd, 1H), 7.04 (t, 1H), 6.50 (d, 1H), 6.38 (d, 1H), 4.12 (dd, 1H), 3.92 (t, 2H), 3.71 (s, 3H), 3.62 (t, 1H), 3.52 (m, 2H), 3.06 (m, 4H), 2.78 (m, 2H), 2.25 (m, 1H), 1.76 (m, 2H), 1.64 (m, 2H), 1.54 (m, 1H). MS (DCI/NH₃) m/e 493 (M+H)⁺. Anal calcd for C₂₆H₂₈N₄O₄S.2HCl: C, 51.88; H, 5.19; N, 9.31. Found: C, 52.24; H, 5.52; N, 9.32.

EXAMPLE 86

3-[4-((±)-trans-10-Methoxy-1,3,4,4a,5,10b-hexahydro-2H-[1]-benzopyrano[3,4-c]pyrido-3-yl) butyl]-6,7-dimethoxy-quinazoline-2,4(1H,3H)-dione hydrochloride Methyl 2-amino-4,5-dimethoxybenzoate (0.196 g, 0.83 mmol) and the product from Example 85B (0.200 g, 0.69 mmol) were treated as described in Example 1F to yield the title compound (0.140 g, 37%): m.p. 220° C. ¹H NMR (300 MHz, DMSO) δ 11.27 (s, 1H), 10.54 (br s, 1H), 7.25 (s, 1H), 7.04 (t, 1H), 6.68 (s, 1H), 6.50 (d, 1H), 6.39 (d, 1H), 4.12 (dd, 1H), 3.87 (t, 2H), 3.79 (s, 3H), 3.76 (s, 3H), 3.71 (s, 3H), 3.62 (t, 1H), 3.62 ( m, 2H), 3.06 (m, 4H), 2.76 (m, 2H), 2.21 (m, 1H), 1.71 (m, 2H), 1.59 (m, 2H), 1.51 (m, 1H). MS (DCI/NH₃) m/e 496 (M+H)⁺. Anal calcd for C₂₇H₃₃N₃O₆.1.4HCl: C, 59.37; H, 6.35; N, 7.69. Found: C, 59.36; H, 6.56; N, 7.57.

EXAMPLE 87

3-[4-((±)-trans-10-Methoxy-1,3,4,4a,5,10b-hexahydro-2H-[1]-benzopyrano[3,4-c]pyrido-3-yl) butyl]-[1]-benzthieno[3,2-d]pyrimidine-2,4(1H,3H)-dione hydrochloride Methyl 3-amino-benzo[b]thiophene-2-carboxylate (0.143 g, 58 mmol) and the product from Example 85B (0.14 g, 0.48 mmol) were treated as described in Example 1F to yield the title compound (0.121 g, 48%): m.p. >305° C. ¹H NMR (300 MHz, DMSO) δ 12.56 (s, 1H), 10.44 (br s, 1H), 8.37 (d, 1H), 8.07 (d, 1H), 7.60 (t, 1H), 7.52 (t, 1H), 7.04 (t, 1H), 6.50 (d, 1H), 6.38 (d, 1H), 4.12 (dd, 1H), 3.93 (t, 2H), 3.71 (s, 3H), 3.62 (t, 1H), 3.53 (m, 2H), 3.06 (m, 4H), 2.77 (m, 2H), 2.20 (m, 1H), 1.76 (m, 2H), 1.65 (m, 2H), 1.52 (m, 1H). MS (DCI/NH₃) m/e 492 (M+H)⁺. Anal calcd for C₂₇H₂₉N₃O₄S.HCl: C, 61.41; H, 5.73; N, 7.96. Found: C, 61.16; H, 5.48; N, 7.79.

EXAMPLE 88

3-[4-((±)-trans-10-Methoxy-1,3,4,4a,5,10b-hexahydro-2H-[1]-benzopyrano[3,4-c]pyrido-3-yl) butyl]-pyrido[2',3':4,5]thieno[3,2-d]pyrimidine-2,4 (1H,3H)-dione hydrochloride Methyl 3-amino-thieno[3,2-b]pyridine-2-carboxylate (0.135 g, 0.58 mmol) and the product from Example 85B (0.14 g, 0.48 mmol) were treated as described in Example 1F to yield the title compound (0.15 g, 54%): m.p. >325° C. ¹H NMR (300 MHz, DMSO) δ 12.68 (s, 1H), 10.65 (br s, 1H), 8.85 (d, 1H), 8.66 (d, 1H), 7.68 (dd, 1H), 7.09 (t, 1H), 6.54 (d, 1H), 6.42 (d, 1H), 4.17 (dd, 1H), 3.97 (t, 2H), 3.76 (s, 3H), 3.67 (t, 1H), 3.58 (m, 2H), 3.11 (m, 4H), 2.81 (m, 2H), 2.28 (m, 1H), 1.79 (m, 2H), 1.69 (m, 2H), 1.58 (m, 1H). MS (DCI/NH₃) m/e 493 (M+H)⁺. Anal calcd for C₂₆H₂₈N₄O₄S.2HCl.0.5H₂O: C, 54.36; H, 5.44; N, 9.75. Found: C, 54.25; H, 5.59; N, 9.68.

EXAMPLE 89

3-[3-((±)-trans-10-Methoxy-1,3,4,4a,5,10b-hexahydro-2H-[1]-benzopyrano[3,4-c]pyrido-3-yl) propyl]-[1]-benzthieno[3,2-d]pyrimidine-2,4(1H,3H)-dione hydrochloride Methyl 3-amino-benzo[b]thiophene-2-carboxylate (0.177 g, 0.72 mmol) and the product from Example 83E (0.165 g, 0.60 mmol) were treated as described in Example 1F to yield the title compound (0.187 g, 61%): m.p. >300° C. ¹H NMR (300 MHz, DMSO) δ 12.65 (s, 1H), 10.41 (br s, 1H), 8.43 (d, 1H), 8.13 (d, 1H), 7.66 (t, 1H), 7.57 (t, 1H), 7.08 (t, 1H), 6.54 (d, 1H), 6.42 (d, 1H), 4.14 (dd, 1H), 4.02 (m, 2H), 3.76 (s, 3H), 3.63 (m, 1H), 3.59 (m, 2H), 3.22–3.03 (m, 4H), 2.86 (m, 1H), 2.77 (m, 1H), 2.22 (m, 1H), 2.13 (m, 2H), 1.54 (m, 1H). MS (DCI/NH₃) m/e 478 (M+H)⁺. Anal calcd for C₂₆H₂₇N₃O₄S.1.0HCl: C, 60.75; H, 5.49; N, 8.17. Found: C, 60.48; H, 5.50; N, 8.02.

EXAMPLE 90

3-[3-((±)-trans-10-Methoxy-1,3,4,4a,5,10b-hexahydro-2H-[1]-benzopyrano[3,4-c]pyrido-3-yl) ethyl]-[1]-benzthieno[3,2-d]pyrimidine-2,4(1H,3H)-dione hydrochloride

EXAMPLE 90A (±)-trans-3-(Cyanomethyl)-10-Methoxy-1,3,4,4a,5, 10b-hexahydro-2H-[1]-benzopyrano[3,4-c]pyridine To a solution of the product from Example 83C (0.80 g, 3.65 mmol) and K₂CO₃ (1.21 g, 8.8 mmol) in acetone (20 mL) and water (2 mL) was added chloroacetonitrile (278 μL, 4.4 mmol), and the solution stirred at reflux for 18 hours. The reaction was cooled and poured into brine, the solution was extracted with 3× EtOAc, and the combined extracts were dried over MgSO₄. The solvent was condensed in vacuo, and the crude product was chromatographed on SiO₂ using 30% EtOAc/hexanes to yield the title compound (0.55 g, 58%). ¹H NMR (300 MHz, DMSO) δ 7.04 (dd, 1H), 6.50 (d, 1H), 6.38 (d, 1H), 4.08 (dd, 1H), 3.74 (s, 3H), 3.68 (t, 1H), 2.91 (m, 2H), 2.39 (ddt, 2H), 2.03 (m, 1H), 1.83 (m, 1H), 1.24 (m, 1H). MS (DCI/NH₃) m/e 259 (M+H)⁺.

EXAMPLE 90B (±)-trans-3-(2-Aminoethyl)-10-Methoxy-1,3,4,4a,5, 10b-hexahydro-2H-[1]-benzopyrano[3,4-c]pyridine To a solution of LiAlH₄ (285 mg, 7.50 mmol) in Et₂O (25 mL) was added dropwise a solution of AlCl₃ (333 mg, 2.50 mmol) in Et₂O (10 mL), and the reaction was stirred for 10 min. A solution of the product from Example 90A (259 mg, 1.00 mmol) in THF (10 mL) was added via syringe, and the reaction stirred for 1 hour. The reaction was cooled to 0° C. and quenched by the consecutive addition of water (2 mL), 1M NaOH (4 mL), and water (4 mL), and stirred for 1 hour. The mixture was filtered through a pad of Celite and rinsed with EtOAc (100 mL) and CHCl$_3$ (100 mL). The organic layer was rinsed with brine, dried over Na$_2$SO$_4$, and condensed in vacuo to yield the title compound (0.225 g, 86%). $^1$H NMR (300 MHz, DMSO) δ 7.02 (dd, 1H), 6.49 (d, 1H), 6.38 (d, 1H), 4.08 (dd, 1H), 3.73 (s, 3H), 3.61 (t, 1H), 2.93 (m, 2H), 2.89 (m, 1H), 2.53 (m, 2H), 2.39 (m, 1H), 2.33 (m, 2H), 2.07 (dt, 1H), 1.79 (m, 1H), 1.62 (m, 2H), 1.19 (m, 1H). MS (DCI/NH$_3$) m/e 263 (M+H)$^+$.

EXAMPLE 90C

3-[2-((±)-trans-10-Methoxy-1,3,4,4a,5,10b-hexahydro-2H-[1]-benzopyrano[3,4-c]pyrido-3-yl)ethyl]-[1]-benzthieno[3,2-d]pyrimidine-2,4(1H,3H)-dione hydrochloride Methyl 3-amino-benzo[b]thiophene-2-carboxylate (0.158 g, 0.64 mmol) and the product from Example 90B (0.140 g, 0.53 mmol) were treated as described in Example 1F to yield the title compound (0.143 g, 54%): m.p. >305° C. $^1$H NMR (300 MHz, DMSO) δ 12.74 (s, 1H), 10.34 (s, 1H), 8.42 (d, 1H), 8.12 (d, 1H), 7.67 (dd, 1H), 7.58 (dd, 1H), 7.09 (dd, 1H), 6.55 (d, 1H), 6.43 (d, 1H), 4.34 (m, 2H), 4.15 (dd, 1H), 3.85 (m, 2H), 3.76 (s, 3H), 3.71 (t, 1H), 3.42 (m, 2H), 3.15 (m, 2H), 2.98 (m, 1H), 2.82 (m, 1H), 2.20 (m, 1H), 1.54 (m, 1H). MS (DCI/NH$_3$) m/e 464 (M+H)$^+$. Anal calcd for C$_{25}$H$_{25}$N$_3$O$_4$S.HCl: C, 60.05; H, 5.24; N, 8.40. Found: C, 59.68; H, 5.21; N, 8.25.

EXAMPLE 91

3-[2-((±)-trans-10-Methoxy-1,3,4,4a,5,10b-hexahydro-2H-[1]-benzopyrano[3,4-c]pyrido-3-yl)ethyl]-6,7-dimethoxy-quinazoline-2,4(1H,3H)-dione hydrochloride Methyl 2-amino-4,5-dimethoxybenzoate (0.152 g, 0.64 mmol) and the product from Example 90B (0.140 g, 0.53 mmol) were treated as described in Example 1F to yield the title compound (0.060 g, 22%): m.p. 291–2° C. $^1$H NMR (300 MHz, DMSO) δ 11.44 (s, 1H), 10.09 (s, 1H), 7.30 (s, 1H), 7.09 (dd, 1H), 6.72 (s, 1H), 6.55 (d, 1H), 6.42 (d, 1H), 4.30 (m, 2H), 4.14 (dd, 1H), 3.85 (m, 2H), 3.84 (s, 3H), 3.79 (s, 3H), 3.75 (s, 3H), 3.71 (t, 1H), 3.42 (m, 2H), 3.15 (m, 2H), 2.95 (m, 1H), 2.81 (m, 1H), 2.16 (m, 1H), 1.50 (m, 1H), MS (DCI/NH$_3$) m/e 468 (M+H)$^+$. Anal. calcd for C$_{24}$H$_{29}$N$_3$O$_6$.1.25HCl: C, 58.52; H, 5.94; N, 8.19. Found: C, 58.79; H, 6.00; N, 8.01.

EXAMPLE 92

3-[3((4aS,10bR)-trans-10-Methoxy-1,3,4,4a,5,10b-hexahydro-2H-[1]-benzopyrano[3,4-c]pyrido-3-yl)propyl]-pyrido[2',3':4,5]thieno[3,2-d]pyrimidine-2,4(1H,3H)-dione dihydrochloride

EXAMPLE 92A (4aS,10bR)-trans-10-Methoxy-1,3,4,4a,5,10b-hexahydro-2H-[1]-benzopyrano[3,4-c]pyridine-4-menthyl carbamate and (4aR,10bS)-trans-10-Methoxy-1,3,4,4a,5,10b-hexahydro-2H-[1]-benzopyrano[3,4-c]pyridine-4-menthyl carbamate To a solution of the product from Example 83C (3.16 g, 14.41 mmol) and ethyldiisopropylamine (5.02 mL, 28.8 mmol) in CH$_2$Cl$_2$ (200 mL) was added at 0° C. (±)-menthyl chloroformate (3.71 mL, 17.3 mmol). The reaction was warmed to 23° C. and stirred for 3 hours. The reaction was then poured into 1M NaOH, the layers separated, and the aqueous layer extracted with 3× Et$_2$O. The combined organic layers were dried over MgSO$_4$, the solvent was condensed in vacuo, and the crude product was chromatographed on SiO$_2$ using 10% EtOAc/hexanes to yield a mixture of diastereomers (5.30 g, 92%). The 1:1 mixture of two diastereomers was separated on a preparatory chiral HLPC column. $^1$H NMR (300 MHz, DMSO) δ 7.04 (dd, 1H), 6.50 (d, 1H), 6.39 (d, 1H), 4.46 (m, 1H), 4.10 (m, 3H), 3.74 (s, 3H), 3.61 (t, 1H), 2.94 (m, 2H), 2.63 (m, 2H), 1.89 (m, 2H), 1.83 (m, 1H), 1.62 (m, 3H), 1.41 (m, 1H), 1.36 (m, 1H), 1.00 (m, 4H), 0.87 (m, 6H), 0.72 (m, 3H). MS (DCI/NH$_3$) m/e 402 (M+H)$^+$.

EXAMPLE 92B (4aS,10bR)-trans-10-Methoxy-1,3,4,4a,5,10b-hexahydro-2H-[1]-benzopyrano[- 3,4-c]pyridine To a solution of (4aS,10bR), slower moving diastereomer from Example 92A (2.38 g, 5.93 mmol) in THF (125 mL) was added at 0° C. a solution of 1.6M n-BuLi (15.0 mL, 24.0 mmol) dropwise, and the reaction was stirred for 15 min. The reaction was quenched with 1M NaOH, poured into brine, and extracted with 3× EtOAc and 2× CH$_2$Cl$_2$. The combined extracts were dried over Na$_2$SO$_4$, the solvent was condensed in vacuo, and the crude product was chromatographed on SiO$_2$ using NH$_3$-saturated 5% MeOH/CH$_2$Cl$_2$ to yield the title compound (1.07 g, 82%); $^1$H NMR (300 MHz, DMSO) δ 7.02 (dd, 1H), 6.48 (d, 1H), 6.36 (d, 1H), 4.03 (dd, 1H), 3.72 (s, 3H), 3.55 (dd, 1H), 3.01 (m, 1H), 2.94 (dd, 1H), 2.83 (ddd, 1H), 2.62 (dt, 1H), 2.51 (dt, 1H), 2.29 (t, 1H), 1.64 (ddt, 1H), 1.05 (ddd, 1H). MS (DCI/NH$_3$) m/e 220 (M+H)$^+$.

EXAMPLE 92C (4aS,10bR)-trans-3-(3-Aminopropyl)-10-Methoxy-1,3,4,4a,5,10b-hexahydro-2H-[1]-benzopyrano[3,4-c]pyridine The product from Example 92B was treated as described in Examples 83 D and 83E to yield the title compound; $^1$H NMR (300 MHz, DMSO) δ 7.02 (dd, 1H), 6.48 (d, 1H), 6.37 (d, 1H), 4.08 (dd, 1H), 3.73 (s, 3H), 3.62 (t, 1H), 2.96 (m, 2H), 2.89 (m, 1H), 2.57 (m, 2H), 2.39 (m, 1H), 2.33 (m, 2H), 2.01 (dt, 1H), 1.77 (m, 1H), 1.66 t, 1H), 1.51 (m, 2H), 1.17 (m, 1H). MS (DCI/NH$_3$) m/e 277 (M+H)$^+$.

EXAMPLE 92D

3-[3-((4aS,10bR)-trans-10-Methoxy-1,3,4,4a,5,10b-hexahydro-2H-[1]-benzopyrano[3,4-c]pyrido-3-yl)propyl]-pyrido[2',3':4,5]thieno[3,2-d]pyrimidine-2,4 (1H,3H)-dione dihydrochloride Methyl 3-amino-thieno[3,2-b]pyridine-2-carboxylate (107 mg, 0.456 mmol) and the product from Example 92C (105 mg, 0.380 mmol) were treated as described in Example 1F to yield the title compound (135 mg, 64%): m.p. 235° C; $^1$H NMR (300 MHz, DMSO) δ 12.72 (s, 1H), 10.66 (br s, 1H), 8.86 (d, 1H), 8.68 (d, 1H), 7.68 (dd, 1H), 7.09 (t, 1H), 6.53 (d, 1H), 6.41 (d, 1H), 4.14 (dd, 1H), 4.00 (m, 2H), 3.76 (s, 3H), 3.63 (m, 1H), 3.59 (m, 2H), 3.21–3.03 (m, 4H), 2.86 (m, 1H), 2.76 (m, 1H), 2.28 (m, 1H), 2.12 (m, 2H), 1.56 (m, 1H). MS (DCI/NH$_3$) m/e 479 (M+H)$^+$. Anal calcd for C$_{25}$H$_{26}$N$_4$O$_4$S.2.0HCl.0.5H$_2$O: C, 53.57; H, 5.22; N, 10.00. Found: C, 53.35; H, 5.05; N, 9.92. [α]$_D^{25.0° C.}$=−79.4°.

EXAMPLE 93

3-[3-((4aR,10bS)-trans-10-Methoxy-1,3,4,4a,5,10b-hexahydro-2H-[1]-benzopyrano[3,4-c]pyrido-3-yl)propyl]-pyrido[2',3':4,5]thieno[3,2-d]pyrimidine-2,4 (1H,3H)-dione dihydrochloride

EXAMPLE 93A (4aR,10bS)-trans-10-Methoxy-1,3,4,4a,5,10b-hexahydro-2H-[1]-benzopyrano[3,4-c]pyridine To a solution of (4aR,10bS), faster moving diastereomer from Example 92A (2.27 g, 5.74 mmol) in THF (125 mL) was added at 0° C. a solution of 1.6M n-BuLi (15.0 mL, 24.0 mmol) dropwise, and the reaction was stirred for 15 min. The reaction was quenched with 1M NaOH, poured into brine, and extracted with 3× EtOAc and 2× $CH_2Cl_2$. The combined extracts were dried over $Na_2SO_4$, the solvent was condensed in vacuo, and the crude product was chromatographed on $SiO_2$ using $NH_3$-saturated 5% $MeOH/CH_2Cl_2$ to yield the title compound (0.96 g, 80%); $^1H$ NMR (300 MHz, DMSO) δ 7.02 (dd, 1H), 6.48 (d, 1H), 6.36 (d, 1H), 4.03 (dd, 1H), 3.72 (s, 3H), 3.55 (dd, 1H), 3.01 (m, 1H), 2.94 (dd, 1H), 2.83 (ddd, 1H), 2.62 (dt, 1H), 2.51 (dt, 1H), 2.29 (t, 1H), 1.64 (ddt, 1H), 1.05 (ddd, 1H). MS ($DCI/NH_3$) m/e 220 $(M+H)^+$.

EXAMPLE 93B (4aR,10bS)-trans-3-(3-Aminopropyl)-10-Methoxy-1,3,4,4a,5,10b-hexahydro-2H-[1]-benzopyrano[3,4-c]pyridine The product from Example 93A was treated as described in Examples 83D and 83E to yield the title compound; $^1H$ NMR (300 MHz, DMSO) δ 7.02 (dd, 1H), 6.48 (d, 1H), 6.37 (d, 1H), 4.08 (dd, 1H), 3.73 (s, 3H), 3.62 (t, 1H), 2.96 (m, 2H), 2.89 (m, 1H), 2.57 (m, 2H), 2.39 (m, 1H), 2.33 (m, 2H), 2.01 (dt, 1H), 1.77 (m, 1H), 1.66 (t, 1H), 1.51 (m, 2H), 1.17 (m, 1H). MS ($DCI/NH_3$) m/e 277 $(M+H)^+$.

EXAMPLE 93C

3-[3-((4aR,10bS)-trans-10-Methoxy-1,3,4,4a,5,10b-hexahydro-2H-[1]-benzopyrano[3,4-c]pyrido-3-yl)propyl]-pyrido[2',3':4,5]thieno[3,2-d]pyrimidine-2,4 (1H,3H)-dione dihydrochloride Methyl 3-amino-thieno[3,2-b]pyridine-2-carboxylate (0.116 g, 0.495 mmol) and the product from Example 93B (0.114 g, 0.413 mmol) were treated as described in Example 1F to yield the title compound (0.091 g, 39%): m.p. 235° C. $^1H$ NMR (300 MHz, DMSO) δ 12.72 (s, 1H), 10.66 (br s, 1H), 8.86 (d, 1H), 8.68 (d, 1H), 7.68 (dd, 1H), 7.09 (t, 1H), 6.53 (d, 1H), 6.41 (d, 1H), 4.14 (dd, 1H), 4.00 (m, 2H), 3.76 (s, 3H), 3.63 (m, 1H), 3.59 (m, 2H), 3.21–3.03 (m, 4H), 2.86 (m, 1H), 2.76 (m, 1H), 2.28 (m, 1H), 2.12 (m, 2H), 1.56 (m, 1H). MS ($DCI/NH_3$) m/e 479 $(M+H)^+$. Anal calcd for $C_{25}H_{26}N_4O_4S.2.0HCl.H_2O$: C, 52.73; H, 5.31; N, 9.84. Found: C, 52.59; H, 5.04; N, 9.75. $[\alpha]_D^{25.0° C.}=+77.7°$.

EXAMPLE 94

3-[4-((4aR,10bS)-trans-10-Methoxy-1,3,4,4a,5,10b-hexahydro-2H-[1]-benzopyrano[3,4-c]pyrido-3-yl)butyl]-pyrido[2',3':4,5]thieno[3,2-d]pyrimidine-2,4 (1H,3H)-dione dihydrochloride

EXAMPLE 94A (4aR,10bS)-trans-3-(4-Aminobutyl)-10-Methoxy-1,3,4,4a,5,10b-hexahydro-2H-[1]-benzopyrano[3,4-c]pyridine The product from Example 93A was treated as described in Examples 85A and 85B to yield the title compound; $^1H$ NMR (300 MHz, DMSO) δ 7.02 (dd, 1H), 6.48 (d, 1H), 6.37 (d, 1H), 4.08 (dd, 1H), 3.73 (s, 3H), 3.62 (t, 1H), 2.97 (m, 2H), 2.89 (m, 1H), 2.53 (m, 2H), 2.38 (m, 1H), 2.29 (m, 2H), 2.01 (dt, 1H), 1.78 (m, 1H), 1.67 (t, 1H), 1.46 (m, 2H), 1.34 (m, 2H), 1.18 (m, 1H). MS ($DCI/NH_3$) m/e 291 $(M+H)^+$.

EXAMPLE 94B

3-[4-((4aR,10bS)-trans-10-Methoxy-1,3,4,4a,5,10b-hexahydro-2H-[1]-benzopyrano[3,4-c]pyrido-3-yl)butyl]-pyrido[2',3':4,5]thieno[3,2-d]pyrimidine-2,4 (1H,3H)-dione dihydrochloride Methyl 3-amino-thieno[3,2-b]pyridine-2-carboxylate (0.087 g, 0.372 mmol) and the product from Example 94A (0.090 g, 0.310 mmol) were treated as described in Example 1F to yield the title compound (0.080 g, 43%): $^1H$ NMR (300 MHz, DMSO) δ 12.68 (s, 1H), 10.65 (br s, 1H), 8.85 (d, 1H), 8.66 (d, 1H), 7.68 (dd, 1H), 7.09 (t, 1H), 6.54 (d, 1H), 6.42 (d, 1H), 4.17 (dd, 1H), 3.97 (t, 2H), 3.76 (s, 3H), 3.67 (t, 1H), 3.58 (m, 2H), 3.11 (m, 4H), 2.81 (m, 2H), 2.28 (m, 1H), 1.79 (m, 2H), 1.69 (m, 2H), 1.58 (m, 1H). MS ($DCI/NH_3$) m/e 493 $(M+H)^+$. Anal calcd for $C_{26}H_{28}N_4O_4S.2.0HCl.2.0H_2O$: C, 51.92; H, 5.70; N, 9.31. Found: C, 52.27; H, 5.56; N, 9.24. $[\alpha]_D^{25.0° C.}=+83.2°$.

EXAMPLE 95

3-[4-((4aS,10bR)-trans-10-Methoxy-1,3,4,4a,5,10b-hexahydro-2H-[1]-benzopyrano[3,4-c]pyrido-3-yl)butyl]-pyrido[2',3':4,5]thieno[3,2-d]pyrimidine-2,4 (1H,3H)-dione dihydrochloride

EXAMPLE 95A (4aS,10bR)-trans-3-(4-Aminobutyl)-10-Methoxy-1,3,4,4a,5,10b-hexahydro-2H-[1]-benzopyrano[3,4-c]pyridine The product from Example 92B was treated as described in Examples 85A and 85B to yield the title compound; $^1H$ NMR (300 MHz, DMSO) δ 7.02 (dd, 1H), 6.48 (d, 1H), 6.37 (d, 1H), 4.08 (dd, 1H), 3.73 (s, 3H), 3.62 (t, 1H), 2.97 (m, 2H), 2.89 (m, 1H), 2.53 (m, 2H), 2.38 (m, 1H), 2.29 (m, 2H), 2.01 (dt, 1H), 1.78 (m, 1H), 1.67 (t, 1H), 1.46 (m, 2H), 1.34 (m, 2H), 1.18 (m, 1H). MS (DCI/NH$_3$) m/e 291 (M+H)$^+$.

EXAMPLE 95B

3-[4-((4aS10bR)-trans-10-Methoxy-1,3,4,4a,5,10b-hexahydro-2H-[1]-benzopyrano[3,4-c]pyrido-3-yl)butyl]-pyrido[2',3':4,5]thieno[3,2-d]pyrimidine-2,4(1H,3H)-dione dihydrochloride Methyl 3-amino-thieno[3,2-b]pyridine-2-carboxylate (0.097 g, 0.413 mmol) and the product from Example 95A (0.100 g, 0.344 mmol) were treated as described in Example 1F to yield the title compound (0.114 g, 55%): $^1$H NMR (300 MHz, DMSO) δ 12.68 (s, 1H), 10.65 (br s, 1H), 8.85 (d, 1H), 8.66 (d, 1H), 7.68 (dd, 1H), 7.09 (t, 1H), 6.54 (d, 1H), 6.42 (d, 1H), 4.17 (dd, 1H), 3.97 (t, 2H), 3.76 (s, 3H), 3.67 (t, 1H), 3.58 (m, 2H), 3.11 (m, 4H), 2.81 (m, 2H), 2.28 (m, 1H), 1.79 (m, 2H), 1.69 (m, 2H), 1.58 (m, 1H). MS (DCI/NH$_3$) m/e 493 (M+H)$^+$. Anal calcd for C$_{26}$H$_{28}$N$_4$O$_4$S.2.0HCl.2.0H$_2$O: C, 51.92; H, 5.70; N, 9.31. Found: C, 51.48; H, 5.62; N, 9.05. [α]$_D^{25.0° C.}$=−82.4°.

EXAMPLE 96

3-[4-((4aR,10bS)-trans-10-Methoxy-1,3,4,4a,5,10b-hexahydro-2H-[1]-benzopyrano[3,4-c]pyrido-3-yl)butyl]-8-chloro-pyrazino[2',3':4,5]thieno[3,2-d]pyrimidine-2,4(1H,3H)-dione dihydrochloride The product from Example 10C (0.106 g, 0.372 mmol) and the product from Example 94A (0.090 g, 0.310 mmol) were treated as described in Example 1F to yield the title compound (0.020 g, 11%): m.p. 253–4° C. $^1$H NMR (300 MHz, DMSO) δ 12.92 (s, 1H), 10.45 (br s, 1H), 9.02 (s, 1H), 7.09 (t, 1H), 6.54 (d, 1H), 6.42 (d, 1H), 4.17 (dd, 1H), 3.97 (t, 2H), 3.76 (s, 3H), 3.67 (t, 1H), 3.57 (m, 2H), 3.11 (m, 4H), 2.81 (m, 2H), 2.25 (m, 1H), 1.78 (m, 2H), 1.69 (m, 2H), 1.56 (m, 1H). MS (DCI/NH$_3$) m/e 528 (M+H)$^+$. Anal calcd for C$_{25}$H$_{26}$N$_5$O$_4$SCl.2.0HCl.0.5H$_2$O: C, 49.23; H, 4.79; N, 11.48. Found: C, 48.95; H, 4.77; N, 11.22. [α]$_D^{25.0° C.}$=+57.6°.

EXAMPLE 97

3-[4-((4aS,10bR)-trans-10-Methoxy-1,3,4,4a,5,10b-hexahydro-2H-[1]-benzopyrano[3,4-c]pyrido-3-yl)butyl]-8-chloro-pyrazino[2',3':4,5]thieno[3,2-d]pyrimidine-2,4(1H,3H)-dione dihydrochloride The product from Example 10C (0.189 g, 0.667 mmol) and the product from Example 95A (0.176 g, 0.606 mmol) were treated as described in Example 1F to yield the title compound (0.192 g, 55%): m.p. 254–5° C. $^1$H NMR (300 MHz, DMSO) δ 12.92 (s, 1H), 10.45 (br s, 1H), 9.02 (s, 1H), 7.09 (t, 1H), 6.54 (d, 1H), 6.42 (d, 1H), 4.17 (dd, 1H), 3.97 (t, 2H), 3.76 (s, 3H), 3.67 (t, 1H), 3.57 (m, 2H), 3.11 (m, 4H), 2.81 (m, 2H), 2.25 (m, 1H), 1.78 (m, 2H), 1.69 (m, 2H), 1.56 (m, 1H). MS (DCI/NH$_3$) m/e 528 (M+H)$^+$. Anal calcd for C$_{25}$H$_{26}$N$_4$O$_4$S.2.0HCl.3.0H$_2$O: C, 45.84; H, 5.23; N, 10.69. Found: C, 45.47; H, 5.03; N, 10.51. [α]$_D^{25.0° C.}$=−58.4°.

EXAMPLE 98

3-[4-((4aS,10bR)-trans-10-Methoxy-1,3,4,4a,5,10b-hexahydro-2H-[1]-benzopyrano[3,4-c]pyrido-3-yl)butyl]-8-methoxy-pyrido[2',3':4,5]thieno[3,2-d]pyrimidine-2,4(1H,3H)-dione hydrochloride The product from Example 7A (0.24 g, 1.00 mmol) and the product from Example 95A (0.276 g, 1.00 mmol) were treated as described in Example 1F to yield the title compound (0.30 g, 57%): m.p. >250°; $^1$H NMR (300 MHz, CDCl$_3$(free base)) δ 8.04 (d, 1H), 7.03 (t, 1H), 6.98 (d, 1H), 6.46 (d, 1H), 6.41 (d, 1H), 4.12 (t, 2H), 4.08 (dd, 1H), 4.04 (s, 3H), 3.79 (s, 3H), 3.67 (m, 1H), 3.08 (m, 1H), 2.98 (m, 2H), 2.42 (m, 3H), 2.13 (m, 1H), 2.02 (m, 1H), 1.76 (m, 3H), 1.62 (m, 2H), 1.38 (m, 1H); MS (DCI/NH$_3$) m/e 523(M+H)$^+$; Analysis calc'd for C$_{27}$H$_{30}$N$_4$O$_5$S.HCl.0.5H$_2$O: C, 57.09; H, 5.68; N, 9.86; found: C, 57.01; H, 5.43; N, 9.64.

EXAMPLE 99

3-[4-((4aS,10bR)-trans-10-Methoxy-1,3,4,4a,5,10b-hexahydro-2H-[1]-benzopyrano[3,4-c]pyrido-3-yl)butyl]-8-methoxy-pyrazino[2',3':4,5]thieno[3,2-d]pyrimidine-2,4(1H,3H)-dione hydrochloride The product from Example 31A (0.167 g, 0.70 mmol) and the product from Example 95A (0.195 g, 0.70 mmol) were treated as described in Example 1F to yield the title compound (0.29 g, 78%): m.p. 220–224°; $^1$H NMR (300 MHz, CDCl$_3$(free base)) δ 8.39 (s, 1H), 7.04 (t, 1H), 6.46 (d, 1H), 6.41 (d, 1H), 4.11 (m, 3H), 4.08 (s, 3H), 3.79 (s, 3H), 3.67 (t, 1H), 3.08 (m, 1H), 2.98 (m, 2H), 2.42 (m, 3H), 2.15 (m, 1H), 2.0 (m, 1H), 1.78 (m, 3H), 1.6 (m, 2H), 1.4 (m, 1H); MS (DCI/NH$_3$) m/e 524 (M+H)$^+$; Analysis calc'd for C$_{26}$H$_{29}$N$_5$O$_5$S.HCl.2H$_2$O: C, 52.39; H, 5.75; N, 11.75; found: C, 52.59; H, 5.70; N, 11.65.

EXAMPLE 100

3-[4-((4aS,10bR)-trans-10-Methoxy-1,3,4,4a,5,10b-hexahydro-2H-[1]-benzopyrano[3,4-c]pyrido-3yl)butyl]-8-phenyl-pyrazino[2',3':4,5]thieno[3,2-d]pyrimidine-2,4(1H,3H)-dione hydrochloride The product from Example 9B (0.16 g, 0.56 mmol) and the product from Example 95A (0.154 g, 0.56 mmol) were treated as described in Example 1F to yield the title compound (0.17 g, 53%): m.p. >250°; $^1$H NMR (300 MHz, CDCl$_3$(free base)) δ 9.16 (s, 1H), 8.08 (m, 2H), 7.59 (m, 3H), 7.02 (t, 1H), 6.42 (d, 1H), 6.38 (d, 1H), 4.18 (m, 2H), 3.93 (dd, 1H), 3.77 (s, 3H), 3.6 (t, 1H), 3.18 (m, 1H), 3.07 (m, 1H), 2.93 (m, 1H), 2.5 (m, 2H), 2.41 (m, 1H), 2.16 (m, 1H), 1.97 (m, 1H), 1.8 (m, 3H), 1.76 (m, 2H), 1.18 (m, 1H); MS (DCI/NH$_3$) m/e 570 (M+H)$^+$; Analysis calc'd for C$_{31}$H$_{31}$N$_5$SO$_4$.HCl.1.5H$_2$O: C, 58.81; H, 5.57; N, 11.06; found: C, 58.69; H, 5.52; N, 11.03.

EXAMPLE 101

3-[4-((4aS,10bR)-trans-10-Methoxy-1,3,4,4a,5,10b-hexahydro-2H-[1]-benzopyrano[3,4-c]pyrido-3yl)butyl]-8-phenyl-pyrido[2',3':4,5]thieno[3,2-d]pyrimidine-2,4(1H,3H)-dione dihydrochloride The product from Example 95B (0.145 g, 0.50 mmol) and the product from Example 52A (0.15 g, 0.53 mmol) were treated as described in Example 1F to yield 0.230 g (80%) of the title compound: m.p. >255°; $^1$H NMR (300 MHz, CDCl$_3$(free base)) δ 1.35 (dd, J=3, 12 Hz, Hz, 1H), 1.58–1.72 (m, 2H), 1.72–1.87 (m, 3H), 1.91–2.05 (m, 1H), 2.12 (dd, J=3, 12 Hz, 1H), 2.36–2.50 (m, 3H), 2.89–3.02 (m, 2H), 3.04–3.13 (m, 1H), 3.63 (dd, J=10, 11 Hz, 1H), 3.77 (s, 3H), 4.03 (dd, J=3, 10 Hz, 1H), 4.18 (t, J=7 Hz, 2H), 6.39 (dd, J=1, 8 Hz, 1H), 6.45 (dd, J=1, 8 Hz, 1H), 7.03 (t, J=8 Hz, 1H), 7.45–7.56 (m, 3H), 7.93 (d, J=9 Hz, 1H), 8.05–8.11 (m, 2H), 8.27 (d, J=9 Hz, 1H); MS (CI(NH$_3$)) m/e (M+H)$^+$ at 569; Analysis calc'd for C$_{32}$H$_{32}$N$_4$O$_4$S.(HCl)$_2$.(H$_2$O)$_{0.5}$: C, 59.07; H, 5.42; N, 8.61; found: C, 59.04; H, 5.53; N, 8.35.

EXAMPLE 102

3-[4-((4aS,10bR)-trans-10-Methoxy-1,3,4,4a,5,10b-hexahydro-2H-[1]-benzopyrano[3,4-c]pyrido-3yl)butyl]-7-chloro-pyrido[3',2':4,5]thieno[3,2-d]pyrimidine-2,4(1H,3H)-dione hydrochloride The product from Example 95B (0.290 g, 1.0 mmol) and methyl 3-amino-6-chloro-thieno[2,3-b]pyridine-2-carboxylate (0.242 g, 1.00 mmol) were treated as described in Example 1F to yield 0.375 g (66%) of the title compound: m.p. 236° (d); $^1$H NMR (300 MHz, DMSO-d$_6$) δ 1.4–1.6 (m, 2H), 1.6–1.85 (n, 4H), 2.04–2.24 (m, 2H), 2.7–3.6 (m, 6H), 3.66 (t, 2H), 3.77 (s, 3H), 3.95 (t, 2H), 4.15 (m, 1H), 6.41 (d, 1H), 6.52 (d, 1H), 7.07 (t, 1H), 7.78 (d, 1H), 8.77 (d, 1H); MS (DCI/NH3) m/e 527 (529 (M+H)+); Analysis calc'd for $C_{26}H_{28}Cl_2N_4O_4S \cdot 1.25H_2O$: C, 53.29; H, 5.25; N, 9.56; Cl, 12.10; found: C, 53.26; H, 5.28; N, 9.27; Cl, 11.82.

EXAMPLE 103

3-[4-((4aS,10bR)-trans-10-Methoxy-1,3,4,4a,5,10b-hexahydro-2H-[1]-benzopyrano[3,4-c]pyrido-3yl)butyl]-7-methoxy-pyrido[3',2':4,5]thieno[3,2-d]pyrimidine-2,4(1H,3H)-dione hydrochloride The product from Example 95B (0.290 g, 1.0 mmol) and methyl 3-amino-6-methoxy-thieno[2,3-b]pyridine-2-carboxylate (0.238 g, 1.00 mmol) were treated as described in Example 1F to yield 0.315 g (56%) of the title compound: m.p. 224° (d); $^1$H NMR (300 MHz, DMSO-d$_6$) δ 1.4–1.6 (m, 2H), 1.6–1.85 (m, 4H), 2.04–2.15 (m, 2H), 2.7–3.6 (m, 6H), 3.67 (t, 2H), 3.77 (s, 3H), 3.96 (m, 2H), 3.98 (s, 3H), 4.15 (m, 1H), 6.41 (d, 1H), 6.54 (d, 1H), 7.07 (d, 1H), 7.08 (t, 1H), 8.58 (d, 1H); MS (DCI/NH3) m/e 523 (M+H)+; Analysis calc'd for $C_{27}H_{31}ClN_4O_5S \cdot 1.4H_2O$: C, 54.65; H, 5.78; N, 9.44; Cl, 7.47; found: C, 54.52; H, 5.91; N, 9.31; Cl, 7.55.

The foregoing is merely illustrative of the invention and is not intended to limit the invention to the disclosed compounds. Variations and changes which are obvious to one skilled in the art are intended to be within the scope and nature of the invention which are defined in the appended claims.

We claim:
1. A compound of formula I:

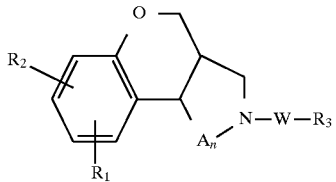

or a pharmaceutically acceptable salt thereof, wherein $R_1$ and $R_2$ are independently selected from the group consisting of hydrogen, alkyl, alkenyl, alkynyl, alkoxyalkyl, alkoxy, alkoxycarbonyl, hydroxy, hydroxyalkyl, carboxy, carboxyalkyl, halogen nitro, amino and aminoalkyl, A is methylene, n is a 1 or 2, W is alkylene of from 2 to 10 carbon atoms, and $R_3$ is selected from the group consisting of,

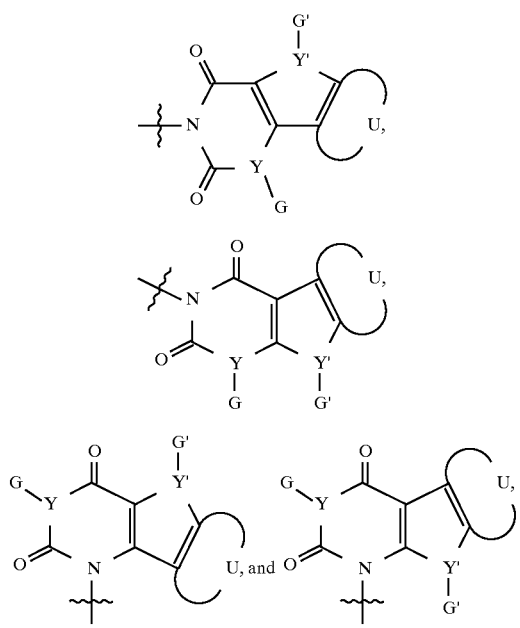

wherein G and G' are independently selected from the group consisting of hydrogen, alkyl, alkynyl, alkynyl, alkoxy, alkoxyalkyl, alkoxycarbonyl, hydroxy, hydroxyalkyl, carboxy, carboxyalkyl, halogen, alkylsulfonyl, and aminoalkyl, Y is nitrogen and Y' is selected from the group consisting of oxygen, nitrogen, and sulfur, with the proviso that when Y' is oxygen or sulfur, G' is absent, and U is a ring that is fused to its adjacent ring and is selected from the group consisting of (a) an unsubstituted or substituted five member ring having five carbon atoms; (b) an unsubstituted or substituted five membered ring having four carbon atoms and one heteroatom selected from the group consisting of nitrogen, oxygen, and sulfur; (c) an unsubstituted or substituted five membered ring having three carbon atoms and two heteroatoms independently selected from the group consisting of nitrogen, oxygen, and sulfur; (d) a substituted or unsubstituted six membered ring having six carbon atoms; (e) a substituted or unsubstituted six membered ring having 5 carbon atoms and one heteroatom selected from the group consisting of nitrogen, oxygen, and sulfur; (f) a substituted or unsubstituted 6 membered ring having 4 carbon atoms and two heteroatom selected from the group consisting of nitrogen, oxygen, and sulfur; and (g) a substituted or unsubstituted 6 membered ring having three carbon atoms and three heteroatoms selected from the group consisting of nitrogen, oxygen, and sulfur. The five membered rings constituting U may contain 0, 1, or 2 double bonds. The six membered rings constituting U may contain 0, 1, 2, or 3 double bonds. The rings (a)–(g) of the group constituting U may be mono or di-substituted with substituents independently selected from the group consisting of alkyl, alkoxy, cyano, nitro, carboxy, alkoxycarbonyl of two to eight carbon atoms, halogen, cycloalkyl, aryl, and heterocyclic; or a pharmaceutically acceptable salt thereof.

2. A compound of claim 1 wherein said five and six membered ring comprising U contains at least 1 double bond.

3. A compound according to claim 1 of formula II:

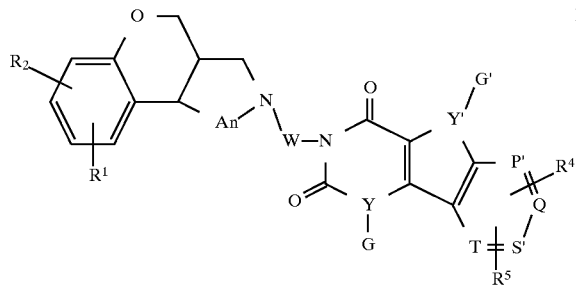

wherein

R₁ and R₂ are independently selected from the group consisting of hydrogen, alkyl, alkenyl, alkynyl, alkoxyalkyl, alkoxy, alkoxycarbonyl, hydroxy, hydroxyalkyl, carboxy, carboxyalkyl, halogen, nitro, amino, and aminoalkyl, A is methylene, n is 1 or 2, W is alkylene of from 2 to 10 carbon atoms, G and G' are independently selected from the group consisting of hydrogen, alkyl, alkenyl, alkynyl, alkoxy, alkoxyalkyl, alkoxycarbonyl, hydroxy, hydroxyalkyl, carboxy, carboxyalkyl, halogen, alkylsulfonyl, and aminoalkyl, Y is nitrogen and Y' is selected from the group consisting of oxygen, nitrogen, and sulfur, with the proviso that when Y' is oxygen or sulfur, G' is absent, P', Q, S', and T are independently selected from the group consisting of nitrogen and methine, with the proviso that no more than two of P', Q, S', and T can be nitrogen, and R₄ and R₅ are independently selected from hydrogen, alkyl, alkoxy, halogen, hydroxy, amino, cycloalkyl, aryl and heterocyclic; or a pharmaceutically acceptable salt thereof.

4. A compound according to claim 1 of the formula III:

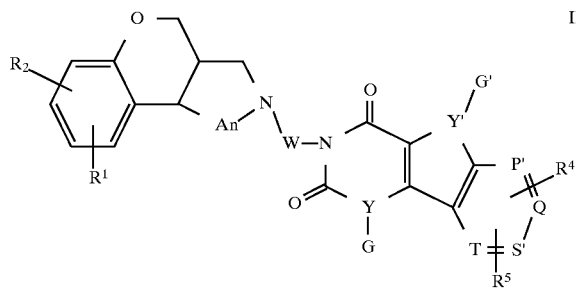

wherein R₁ and R₂ are independently selected from the group consisting of hydrogen, alkyl, alkenyl, alkynyl, alkoxyalkyl, alkoxy, alkoxycarbonyl, hydroxy, hydroxyalkyl, carboxy, carboxyalkyl, halogen, nitro, amino, and aminoalkyl, A is methylene, n is 1 or 2, W is alkylene of from 2 to 10 carbon atoms, G and G' are independently selected from the group consisting hydrogen, alkyl, alkenyl, alkynyl, alkoxy, alkoxyalkyl, alkoxycarbonyl, hydroxy, hydroxyalkyl, carboxy, carboxyalkyl, halogen, alkylsulfonyl, and aminoalkyl, Y is nitrogen and Y' is selected from the group consisting of oxygen, nitrogen, and sulfur, with the proviso that when Y' is oxygen or sulfur, G' is absent, P' and T are nitrogen, Q and S' are methine, and R₄ and R₅ are independently selected from hydrogen, alkyl, alkoxy, halogen, hydroxy, amino, cycloalkyl, aryl and heterocyclic; or a pharmaceutically acceptable salt thereof.

5. A compound according to claim 1 of formula IV:

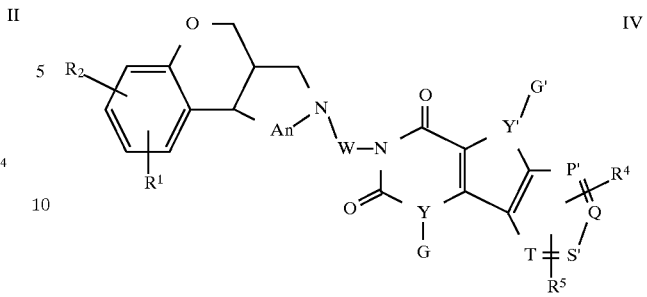

wherein R₁ and R₂ are independently selected from the group consisting of hydrogen, alkyl, alkenyl, alkynyl, alkoxyalkyl, alkoxy, alkoxycarbonyl, hydroxy, hydroxyalkyl, carboxy, carboxyalkyl, halogen, nitro, amino, and aminoalkyl, A is methylene, n is 1 or 2, W is alkylene of from 2 to 10 carbon atoms, G and G' are independently selected from the group consisting hydrogen, alkyl, alkenyl, alkynyl, alkoxy, alkoxyalkyl, alkoxycarbonyl, hydroxy, hydroxyalkyl, carboxy, carboxyalkyl, halogen, alkylsulfonyl, and aminoalkyl, Y is nitrogen and Y' is selected from the group consisting of oxygen, nitrogen, and sulfur, with the proviso that when Y' is oxygen or sulfur, G' is absent, P' is nitrogen, Q, S', and T are methine, and R₄ and R₅ are independently selected from hydrogen, alkyl, alkoxy, halogen, hydroxy, amino, cycloalkyl, aryl and heterocyclic; or a pharmaceutically acceptable salt thereof.

6. A compound according to claim 1 of formula V:

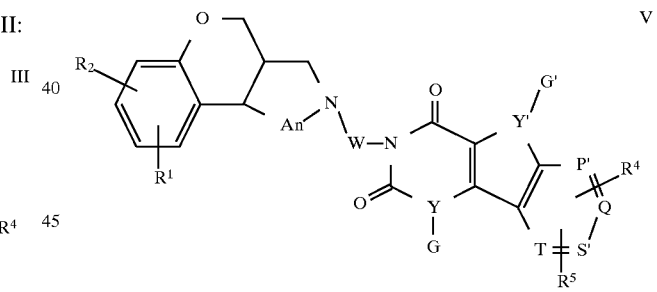

wherein R₁ and R₂ are independently selected from the group consisting of hydrogen, alkyl, alkenyl, alkynyl, alkoxyalkyl, alkoxy, alkoxycarbonyl, hydroxy, hydroxyalkyl, carboxy, carboxyalkyl, halogen, nitro, amino, and aminoalkyl, A is methylene, n is 1 or 2, W is alkylene of from 2 to 10 carbon atoms, G and G' are independently selected from the group consisting hydrogen, alkyl, alkenyl, alkynyl, alkoxy, alkoxyalkyl, alkoxycarbonyl, hydroxy, hydroxyalkyl, carboxy, carboxyalkyl, halogen, alkylsulfonyl, and aminoalkyl, Y is nitrogen and Y' is selected from the group consisting of oxygen, nitrogen, and sulfur, with the proviso that when Y' is oxygen or sulfur, G' is absent, Q is nitrogen, P', S', and T are methine, and R₄ and R₅ are independently selected from hydrogen, alkyl, alkoxy, halogen, hydroxy, amino, cycloalkyl, aryl and heterocyclic; or a pharmaceutically acceptable salt thereof.

7. A compound according to claim 1 of formula VI:

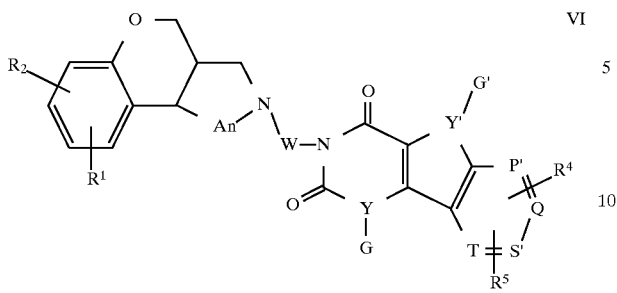

wherein R₁ and R₂ are independently selected from the group consisting of hydrogen, alkyl, alkenyl, alkynyl, alkoxyalkyl, alkoxy, alkoxycarbonyl, hydroxy, hydroxyalkyl, carboxy, carboxyalkyl, halogen, nitro, amino, and aminoalkyl, A is methylene, n is 1 or 2, W is alkylene of from 2 to 10 carbon atoms, G and G' are independently selected from the group consisting hydrogen, alkyl, alkenyl, alkynyl, alkoxy, alkoxyalkyl, alkoxycarbonyl, hydroxy, hydroxyalkyl, carboxy, carboxyalkyl, halogen, alkylsulfonyl, and aminoalkyl, Y is nitrogen and Y' is selected from the group consisting of oxygen, nitrogen, and sulfur, with the proviso that when Y' is oxygen or sulfur, G' is absent, S' is nitrogen, P', Q, and T are methine, and R₄ and R₅ are independently selected from hydrogen alkyl, alkoxy, halogen, hydroxy, amino, cycloalkyl, aryl and heterocyclic; or a pharmaceutically acceptable salt thereof.

8. A compound according to claim 1 of formula VII:

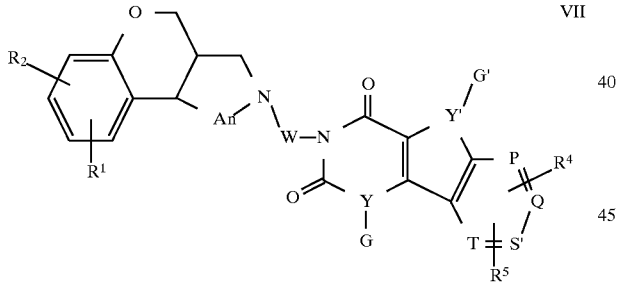

wherein R₁ and R₂ are independently selected from the group consisting of hydrogen, alkyl, alkenyl, alkynyl, alkoxyalkyl, alkoxy, alkoxycarbonyl, hydroxy, hydroxyalkyl, carboxy, carboxyalkyl, halogen, nitro, amino, and aminoalkyl, A is methylene, n is 1 or 2, W is alkylene of from 2 to 10 carbon atoms, G and G' are independently selected from the group consisting hydrogen, alkyl, alkenyl, alkynyl, alkoxy, alkoxyalkyl, alkoxycarbonyl, hydroxy, hydroxyalkyl carboxy, carboxyalkyl, halogen, alkylsulfonyl, and aminoalkyl, Y is nitrogen and Y' is selected from the group consisting of oxygen, nitrogen, and sulfur, with the proviso that when Y' is oxygen or sulfur, G' is absent, T is nitrogen, P', Q, and S' are methine and R₄ and R₅ are independently selected from hydrogen, alkyl, alkoxy, halogen, hydroxy, amino, cycloalkyl, aryl and heterocyclic; or a pharmaceutically acceptable salt thereof.

9. A compound according to claim 1 of formula VIII:

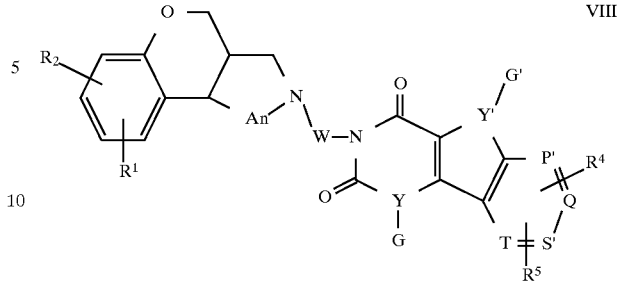

wherein
R₁ and R₂ are independently selected from the group consisting of hydrogen, alkyl, alkenyl, alkynyl, alkoxyalkyl, alkoxy, alkoxycarbonyl, hydroxy, hydroxyalkyl, carboxy, carboxyalkyl, halogen, nitro, amino, and aminoalkyl, A is methylene, n is 1 or 2, W is alkylene of from 2 to 10 carbon atoms, G and G' are independently selected from the group consisting hydrogen, alkyl, alkenyl, alkynyl, alkoxy, alkoxyalkyl, alkoxycarbonyl, hydroxy, hydroxyalkyl, carboxy, carboxyalkyl, halogen, alkylsulfonyl, and aminoalkyl, Y is nitrogen and Y' is selected from the group consisting of oxygen, nitrogen, and sulfur, with the proviso that when Y' is oxygen or sulfur, G' is absent, P', Q, S', and T are methine, and R₄ and R₅ are independently selected from hydrogen, alkyl, alkoxy, halogen, hydroxy, amino, cycloalkyl, aryl and heterocyclic; or a pharmaceutically acceptable salt thereof.

10. A compound according to claim 1 of formula I selected from the group consisting of:
3-[4-((3aR,9bR)-cis-9-Methoxy-1,2,3,3a,4,9b-hexahydro-[1]-benzopyrano[3,4-c]pyrrol-2-yl)butyl]-pyrido[2',3':4,5]thieno[3,2-d]pyrimidine-2,4(1H,3H)-dione,
3-[4-((3aS,9bR)-trans-9-Methoxy-1,2,3,3a,4,9b-hexahydro-[1]-benzopyrano[3,4-c]pyrrol-2-yl)butyl]-pyrido[2',3':4,5]thieno[3,2-d]pyrimidine-2,4(1H,3H)-dione,
3-[4-((3aS,9bR)-trans-9-Methoxy-1,2,3,3a,4,9b-hexahydro-[1]-benzopyrano[3,4-c]pyrrol-2-yl)butyl]-8-chloro-pyrazino[2',3':4,5]thieno[3,2-dyrimidine-2,4(1H,3H)-dione,
3-[4-((3aR,9bR)-cis-9-Methoxy-1,2,3,3a,4,9b-hexahydro-[1]-benzopyrano[3,4-c]pyrrol-2-yl)butyl]-8-chloro-pyrazino[2',3':4,5]thieno[3,2-d]pyrimidine-2,4(1H,3H)-dione,
3-[4-((3aR,9bR)-cis-9-Methoxy-1,2,3,3a,4,9b-hexahydro-[1]-benzopyrano[3,4c]pyrrol-2-yl)butyl]-8-methoxy-pyrido[2',3':4,5]thieno[3,2-d]pyrimidine-2,4(1H,3H)-dione,
3-[4-((3aR,9bR)-cis-9-Methoxy-1,2,3,3a,4,9b-hexahydro-[1]-benzopyrano[3,4c]pyrrol-2-yl)butyl]-8-methoxy-pyrazino[2',3':4,5]thieno[3,2-d]pyrimidine-2,4(1H,3H)-dione,
3-[4-((3aR,9bR)-cis-9-Methoxy-1,2,3,3a,4,9b-hexahydro-[1]-benzopyrano[3,4-c]pyrrol-2-yl)butyl]-7-methoxy-pyrido[3',2':4,5]thieno[3,2-d]pyrimidine-2,4(1H,3H)-dione,
3-[4-((3aR,9bR)-cis-9-Methoxy-1,2,3,3a,4,9b-hexahydro-[1]-benzopyrano[3,4c]pyrrol-2-yl)butyl]-7-chloro-pyrido[3',2':4,5]thieno[3,2-d]pyrimidine-2,4(1H,3H)-dione,
3-[4-((3aR,9bR)-cis-9-Methoxy-1,2,3,3a,4,9b-hexahydro-[1]-benzopyrano[3,4c]pyrrol-2-yl)butyl]-8-chloro-pyrido[2',3':4,5]thieno[3,2-d]pyrimidine-2,4(1H,3H)-dione,
3-[4-((3aR,9bR)-cis-9-Methoxy-1,2,3,3a,4,9b-hexahydro-[1]-benzopyrano[3,4-c]pyrrol-2-yl)butyl]-8-phenyl-pyrazino[2',3':4,5]thieno[3,2-d]pyrimidine-2,4(1H,3H)-dione, 3-[4-((3aS,9bR)-trans-9-Methoxy-1,2,3,3a,4,9b-hexahydro-[1]-benzopyrano[3,4-c]pyrrol-2-yl)butyl]-8-methoxy-pyrazino[2',3':4,5]thieno[3,2-d]pyrimidine-2,4(1H,3H)-dione, 3-[4-((3aS,9bR)-trans-9-Methoxy-1,2,3,3a,4,9b-hexahydro-[1]-benzopyrano[3,4c]pyrrol-2-yl)butyl]-7-methoxy-pyrido[3',2':4,5]thieno[3,2-d]pyrimidine-2,4(1H,3H)-dione, 3-[4-((3aS,9bR)-trans-9-Methoxy-1,2,3,3a,4,9b-hexahydro-[1]-benzopyrano[3,4-c]pyrrol-2-yl)butyl]-7-chloro-pyrido[3',2':4,5]thieno[3,2-d]pyrimidine-2,4(1H,3H)-dione, 3-[4-((3aS,9bR)-trans-9-Methoxy-1,2,3,3a,4,9b-hexahydro-[1]-benzopyrano[3,4-c]pyrrol-2-yl)butyl]-8-phenyl-pyrazino[2',3':4,5]thieno[3,2-d]pyrimidine-2,4(1H,3H)-dione, 3-[4-((3aS,9bR)-trans-9-Methoxy-1,2,3,3a,4,9b-hexahydro-[1]-benzopyrano[3,4-c]pyrrol-2-yl)butyl]-8-isopropoxy-pyrido[2',3':4,5]thieno[3,2-d]pyrimidine-2,4(1H,3H)-dione, 3-[4-((3aS,9bR)-trans-9-Methoxy-1,2,3,3a,4,9b-hexahydro-[1]-benzopyrano[3,4-c]pyrrol-2-yl)butyl]-8-phenyl-pyrido[2',3':4,5]thieno[3,2-d]pyrimidine-2,4(1H,3H)-dione, 3-[3-((4aS,10bR)-trans-10-Methoxy-1,3,4,4a,5,10b-hexahydro-2H-[1]-benzopyrano[3,4-c]pyrido-3-yl) propyl]-pyrido[2',3':4,5]thieno[3,2-d]pyrimidine-2,4(1H,3H)-dione, 3-[4-((4aS,10bR)-trans-10-Methoxy-1,3,4,4a,5,10b-hexahydro-2H-[1]-benzopyrano[3,4-c]pyrido-3-yl)butyl]-pyrido[2',3':4,5]thieno[3,2-d]pyrimidine-2,4(1H,3H)-dione, 3-[4-((4aS,10bR)-trans-10-Methoxy-1,3,4,4a,5,10b-hexahydro-2H-[1]-benzopyrano[3,4-c]pyrido-3-yl)butyl]-8-methoxy-pyrido[2',3':4,5]thieno[3,2-d]pyrimidine-2,4(1H,3H)-dione, 3-[4-((4aS,10bR)-trans-10-Methoxy-1,3,4,4a,5,10b-hexahydro-2H-[1]-benzopyrano[3,4-c]pyrido-3-yl)butyl]-8-methoxy-pyrazino[2',3':4,5]thieno[3,2-d]pyrimidine-2,4(1H,3H)-dione, 3-[4-((4aS,10bR)-trans-10-Methoxy-1,3,4,4a,5,10b-hexahydro-2H-[1]-benzopyrano[3,4-c]pyrido-3-yl)butyl]-8-phenyl-pyrazino[2',3':4,5]thieno[3,2-d]pyrimidine-2,4(1H,3H)-dione, 3-[4-((4aS,10bR)-trans-10-Methoxy-1,3,4,4a,5,10b-hexahydro-2H-[1]-benzopyrano[3,4-c]pyrido-3-yl)butyl]-8-phenyl-pyrido[2',3':4,5]thieno[3,2-d]pyrimidine-2,4(1H,3H)-dione, 3-[4-((3aR,9bR)-cis-9-Methoxy-1,2,3,3a,4,9b-hexahydro-[1]-benzopyrano[3,4-c]pyrrol-2-yl)butyl]-8-(3-thienyl)-pyrazino[2',3':4,5]thieno[3,2-d]pyrimidine-2,4(1H,3H)-dione, 3-[4-((3aR,9bR)-cis-9-Methoxy-1,2,3,3a,4,9b-hexahydro-[1]-benzopyrano[3,4-c]pyrrol-2-yl)butyl]-8-(3-pyridyl)-pyrido[2',3':4,5]thieno[3,2-d]pyrimidine-2,4(1H,3H)-dione, 3-[4-((3aR,9bR)-cis-9-Methoxy-1,2,3,3a,4,9b-hexahydro-[1]-benzopyrano[3,4-c]pyrrol-2-yl)butyl]-8-(3-pyridyl)-pyrazino[2',3':4,5]thieno[3,2-d]pyrimidine-2,4(1H,3H)-dione, 3-[4-((3aS,9bR)-trans-9-Methoxy-1,2,3,3a,4,9b-hexahydro-[1]-benzopyrano[3,4-c]pyrrol-2-yl)butyl)-8-(3-pyridyl)-pyrazino[2',3':4,5]thieno[3,2-d]pyrimidine-2,4(1H,3H)-dione, 3-[4-((3aR,9bR)-cis-9-Methoxy-1,2,3,3a,4,9b-hexahydro-[1]-benzopyrano[3,4-c]pyrrol-2-yl)butyl]-8-(3-furyl)-pyrazino[2',3':4,5]thieno[3,2-d]pyrimidine-2,4(1H,3H)-dione, and 3-[4-((3aS,9bR)-trans-9-Methoxy-1,2,3,3a,4,9b-hexahydro-[1]-benzopyrano[3,4-c]pyrrol-2-yl)butyl]-8-(3-thienyl)-pyrazino[2',3':4,5]thieno[3,2-d]pyrimidine-2,4(1H,3H)-dione, or a pharmaceutically acceptable salt thereof.

11. A compound according to claim 1 of formula IX:

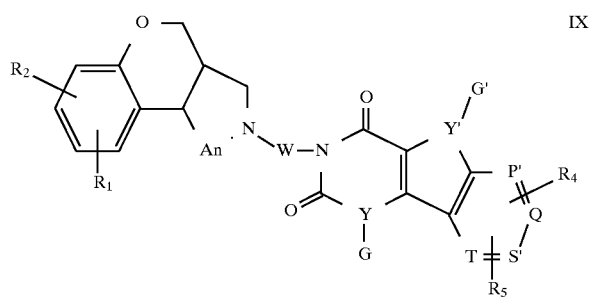

wherein $R_1$ and $R_2$ are independently selected from the group consisting of hydrogen, and alkoxy, A is methylene, n is 1, W is an alkylene of 2 to 10 carbon atoms, G is hydrogen, G' is absent, Y is nitrogen, Y' is sulfur, P', Q, S', are methine, T is nitrogen, and $R_4$ and $R_5$ are independently selected from hydrogen, alkyl, alkoxy, halogen, hydroxy, amino, cycloalkyl, aryl and heterocyclic; or a pharmaceutically acceptable salt thereof.

12. A compound of formula IX according to claim 11 wherein said compound is selected from the group of:

3-[4-((3aR,9bR)-cis-9-Methoxy-1,2,3,3a,4,9b-hexahydro-[1]-benzopyrano[3,4-c]pyrrol-2-yl)butyl]-pyrido[2',3':4,5]thieno[3,2-d]pyrimidine-2,4(1H,3H)-dione, 3-[4-((3aS,9bR)-trans-9-Methoxy-1,2,3,3a,4,9b-hexahydro-[1]-benzopyrano[3,4-c]pyrrol-2-yl)butyl]-pyrido[2',3':4,5]thieno[3,2-d]pyrimidine-2,4(1H,3H)-dione, 3-[4-((3aR,9bR)-cis-9-Methoxy-1,2,3,3a,4,9b-hexahydro-[1]-benzopyrano[3,4-c]pyrrol-2-yl)butyl]-8-methoxy-pyrido[2',3':4,5]thieno[3,2-d]pyrimidine-2,4(1H,3H)-dione, 3-[4-((3aR,9bR)-cis-9-Methoxy-1,2,3,3a,4,9b-hexahydro-[1]-benzopyrano[3,4-c]pyrrol-2-yl)butyl]-8-chloro-pyrido[2',3':4,5]thieno[3,2-d]pyrimidine-2,4(1H,3H)-dione, 3-[4-((3 aS,9bR)-trans-9-Methoxy-1,2,3,3a,4,9b-hexahydro-[1]-benzopyrano[3,4-c]pyrrol-2-yl)butyl]-8-isopropoxy-pyrido[2',3':4,5]thieno[3,2-d]pyrimidine-2,4(1H,3H)-dione, 3-[4-((3aS,9bR)-trans-9-Methoxy 1,2,3,3a,4,9b-hexahydro-[1]-benzopyrano[3,4-c]pyrrol-2-yl)butyl]-8-phenyl-pyrido[2',3':4,5]thieno[3,2-d]pyrimidine-2,4(1H,3H)-dione, and 3-[4-((3aR,9bR)-cis-9-Methoxy-1,2,3,3a,4,9b-hexahydro-[1]-benzopyrano[3,4-c]pyrrol-2-yl)butyl]-8-(3-pyridyl)-pyrido[2',3':4,5]thieno[3,2-d]pyrimidine-2,4(1H,3H)-dione, or a pharmaceutically acceptable salt thereof.

13. A compound according to claim 1 of formula X:

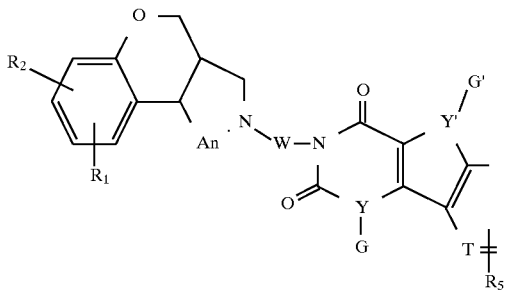

wherein $R_1$ and $R_2$ are independently selected from the group consisting of hydrogen, and alkoxy, A is methylene, n is 2, W is an alkylene of 2 to 10 carbon atoms, G is hydrogen, G' is absent, Y is nitrogen, Y' is sulfur, P', Q and S', are methine, T is nitrogen, and $R_4$ and $R_5$ are independently selected from hydrogen, alkyl, alkoxy, halogen, hydroxy, amino, cycloalkyl, aryl and heterocyclic; or a pharmaceutically acceptable salt thereof.

14. A compound of formula X according to claim 13 selected from the group consisting of:
3-[3-((4aS,10bR)-trans-10-Methoxy-1,3,4,4a,5,10b-hexahydro-2H-[1]-benzopyrano[3,4-c]pyrido-3-yl)propyl]-pyrido[2',3':4,5]thieno[3,2-d]pyrimidine-2,4(1H, 3H)-dione,
3-[4-((4aS,10bR)-trans-10-Methoxy-1,3,4,4a,5,10b-hexahydro-2H-[1]-benzopyrano[3,4-c]pyrido-3-yl)butyl]-pyrido[2',3':4,5]thieno[3,2-d]pyrimidine-2,4(1H,3H)-dione,
3-[4-((4aS,10bR)-trans-10-Methoxy-1,3,4,4a,5,10b-hexahydro-2H-[1]-benzopyrano[3,4-c]pyrido-3-yl)butyl]-8-methoxy-pyrido[2',3':4,5]thieno[3,2-d]pyrimidine-2,4(1H,3H)-dione, and
3-[4-((4aS,10bR)-trans-10-Methoxy-1,3,4,4a,5,10b-hexahydro-2H-[1]-benzopyrano]3,4-c]pyrido-3-yl)butyl]-8-phenyl-pyrido[2',3':4,5]thieno[3,2-d]pyrimidine-2,4(1H,3H)-dione,
or a pharmaceutically acceptable salt thereof.

15. A compound according to claim 1 of formula XI:

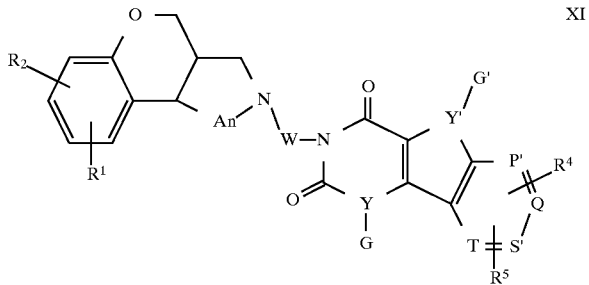

wherein $R_1$ and $R_2$ are independently selected from the group consisting of hydrogen, and alkoxy, A is methylene, n is 2, W is an alkylene of 2 to 10 carbon atoms, G is hydrogen, G' is absent, Y is nitrogen, Y' is sulfur, Q and S' are methine, P' and T are nitrogen, and $R_4$ and $R_5$ are independently selected from hydrogen, alkyl, alkoxy, halogen, hydroxy, amino, cycloalkyl, aryl and heterocyclic; or a pharmaceutically acceptable salt thereof.

16. A compound of formula XI according to claim 15 wherein said compound is selected from the group consisting of:
3-[4-((4aS,10bR)-trans-10-Methoxy-1,3,4,4a,5,10b-hexahydro-2H-[1]-benzopyrano[3,4-c]pyrido-3-yl)butyl]-8-methoxy-pyrazino[2',3':4,5]thieno[3,2-d]pyrimidine-2,4(1H,3H)-dione, and
3-[4-((4aS,10bR)-trans-10-Methoxy-1,3,4,4a,5,10b-hexahydro-2H-[1]-benzopyrano[3,4-c]pyrido-3-yl)butyl]-8-phenyl-pyrazino[2',3':4,5]thieno[3,2-d]pyrimidine-2,4(1H,3H)-dione,
or a pharmaceutically acceptable salt thereof.

17. A compound according to claim 1 of formula XII:

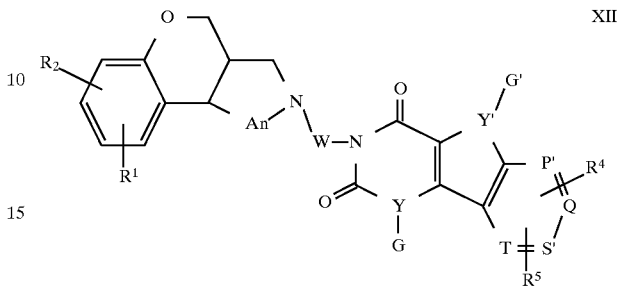

wherein $R_1$ and $R_2$ are independently selected from the group consisting of hydrogen, and alkoxy, A is methylene, n is 1, W is an alkylene of 2 to 10 carbon atoms, G is hydrogen, G' is absent, Y is nitrogen, Y' is sulfur, Q and S', are methine, P' and T are nitrogen, and $R_4$ and $R_5$ are independently selected from hydrogen, alkyl, alkoxy, halogen, hydroxy, amino, cycloalkyl, aryl and heterocyclic, or a pharmaceutically acceptable salt thereof.

18. A compound of formula XII according to claim 17 wherein said compound is selected from the group consisting of:
3-[4-((3aS,9bR)-trans-9-Methoxy-1,2,3,3a,4,9b-hexahydro-[1]-benzopyrano[3,4-c]pyrrol-2-yl)butyl]-8-chloro-pyrazino[2',3':4,5]thieno[3,2-d]pyrimidine-2,4(1H, 3H)-dione,
3-[4-((3aR,9bR)-cis-9-Methoxy-1,2,3,3a,4,9b-hexahydro-[1]-benzopyrano[3,4-c]pyrrol-2-yl)butyl]-8-chloro-pyrazino[2',3':4,5]thieno[3,2-d]pyrimidine-2,4(1H,3H)-dione,
3-[4-((3aR,9bR)-cis-9-Methoxy-1,2,3,3a,4,9b-hexahydro-[1]-benzopyrano[3,4-c]pyrrol-2-yl)butyl]-8-methoxy-pyrazino[2',3':4,5]thieno[3,2-d]pyrimidine-2,4(1H,3H)-dione,
3-[4-((3aR,9bR)-cis-9-Methoxy-1,2,3,3a,4,9b-hexahydro-[1]-benzopyrano[3,4-c]pyrrol-2-yl)butyl]-8-phenyl-pyrazino[2',3':4,5]thieno[3,2-d]pyrimidine-2,4(1H,3H)-dione,
3-[4-((3aS,9bR)-trans-9-Methoxy-1,2,3,3a,4,9b-hexahydro-[1]-benzopyrano[3,4-c]pyrrol-2-yl)butyl]-8-methoxy-pyrazino[2',3':4,5]thieno[3,2-d]pyrimidine-2,4(1H,3H)-dione,
3-[4-((3aS,9bR)-trans-9-Methoxy-1,2,3,3a,4,9b-hexahydro-[1]-benzopyrano[3,4-c]pyrrol-2-yl)butyl]-8-phenyl-pyrazino[2',3':4,5]thieno[3 ,2-d]pyrimidine-2,4(1H,3H)-dione,
3-[4-((3aR,9bR)-cis-9-Methoxy-1,2,3,3a,4,9b-hexahydro-[1]-benzopyrano[3,4-c]pyrrol-2-yl)butyl]-1-8-(3-thienyl)-pyrazino[2',3':4,5]thieno[3,2-d]pyrimidine-2,4(1H,3H)-dione,
3-[4-((3aR,9bR)-cis-9-Methoxy-1,2,3,3a,4,9b-hexahydro-[1]-benzopyrano[3,4-c]pyrrol-2-yl)butyl]-8-(3-pyridyl)-pyrazino[2',3':4,5]thieno[3,2-d]pyrimidine-2,4(1H,3H)-dione,
3-[4-((3aS,9bR)-trans-9-Methoxy-1,2,3,3a,4,9b-hexahydro-[1]-benzopyrano[3,4-c]pyrrol-2-yl)butyl]-8-(3-pyridyl)-pyrazino[2',3':4,5]thieno[3,2-d]pyrimidine-2,4(1H,3H)-dione,
3-[4-((3aR,9bR)-cis-9-Methoxy-1,2,3,3a,4,9b-hexahydro-[1]-benzopyrano[3,4-c]pyrrol-2-yl)butyl]8-(3-furyl)-pyrazino[2',3':4,5]thieno[3,2-d]pyrimidine-2,4(1H,3H)-dione, and 3-[4-((3aS,9bR)-trans-9-Methoxy-1,2,3,3a,4,9b-hexahydro-[1]-benzopyrano[3,4-c]pyrrol-2-yl)butyl]-8-(3-thienyl)-pyrazino[2',3':4,5]thieno[3,2-d]pyrimidine-2,4(1H,3H)-dione, or a pharmaceutically acceptable salt thereof.

19. A compound according to claim 1 of formula XIII:

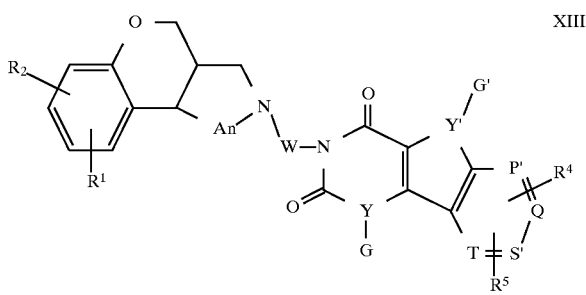

XIII wherein $R_1$ and $R_2$ are independently selected from the group consisting of hydrogen, and alkoxy, A is methylene, n is 1, W is an alkylene of 2 to 10 carbon atoms, G is hydrogen, G' is absent, Y is nitrogen, Y' is sulfur, Q, S', and T are methine, P' is nitrogen, and $R_4$ and $R_5$ are independently selected from hydrogen, alkyl, alkoxy, halogen, hydroxy, amino, cycloalkyl, aryl and heterocyclic, or a pharmaceutically acceptable salt thereof.

20. A compound of the formula XIII according to claim 19 wherein said compound is selected from the group consisting of:

3-[4-((3aR,9bR)-cis-9-Methoxy-1,2,3,3a,4,9b-hexahydro-[1]-benzopyrano[3,4-c]pyrrol-2-yl)butyl]-7-methoxy-pyrido[3',2':4,5]thieno[3,2-d]pyrimidine-2,4(1H,3H)-dione, 3-[4((3aR,9bR)-cis-9-Methoxy-1,2,3,3a,4,9b-hexahydro-[1]-benzopyrano[3,4-c]pyrrol-2-yl)butyl]-7-chloro-pyrido[3',2':4,5]thieno[3,2-d]pyrimidine-2,4(1H,3H)-dione, 3-[4-((3aS,9bR)-trans-9-Methoxy-1,2,3,3a,4,9b-hexahydro-[1]-benzopyrano[3,4-c]pyrrol-2-yl)butyl]-7-methoxy-pyrido[3',2':4,5]thieno[3,2-d]pyrimidine-2,4(1H,3H)-dione, and 3-[4-((3aS,9bR)-trans-9-Methoxy-1,2,3,3a,4,9b-hexahydro-[1]-benzopyrano[3,4-c]pyrrol-2-yl)butyl]-7-chloro-pyrido[3',2':4,5]thieno[3,2-d]pyrimidine-2,4(1H,3H)-dione, or a pharmaceutically acceptable salt thereof.

21. A compound according to claim 1 of formula XIV:

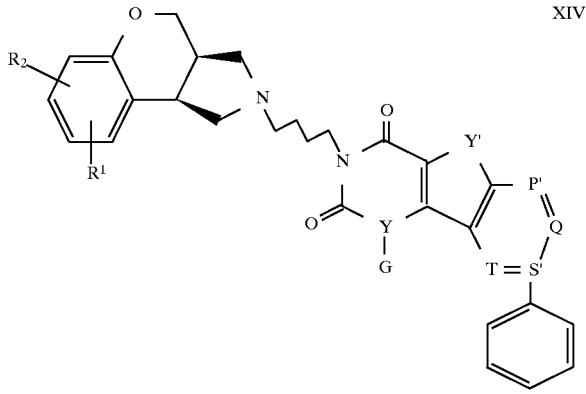

XIV wherein $R_1$ and $R_2$ are independently selected from the group consisting of hydrogen, and alkoxy, Y is nitrogen, G is hydrogen, Y' is sulphur, P' and T are nitrogen, and Q and S' are methine.

22. A compound of formula XIV according to claim 21 wherein said compound is 3-[4-((3aR,9bR)-cis-9-Methoxy-1,2,3,3a,4,9b-hexahydro-[1]-benzopyrano[3,4-c]pyrrol-2-yl)butyl]-8-phenyl-pyrazino[2',3':4,5]thieno[3,2-d]pyrimidine-2,4(1H,3H)-dione, or pharmaceutically acceptable salt thereof.

23. A compound of formula XIV according to claim 22 wherein said compound is 3-[4-((3aR,9bR)-cis-9-Methoxy-1,2,3,3a,4,9b-hexahydro-[1]-benzopyrano[3,4-c]pyrrol-2-yl)butyl]-8-phenyl-pyrazino[2',3':4,5]thieno[3,2-d]pyrimidine-2,4(1H,3H)-dione hydrochloride.

24. A pharmaceutical composition comprising a therapeutically effective amount of a compound of claim 1 in combination with a pharmaceutically acceptable carrier.

25. A pharmaceutical composition comprising a therapeutically effective amount of a compound of claim 22 in combination with a pharmaceutically acceptable carrier.

26. A method of treating benign prostatic hyperplasia (BPH) in a host mammal in need of such treatment comprising administering a therapeutically effective amount of a compound of claim 1.

27. A method of treating benign prostatic hyperplasia (BPH) in a host mammal in need of such treatment comprising administering a therapeutically effective amount of a compound of claim 22.

28. A method of treating bladder outlet obstruction (BOO) in a host mammal in need of such treatment comprising administering a therapeutically effective amount of a compound of claim 1.

29. A method of treating bladder outlet obstruction (BOO) in a host mammal in need of such treatment comprising administering a therapeutically effective amount of a compound of claim 22.

30. A method of treating neurogenic bladder in a host mammal in need of such treatment comprising administering a therapeutically effective amount of a compound of claim 1.

31. A method of treating neurogenic bladder in a host mammal in need of such treatment comprising administering a therapeutically effective amount of a compound of claim 22.

32. A method of treating uterine smooth muscle contraction in a host mammal in need of such treatment comprising administering a therapeutically effective amount of a compound of claim 1.

33. A method of treating uterine smooth muscle contraction in a host mammal in need of such treatment comprising administering a therapeutically effective amount of a compound of claim 22.

* * * * *